US012617822B2

(12) United States Patent
Malone et al.

(10) Patent No.: US 12,617,822 B2
(45) Date of Patent: **\*May 5, 2026**

(54) ARC-BASED CAPSIDS AND USES THEREOF

(71) Applicant: VNV NEWCO INC., Boston, MA (US)

(72) Inventors: Colin Malone, South Orange, NJ (US); Ian Peikon, Bethpage, NY (US); Zachary Gilbert, Brooklyn, NY (US); Andrey Pisarev, Brooklyn, NY (US); Adam Fraites, Boston, MA (US); Jessica Crisp, Phoenix, AZ (US)

(73) Assignee: Aera Therapeutics, Inc., Cambridge, MA (US)

( * ) Notice: Subject to any disclaimer, the term of this patent is extended or adjusted under 35 U.S.C. 154(b) by 677 days.

This patent is subject to a terminal disclaimer.

(21) Appl. No.: 18/046,354

(22) Filed: Oct. 13, 2022

(65) Prior Publication Data

US 2023/0312657 A1     Oct. 5, 2023

Related U.S. Application Data

(63) Continuation of application No. 17/382,102, filed on Jul. 21, 2021, now Pat. No. 11,505,578, which is a continuation of application No. 17/277,119, filed as application No. PCT/US2019/051786 on Sep. 18, 2019, now abandoned.

(60) Provisional application No. 62/733,015, filed on Sep. 18, 2018.

(51) Int. Cl.

| | |
|---|---|
| *C12N 15/11* | (2006.01) |
| *A61K 9/16* | (2006.01) |
| *A61K 38/00* | (2006.01) |
| *A61K 39/39* | (2006.01) |
| *A61K 48/00* | (2006.01) |
| *C07K 14/005* | (2006.01) |
| *C07K 14/15* | (2006.01) |
| *C07K 14/16* | (2006.01) |
| *C07K 14/435* | (2006.01) |
| *C07K 14/46* | (2006.01) |
| *C07K 16/00* | (2006.01) |
| *C12N 9/22* | (2006.01) |
| *C12N 15/85* | (2006.01) |
| *C12N 15/87* | (2006.01) |
| *C12N 15/90* | (2006.01) |
| *A61K 39/00* | (2006.01) |

(52) U.S. Cl.
CPC ............ *C07K 14/15* (2013.01); *A61K 9/1658* (2013.01); *A61K 38/00* (2013.01); *A61K 39/39* (2013.01); *A61K 48/0008* (2013.01); *C07K 14/005* (2013.01); *C07K 14/16* (2013.01); *C07K 14/161* (2013.01); *C07K 14/435* (2013.01); *C07K 14/46* (2013.01); *C07K 16/00* (2013.01); *C12N 9/22* (2013.01); *C12N 15/11* (2013.01); *C12N 15/111* (2013.01); *C12N*

*15/85* (2013.01); *C12N 15/87* (2013.01); *C12N 15/907* (2013.01); *A61K 39/0011* (2013.01); *A61K 2039/55555* (2013.01); *A61K 2039/80* (2018.08); *C12N 2310/12* (2013.01); *C12N 2310/141* (2013.01); *C12N 2310/20* (2017.05); *C12N 2310/3519* (2013.01); *C12N 2310/531* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 4,510,245 | A | 4/1985 | Cousens et al. |
| 4,737,323 | A | 4/1988 | Martin et al. |
| 4,837,028 | A | 6/1989 | Allen |
| 4,897,355 | A | 1/1990 | Eppstein et al. |
| 4,968,615 | A | 11/1990 | Koszinowski et al. |
| 5,000,960 | A | 3/1991 | Wallach |
| 5,168,062 | A | 12/1992 | Stinski |
| 5,260,065 | A | 11/1993 | Mathur |
| 5,543,158 | A | 8/1996 | Gref et al. |
| 5,855,913 | A | 1/1999 | Hanes et al. |
| 5,869,326 | A | 2/1999 | Hofmann |
| 5,985,309 | A | 11/1999 | Edwards et al. |
| 6,007,845 | A | 12/1999 | Domb |
| 6,479,626 | B1 | 11/2002 | Kim et al. |
| 6,534,261 | B1 | 3/2003 | Cox, III et al. |
| 6,607,882 | B1 | 8/2003 | Cox, III et al. |
| 6,746,838 | B1 | 6/2004 | Choo et al. |
| 6,794,136 | B1 | 9/2004 | Eisenberg et al. |
| 6,824,978 | B1 | 11/2004 | Cox, III et al. |
| 6,866,997 | B1 | 3/2005 | Choo et al. |

(Continued)

FOREIGN PATENT DOCUMENTS

| | | |
|---|---|---|
| CA | 2331923 C | 2/2014 |
| CA | 2383877 C | 4/2014 |

(Continued)

OTHER PUBLICATIONS

Abed et al. The Gag protein PEG10 binds to RNA and regulates trophoblast stem cell lineage specification. PLoS One 14(4):e0214110 (2019).

(Continued)

*Primary Examiner* — Carla J Myers

(74) *Attorney, Agent, or Firm* — Blank Rome LLP

(57) ABSTRACT

Disclosed herein, in certain embodiments, are recombinant Arc and endogenous Gag polypeptides, and methods of using recombinant Arc and endogenous Gag polypeptides.

11 Claims, 8 Drawing Sheets

Specification includes a Sequence Listing.

(56) References Cited

U.S. PATENT DOCUMENTS

| | | | |
|---|---|---|---|
| 6,903,185 B2 | 6/2005 | Kim et al. | |
| 6,919,438 B1 | 7/2005 | Alliel et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,030,215 B2 | 4/2006 | Liu et al. | |
| 7,220,719 B2 | 5/2007 | Case et al. | |
| 7,241,573 B2 | 7/2007 | Choo et al. | |
| 7,241,574 B2 | 7/2007 | Choo et al. | |
| 7,442,550 B1 | 10/2008 | Mallet et al. | |
| 7,534,439 B2 | 5/2009 | Alliel et al. | |
| 7,585,849 B2 | 9/2009 | Liu et al. | |
| 7,595,376 B2 | 9/2009 | Kim et al. | |
| 7,776,321 B2 | 8/2010 | Cascalho et al. | |
| 8,021,867 B2 | 9/2011 | Smith et al. | |
| 8,084,213 B2 | 12/2011 | Sepp et al. | |
| 8,119,361 B2 | 2/2012 | Smith et al. | |
| 8,119,381 B2 | 2/2012 | Smith et al. | |
| 8,124,369 B2 | 2/2012 | Smith et al. | |
| 8,129,134 B2 | 3/2012 | Smith et al. | |
| 8,133,697 B2 | 3/2012 | Smith et al. | |
| 8,163,514 B2 | 4/2012 | Smith et al. | |
| 8,318,173 B2 | 11/2012 | August et al. | |
| 8,440,431 B2 | 5/2013 | Voytas et al. | |
| 8,440,432 B2 | 5/2013 | Voytas et al. | |
| 8,450,471 B2 | 5/2013 | Voytas et al. | |
| 8,518,694 B2 | 8/2013 | Hardy et al. | |
| 8,597,657 B2 | 12/2013 | Renard et al. | |
| 8,697,359 B1 | 4/2014 | Zhang | |
| 8,709,843 B2 | 4/2014 | Shakuda | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,418 B2 | 11/2014 | Zhang et al. | |
| 8,895,308 B1 | 11/2014 | Zhang et al. | |
| 8,906,616 B2 | 12/2014 | Zhang et al. | |
| 8,932,814 B2 | 1/2015 | Cong et al. | |
| 8,945,839 B2 | 2/2015 | Zhang | |
| 8,993,233 B2 | 3/2015 | Zhang et al. | |
| 8,999,641 B2 | 4/2015 | Zhang et al. | |
| 9,254,311 B2 | 2/2016 | Bancel et al. | |
| 9,481,905 B2 | 11/2016 | Chen et al. | |
| 9,555,091 B2 | 1/2017 | Kim et al. | |
| 9,827,332 B2 | 11/2017 | Bancel et al. | |
| 11,129,892 B1 | 9/2021 | Gilbert et al. | |
| 11,447,527 B2 | 9/2022 | Malone et al. | |
| 11,505,578 B2 | 11/2022 | Malone et al. | |
| 2004/0171156 A1 | 9/2004 | Hartley et al. | |
| 2011/0027239 A1 | 2/2011 | Paek | |
| 2011/0265198 A1 | 10/2011 | Gregory et al. | |
| 2011/0293703 A1 | 12/2011 | Mahon et al. | |
| 2012/0017290 A1 | 1/2012 | Cui et al. | |
| 2012/0251560 A1 | 10/2012 | Dahlman et al. | |
| 2013/0236946 A1 | 9/2013 | Gouble | |
| 2013/0302401 A1 | 11/2013 | Ma et al. | |
| 2014/0170753 A1 | 6/2014 | Zhang | |
| 2014/0179006 A1 | 6/2014 | Zhang | |
| 2014/0179770 A1 | 6/2014 | Zhang et al. | |
| 2014/0186843 A1 | 7/2014 | Zhang et al. | |
| 2014/0186919 A1 | 7/2014 | Zhang et al. | |
| 2014/0186958 A1 | 7/2014 | Zhang et al. | |
| 2014/0189896 A1 | 7/2014 | Zhang et al. | |
| 2014/0227787 A1 | 8/2014 | Zhang | |
| 2014/0234972 A1 | 8/2014 | Zhang | |
| 2014/0242664 A1 | 8/2014 | Zhang et al. | |
| 2014/0242699 A1 | 8/2014 | Zhang | |
| 2014/0242700 A1 | 8/2014 | Zhang et al. | |
| 2014/0248702 A1 | 9/2014 | Zhang et al. | |
| 2014/0256046 A1 | 9/2014 | Zhang et al. | |
| 2014/0273231 A1 | 9/2014 | Zhang et al. | |
| 2014/0273232 A1 | 9/2014 | Zhang et al. | |
| 2014/0273234 A1 | 9/2014 | Zhang et al. | |
| 2014/0287938 A1 | 9/2014 | Zhang et al. | |
| 2014/0308304 A1 | 10/2014 | Manoharan | |
| 2014/0310830 A1 | 10/2014 | Zhang et al. | |
| 2014/0328759 A1 | 11/2014 | Cullis et al. | |
| 2014/0348900 A1 | 11/2014 | Zhu | |
| 2015/0184139 A1 | 7/2015 | Zhang et al. | |
| 2017/0087087 A1 | 3/2017 | Leonard et al. | |
| 2018/0135025 A1 | 5/2018 | Bouille et al. | |
| 2019/0240351 A1 | 8/2019 | Bancel et al. | |
| 2019/0300902 A1 | 10/2019 | Galy | |
| 2020/0330586 A1 | 10/2020 | Holst et al. | |
| 2020/0347100 A1 | 11/2020 | Zhang | |
| 2021/0047375 A1 | 2/2021 | Lu et al. | |
| 2021/0189432 A1 | 6/2021 | Shepherd et al. | |
| 2021/0261957 A1 | 8/2021 | Petris et al. | |
| 2021/0403907 A1 | 12/2021 | Malone et al. | |
| 2022/0016032 A1 | 1/2022 | Malone et al. | |
| 2022/0088224 A1 | 3/2022 | Malone et al. | |

FOREIGN PATENT DOCUMENTS

| | | | |
|---|---|---|---|
| CN | 101952436 B | 3/2013 | |
| CN | 109563139 A | 4/2019 | |
| EP | 1090122 B1 | 7/2008 | |
| EP | 2241626 A2 | 10/2010 | |
| EP | 2385058 B1 | 11/2013 | |
| EP | 2764103 A2 | 8/2014 | |
| EP | 2771468 A1 | 9/2014 | |
| EP | 2784162 A1 | 10/2014 | |
| EP | 2241626 B1 | 1/2016 | |
| EP | 3445774 A1 | 2/2019 | |
| EP | 3452101 A2 | 3/2019 | |
| JP | 4283475 B2 | 6/2009 | |
| JP | 4824731 B2 | 11/2011 | |
| JP | 5309159 B2 | 10/2013 | |
| JP | 2016526045 A | 9/2016 | |
| JP | 2019514369 A | 6/2019 | |
| KR | 101164602 B1 | 7/2012 | |
| KR | 20180135034 A | 12/2018 | |
| WO | WO-9212237 A1 | 7/1992 | |
| WO | WO-9400588 A1 | 1/1994 | |
| WO | WO-9749450 A1 | 12/1997 | |
| WO | WO-9852609 A1 | 11/1998 | |
| WO | WO-2004087748 A1 | 10/2004 | |
| WO | 2007072056 A2 | 6/2007 | |
| WO | WO-2009042727 A1 | 4/2009 | |
| WO | WO-2011028929 A2 | 3/2011 | |
| WO | WO-2012135025 A2 | 10/2012 | |
| WO | WO-2013151663 A1 | 10/2013 | |
| WO | WO-2013151664 A1 | 10/2013 | |
| WO | WO-2013158141 A1 | 10/2013 | |
| WO | WO-2014018423 A2 | 1/2014 | |
| WO | WO-2014093595 A1 | 6/2014 | |
| WO | WO-2014093622 A2 | 6/2014 | |
| WO | WO-2014093635 A1 | 6/2014 | |
| WO | WO-2014093655 A2 | 6/2014 | |
| WO | WO-2014093661 A2 | 6/2014 | |
| WO | WO-2014093694 A1 | 6/2014 | |
| WO | WO-2014093701 A1 | 6/2014 | |
| WO | WO-2014093709 A1 | 6/2014 | |
| WO | WO-2014093712 A1 | 6/2014 | |
| WO | WO-2014093718 A1 | 6/2014 | |
| WO | WO-2014118272 A1 | 8/2014 | |
| WO | WO-2014204723 A1 | 12/2014 | |
| WO | WO-2014204724 A1 | 12/2014 | |
| WO | WO-2014204725 A1 | 12/2014 | |
| WO | WO-2014204726 A1 | 12/2014 | |
| WO | WO-2014204727 A1 | 12/2014 | |
| WO | WO-2014204728 A1 | 12/2014 | |
| WO | WO-2014204729 A1 | 12/2014 | |
| WO | WO-2015058052 A1 | 4/2015 | |
| WO | WO-2015070083 A1 | 5/2015 | |
| WO | 2015089406 A1 | 6/2015 | |
| WO | WO-2015089351 A1 | 6/2015 | |
| WO | WO-2015089354 A1 | 6/2015 | |
| WO | WO-2015089364 A1 | 6/2015 | |
| WO | WO-2015089419 A2 | 6/2015 | |
| WO | WO-2015089427 A1 | 6/2015 | |
| WO | WO-2015089462 A1 | 6/2015 | |
| WO | WO-2015089465 A1 | 6/2015 | |

(56) References Cited

FOREIGN PATENT DOCUMENTS

| WO | WO-2015089473 A1 | 6/2015 | | |
| WO | WO-2015089486 A2 | 6/2015 | | |
| WO | WO-2016049258 A2 | 3/2016 | | |
| WO | WO-2016094867 A1 | 6/2016 | | |
| WO | WO-2016094872 A1 | 6/2016 | | |
| WO | WO-2016094874 A1 | 6/2016 | | |
| WO | WO-2016106236 A1 | 6/2016 | | |
| WO | WO-2016106244 A1 | 6/2016 | | |
| WO | WO-2016149426 A1 | 9/2016 | | |
| WO | WO-2016161516 A1 | 10/2016 | | |
| WO | WO-2017068077 A1 | 4/2017 | | |
| WO | WO-2017165859 A1 * | 9/2017 | .......... | A61K 48/005 |
| WO | WO-2017182607 A1 | 10/2017 | | |
| WO | WO-2017191274 A2 | 11/2017 | | |
| WO | WO-2018209113 A1 | 11/2018 | | |
| WO | WO-2018213708 A1 | 11/2018 | | |
| WO | WO-2018213726 A1 | 11/2018 | | |
| WO | WO-2018234576 A1 | 12/2018 | | |
| WO | WO-2019005884 A1 | 1/2019 | | |
| WO | WO-2019005886 A1 | 1/2019 | | |
| WO | WO-2019018423 A1 | 1/2019 | | |
| WO | WO-2019060746 A1 | 3/2019 | | |
| WO | WO-2019067225 A1 | 4/2019 | | |
| WO | WO-2019071048 A1 | 4/2019 | | |
| WO | WO-2019077149 A1 | 4/2019 | | |
| WO | WO-2019077150 A1 | 4/2019 | | |
| WO | WO-2019118497 A1 | 6/2019 | | |
| WO | WO-2019126709 A1 | 6/2019 | | |
| WO | WO-2019126762 A2 | 6/2019 | | |
| WO | WO-2020043908 A1 | 3/2020 | | |
| WO | WO-2020061229 A2 | 3/2020 | | |
| WO | WO-2020131862 A1 | 6/2020 | | |
| WO | WO-2020252455 A1 | 12/2020 | | |
| WO | WO-2021055855 A1 | 3/2021 | | |
| WO | WO-2021236513 A1 | 11/2021 | | |
| WO | WO-2022164942 A1 | 8/2022 | | |

OTHER PUBLICATIONS

Abudayeh et al. C2c2 is a single-component programmable RNA-guided RNA-targeting CRISPR effector. Science 353(6299):aaf5573 (2016).
Akinc et al. Targeted Delivery of RNAi Therapeutics With Endogenous and Exogenous Ligand-Based Mechanisms. Mol Ther 18(7):1357-1364 (2010).
Alhasan et al. Exosome encased spherical nucleic acid gold nanoparticle conjugates as potent microRNA regulation agents. Small. 10(1):186-192 (2014).
Allerson et al. Fully 2'-modified oligonucleotide duplexes with improved in vitro potency and stability compared to unmodified small interfering RNA. J Med Chem. 48:901-904 (2005).
Altinoglu et al. Intracellular delivery of the PTEN protein using cationic lipoids for cancer therapy. Biomater Sci. 4(12):1773-80 (2016).
Altschul et al. Basic local alignment search tool. J Mol Biol 215(3):403-410 (1990).
Alvarez-Erviti et al. Delivery of siRNA to the mouse brain by systemic injection of targeted exosomes. Nature Biotechnol. 29:341-345 (2011).
An et al. Envelope gene of the human endogenous retrovirus HERV-W encodes a functional retrovirus envelope. J. Virol. 75:3488-3489 (2001).
Antony et al. The human endogenous retrovirus envelope glycoprotein, Syncytin-1, regulates neuroinflammation and its receptor expression in multiple sclerosis: a role for endoplasmic reticulum chaperones in astrocytes. J Immunology 179(2):1210-1224 (2007).
Anzalone, et al. Search-and-replace genome editing without double-strand breaks or donor DNA. Nature 576:149-157 (2019).
Ashley et al. Retrovirus-like Gag protein Arc1 binds RNA and traffics across synaptic boutons. Cell 172:262-274 (2018).

Balachandran et al. Vesicular stomatitis virus (VSV) therapy of tumors. IUBMB Life 50:135-8 (2000).
Baldrick. Pharmaceutical Excipient Development: The Need for Preclinical Guidance. Regul Toxicol Pharmacology 32(2):210-218 (2000).
Balvay et al. Translational control of retroviruses. Nat rev Microbiol 5(2):128-49 (2007).
Bartlett et al. Impact of tumor-specific targeting on the biodistribution and efficacy of siRNA nanoparticles measured by multimodality in vivo imaging. PNAS USA 104(39):15549-15554 (2007).
Basha et al. Influence of cationic lipid composition on gene silencing properties of lipid nanoparticle formulations of siRNA in antigen-presenting cells. Molecular Therapy 19(12):2186-200 (2011).
Becker et al. Extracellular vesicles in cancer: cell-to-cell mediators of metastasis. Cancer Cell 30:836-848 (2016).
Benit et al. Identification, phylogeny, and evolution of retroviral elements based on their envelope genes. J. Virol. 75:11709-11719 (2001).
Besser et al. Clinical Responses in a Phase II Study Using Adoptive Transfer of Short-term Cultured Tumor Infiltration Lymphocytes in Metastatic Melanoma Patients. Clinical Cancer Research 16(9):2646-2655 (2010).
Boch et al. Breaking the Code of DNA Binding Specificity of TAL-Type III Effectors. Science 326:1509-1512 (Dec. 11, 2009).
Boshart et al. A very strong enhancer is located upstream of an immediate early gene of human cytomegalovirus. Cell. 41(2):521-30 (1985).
Bramham et al. The Arc of synaptic memory. Exp. Brain Res. 200:125-140 (2010).
Bramsen et al. Development of Therapeutic-Grade Small Interfering RNAs by Chemical Engineering. Front Genet. 3:154 (2012).
Brandt et al. A family of neofunctionalized Ty3/gypsy retrotransposon genes in mammalian genomes. Cytogenet Genome Res 110(1-4):307-17 (2005).
Brandt et al. Transposable elements as a source of genetic innovation: expression and evolution of a family of retrotransposon-derived neogenes in mammals. Gene 345:101-111 (2005).
Brigham et al. Expression of a prokaryotic gene in cultured lung endothelial cells after lipofection with a plasmid vector. Am. J. Resp. Cell. Mol. Biol. 1:95-100 (1989).
Brown. Propellant-Driven Aerosols of Proteins. Aerosol Science and Technology 24(1):45-56 (1994).
Budnik et al. Extracellular vesicles round off communication in the nervous system. Nat. Rev. Neurosci. 17:160-172 (2016).
Campbell et al. In vitro assembly properties of human immunodeficiency virus type 1 Gag protein lacking the p6 domain. J. Virol. 73:2270-2279 (1999).
Campillos et al. Computational characterization of multiple Gag-like human proteins. Trends Genet. 22(11):585-9 (2006).
Canver et al. BCL11A enhancer dissection by Cas9-mediated in situ saturating mutagenesis. Nature. 527(7577): 192-197 (2015).
Carlson et al. Reconstitution of selective HIV-1 RNA packaging in vitro by membrane-bound Gag assemblies. eLife 5:e14663 (2016).
Carr et al. Genome engineering. Nat Biotechnol. 27(12):1151-62 (2009).
Cermak et al., Efficient design and assembly of custom TALEN and other TAL effector-based constructs for DNA targeting. Nucleic Acids Research 39(12):e82 (2011).
Chen et al. Dynamic Imaging of Genomic Loci in Living Human Cells by an Optimized CRISPR/Cas System. Cell. 155(7):1479-1491 (2013).
Chen et al. Genome-wide CRISPR screen in a mouse model of tumor growth and metastasis. Cell. 160(6):1246-60 (2015).
Choi et al. Mechanism for the endocytosis of spherical nucleic acid nanoparticle conjugates. PNAS USA 110(19):7625-7630 (2013).
Chowdhury et al. Arc/Arg3.1 interacts with the endocytic machinery to regulate AMPA receptor trafficking. Neuron 52:445-459 (2006).
Chung et al. Polycistronic RNA polymerase II expression vectors for RNA interference based on BIC/miR-155. Nucleic Acids Res 34(7):e53 (2006).
Chuong et al. Regulatory activities of transposable elements: from conflicts to benefits. Nat. Rev. Genet. 18:71-8 (2017).

(56)  References Cited

OTHER PUBLICATIONS

Cloud-Clone Corp., Recombinant Paraneoplastic Antigen MA2 (PNMA2). Instruction manual, 20.16.08, 1-3 sheets, URL:http://www.cloud-clone.com/products/RPH343Hu01.html.

Coelho et al. Safety and efficacy of RN Ai therapy for transthyretin amyloidosis. New Engl J Med. 369(9):819-829 (2013).

Comas-Garcia et al. On the selective packaging of genomic RNA by HIV-1. Viruses 8(9):246 (2016).

Cong et al. Multiplex genome engineering using CRISPR/Cas systems. Science 339:819-823 (2013).

Cornelis et al. Retro-viral envelope gene captures and syncytin exaptation for placentation in marsupials. PNAS USA 112:E487-E496 (2015).

Cox et al. RNA editing with CRISPR-Cas13. Science 358:1019-1027 (2017).

Craven et al. Dynamic interactions of the Gag polyprotein. Morphogenesis and maturation of retroviruses. pp. 65-94 (1996).

Cutler et al. Polyvalent nucleic acid nanostructures. J Am Chem Soc. 133(24):9254-9257 (2011).

Cutler et al. Spherical nucleic acids. J Am Chem Soc. 134(3):1376-1391 (2012).

Daberkow et al. Arc mRNA induction in striatal efferent neurons associated with response learning. Eur. J. Neurosci. 26:228-241 (2007).

Dahlman et al. In vivo endothelial siRNA delivery using polymeric nanoparticleswith low molecular weight. Nat Nanotechnol, 9(8):648-655 (2014).

Day et al. Arc: Building a bridge from viruses to memory. Biochem. J. 469(1):p. el-e3 (2015).

De Solis et al. Is Arc mRNA unique: a search for mRNAs that localize to the distal dendrites of dentate gyrus granule cells following neural activity. Front. Mol. Neurosci. 10:314 (2017).

Delamarre et al. A Novel Human T-leukemia Virus Type 1 Cell-To-Cell Transmission Assay Permits Definition of SU Glycoprotein Amino Acids Important for Infectivity. J. Virol. 71(1):259-266 (1997).

Delchambre et al., The Gag Precursor of Simian Immunodeficiency Virus Assembles Into Virus-Like Particles. The EMBO Journal 8(9):2653-26660 (1989).

Dellinger et al. Streamlined process for the chemical synthesis of RNA using 2'-O-thionocarbamate-protected nucleoside phosphoramidites in the solid phase. J Am Chem Soc 133(30):11540-11556 (Jun. 20, 2011).

Deng et al. CASFISH: CRISPR/Cas9-mediated in situ labeling of genomic loci in fixed cells. PNAS USA 112:11870-11875 (2015).

Dickson et al. Protein biosynthesis and assembly. RNA tumor viruses (Weiss, N. Teich, H. Varmus, and J. Coffin, Eds. Cold Spring Harbor Laboratory, Cold Spring Harbor, N.Y. 1:513-648 (1984).

Doench et al. Rational design of highly active sgRNAs for CRISPR-Cas9-mediated gene inactivation. Nat Biotechnol 32:1262-1267 (2014).

Doyon et al. Enhancing zinc-finger-nuclease activity with improved obligate heterodimeric architectures. Nat Methods. 8(1):74-9 (2011).

Dudley et al. Cancer Regression and Autoimmunity in Patients After Clonal Repopulation with Antitumor Lvmohocytes. Science 298:850-854 (2002).

Dudley et al. Adoptive Cell Transfer Therapy Following Non-Myeloablative but Lymphodepleting Chemotherapy for the Treatment of Patients With Refractory Metastatic Melanoma. J Clin Oncol. 23(10):2346-2357 (2005).

Faure et al. Exosomes are released by cultured cortical neurones. Mol. Cell. Neurosci. 31:642-648 (2006).

Feigner et al. Lipofection: A Highly Efficient, Lipid-Mediated DNA-Transfection Procedure. PNAS USA 84(21):7413-7417 (1987).

Feschotte et al. Endogenous viruses: insights into viral evolution and impact on host biology. Nat. Rev. Genet. 13:283-296 (2012).

File History for U.S. Appl. No. 16/876,731, filed Oct. 8, 2021 entitled Vaccine Compositions Comprising Endogenous Gag Polypeptides (downloaded Dec. 7, 2021).

File History for U.S. Appl. No. 17/277,119, filed Mar. 17, 2021 entitled Arc-Based Capsids and Uses Thereof (downloaded Dec. 7, 2021).

File History for U.S. Appl. No. 17/382,102, filed Jul. 21, 2021 entitled Arc-Based Capsids and Uses Thereof (downloaded Dec. 7, 2021).

File History for U.S. Appl. No. 17/473,209, filed Sep. 13, 2021 entitled Arc-Based Capsids and Uses Thereof (downloaded Dec. 7, 2021).

File History for U.S. Appl. No. 17/497,174, filed Oct. 8, 2021 entitled Arc-Based Capsids and Uses Thereof (downloaded Dec. 7, 2021).

Freed. HIV-1 assembly, release and maturation. Nat. Rev. Microbiol. 13:484-496 (2015).

Fromer et al. De novo mutations in schizophrenia implicate synaptic networks. Nature 506:179-184 (2014).

Gallagher et al. Characterization of the disassembly and reassembly of the HBV glycoprotein surface antigen, a pliable nanoparticle vaccine platform. Virology 502:176-187 (2017).

Ganser et al. Assembly and analysis of conical models for the HIV-1 core. Science 283:80-83 (1999).

Gao et al. Antibody-targeted immunoliposomes for cancer treatment. Mini. Rev. Med. Chem. 13(14):2026-2035 (2013).

Gao et al. Engineered Cpf1 variants with altered PAM specificities. Nat Biotechnol 35(8):789-792 (2017).

Gaudeli et al. Programmable base editing of A•T to G•C in genomic DNA without DNA cleavage. Nature 551:464-471 (2017).

Gibson et al. Enzymatic assembly of DNA molecules up to several hundred kilobases. Nat Methods. 6(5):343-5 (2009).

Greer et al. The Angelman syndrome protein Ube3A regulates synapse development by ubiquitinating arc. Cell 140:704-716 (2010).

Gross et al., In vitro assembly properties of purified bacterially expressed capsid proteins of human immunodeficiency virus. Eur J Biochem. 249(2):592-600 (1997).

Gsheysen et al, Assembly and Release of Hiv-1 Precursor Pr55Gag Virus-Like Particles from Recombinant 3aculovirus-Infected Insect Cells. Cell 59(1):103-112 (1989).

Guzowski et al. Environment-specific expression of the immediate-early gene Arc in hippo-campal neuronal ensembles. Nat. Neurosci. 2:1120-1124 (1999).

Guzowski et al. Inhibition of activity-dependent arc protein expression in the rat hippocampus impairs the maintenance of long-term potentiation and the consolidation of long-term memory. J. Neurosci. 20:3993-4001 (2000).

Haffar et al. Human immunodeficiency virus-like, non-replication, Gag-Env particles assemble in a recombinant vaccinia virus expression system. J. Virol. 64:2653-59 (1990).

Hamann et al. Foamy virus protein-nucleic acid interactions during particle morphogenesis. Viruses 8(9):243 (2016).

Hansen et al. Ty3 GAG3 and POL3 genes encode the components of intracellular particles. J. Virol. 66:1414-1424 (1992).

Hao et al. Nucleic acid-gold nanoparticle conjugates as mimics of microRNA. Small. 7(22):3158-3162 (2011).

Hendel et al. Chemically modified guide RN As enhance CRISPR-Cas genomeediting in human primary cells. Nat. Biotechnol. 33:985-989 (2015).

Heraud-Farlow et al. The multifunctional Staufen proteins: conserved roles from neurogenesis to synaptic plasticity. Trends Neurosci. 37:470-479 (2014).

Hicke et al. Escort aptamers: a delivery service for diagnosis and therapy. J Clin Invest 106:923-928 (2000).

Howard, et al. Intracerebral drug delivery in rats with lesion-induced memory deficits. J Neurosurg. Jul. 1989;71(1):105-12.

Hsu et al. Development and applications of CRISPR-Cas9 for genome engineering. Cell 157(6):1262-1278 (2014).

Hsu et al. DNA targeting specificity of RNA-guided Cas9 nucleases. Nat Biotechnol 31(9):827- 832 (2013).

Hugo. Retrotransposon Gag like (RLT). Gene Nomenclature Committee. Available at https://www.genenames.org/data/genegroup/#!/group/1409 (Accessed Dec. 3, 2021).

Hunter. Macromolecular interactions in the assembly of HIV and other retroviruses. Seminars in Virology 5:71-83 (1994).

(56)            References Cited

OTHER PUBLICATIONS

Inoue et al. An inducible translocation strategy to rapidly activate and inhibit small GTPase signaling pathways. Nat Methods 2(6):415-418 (2005).

Irie et al. Cognitive Function Related to the Sirh11/Zcchc16 Gene Acquired from an LTR Retro-transposon in Eutherians. PLoS Genet. 11:e1005521 (2015).

Jensen et al. Spherical nucleic acid nanoparticle conjugates as an RNAi-based therapy for glioblastoma. Sci Transl Med. 5(209):209ra152 (2013).

Jiang et al. RNA-guided editing of bacterial genomes using CRISPR-Cas systems. Nat Biotechnol. 31(3):233-9 (2013).

Johnson et al., Gene Therapy with Human and Mouse T-Cell Receptors Mediates Cancer Regression and Targets gormal Tissues Expressing Cognate Antigen. Blood 114(3):535-546 (2009).

Kalos et al. T cells with chimeric antigen receptors have potent antitumor effects and can establish memory in patients with advanced leukemia. Sci Transl Med 3(95):95ra73 (2011).

Kaneko-Ishino et al. The role of genes domesticated from LTR retrotransposons and retroviruses in mammals. Front. Microbiol. 3:262 (2012).

Karlin, et al. Applications and statistics for multiple high-scoring segments in molecular sequences. PNAS USA 90:5873-5877 (1993).

Karlin et al. Methods for assessing the statistical significance of molecular sequence features by using general scoring schemes. PNAS USA 87:2264-2268 (1990).

Keefe et al. Aptamers as therapeutics. Nat. Rev. Drug Discov. 9:537-550 (2010).

Kim et al. Chimeric restriction endonuclease. PNAS USA. 91(3):883-7 (1994).

Kim et al. Highly efficient RNA-guided genome editing in human cells via delivery of purified Cas9 ribonucleoproteins. Genome Res. 24(6):1012-9 (2014).

Kim et al., Hybrid restriction enzymes: Zinc finger fusions to Fok I cleavage domain. PNAS USA 93:1156-1160 (1996).

Kleinstiver et al. Engineered CRISPR-Cas9 nucleases with altered PAM specificities. Nature 523(7561):481-485 (2015).

Komor, et al. Programmable editing of a target base in genomic DNA without double-stranded DNA cleavage. Nature 533, 420-424 (2016).

Konermann et al. Genome-scale transcriptional activation by an engineered CRISPR-Cas9 complex. Nature 517(7536):583-588 (2015).

Konermann et al. Optical control of mammalian endogenous transcription and epigenetic states. Nature. 500(7463):472-476 (2013).

Koonin et al., Origins and evolution of CRISPR-Cas systems. Phil Trans R. Soc. B 374(1772) 6 pages (2019).

Korkut et al. Trans-synaptic transmission of vesicular Wnt signals through Evi/Wntless. Cell 139:393-404 (2009).

Kraft et al. Visual experience sculpts whole-cortex spontaneous infraslow activity patterns through an Arc-dependent mechanism. PNAS USA 114:E9952-E9961 (2017).

Krausslich et al. Intracellular transport of retroviral capsid components. Morphogenesis and Maturation of Retroviruses pp. 25-64 (1996).

Kutluay et al. Global changes in the RNA binding specificity of HIV-1 gag regulate virion genesis. Cell 159:1096-1109 (2014).

Lachenal et al. Release of exosomes from differentiated neurons and its regulation by synaptic glutamatergic activity. Mol. Cell. Neurosci. 46:409-418 (2011).

Lavillette et al. The envelope glycoprotein of human endogenous retrovirus type W uses a divergent family of amino acid transporters/ cell surface receptors. J. Virol. 76:6442-6452 (2002).

Le et al. In Vitro Assembly of Virus-Like Particles and Their Applications. Life (Basel) 11(4):334 (2021).

Lee et al. Synthetically modified guide RNA and donor DNA are a versatile platform for CRISPR-Cas9 engineering. eLife. 6:e25312 (2017).

Lefebvre et al. Comparative transcriptomic analysis of human and *Drosophila* extracellular vesicles. Sci. Rep. 6:27680 (2016).

Levy et al. Cytosine and adenine base editing of the brain, liver, retina, heart and skeletal muscle of mice via adeno-associated viruses. Nat Biomed Eng 4(1):97-110 (2020).

Levy-Nissenbaum et al. Nanotechnology and aptamers: applications in drug delivery. Trends Biotechnol 26.8:442-449 (2008).

Li, et al. Base editing with a Cpf1—cytidine deaminase fusion. Nat. Biotechnol. 36:324-327 (2018).

Li et al. Cell culture processes for monoclonal antibody production. Mabs. 2(5):466-477 (2010).

Li et al., Engineering CRISPR-Cpf1 crRNAs and mRNAs to maximize genome editing efficiency. Nat Biomed Eng. 1(5):0066 (2017).

Liang et al. Engineering the ABA Plant Stress Pathway for Regulation of Induced Proximity. Sci Signla 4(164):rs2 (2011).

Lim et al. Altering the RNA binding specificity of a translational repressor. J Biol Chem 269(12):9006-9010 (1994).

Liu. CRISPR pioneer Feng Zhang's latest work delivers mRNA, gene therapy with a human protein. FierceBiotech Available at https://www.fiercebiotech.com/research/crispr-pioneer-feng-zhang-s-latest-work-delivers-mrna-gene-therapy-human-protein (Aug. 19, 2021).

Liu et al. Engineering cell signaling using tunable CRISPR-Cpf1-based transcription factors. Nat Commun 8:2095 (2017).

Lizatovic et al. A Protein-Based Encapsulation System with Calcium-Controlled Cargo Loading and Detachment. Angew Chem Int Ed Engl 57(35):11334-11338 (2018).

Lyu et al. Delivering Cas9/sgRNA ribonucleoprotein (RNP) by lentiviral capsid-based bionanoparticles for efficient 'hit-and-run' genome editing. Nucleic Acids Res 1:1-13 (2019).

Mach et al. Disassembly and reassembly of yeast-derived recombinant human papillomavirus virus-like particles (HPV VLPs). J Pharm Sci 95(10):2195-206 (2006).

Macia et al. Dynasore, a cell-permeable inhibitor of dynamin. Dev. Cell 10:839-850 (2006).

Madisen et al. Expression of the human immunodeficiency virus gag gene in insect cells. Virology 158:248-250 (1987).

Mailler et al. The life-cycle of the HIV-1 Gag-RNA complex. Viruses 8(9):248 (2016).

Makarova et al. Classification and nomenclature of CRISPR-Cas systems: where from here?. The CRISPR Journal 1(5):325-336 (2018).

Makarova et al. Evolutionary classification of CRISPR-Cas systems: a burst of class 2 and derived variants. Nat Rev Microbiol. 18(2):67-83 (2020).

Malik et al. Poised for contagion: evolutionary origins of the infectious abilities of invertebrate retroviruses. Genome Res. 10:1307-1318 (2000).

Manago et al. Genetic disruption of Arc/Arg3.1 in mice causes alterations in dopamine and neurobehavioral phenotypes related to schizophrenia. Cell Rep. 16:2116-2128 (2016).

Manjappa et al. Antibody derivatization and conjugation strategies: application in preparation of stealth immunoliposome to target chemotherapeutics to tumor, J. Control. Release 150(1):2-22 (2011).

Maruyama et al. Targetability of Novel Immunoliposomes Modified with Amphipathic Poly(Ethylene Glycol) S Sonjugated at their Distal Terminals to Monoclonal Antibodies. Biochimica et Biophysica Acta (BBA)—Biomembranes 1234(1):74-80 (1995).

Matsuda et al. Controlled expression of transgenes introduced by in vivo electroporation. PNAS 104(3):1027-2032 (2007).

Mattei et al. Retrovirus maturation-an extraordinary structural transformation. Curr. Opin. Virol. 18:27-35 (2016).

McCurry et al. Loss of Arc renders the visual cortex impervious to the effects of sensory experience or deprivation. Nat. Neurosci. 13:450-457 (2010).

Mikuni et al. Arc/Arg3.1 is a postsynaptic mediator of activity-dependent synapse elimination in the developing cerebellum. Neuron 78:1024-1035 (2013).

Mirkin. Interview: An interview with Chad Mirkin: nanomedicine expert. Interviewed by Hannah Stanwix. Nanomedicine (Lond). 7(5):635-638 (2012).

Miyamoto et al. Rapid and orthogonal logic gating with a gibberellin-induced dimerization system. Nat Chem Biol 8(5):465-70 (2012).

(56)          References Cited

OTHER PUBLICATIONS

Mokany et al. MNAzymes, a versatile new class of nucleic acid enzymes that can function as biosensors and molecular switches. J Am Chem Soc 132(2):1051-1059 (2010).

Molavi et al. Anti-CD30 antibody conjugated liposomal doxorubicin with significantly improved therapeutic efficacy against anaplastic large cell lymphoma, Biomaterials 34(34):8718-25 (2013).

Montagna et al. VSV-G-Enveloped Vesicles for Traceless Delivery of CRISPR-Cas9. Mol Ther Nucleic Acids. 12:453-462 (2018).

Morgan et al. Cancer regression in patients after transfer of genetically engineered lymphocytes. Science 314(5796):126-129 (2006).

Moscou et al. A simple cipher governs DNA recognition by TAL effectors. Science 326(5959):1501 (2009).

Mouland et al. The double-stranded RNA-binding protein Staufen is incorporated in human immunodeficiency virus type 1: evidence for a role in genomic RNA encapsidation. J. Virol. 74:5441-5451(2000).

Myrum et al. Arc is a flexible modular protein capable of reversible self-oligomerization. Biochem. J. 468(1):145-158 (2015).

Nair et al. Multivalent N-acetylgalactosamine-conjugated siRNA localizes in hepatocytes and elicits robust RNAi-mediated gene silencing. J Am Chem Soc. 136(49):16958-16961 (2014).

Nakamura, et al., Codon usage tabulated from international DNA sequence databases: status for the year 2000. Nucleic Acids Res. 28(1):292 (2000).

Naville et al. Not so bad after all: retroviruses and long terminal repeat retrotransposons as a source of new genes in vertebrates. Clin Microbiol Infect 22(4):312-323 (2016).

NCBI, GenBank accession No. NP_001269464.1, 'paraneoplastic antigen Ma3 isoform 2 [*Homo sapiens*]' (Jun. 30, 2018).

NCBI, GenBank accession No. XP_018887452.1, 'activity-regulated cytoskeleton-associated protein [Gorilla gorilla gorilla]' (Nov. 4, 2016).

NCBI, GenBank accession No. XP_020755692.1, 'activity-regulated cytoskeleton-associated protein [Odocoileus virginianus texanus]' (Apr. 28, 2017).

Nielsen et al. The Capsid Domain of Arc Changes Its Oligomerization Propensity through Direct Interaction with the NMDA Receptor. Structure 27(7):1071 (2019).

Nishida et al., Targeted nucelotide editing using hybrid prokaryotic and vertebrate adaptive immune systems. Science 353(6305):aaf8729 (2016).

Nishimasu et al. Crystal Structure of Cas9 in Complex with Guide RNA and Target DNA. Cell 156(5):935-949 (2014).

Nishimasu et al. Crystal Structure of *Staphylococcus aureus* Cas9. Cell 162:1113-1126 (2015).

Nolte-'t Hoen et al. Extracellular vesicles and viruses: Are they close relatives? PNAS USA 113:9155-9161 (2016).

Nowak et al. Guide RNA engineering for versatile Cas9 functionality. Nucleic Acids Res. 44(20):9555-9564 (2016).

O'Hare et al. Transformation of mouse fibroblasts to methotrexate resistance by a recombinant plasmid expressing a prokaryotic dihydrofolate reductase. PNAS USA 78(3):1527-31 (1981).

Okuno et al. Inverse synaptic tagging of inactive synapses via dynamic interaction of Arc/Arg3.1 with CaMKIIβ. Cell 149:886-898 (2012).

Ostergaard et al. Efficient Synthesis and Biological Evaluation of 5'-GalNAc Conjugated Antisense Oligonucleotides. Bioconjugate Chem., 26(8):1451-1455 (2015).

Paige et al. RNA mimics of green fluorescent protein. Science 333(6042):642-6 (2011).

Paix et al. High Efficiency, Homology-Directed Genome Editing in Caenorhabditis elegans Using CRISPR-Cas9 Ribonucleoprotein Complexes. Genetics 201(1):47-54 (Sep. 2015).

Pang et al. PNMA family: Protein interaction network and cell signalling pathways implicated in cancer and apoptosis. Cell Signal 45:54-62 (2018).

Pardridge. Preparation of Trojan Horse Liposomes (THLs) for Gene Transfer across the Blood-Brain Barrier. Cold Spring Harb Protoc 2010(4):pdb.prot5407 (2010).

Park et al. Elongation factor 2 and fragile X mental retardation protein control the dynamic translation of Arc/Arg3.1 essential for mGluR-LTD. Neuron 59:70-83 (2008).

Parnas et al. A Genome-wide CRISPR Screen in Primary Immune Cells to Dissect Regulatory Networks. Cell 162:675-686 (Jul. 30, 2015).

Pastuzyn et al. Activity-dependent Arc expression and homeostatic synaptic plasticity are altered in neurons from a mouse model of Angelman syndrome. Front. Mol. Neurosci. 10:234 (2017).

Pastuzyn et al. The Neuronal Gene Arc Encodes a Repurposed Retrotransposon Gag Protein that Mediates Intercellular RNA Transfer. Cell 172:275-288 (2018).

PCT/US2018/032105 International Search Report and Written Opinion dated Aug. 1, 2018.

PCT/US2019/051786 International Search Report and Written Opinion dated Mar. 20, 2020.

PCT/US2020/051637 International Search Report and Written Opinion dated Feb. 3, 2021.

PCT/US2021/032757 International Search Report and Written Opinion dated Sep. 14, 2021.

PCT/US2022/013954 International Search Report and Written Opinion dated May 11, 2022.

Peters et al. Recruitment of CRISPR-Cas systems by Tn7-like transposons. PNAS USA 114(35):E7358-E7366 (2017).

Piazza et al. Immunotherapy of Respiratory Syncytial Virus Infection in Cotton Rats (*Sigmodon fulviventer*) Using gG in a Small-Particle Aerosol. The Journal of Infectious Diseases 166(6):1422-4 (1992).

Pinkstaff et al. Internal initiation of translation of five dendritically localized neuronal mRNAs. PNAS USA 98:2770-2775 (2001).

Plath et al. Arc/Arg3.1 is essential for the consolidation of synaptic plasticity and memories. Neuron 52:437-444 (2006).

Platt, et al. CRISPR-Cas9 knockin mice for genome editing and cancer modeling. Cell 159(2):440-455 (2014).

Poulter et al. A retrotransposon family from the pufferfish (*Fugu*) *Fugu rubripes*1. Gene 215:241-249 (1998).

Purcell et al. A poly-genic burden of rare disruptive mutations in schizophrenia. Nature 506:185-190 (2014).

Purdy et al. Critical role of conserved hydrophobic residues within the major homology region in mature retroviral capsid assembly. J. Virol. 82:5951-5961 (2008).

Qiu et al. Mutation detection using Surveyor nuclease. Biotechniques 36:702-707 (2004).

Rajendran et al. Alzheimer's disease β-amyloid peptides are released in association with exosomes. PNAS USA 103:11172-11177 (2006).

Ramanan et al. CRISPR/Cas9 cleavage of viral DNA efficiently suppresses hepatitis B virus. Sci Rep 5:10833 (2015).

Ran et al. Double nicking by RNA-guided CRISPR Cas9 for enhanced genome editing specificity. Cell 154:1380-1389 (2013).

Ran et al. Genome engineering using the CRISPR-Cas9 system. Nature Protocols 8:2281-2308 (2013).

Ran et al. In vivo genome editing using Staphylococcus aureus Cas9. Nature. 520(7546):186-191 (2015).

Raposo et al. Extracellular vesicles: exosomes, microvesicles, and friends. J. Cell Biol. 200:373-383 (2013).

Rees et al. Base editing: precision chemistry on the genome and transcriptome of living cells. Nat. Rev. Genet. 19(12):770-788 (2018).

Rosenberg et al. Early Assembly Step of a Retroviral Envelope Glycoprotein: Analysis Using a Dominant Negative Assay. J. Cell Biol. 145:57-68 (1999).

Rueckert. Chapter 32: Picornaviruses and Their Replication. Virology. B. N. Fields et al. (eds.) Raven Press, New York, pp. 705-738 (1985).

Saudek et al. A preliminary trial of the programmable implantable medication system for insulin delivery. N. Engl. J. Med. 321:574 (1989).

Scaringe. Advanced 5'-Silyl-2'-Orthoester Approach to RNA Oligonucleotide Synthesis. Methods Enzymology. 317:3-18 (2000).

Scaringe et al. Novel RNA synthesis method using 5'-0-silyl-2'-0-orthoester protecting groups. J Am Chem Soc 120:11820-11821 (1998).

(56)         References Cited

OTHER PUBLICATIONS

Schiffelers et al. Cancer siRNA therapy by tumor selective delivery with ligand-targeted sterically stabilized nanoparticle. Nucleic Acids Res 32(19):e149 (2004).

Segel et al. Mammalian retrovirus-like protein PEG10 packages its own mRNA and can be pseudotyped for mRNA delivery. Science 373(6557):882-889 (2021).

Shalem et al. Genome-scale CRISPR-Cas9 knockout screening in human cells. Science 343(6166):84-87 (2014).

Shalem et al. High-throughput functional genomics using CRISPR-Cas9. Nature Reviews Genetics16(5):299 (2015).

Shepherd et al. Arc/Arg3.1 mediates homeostatic synaptic scaling of AMPA receptors. Neuron 52:475-484 (2006).

Shepherd et al. New views of Arc, a master regulator of synaptic plasticity. Nat. Neurosci. 14:279-284 (2011).

Shmakov et al. Discovery and Functional Characterization of Diverse Class 2 CRISPR-Cas Systems. Mol Cell 60(3):385-397 (2015).

Slaymaker et al. Rationally engineered Cas9 nucleases with improved specificity. Science 351(6268):84-88 (Jan. 1, 2016).

Smit. Interspersed repeats and other mementos of transposable elements in mammalian genomes. Curr. Opin. Genet. Dev. 9:657-663 (1999).

Smith et al. Human immunodeficiency virus type 1 Pr55gag and Prl60gag-pol expressed from a simian virus 40 late-replacement vector are efficiently processed and assembled into virus-like particles, J. Virol. 64:2743-50 (1990).

Sofou et al. Antibody-targeted liposomes in cancer therapy and imaging, Expert Opin. Drug Deliv. 5(2):189-204 (2008).

Sommerfelt et al. Importance of the pl2 protein in Mason-Pfizer monkey virus assembly and infectivity. J. Virol. 66:7005-11 (1992).

Sonoke et al. Galactose-modified cationic liposomes as a liver-targeting delivery system for small interfering RNA. Biol Pharm Bull. 34(8):1338-42 (2011).

Spuch et al. Liposomes for Targeted Delivery of Active Agents against Neurodegenerative Diseases (Alzheimer's Disease and Parkinson's Disease). Journal of Drug Delivery 2011:469679 (2011).

Steward et al. Synaptic activation causes the mRNA for the IEG Arc to localize selectively near activated postsynaptic sites on dendrites. Neuron 21:741-751 (1998).

Strecker et al. RNA-guided DNA insertion with CRISPR-associated transposases. Science 365:48-53 (2019).

Sun et al. Cocoon-like self-degradable DNA nanoclew for anticancer drug delivery. J Am. Chem. Soc. 136:14722-14725 (2014).

Sun et al. Self-assembled DNA nanoclews for the efficient delivery of CRISPR-Cas9 for genome editing. Angew. Chem. Int. Ed.54(41):12029-12033 (2015).

Surace et al. Lipoplexes targeting the CD44 hyaluronic acid receptor for efficient transfection of breast cancer cells. J. Mol Pharm 6(4):1062-73 (2009).

Suzuki et al. In vivo genome editing via CRISPR/Cas9 mediated homology-independent targeted integration. Nature 540(7631):144-149 (2016).

Swiech et al. In vivo interrogation of gene function in the mammalian brain using CRISPR-Cas9. Nat Biotechnol 33:102-106 (2015).

Tabernero et al. First-in-Human Trial of an RNA Interference Therapeutic Targeting VEGF and KSP in Cancer Patients with Liver Involvement. Cancer Discovery 3(4):363-470 (Apr. 2013).

Takebe et al. SR alpha promoter: an efficient and versatile mammalian cDNA expression system composed of the simian virus 40 early promoter and the R-U5 segment of human T-cell leukemia virus type 1 long terminal repeat. Mol. Cell. Biol. 8(1):466-472 (1988).

Takeda et al. Synthetic and nature-derived lipid nanoparticles for neural regeneration. Neural Regen Res. 10(5):689-90 (May 2015).

Tato et al. A mutant of Rous sarcoma virus with a thermolabile defect in the virus envelope. Virology 88:71-81 (1978).

Taylor et al. A comparative analysis of the foamy and ortho virus capsid structures reveals an ancient domain duplication. BMC Struct. Biol. 17(1):3 (2017).

Tkach et al. Communication by extracellular vesicles: where we are and where we need to go. Cell 164:1226-1232 (2016).

Tonjes et al. Characterization of Human Endogenous Retrovirus Type K Virus-like Particles Generated from Recombinant Baculoviruses. Virology 233(2):280-291 (1997).

Topuzoğullari et al. An insight into the epitope-based peptide vaccine design strategy and studies against COVID-19. Turk J. Biol 44(3):215-227 (2020).

Torchilin. Antibody-modified liposomes for cancer chemotherapy. Expert Opin. Drug Deliv. 5(9):1003-1025 (2008).

Tristem. Identification and characterization of novel human endogenous retrovirus families by phylogenetic screening of the human genome mapping project database. J. Virol. 74:3715-3730 (2000).

Tsai et al., Dimeric CRISPR RNA-guided Fokl nucleases for highly specific genome editing Nat. Biotechnol., 32(6):569-576 (2014).

Tsai. Penetration of nonenveloped viruses into the cytoplasm. Annu. Rev. Cell Dev. Biol. 23:23-43 (2007).

Tuerk. Systematic evolution of ligands by exponential enrichment: RNA ligands to bacteriophage T4 DNA polymerase. Science 249:505-510 (1990).

Ufer et al. Arc/Arg3.1 governs inflammatory dendritic cell migration from the skin and thereby controls T cell activation. Sci. Immunol. 1:eaaf8665 (2016).

U.S. Appl. No. 16/876,731 Office Action dated Apr. 5, 2021.

U.S. Appl. No. 16/876,731 Office Action dated Jan. 12, 2021.

U.S. Appl. No. 16/876,731 Office Action dated Nov. 17, 2020.

U.S. Appl. No. 17/382,092 Office Action dated Nov. 12, 2021.

U.S. Appl. No. 17/382,102 Office Action dated Feb. 22, 2022.

U.S. Appl. No. 17/497,174 Restriction Requirement dated Apr. 4, 2022.

Valadi et al. Exosome-mediated transfer of mRNAs and microRNAs is a novel mechanism of genetic exchange between cells. Nat. Cell Biol. 9:654-659 (2007).

Vaux et al. Spike—nucleocapsid interaction in Semliki Forest virus reconstructed using network antibodies. Nature 336:36-42 (1988).

Vlach et al. Structural and molecular determinants of HIV-1 Gag binding to the plasma membrane. Front Microbiol 6:232 (2015).

Volff et al. Cellular Genes Derived from Gypsy/Ty3 Retrotransposons in Mammalian Genomes. An N Y Acad Sci 1178(1):233-243 (2009).

Wahlgren et al. Plasma Exosomes can Deliver Exogenous Short Interfering RNA to Monocytes and Lymphocytes. Nucleic Acids Res 40(17):e130 (2012).

Wang et al. Combinatorially designed lipid-like nanoparticles for intracellular delivery of cytotoxic protein for cancer therapy. Agnew Chem Int Ed Engl., 53(11):2893-8 (2014).

Wang et al. Efficient delivery of genome-editing proteins using bioreducible lipid nanoparticles. PNAS USA 113:2868-2873 (2016).

Wang et al. Enhanced intracellular siRNA delivery using bioreducible lipid-like nanoparticles. Adv. Healthc Mater. 3(9):1398-403 (2014).

Wang et al. Genetic screens in human cells using CRISPR-Cas9 system. Science 343:80-84 (2014).

Wang et al. Hyaluronic Acid Modification of RNase A and its Intracellular Delivery Using Lipid-like Nanoparticles. J Control Release 263:39-45 (2017).

Wang et al. In vivo two-photon imaging reveals a role of arc in enhancing orientation specificity in visual cortex. Cell 126:-389-402 (2006).

Wang et al. Integrating Protein Engineering and Bioorthogonal Click Conjugation for Extracellular Vesicle Modulation and Intracellular Delivery. PloS One 10(11):e0141860 (2015).

Wang et al. One-step generation of mice carrying mutations in multiple genes by CRISPR/Cas-mediated genome engineering. Cell 153:910-918 (2013).

Wang. Lyophilization and development of solid protein pharmaceuticals. Int. J. Pharm., 203(1-2):1-60 (2000).

Waung et al. Rapid translation of Arc/Arg3.1 selectively mediates mGluR-dependent LTD through persistent increases in AMPAR endocytosis rate. Neuron 59:84-97 (2008).

Weintraub. Biomedicine: The new gold standard. Nature. 495(7440):S14-S16 (2013).

(56)          References Cited

OTHER PUBLICATIONS

Wills et al. Creation and expression of myristylated forms of Rous sarcoma virus Gag protein in mammalian cells. J. Virol. 63:4331-43 (1989).

Woycechowsky. Protein capsids as molecular containers: Cargo Loading and controlled release. J Nanomater Mol Nanotechnol 6:5 (2017).

Wu et al. Arc/Arg3.1 regulates an endosomal pathway essential for activity-dependent b-amyloid generation. Cell 147:615-628 (2011).

Wu et al. Genome-wide binding of the CRISPR endonuclease Cas9 in mammalian cells. Nat Biotechnol. 32(7):670-676 (2014).

Xu et al. Sequence determinants of improved CRISPR sgRNA design. Genome Res 25:1147-1157 (Aug. 2015).

Yan et al. Cas13d Is a Compact RNA-Targeting Type VI CRISPR Effector Positively Modulated by a WYL-Domain-Containing Accessory Protein. Molecular Cell 70(2):327-339 (2018).

Yoshida et al. SARS-CoV-2-induced humoral immunity through B cell epitope analysis and neutralizing activity in COVID-19 infected individuals in Japan. bioRxiv (2020).

Young et al. Hollow spherical nucleic acids for intracellular gene regulation based upon biocompatible silica shells. Nano Lett. 12(7):3867-3871 (2012).

Zappulli et al. Extracellular vesicles and intercellular communication within the nervous system. J. Clin. Invest. 126:1198-1207 (2016).

Zetsche et al. A split-Cas9 architecture for inducible genome editing and transcription modulation. Nat Biotechnol 33:139-142 (2015).

Zetsche et al. Cpf1 is a single RNA-guided endonuclease of a class 2 CRISPR-Cas system. Cell 163:759-771 (2015).

Zhang et al. A Strategy for increasing drug solubility and efficacy through covalent attachment to polyvalent DNA-nanoparticle conjugates. ACS Nano. 5(9):6962-6970 (2011).

Zhang et al. Antibody-linked spherical nucleic acids for cellular targeting. J. Am. Chem. Soc. 134:16488-1691 (2012).

Zhang et al. Structural Basis of Arc Binding to Synaptic Proteins: Implications for Cognitive Diseases. Neuron 86(2):490-500 (2015).

Zheng et al. Topical delivery of siRNA-based spherical nucleic acid nanoparticle conjugates for gene regulation. PNAS USA 109(30):11975-11980 (2012).

Zhou et al. Aptamer-targeted cell-specific RNA interference. Silence 1(1):4 (2010).

Zhou et al. Novel reference genes for quantifying transcriptional responses of *Escherichia coli* to protein overexpression by quantitative PCR. BMC Mol. Biol. 12:18 (2011).

Zuker et al. Optimal computer folding of large RNA sequences using thermodynamics and auxiliary information. Nucleic Acids Res. 9:133-148 (1981).

* cited by examiner

Engineered Arc

Reengineering Arc to carry specific RNA payload

Reengineering Arc to remove off-function effects

Endogenous Human Gag-Like Genes

Delivering Cre-Loaded Capsids

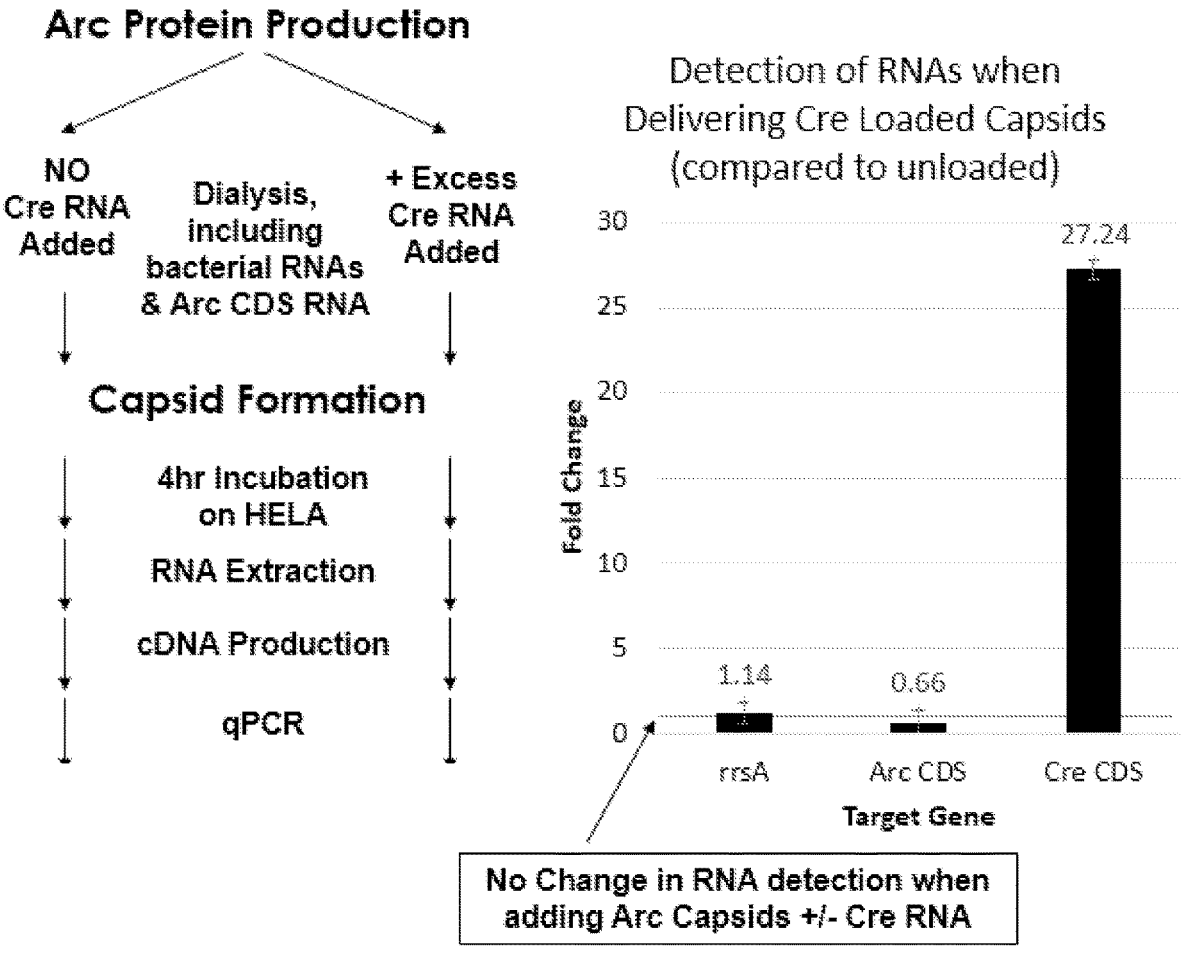

Arc Protein Production

NO Cre RNA Added

Dialysis, including bacterial RNAs & Arc CDS RNA

+ Excess Cre RNA Added

Capsid Formation

4hr Incubation on HELA

RNA Extraction cDNA Production qPCR

Detection of RNAs when Delivering Cre Loaded Capsids (compared to unloaded)

Fold Change rrsA    1.14
Arc CDS    0.66
Cre CDS    27.24

Target Gene

No Change in RNA detection when adding Arc Capsids +/- Cre RNA

FIG. 10

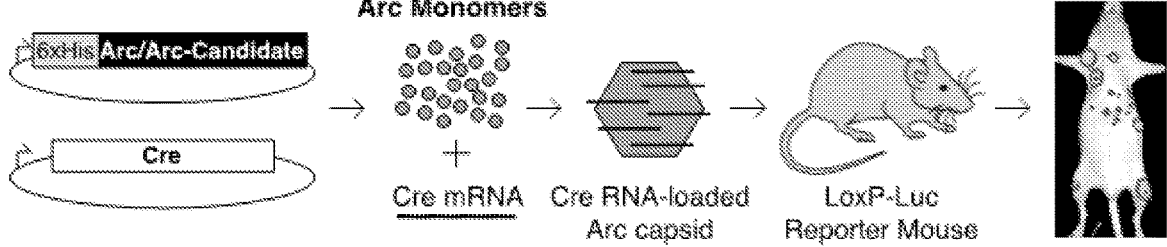

6x-his Arc/Arc-Candidate

Cre

Arc Monomers

+

Cre mRNA

Cre RNA-loaded Arc capsid

LoxP-Luc Reporter Mouse

ARC-BASED CAPSIDS AND USES THEREOF

CROSS REFERENCE

This application is a continuation of U.S. application Ser. No. 17/382,102, filed Jul. 21, 2021, which is a continuation of U.S. application Ser. No. 17/277,119, filed Mar. 17, 2021, which is a U.S. national phase entry of International Application No. PCT/US2019/051786, filed Sep. 18, 2019, which claims the benefit of U.S. Provisional Patent Application No. 62/733,015, filed Sep. 18, 2018, each of which is incorporated herein by reference in its entirety.

SEQUENCE LISTING

The instant application contains a Sequence Listing which has been submitted electronically in XML format and is hereby incorporated by reference in its entirety. Said XML copy, created on Oct. 25, 2022, is named 54838-702-306_SL.xml and is 131,736 bytes in size.

SUMMARY OF THE DISCLOSURE

Disclosed herein, in certain embodiments, are recombinant and engineered Arc polypeptides and recombinant and engineered endogenous Gag (endo-Gag) polypeptides. In some embodiments, also included are Arc-based capsids and endo-Gag based capsids, either loaded or empty, and methods of preparing the capsids. Additionally included are methods of delivery of the Arc-based capsids and endo-Gag-based capsids to a site of interest.

Disclosed herein, in certain embodiments, is a capsid comprising a recombinant Arc polypeptide or a recombinant endogenous Gag polypeptide and a therapeutic agent. In some embodiments, the therapeutic agent is a nucleic acid. In some embodiments, the nucleic acid is an RNA. In some embodiments, the recombinant Arc polypeptide is a human Arc polypeptide comprising an amino acid sequence that is SEQ ID NO: 1 or an amino acid sequence that is at least 90% identical to the SEQ ID NO: 1. In some embodiments, the recombinant Arc polypeptide is an Arc polypeptide comprising: a) an amino acid sequence that is SEQ ID NO: 2 or an amino acid sequence that is at least 90% identical to the SEQ ID NO: 2; b) an amino acid sequence that is SEQ ID NO: 3 or an amino acid sequence that is at least 90% identical to the SEQ ID NO: 3; c) an amino acid sequence that is SEQ ID NO: 4 or an amino acid sequence that is at least 90% identical to the SEQ ID NO: 4; d) an amino acid sequence that is SEQ ID NO: 5 or an amino acid sequence that is at least 90% identical to the SEQ ID NO: 5; e) an amino acid sequence that is SEQ ID NO: 6 or an amino acid sequence that is at least 90% identical to the SEQ ID NO: 6; f) an amino acid sequence that is SEQ ID NO: 7 or an amino acid sequence that is at least 90% identical to the SEQ ID NO: 7; g) an amino acid sequence that is SEQ ID NO: 8 or an amino acid sequence that is at least 90% identical to the SEQ ID NO: 8; h) an amino acid sequence that is SEQ ID NO: 9 or an amino acid sequence that is at least 90% identical to the SEQ ID NO: 9; i) an amino acid sequence that is SEQ ID NO: 10 or an amino acid sequence that is at least 90% identical to the SEQ ID NO: 10; or j) an amino acid sequence that is SEQ ID NO: 11 or an amino acid sequence that is at least 90% identical to the SEQ ID NO: 11; or k) an amino acid sequence that is SEQ ID NO: 12 or an amino acid sequence that is at least 90% identical to the SEQ ID NO: 12; or l) an amino acid sequence that is SEQ ID NO: 13 or an amino acid sequence that is at least 90% identical to the SEQ ID NO: 13; or m) an amino acid sequence that is SEQ ID NO: 14 or an amino acid sequence that is at least 90% identical to the SEQ ID NO: 14; or n) an amino acid sequence that is SEQ ID NO: 15 or an amino acid sequence that is at least 90% identical to the SEQ ID NO: 15. In some embodiments, the recombinant endogenous Gag polypeptide is a human endogenous Gag polypeptide. In some embodiments, the recombinant endogenous Gag polypeptide is an endogenous Gag polypeptide comprising: a) an amino acid sequence that is SEQ ID NO: 16 or an amino acid sequence that is at least 90% identical to the SEQ ID NO: 16; b) an amino acid sequence that is SEQ ID NO: 17 or an amino acid sequence that is at least 90% identical to the SEQ ID NO: 17; c) an amino acid sequence that is SEQ ID NO: 18 or an amino acid sequence that is at least 90% identical to the SEQ ID NO: 18; d) an amino acid sequence that is SEQ ID NO: 19 or an amino acid sequence that is at least 90% identical to the SEQ ID NO: 19; e) an amino acid sequence that is SEQ ID NO: 20 or an amino acid sequence that is at least 90% identical to the SEQ ID NO: 20; f) an amino acid sequence that is SEQ ID NO: 21 or an amino acid sequence that is at least 90% identical to the SEQ ID NO: 21; or g) an amino acid sequence that is SEQ ID NO: 22 or an amino acid sequence that is at least 90% identical to the SEQ ID NO: 22; or h) an amino acid sequence that is SEQ ID NO: 23 or an amino acid sequence that is at least 90% identical to the SEQ ID NO: 23; or i) an amino acid sequence that is SEQ ID NO: 24 or an amino acid sequence that is at least 90% identical to the SEQ ID NO: 24; or j) an amino acid sequence that is SEQ ID NO: 25 or an amino acid sequence that is at least 90% identical to the SEQ ID NO: 25; or k) an amino acid sequence that is SEQ ID NO: 26 or an amino acid sequence that is at least 90% identical to the SEQ ID NO: 26; or l) an amino acid sequence that is SEQ ID NO: 27 or an amino acid sequence that is at least 90% identical to the SEQ ID NO: 27 or m) an amino acid sequence that is SEQ ID NO: 28 or an amino acid sequence that is at least 90% identical to the SEQ ID NO: 28.

Disclosed herein, in certain embodiments, is a capsid comprising a recombinant Arc polypeptide or a recombinant endogenous Gag polypeptide, wherein the recombinant Arc polypeptide is not a rat Arc polypeptide or a human Arc polypeptide. In some embodiments, the capsid further comprises a cargo. In some embodiments, the cargo is a nucleic acid. In some embodiments, the cargo is an RNA. In some embodiments, the cargo is a therapeutic agent. In some embodiments, the recombinant Arc polypeptide is an Arc polypeptide comprising: a) an amino acid sequence that is SEQ ID NO: 2 or an amino acid sequence that is at least 90% identical to the SEQ ID NO: 2; b) an amino acid sequence that is SEQ ID NO: 3 or an amino acid sequence that is at least 90% identical to the SEQ ID NO: 3; c) an amino acid sequence that is SEQ ID NO: 4 or an amino acid sequence that is at least 90% identical to the SEQ ID NO: 4; d) an amino acid sequence that is SEQ ID NO: 5 or an amino acid sequence that is at least 90% identical to the SEQ ID NO: 5; e) an amino acid sequence that is SEQ ID NO: 6 or an amino acid sequence that is at least 90% identical to the SEQ ID NO: 6; f) an amino acid sequence that is SEQ ID NO: 7 or an amino acid sequence that is at least 90% identical to the SEQ ID NO: 7; g) an amino acid sequence that is SEQ ID NO: 8 or an amino acid sequence that is at least 90% identical to the SEQ ID NO: 8; h) an amino acid sequence that is SEQ ID NO: 9 or an amino acid sequence that is at least 90% identical to the SEQ ID NO: 9; i) an amino acid sequence that is SEQ ID NO: 10 or an amino acid sequence that is at least 90% identical to the SEQ ID NO: 10; or j) an amino acid sequence that is SEQ ID NO: 11 or an amino acid sequence that is at least 90% identical to the SEQ ID NO: 11; or k) an amino acid sequence that is SEQ ID NO: 12 or an amino acid sequence that is at least 90% identical to the SEQ ID NO: 12; or 1) an amino acid sequence that is SEQ ID NO: 13 or an amino acid sequence that is at least 90% identical to the SEQ ID NO: 13; or m) an amino acid sequence that is SEQ ID NO: 14 or an amino acid sequence that is at least 90% identical to the SEQ ID NO: 14; or n) an amino acid sequence that is SEQ ID NO: 15 or an amino acid sequence that is at least 90% identical to the SEQ ID NO: 15. In some embodiments, the recombinant endogenous Gag polypeptide is an endogenous Gag polypeptide comprising: a) an amino acid sequence that is SEQ ID NO: 16 or an amino acid sequence that is at least 90% identical to the SEQ ID NO: 16; b) an amino acid sequence that is SEQ ID NO: 17 or an amino acid sequence that is at least 90% identical to the SEQ ID NO: 17; c) an amino acid sequence that is SEQ ID NO: 18 or an amino acid sequence that is at least 90% identical to the SEQ ID NO: 18; d) an amino acid sequence that is SEQ ID NO: 19 or an amino acid sequence that is at least 90% identical to the SEQ ID NO: 19; e) an amino acid sequence that is SEQ ID NO: 20 or an amino acid sequence that is at least 90% identical to the SEQ ID NO: 20; f) an amino acid sequence that is SEQ ID NO: 21 or an amino acid sequence that is at least 90% identical to the SEQ ID NO: 21; or g) an amino acid sequence that is SEQ ID NO: 22 or an amino acid sequence that is at least 90% identical to the SEQ ID NO: 22; or h) an amino acid sequence that is SEQ ID NO: 23 or an amino acid sequence that is at least 90% identical to the SEQ ID NO: 23; or i) an amino acid sequence that is SEQ ID NO: 24 or an amino acid sequence that is at least 90% identical to the SEQ ID NO: 24; or j) an amino acid sequence that is SEQ ID NO: 25 or an amino acid sequence that is at least 90% identical to the SEQ ID NO: 25; or k) an amino acid sequence that is SEQ ID NO: 26 or an amino acid sequence that is at least 90% identical to the SEQ ID NO: 26; or 1) an amino acid sequence that is SEQ ID NO: 27 or an amino acid sequence that is at least 90% identical to the SEQ ID NO: 27 or m) an amino acid sequence that is SEQ ID NO: 28 or an amino acid sequence that is at least 90% identical to the SEQ ID NO: 28.

Disclosed herein, in certain embodiments, is a vector comprising DNA encoding a recombinant Arc polypeptide or a recombinant endogenous Gag polypeptide. In some embodiments, the vector further encodes a therapeutic agent. In some embodiments, the therapeutic agent is a nucleic acid. In some embodiments, the nucleic acid is an RNA. In some embodiments, the recombinant Arc polypeptide is a human Arc polypeptide comprising an amino acid sequence that is SEQ ID NO: 1 or an amino acid sequence that is at least 90% identical to the SEQ ID NO: 1. In some embodiments, the recombinant Arc polypeptide is an Arc polypeptide comprising: a) an amino acid sequence that is SEQ ID NO: 2 or an amino acid sequence that is at least 90% identical to the SEQ ID NO: 2; b) an amino acid sequence that is SEQ ID NO: 3 or an amino acid sequence that is at least 90% identical to the SEQ ID NO: 3; c) an amino acid sequence that is SEQ ID NO: 4 or an amino acid sequence that is at least 90% identical to the SEQ ID NO: 4; d) an amino acid sequence that is SEQ ID NO: 5 or an amino acid sequence that is at least 90% identical to the SEQ ID NO: 5; e) an amino acid sequence that is SEQ ID NO: 6 or an amino acid sequence that is at least 90% identical to the SEQ ID NO: 6; f) an amino acid sequence that is SEQ ID NO: 7 or an amino acid sequence that is at least 90% identical to the SEQ ID NO: 7; g) an amino acid sequence that is SEQ ID NO: 8 or an amino acid sequence that is at least 90% identical to the SEQ ID NO: 8; h) an amino acid sequence that is SEQ ID NO: 9 or an amino acid sequence that is at least 90% identical to the SEQ ID NO: 9; i) an amino acid sequence that is SEQ ID NO: 10 or an amino acid sequence that is at least 90% identical to the SEQ ID NO: 10; or j) an amino acid sequence that is SEQ ID NO: 11 or an amino acid sequence that is at least 90% identical to the SEQ ID NO: 11; or k) an amino acid sequence that is SEQ ID NO: 12 or an amino acid sequence that is at least 90% identical to the SEQ ID NO: 12; or 1) an amino acid sequence that is SEQ ID NO: 13 or an amino acid sequence that is at least 90% identical to the SEQ ID NO: 13; or m) an amino acid sequence that is SEQ ID NO: 14 or an amino acid sequence that is at least 90% identical to the SEQ ID NO: 14; or n) an amino acid sequence that is SEQ ID NO: 15 or an amino acid sequence that is at least 90% identical to the SEQ ID NO: 15. In some embodiments, the recombinant endogenous Gag polypeptide is a human endogenous Gag polypeptide. In some embodiments, the recombinant endogenous Gag polypeptide is an endogenous Gag polypeptide comprising: a) an amino acid sequence that is SEQ ID NO: 16 or an amino acid sequence that is at least 90% identical to the SEQ ID NO: 16; b) an amino acid sequence that is SEQ ID NO: 17 or an amino acid sequence that is at least 90% identical to the SEQ ID NO: 17; c) an amino acid sequence that is SEQ ID NO: 18 or an amino acid sequence that is at least 90% identical to the SEQ ID NO: 18; d) an amino acid sequence that is SEQ ID NO: 19 or an amino acid sequence that is at least 90% identical to the SEQ ID NO: 19; e) an amino acid sequence that is SEQ ID NO: 20 or an amino acid sequence that is at least 90% identical to the SEQ ID NO: 20; f) an amino acid sequence that is SEQ ID NO: 21 or an amino acid sequence that is at least 90% identical to the SEQ ID NO: 21; or g) an amino acid sequence that is SEQ ID NO: 22 or an amino acid sequence that is at least 90% identical to the SEQ ID NO: 22; or h) an amino acid sequence that is SEQ ID NO: 23 or an amino acid sequence that is at least 90% identical to the SEQ ID NO: 23; or i) an amino acid sequence that is SEQ ID NO: 24 or an amino acid sequence that is at least 90% identical to the SEQ ID NO: 24; or j) an amino acid sequence that is SEQ ID NO: 25 or an amino acid sequence that is at least 90% identical to the SEQ ID NO: 25; or k) an amino acid sequence that is SEQ ID NO: 26 or an amino acid sequence that is at least 90% identical to the SEQ ID NO: 26; or 1) an amino acid sequence that is SEQ ID NO: 27 or an amino acid sequence that is at least 90% identical to the SEQ ID NO: 27 or m) an amino acid sequence that is SEQ ID NO: 28 or an amino acid sequence that is at least 90% identical to the SEQ ID NO: 28.

Disclosed herein, in certain embodiments, is a vector comprising DNA encoding a recombinant Arc polypeptide or a recombinant endogenous Gag polypeptide, wherein the recombinant Arc polypeptide is not a rat Arc polypeptide or a human Arc polypeptide. In some embodiments, the vector further encodes a cargo. In some embodiments, the cargo is a nucleic acid. In some embodiments, the cargo is an RNA. In some embodiments, the cargo is a therapeutic agent. In some embodiments, the recombinant Arc polypeptide is an Arc polypeptide comprising: a) an amino acid sequence that is SEQ ID NO: 2 or an amino acid sequence that is at least 90% identical to the SEQ ID NO: 2; b) an amino acid sequence that is SEQ ID NO: 3 or an amino acid sequence that is at least 90% identical to the SEQ ID NO: 3; c) an amino acid sequence that is SEQ ID NO: 4 or an amino acid sequence that is at least 90% identical to the SEQ ID NO: 4; d) an amino acid sequence that is SEQ ID NO: 5 or an amino acid sequence that is at least 90% identical to the SEQ ID NO: 5; e) an amino acid sequence that is SEQ ID NO: 6 or an amino acid sequence that is at least 90% identical to the SEQ ID NO: 6; f) an amino acid sequence that is SEQ ID NO: 7 or an amino acid sequence that is at least 90% identical to the SEQ ID NO: 7; g) an amino acid sequence that is SEQ ID NO: 8 or an amino acid sequence that is at least 90% identical to the SEQ ID NO: 8; h) an amino acid sequence that is SEQ ID NO: 9 or an amino acid sequence that is at least 90% identical to the SEQ ID NO: 9; i) an amino acid sequence that is SEQ ID NO: 10 or an amino acid sequence that is at least 90% identical to the SEQ ID NO: 10; or j) an amino acid sequence that is SEQ ID NO: 11 or an amino acid sequence that is at least 90% identical to the SEQ ID NO: 11; or k) an amino acid sequence that is SEQ ID NO: 12 or an amino acid sequence that is at least 90% identical to the SEQ ID NO: 12; or l) an amino acid sequence that is SEQ ID NO: 13 or an amino acid sequence that is at least 90% identical to the SEQ ID NO: 13; or m) an amino acid sequence that is SEQ ID NO: 14 or an amino acid sequence that is at least 90% identical to the SEQ ID NO: 14; or n) an amino acid sequence that is SEQ ID NO: 15 or an amino acid sequence that is at least 90% identical to the SEQ ID NO: 15. In some embodiments, the recombinant endogenous Gag polypeptide is an endogenous Gag polypeptide comprising: a) an amino acid sequence that is SEQ ID NO: 16 or an amino acid sequence that is at least 90% identical to the SEQ ID NO: 16; b) an amino acid sequence that is SEQ ID NO: 17 or an amino acid sequence that is at least 90% identical to the SEQ ID NO: 17; c) an amino acid sequence that is SEQ ID NO: 18 or an amino acid sequence that is at least 90% identical to the SEQ ID NO: 18; d) an amino acid sequence that is SEQ ID NO: 19 or an amino acid sequence that is at least 90% identical to the SEQ ID NO: 19; e) an amino acid sequence that is SEQ ID NO: 20 or an amino acid sequence that is at least 90% identical to the SEQ ID NO: 20; f) an amino acid sequence that is SEQ ID NO: 21 or an amino acid sequence that is at least 90% identical to the SEQ ID NO: 21; or g) an amino acid sequence that is SEQ ID NO: 22 or an amino acid sequence that is at least 90% identical to the SEQ ID NO: 22; or h) an amino acid sequence that is SEQ ID NO: 23 or an amino acid sequence that is at least 90% identical to the SEQ ID NO: 23; or i) an amino acid sequence that is SEQ ID NO: 24 or an amino acid sequence that is at least 90% identical to the SEQ ID NO: 24; or j) an amino acid sequence that is SEQ ID NO: 25 or an amino acid sequence that is at least 90% identical to the SEQ ID NO: 25; or k) an amino acid sequence that is SEQ ID NO: 26 or an amino acid sequence that is at least 90% identical to the SEQ ID NO: 26; or l) an amino acid sequence that is SEQ ID NO: 27 or an amino acid sequence that is at least 90% identical to the SEQ ID NO: 27 or m) an amino acid sequence that is SEQ ID NO: 28 or an amino acid sequence that is at least 90% identical to the SEQ ID NO: 28.

Disclosed herein, in certain embodiments, is a method of delivering a cargo to a cell comprising administering to the cell a capsid comprising a recombinant Arc polypeptide or a recombinant endogenous Gag polypeptide and a therapeutic agent. In some embodiments, the therapeutic agent is a nucleic acid. In some embodiments, the nucleic acid is an RNA. In some embodiments, the recombinant Arc polypeptide is a human Arc polypeptide comprising an amino acid sequence that is SEQ ID NO: 1 or an amino acid sequence that is at least 90% identical to the SEQ ID NO: 1. In some embodiments, the recombinant Arc polypeptide is an Arc polypeptide comprising: a) an amino acid sequence that is SEQ ID NO: 2 or an amino acid sequence that is at least 90% identical to the SEQ ID NO: 2; b) an amino acid sequence that is SEQ ID NO: 3 or an amino acid sequence that is at least 90% identical to the SEQ ID NO: 3; c) an amino acid sequence that is SEQ ID NO: 4 or an amino acid sequence that is at least 90% identical to the SEQ ID NO: 4; d) an amino acid sequence that is SEQ ID NO: 5 or an amino acid sequence that is at least 90% identical to the SEQ ID NO: 5; e) an amino acid sequence that is SEQ ID NO: 6 or an amino acid sequence that is at least 90% identical to the SEQ ID NO: 6; f) an amino acid sequence that is SEQ ID NO: 7 or an amino acid sequence that is at least 90% identical to the SEQ ID NO: 7; g) an amino acid sequence that is SEQ ID NO: 8 or an amino acid sequence that is at least 90% identical to the SEQ ID NO: 8; h) an amino acid sequence that is SEQ ID NO: 9 or an amino acid sequence that is at least 90% identical to the SEQ ID NO: 9; i) an amino acid sequence that is SEQ ID NO: 10 or an amino acid sequence that is at least 90% identical to the SEQ ID NO: 10; or j) an amino acid sequence that is SEQ ID NO: 11 or an amino acid sequence that is at least 90% identical to the SEQ ID NO: 11; or k) an amino acid sequence that is SEQ ID NO: 12 or an amino acid sequence that is at least 90% identical to the SEQ ID NO: 12; or l) an amino acid sequence that is SEQ ID NO: 13 or an amino acid sequence that is at least 90% identical to the SEQ ID NO: 13; or m) an amino acid sequence that is SEQ ID NO: 14 or an amino acid sequence that is at least 90% identical to the SEQ ID NO: 14; or n) an amino acid sequence that is SEQ ID NO: 15 or an amino acid sequence that is at least 90% identical to the SEQ ID NO: 15. In some embodiments, the recombinant endogenous Gag polypeptide is a human endogenous Gag polypeptide. In some embodiments, the recombinant endogenous Gag polypeptide is an endogenous Gag polypeptide comprising: a) an amino acid sequence that is SEQ ID NO: 16 or an amino acid sequence that is at least 90% identical to the SEQ ID NO: 16; b) an amino acid sequence that is SEQ ID NO: 17 or an amino acid sequence that is at least 90% identical to the SEQ ID NO: 17; c) an amino acid sequence that is SEQ ID NO: 18 or an amino acid sequence that is at least 90% identical to the SEQ ID NO: 18; d) an amino acid sequence that is SEQ ID NO: 19 or an amino acid sequence that is at least 90% identical to the SEQ ID NO: 19; e) an amino acid sequence that is SEQ ID NO: 20 or an amino acid sequence that is at least 90% identical to the SEQ ID NO: 20; f) an amino acid sequence that is SEQ ID NO: 21 or an amino acid sequence that is at least 90% identical to the SEQ ID NO: 21; or g) an amino acid sequence that is SEQ ID NO: 22 or an amino acid sequence that is at least 90% identical to the SEQ ID NO: 22; or h) an amino acid sequence that is SEQ ID NO: 23 or an amino acid sequence that is at least 90% identical to the SEQ ID NO: 23; or i) an amino acid sequence that is SEQ ID NO: 24 or an amino acid sequence that is at least 90% identical to the SEQ ID NO: 24; or j) an amino acid sequence that is SEQ ID NO: 25 or an amino acid sequence that is at least 90% identical to the SEQ ID NO: 25; or k) an amino acid sequence that is SEQ ID NO: 26 or an amino acid sequence that is at least 90% identical to the SEQ ID NO: 26; or l) an amino acid sequence that is SEQ ID NO: 27 or an amino acid sequence that is at least 90% identical to the SEQ ID NO: 27 or m) an amino acid sequence that is SEQ ID NO: 28 or an amino acid sequence that is at least 90% identical to the SEQ ID NO: 28. In some embodiments, the cell is a eukaryotic cell. In some embodiments, the cell is a vertebrate cell. In some embodiments, the cell is a mammalian cell. In some embodiments, the cell is a human cell. In some embodiments, the cargo is a nucleic acid. In some embodiments, the cell expresses a gene encoded by the nucleic acid. In some embodiments, the cargo is a therapeutic agent.

Disclosed herein, in certain embodiments, is a method of delivering a cargo to a cell comprising administering to the cell a capsid comprising a recombinant Arc polypeptide or a recombinant endogenous Gag polypeptide, wherein the recombinant Arc polypeptide is not a rat Arc polypeptide or a human Arc polypeptide. In some embodiments, the capsid further comprises a cargo. In some embodiments, the cargo is a nucleic acid. In some embodiments, the cargo is an RNA. In some embodiments, the cargo is a therapeutic agent. In some embodiments, the recombinant Arc polypeptide is an Arc polypeptide comprising: a) an amino acid sequence that is SEQ ID NO: 2 or an amino acid sequence that is at least 90% identical to the SEQ ID NO: 2; b) an amino acid sequence that is SEQ ID NO: 3 or an amino acid sequence that is at least 90% identical to the SEQ ID NO: 3; c) an amino acid sequence that is SEQ ID NO: 4 or an amino acid sequence that is at least 90% identical to the SEQ ID NO: 4; d) an amino acid sequence that is SEQ ID NO: 5 or an amino acid sequence that is at least 90% identical to the SEQ ID NO: 5; e) an amino acid sequence that is SEQ ID NO: 6 or an amino acid sequence that is at least 90% identical to the SEQ ID NO: 6; f) an amino acid sequence that is SEQ ID NO: 7 or an amino acid sequence that is at least 90% identical to the SEQ ID NO: 7; g) an amino acid sequence that is SEQ ID NO: 8 or an amino acid sequence that is at least 90% identical to the SEQ ID NO: 8; h) an amino acid sequence that is SEQ ID NO: 9 or an amino acid sequence that is at least 90% identical to the SEQ ID NO: 9; i) an amino acid sequence that is SEQ ID NO: 10 or an amino acid sequence that is at least 90% identical to the SEQ ID NO: 10; or j) an amino acid sequence that is SEQ ID NO: 11 or an amino acid sequence that is at least 90% identical to the SEQ ID NO: 11; or k) an amino acid sequence that is SEQ ID NO: 12 or an amino acid sequence that is at least 90% identical to the SEQ ID NO: 12; or 1) an amino acid sequence that is SEQ ID NO: 13 or an amino acid sequence that is at least 90% identical to the SEQ ID NO: 13; or m) an amino acid sequence that is SEQ ID NO: 14 or an amino acid sequence that is at least 90% identical to the SEQ ID NO: 14; or n) an amino acid sequence that is SEQ ID NO: 15 or an amino acid sequence that is at least 90% identical to the SEQ ID NO: 15. In some embodiments, the recombinant endogenous Gag polypeptide is an endogenous Gag polypeptide comprising: a) an amino acid sequence that is SEQ ID NO: 16 or an amino acid sequence that is at least 90% identical to the SEQ ID NO: 16; b) an amino acid sequence that is SEQ ID NO: 17 or an amino acid sequence that is at least 90% identical to the SEQ ID NO: 17; c) an amino acid sequence that is SEQ ID NO: 18 or an amino acid sequence that is at least 90% identical to the SEQ ID NO: 18; d) an amino acid sequence that is SEQ ID NO: 19 or an amino acid sequence that is at least 90% identical to the SEQ ID NO: 19; e) an amino acid sequence that is SEQ ID NO: 20 or an amino acid sequence that is at least 90% identical to the SEQ ID NO: 20; f) an amino acid sequence that is SEQ ID NO: 21 or an amino acid sequence that is at least 90% identical to the SEQ ID NO: 21; or g) an amino acid sequence that is SEQ ID NO: 22 or an amino acid sequence that is at least 90% identical to the SEQ ID NO: 22; or h) an amino acid sequence that is SEQ ID NO: 23 or an amino acid sequence that is at least 90% identical to the SEQ ID NO: 23; or i) an amino acid sequence that is SEQ ID NO: 24 or an amino acid sequence that is at least 90% identical to the SEQ ID NO: 24; or j) an amino acid sequence that is SEQ ID NO: 25 or an amino acid sequence that is at least 90% identical to the SEQ ID NO: 25; or k) an amino acid sequence that is SEQ ID NO: 26 or an amino acid sequence that is at least 90% identical to the SEQ ID NO: 26; or 1) an amino acid sequence that is SEQ ID NO: 27 or an amino acid sequence that is at least 90% identical to the SEQ ID NO: 27 or m) an amino acid sequence that is SEQ ID NO: 28 or an amino acid sequence that is at least 90% identical to the SEQ ID NO: 28. In some embodiments, the cell is a eukaryotic cell. In some embodiments, the cell is a vertebrate cell. In some embodiments, the cell is a mammalian cell. In some embodiments, the cell is a human cell. In some embodiments, the cargo is a nucleic acid. In some embodiments, the cell expresses a gene encoded by the nucleic acid. In some embodiments, the cargo is a therapeutic agent.

Disclosed herein, in certain embodiments, is a method of transfecting a nucleic acid into a cell comprising administering to the cell a capsid comprising a recombinant Arc polypeptide or a recombinant endogenous Gag polypeptide and a therapeutic agent. In some embodiments, the therapeutic agent is a nucleic acid. In some embodiments, the nucleic acid is an RNA. In some embodiments, the recombinant Arc polypeptide is a human Arc polypeptide comprising an amino acid sequence that is SEQ ID NO: 1 or an amino acid sequence that is at least 90% identical to the SEQ ID NO: 1. In some embodiments, the recombinant Arc polypeptide is an Arc polypeptide comprising: a) an amino acid sequence that is SEQ ID NO: 2 or an amino acid sequence that is at least 90% identical to the SEQ ID NO: 2; b) an amino acid sequence that is SEQ ID NO: 3 or an amino acid sequence that is at least 90% identical to the SEQ ID NO: 3; c) an amino acid sequence that is SEQ ID NO: 4 or an amino acid sequence that is at least 90% identical to the SEQ ID NO: 4; d) an amino acid sequence that is SEQ ID NO: 5 or an amino acid sequence that is at least 90% identical to the SEQ ID NO: 5; e) an amino acid sequence that is SEQ ID NO: 6 or an amino acid sequence that is at least 90% identical to the SEQ ID NO: 6; f) an amino acid sequence that is SEQ ID NO: 7 or an amino acid sequence that is at least 90% identical to the SEQ ID NO: 7; g) an amino acid sequence that is SEQ ID NO: 8 or an amino acid sequence that is at least 90% identical to the SEQ ID NO: 8; h) an amino acid sequence that is SEQ ID NO: 9 or an amino acid sequence that is at least 90% identical to the SEQ ID NO: 9; i) an amino acid sequence that is SEQ ID NO: 10 or an amino acid sequence that is at least 90% identical to the SEQ ID NO: 10; or j) an amino acid sequence that is SEQ ID NO: 11 or an amino acid sequence that is at least 90% identical to the SEQ ID NO: 11; or k) an amino acid sequence that is SEQ ID NO: 12 or an amino acid sequence that is at least 90% identical to the SEQ ID NO: 12; or 1) an amino acid sequence that is SEQ ID NO: 13 or an amino acid sequence that is at least 90% identical to the SEQ ID NO: 13; or m) an amino acid sequence that is SEQ ID NO: 14 or an amino acid sequence that is at least 90% identical to the SEQ ID NO: 14; or n) an amino acid sequence that is SEQ ID NO: 15 or an amino acid sequence that is at least 90% identical to the SEQ ID NO: 15. In some embodiments, the recombinant endogenous Gag polypeptide is a human endogenous Gag polypeptide. In some embodiments, the recombinant endogenous Gag polypeptide is an endogenous Gag polypeptide comprising: a) an amino acid sequence that is SEQ ID NO: 16 or an amino acid sequence that is at least 90% identical to the SEQ ID NO: 16; b) an amino acid sequence that is SEQ ID NO: 17 or an amino acid sequence that is at least 90% identical to the SEQ ID NO: 17; c) an amino acid sequence that is SEQ ID NO: 18 or an amino acid sequence that is at least 90% identical to the SEQ ID NO: 18; d) an amino acid sequence that is SEQ ID NO: 19 or an amino acid sequence that is at least 90% identical to the SEQ ID NO: 19; e) an amino acid sequence that is SEQ ID NO: 20 or an amino acid sequence that is at least 90% identical to the SEQ ID NO: 20; f) an amino acid sequence that is SEQ ID NO: 21 or an amino acid sequence that is at least 90% identical to the SEQ ID NO: 21; or g) an amino acid sequence that is SEQ ID NO: 22 or an amino acid sequence that is at least 90% identical to the SEQ ID NO: 22; or h) an amino acid sequence that is SEQ ID NO: 23 or an amino acid sequence that is at least 90% identical to the SEQ ID NO: 23; or i) an amino acid sequence that is SEQ ID NO: 24 or an amino acid sequence that is at least 90% identical to the SEQ ID NO: 24; or j) an amino acid sequence that is SEQ ID NO: 25 or an amino acid sequence that is at least 90% identical to the SEQ ID NO: 25; or k) an amino acid sequence that is SEQ ID NO: 26 or an amino acid sequence that is at least 90% identical to the SEQ ID NO: 26; or l) an amino acid sequence that is SEQ ID NO: 27 or an amino acid sequence that is at least 90% identical to the SEQ ID NO: 27 or m) an amino acid sequence that is SEQ ID NO: 28 or an amino acid sequence that is at least 90% identical to the SEQ ID NO: 28.

Disclosed herein, in certain embodiments, is a method of transfecting a nucleic acid into a cell comprising administering to the cell a capsid comprising a recombinant Arc polypeptide or a recombinant endogenous Gag polypeptide, wherein the recombinant Arc polypeptide is not a rat Arc polypeptide or a human Arc polypeptide. In some embodiments, the capsid further comprises a cargo. In some embodiments, the cargo is a nucleic acid. In some embodiments, the cargo is an RNA. In some embodiments, the cargo is a therapeutic agent. In some embodiments, the recombinant Arc polypeptide is an Arc polypeptide comprising: a) an amino acid sequence that is SEQ ID NO: 2 or an amino acid sequence that is at least 90% identical to the SEQ ID NO: 2; b) an amino acid sequence that is SEQ ID NO: 3 or an amino acid sequence that is at least 90% identical to the SEQ ID NO: 3; c) an amino acid sequence that is SEQ ID NO: 4 or an amino acid sequence that is at least 90% identical to the SEQ ID NO: 4; d) an amino acid sequence that is SEQ ID NO: 5 or an amino acid sequence that is at least 90% identical to the SEQ ID NO: 5; e) an amino acid sequence that is SEQ ID NO: 6 or an amino acid sequence that is at least 90% identical to the SEQ ID NO: 6; f) an amino acid sequence that is SEQ ID NO: 7 or an amino acid sequence that is at least 90% identical to the SEQ ID NO: 7; g) an amino acid sequence that is SEQ ID NO: 8 or an amino acid sequence that is at least 90% identical to the SEQ ID NO: 8; h) an amino acid sequence that is SEQ ID NO: 9 or an amino acid sequence that is at least 90% identical to the SEQ ID NO: 9; i) an amino acid sequence that is SEQ ID NO: 10 or an amino acid sequence that is at least 90% identical to the SEQ ID NO: 10; or j) an amino acid sequence that is SEQ ID NO: 11 or an amino acid sequence that is at least 90% identical to the SEQ ID NO: 11; or k) an amino acid sequence that is SEQ ID NO: 12 or an amino acid sequence that is at least 90% identical to the SEQ ID NO: 12; or l) an amino acid sequence that is SEQ ID NO: 13 or an amino acid sequence that is at least 90% identical to the SEQ ID NO: 13; or m) an amino acid sequence that is SEQ ID NO: 14 or an amino acid sequence that is at least 90% identical to the SEQ ID NO: 14; or n) an amino acid sequence that is SEQ ID NO: 15 or an amino acid sequence that is at least 90% identical to the SEQ ID NO: 15. In some embodiments, the recombinant endogenous Gag polypeptide is an endogenous Gag polypeptide comprising: a) an amino acid sequence that is SEQ ID NO: 12 or an amino acid sequence that is at least 90% identical to the SEQ ID NO: 12; b) an amino acid sequence that is SEQ ID NO: 13 or an amino acid sequence that is at least 90% identical to the SEQ ID NO: 13; c) an amino acid sequence that is SEQ ID NO: 14 or an amino acid sequence that is at least 90% identical to the SEQ ID NO: 14; d) an amino acid sequence that is SEQ ID NO: 15 or an amino acid sequence that is at least 90% identical to the SEQ ID NO: 15; e) an amino acid sequence that is SEQ ID NO: 16 or an amino acid sequence that is at least 90% identical to the SEQ ID NO: 16; f) an amino acid sequence that is SEQ ID NO: 17 or an amino acid sequence that is at least 90% identical to the SEQ ID NO: 17; g) an amino acid sequence that is SEQ ID NO: 18 or an amino acid sequence that is at least 90% identical to the SEQ ID NO: 18; g) an amino acid sequence that is SEQ ID NO: 19 or an amino acid sequence that is at least 90% identical to the SEQ ID NO: 19; g) an amino acid sequence that is SEQ ID NO: 20 or an amino acid sequence that is at least 90% identical to the SEQ ID NO: 20; g) an amino acid sequence that is SEQ ID NO: 21 or an amino acid sequence that is at least 90% identical to the SEQ ID NO: 21; or h) an amino acid sequence that is SEQ ID NO: 22 or an amino acid sequence that is at least 90% identical to the SEQ ID NO: 22.

Disclosed herein, in certain embodiments, is an engineered Arc or endo-Gag polypeptide comprising a cargo binding domain and at least one capsid forming subunit from an Arc or endo-Gag polypeptide. In some embodiments, the cargo binding domain comprises a nucleic acid binding domain. In some embodiments, the cargo binding domain comprises a polypeptide that binds to a small molecule. In some embodiments, the cargo binding domain comprises a polypeptide that binds to a protein, a peptide, or an antibody or binding fragment thereof. In some embodiments, the cargo binding domain comprises a polypeptide that binds to a peptidomimetic or a nucleotidomimetic. In some embodiments, the at least one capsid forming subunit comprises a polypeptide that corresponds to the CA N-lobe and/or CA C-lobe of SEQ ID NO: 1. In some embodiments, the engineered Arc or endo-Gag polypeptide further comprises a second capsid forming subunit from a different species of an Arc or endo-Gag polypeptide. In some embodiments, the second capsid forming subunit comprises a polypeptide that corresponds to the N-lobe and/or C-lobe of SEQ ID NO: 1. In some embodiments, the at least one capsid forming subunit and the second capsid forming subunit are each independently selected from a species of Arc or endo-Gag selected from a mammal, a rodent, a bird, a reptile, a fish, an insect, a fungus, or a plant. In some embodiments, the at least one capsid forming subunit and the second capsid forming subunit are from two different species. In some embodiments, the cargo binding domain is fused either directly or via a linker to the C-terminus of the at least one capsid forming subunit. In some embodiments, the cargo binding domain is fused either directly or via a linker to the N-terminus of the at least one capsid forming subunit. In some embodiments, the second capsid forming subunit is fused either directly or via a linker to the C-terminus of the at least one capsid forming subunit. In some embodiments, the second capsid forming subunit is fused either directly or via a linker to the N-terminus of the at least one capsid forming subunit. In some embodiments, the cargo binding domain is fused either directly or via a linker to the N-terminus of the at least one capsid forming subunit and the second capsid forming subunit is fused either directly or via a linker to the C-terminus of the at least one capsid forming subunit. In some embodiments, the cargo binding domain is fused either directly or via a linker to the C-terminus of the at least one capsid forming subunit and the second capsid forming subunit is fused either directly or via a linker to the N-terminus of the at least one capsid forming subunit. In some embodiments, the engineered Arc or endo-Gag polypeptide further comprises a second polypeptide. In some embodiments, the second polypeptide is fused either directly or via a linker to the at least one capsid forming subunit. In some embodiments, the second polypeptide is fused either directly or via a linker to the cargo binding domain. In some embodiments, the second polypeptide is a protein or an antibody or its binding fragments thereof. In some embodiments, the protein is a human protein or a viral protein. In some embodiments, the protein is a human Gag-like protein. In some embodiments, the protein is a de novo engineered protein designed to bind to a target receptor of interest. In some embodiments, the second polypeptide guides the delivery of a capsid formed by the engineered Arc or endo-Gag polypeptide to a target site of interest.

Disclosed herein, in certain embodiments, is a truncated Arc or endo-Gag polypeptide wherein a portion that is not involved with capsid-formation, nucleic acid binding, or delivery is removed. In some embodiments, the portion comprises a matrix (MA) domain, a reverse transcriptase (RT) domain, a nucleotide binding domain, or a combination thereof, provided that the nucleotide binding domain is not a human Arc RNA binding domain. In some embodiments, the portion comprises a CA C-lobe domain. In some embodiments, the portion comprises an N-terminal deletion, a C-terminal deletion, or a combination thereof. In some embodiments, the N-terminal deletion comprises a deletion of up to 10 amino acids, 20 amino acids, 30 amino acids, or 50 amino acids. In some embodiments, the C-terminal deletion comprises a deletion of up to 10 amino acids, 20 amino acids, 30 amino acids, or 50 amino acids.

Disclosed herein, in certain embodiments, is an Arc or endo-Gag-based capsid comprising an engineered Arc or endo-Gag polypeptide which may be a truncated Arc or endo-Gag polypeptide and a cargo encapsulated by the capsid formed by the engineered Arc or endo-Gag polypeptide. In some embodiments, the cargo is a nucleic acid molecule. In some embodiments, the nucleic acid molecule is DNA, RNA, or a mixture of DNA and RNA. In some embodiments, the DNA and the RNA are each independently single-stranded, double-stranded, or a mixture of single and double stranded. In some embodiments, the cargo is a small molecule. In some embodiments, the cargo is a protein. In some embodiments, the cargo is a peptide. In some embodiments, the cargo is an antibody or binding fragments thereof. In some embodiments, the cargo is a peptidomimetic or a nucleotidomimetic. In some embodiments, the Arc or endo-Gag-based capsid comprises one or more additional capsid subunits from one or more species of Arc or endo-Gag proteins that are different than the engineered Arc or endo-Gag polypeptide. In some embodiments, the Arc-based or endo-Gag-based capsid comprises one or more additional capsid subunits from non-Arc proteins. In some embodiments, the one or more additional capsid subunits comprise Copia protein, ASPRV1 protein, a protein from the SCAN domain family, a protein encoded by the Paraneoplastic Ma antigen family (e.g. PNMA5, PNMA6, PNMA6A, and PNMA6B), a protein from the retrotransposon Gag-like family (e.g. RTL3, RTL6, RTL8A, RTL8B), or a combination thereof. In some embodiments, the one or more additional capsid subunits comprise BOP, LDOC1, MOAP1, PEG10, PNMA3, PNMA5, PNMA6A, PNMA6B, RTL3, RTL6, RTL8A, RTL8B, and ZNF18. In some embodiments, the capsid has a diameter of at least 1 nm, 2 nm, 3 nm, 4 nm, 5 nm, 10 nm, 15 nm, 20 nm, 25 nm, 30 nm, 50 nm, 80 nm, 100 nm, 120 nm, 150 nm, 200 nm, 250 nm, 300 nm, 500 nm, 600 nm, or more. In some embodiments, the capsid has a diameter of from about 1 nm to about 600 nm, from about 1 nm to about 500 nm, from about 1 nm to about 200 nm, from about 1 nm to about 100 nm, from about 1 nm to about 50 nm, or from about 1 nm to about 30 nm. In some embodiments, the capsid has a reduced off-target effect. In some embodiments, the capsid does not have an off-target effect. In some embodiments, the capsid is formed ex-vivo. In some embodiments, the capsid is formed in-vitro.

Disclosed herein, in certain embodiments, is a nucleic acid polymer encoding a recombinant or engineered Arc polypeptide or a recombinant or engineered endogenous Gag polypeptide described herein.

Disclosed herein, in certain embodiments, is a vector comprising a nucleic acid polymer encoding a recombinant or engineered Arc polypeptide or a recombinant or engineered endogenous Gag polypeptide described herein.

Disclosed herein, in certain embodiments, is a method of preparing a loaded Arc-based or endo-Gag-based capsid comprising: incubating a plurality of recombinant or engineered Arc polypeptides or a plurality of recombinant or engineered endo-Gag polypeptides with a cargo in a solution for a time sufficient to generate the loaded capsid. In some embodiments, the method further comprises mixing the solution comprising the plurality of engineered Arc or endo-Gag polypeptides with a plurality of non-Arc or non-endo-Gag capsid forming subunits prior to incubating with the cargo. In some embodiments, the plurality of non-Arc or non-endo-Gag capsid forming subunits are mixed with the plurality of recombinant or engineered Arc or endo-Gag polypeptides at a ratio of 1:1, 2:1, 3:1, 4:1, 5:1, 6:1, 7:1, 8:1, 9:1, or 10:1. In some embodiments, the plurality of non-Arc or non-endo-Gag capsid forming subunits are mixed with the plurality of engineered Arc or endo-Gag polypeptides at a ratio of 1:2, 1:3, 1:4, 1:5, 1:6, 1:7, 1:8, 1:9, or 1:10. In some embodiments, the method further comprises mixing the solution comprising the plurality of truncated Arc or endo-Gag polypeptides with a plurality of non-Arc or endo-Gag capsid forming subunits prior to incubating with the cargo. In some embodiments, the plurality of non-Arc or endo-Gag capsid forming subunits are mixed with the plurality of truncated Arc or endo-Gag polypeptides at a ratio of 1:1, 2:1, 3:1, 4:1, 5:1, 6:1, 7:1, 8:1, 9:1, or 10:1. In some embodiments, the plurality of non-Arc or non-endo-Gag capsid forming subunits are mixed with the plurality of truncated Arc or endo-Gag polypeptides at a ratio of 1:2, 1:3, 1:4, 1:5, 1:6, 1:7, 1:8, 1:9, or 1:10. In some embodiments, the plurality of engineered Arc or endo-Gag polypeptides is obtained from a bacterial cell system, an insect cell system, or a mammalian cell system. In some embodiments, the plurality of engineered Arc or endo-Gag polypeptides is obtained from a cell-free system. In some embodiments, the plurality of truncated Arc or endo-Gag polypeptides is obtained from a bacterial cell system, an insect cell system, or a mammalian cell system. In some embodiments, the plurality of truncated Arc or endo-Gag polypeptides is obtained from a cell-free system. In some embodiments, the loaded Arc-based or endo-Gag capsid is formulated for systemic administration. In some embodiments, the loaded Arc or endo-Gag-based capsid is formulated for local administration. In some embodiments, the loaded Arc or endo-Gag-based capsid is formulated for parenteral administration. In some embodiments, the loaded Arc or endo-Gag-based capsid is formulated for oral administration. In some embodiments, the loaded Arc or endo-Gag-based capsid is formulated for topical administration. In some embodiments, the loaded Arc or endo-Gag-based capsid is formulated for sublingual or aerosol administration.

Disclosed herein, in certain embodiments, is use of an engineered or recombinant Arc-based or endo-Gag-based capsid for delivery of a cargo to a site of interest, comprising contacting a cell at the site of interest with an Arc-based or endo-Gag-based capsid for a time sufficient to facilitate cellular uptake of the capsid. In some embodiments, the cell is a tumor cell. In some embodiments, the tumor cell is a solid tumor cell. In some embodiments, the solid tumor cell is a cell from a bladder cancer, breast cancer, brain cancer, colorectal cancer, kidney cancer, liver cancer, lung cancer, pancreatic cancer, prostate cancer, skin cancer, stomach cancer, or thyroid cancer. In some embodiments, the tumor cell is from a hematologic malignancy. In some embodiments, the hematologic malignancy is a B-cell malignancy, or a T-cell malignancy. In some embodiments, the hematologic malignancy is chronic lymphocytic leukemia (CLL), small lymphocytic lymphoma (SLL), diffuse large B cell lymphoma (DLBCL), follicular lymphoma, mantle cell lymphoma, Burkitt lymphoma, cutaneous T-cell lymphoma, or peripheral T cell lymphoma. In some embodiments, the cell is a somatic cell. In some embodiments, the cell is a stem cell or a progenitor cell. In some embodiments, the cell is a mesenchymal stem or progenitor cell. In some embodiments, the cell is a hematopoietic stem or progenitor cell. In some embodiments, the cell is a muscle cell, a skin cell, a blood cell, or an immune cell. In some embodiments, a target protein is overexpressed or is depleted in the cell. In some embodiments, a target gene in the cell has one or more mutations. In some embodiments, the cell comprises an impaired splicing mechanism. In some embodiments, the use is an in vivo use. In some embodiments, the Arc-based capsid is administered systemically to a subject. In some embodiments, the Arc-based or endo-Gag-based capsid is administered via local administration to a subject. In some embodiments, the Arc-based or endo-Gag-based capsid is administered parenterally to a subject. In some embodiments, the Arc-based capsid is administered orally to a subject. In some embodiments, the Arc-based or endo-Gag-based capsid is administered topically to a subject. In some embodiments, the Arc-based or endo-Gag-based capsid is administered via sublingual or aerosol administration to a subject. In some embodiments, the use is an in vitro or ex vivo use.

Disclosed herein, in certain embodiments, is a kit comprising an engineered Arc or endo-Gag polypeptide, a truncated Arc or endo-Gag polypeptide, a vector encoding a recombinant or engineered Arc or endo-Gag polypeptide, or an Arc-based or endo-Gag-based capsid.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings below.

FIG. 9 shows the delivery of Cre RNA to HeLa cells by Arc capsids.

FIG. 10 illustrates methods for screening Arc and endo-Gag gene candidates for the ability to transmit a heterologous RNA payload.

DETAILED DESCRIPTION OF THE DISCLOSURE

Figure 1:
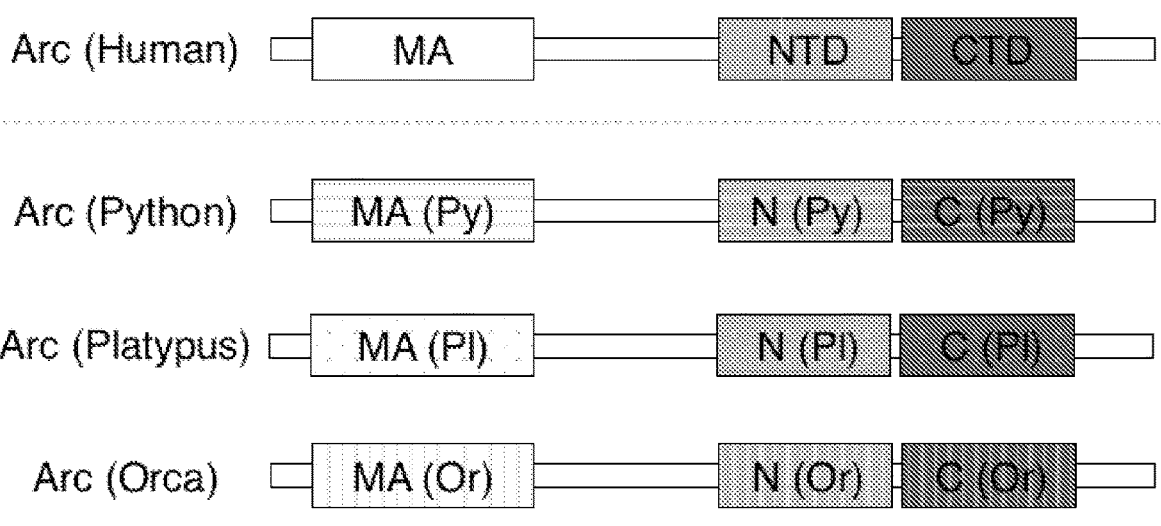
FIG. 1 is a representation of exemplary Arc polypeptides.

Administrating diagnostic or therapeutic agents to a site of interest with precision has presented an ongoing challenge. Available methods of delivering nucleic acids to cells have myriad limitations. For example, AAV viral vectors often used for gene therapy are immunogenic, have a limited payload capacity of <3kb, suffer from poor bio-distribution, can only be administered by direct injection, and pose a risk of disrupting host genes by integration. Non-viral methods have different limitations. Liposomes are primarily delivered to the liver. Extracellular vesicles have a limited payload capacity of <1 kb, limited scalability, and purification difficulties. Thus, there is a recognized need for new methods of delivering therapeutic payloads.

Most molecules do not possess inherent affinity in the body. In other cases, the administered agents accumulate either in the liver and the kidney for clearance or in unintended tissue or cell types. Method for improving delivery includes coating the agent of choice with hydrophobic compounds or polymers. Such an approach increases the duration of said agent in circulation and augments hydrophobicity for cellular uptake. On the other hand, this approach does not actively direct cargo to the site of interest for delivery.

To specifically target sites where therapy is needed, therapeutic compounds are optionally fused to moieties such as ligands, antibodies, and aptamers that recognize and bind to receptors displayed on the surface of targeted cells. Upon reaching a cell of interest, the therapeutic compound is optionally further delivered to an intracellular target. For example, a therapeutic RNA can be translated to a protein if it comes into contact with a ribosome in the cytoplasm of the cell.

Arc (activity-regulated cytoskeleton-associated protein) regulates the endocytic trafficking of α-amino-3-hydroxy-5-methylisoxazole-4-propionic acid (AMPA) type glutamate receptors. Arc activities have been linked to synaptic strength and neuronal plasticity. Phenotypes of loss of Arc in experimental murine model included defective formation of long-term memory and reduced neuronal activity and plasticity.

Arc exhibits similar molecular properties to retroviral Gag proteins. The Arc gene may have originated from the Ty3/gypsy retrotransposon. An endogenous Gag (endo-Gag) protein is any protein endogenous to a eukaryotic organism, including Arc, that has predicted and annotated similarity to viral Gag proteins. Exemplary endo-Gag proteins are disclosed in Campillos M, Doerks T, Shah PK, and Bork P, Computational characterization of multiple Gag-like human proteins, Trends Genet. 2006 November; 22(11):585-9. An endo-Gag protein is optionally recombinantly expressed by any host cell, including a prokaryotic or eukaryotic cell, or a bacterial, yeast, insect, vertebrate, mammalian, or human cell. As described herein, in some embodiments an endo-Gag protein assembles into an endo-Gag capsid.

Disclosed herein, in certain embodiments, are Arc and endo-Gag polypeptides which assemble into a capsid for delivery of a cargo of interest. In some embodiments, also described herein are engineered Arc and endo-Gag polypeptides which assemble into a capsid for delivery of a cargo of interest. In additional embodiments, described herein are capsids, e.g., Arc-based or endo-Gag-based capsids, for delivery of a cargo of interest.

Arc Polypeptides and Endogenous Gag Polypeptides

In certain embodiments, disclosed herein is an Arc polypeptide. In certain embodiments, disclosed herein is an endo-Gag polypeptide. It should be understood that endo-Gag sequences are optional substitutes for Arc sequences to form any type of engineered Arc polypeptide described in this section.

In some instances, Arc is a non-human Arc polypeptide. In some instances, the Arc polypeptide comprises a full-length Arc polypeptide (e.g., a full-length non-human Arc polypeptide). In other instances, the Arc polypeptide comprises a fragment of non-human Arc, such as a truncated Arc polypeptide, that participates in the formation of a capsid. In additional instances, the Arc polypeptide comprises one or more domains of a non-human Arc polypeptide, in which at least one of the domains participates in the formation of a capsid. In further instances, the Arc polypeptide is a recombinant Arc polypeptide.

In some instances, endo-Gag is a non-human endo-Gag polypeptide. In some instances, the endo-Gag polypeptide comprises a full-length endo-Gag polypeptide (e.g., a full-length non-human endo-Gag polypeptide). In other instances, the endo-Gag polypeptide comprises a fragment of non-human endo-Gag, such as a truncated endo-Gag polypeptide, that participates in the formation of a capsid. In additional instances, the endo-Gag polypeptide comprises one or more domains of a non-human endo-Gag polypeptide, in which at least one of the domains participates in the formation of a capsid. In further instances, the endo-Gag polypeptide is a recombinant endo-Gag polypeptide.

In some embodiments, the Arc is a human Arc polypeptide with at least its RNA binding domain modified to bind to a cargo that is not native to the human Arc. In some instances, the Arc polypeptide comprises a full-length human Arc polypeptide with at least its RNA binding domain modified to bind to a cargo that is not native to the human Arc protein. In other instances, the Arc polypeptide comprises a human Arc fragment comprising modification(s) in at least its RNA binding domain. In additional instances, the Arc polypeptide comprises one or more domains of a human Arc polypeptide, in which at least one of the domains participates in the formation of a capsid and in which the RNA binding domain is modified to bind to a cargo that native human Arc protein does not bind to. In further instances, the Arc polypeptide is a recombinant human Arc polypeptide, with at least the RNA binding domain is modified to enable loading of a cargo that is not native to the human Arc protein.

In some embodiments, the Endo-Gag is a human Endo-Gag polypeptide with at least its RNA binding domain modified to bind to a cargo that is not native to the human endo-Gag. In some instances, the endo-Gag polypeptide comprises a full-length human endo-Gag polypeptide with at least its RNA binding domain modified to bind to a cargo that is not native to the human endo-Gag protein. In other instances, the endo-Gag polypeptide comprises a human endo-Gag fragment comprising modification(s) in at least its RNA binding domain to bind to a cargo that a native human endo-Gag protein does not bind to. In additional instances, the endo-Gag polypeptide comprises one or more domains of a human endo-Gag polypeptide, in which at least one of the domains participates in the formation of a capsid and in which the RNA binding domain is modified to bind to a cargo that is not native to the human endo-Gag protein. In further instances, the endo-Gag polypeptide is a recombinant human endo-Gag polypeptide, with at least the RNA binding domain is modified to enable loading of a cargo that is not native to the human endo-Gag protein.

In some instances, the Arc or endo-Gag polypeptide is an engineered Arc or endo-Gag polypeptide. As used herein, an engineered polypeptide is a recombinant polypeptide that is not identical in sequence to a full length, wild-type polypeptide. In some instances, the engineered Arc or endo-Gag polypeptide comprises a fragment of an Arc or endo-Gag polypeptide from a first species and at least an additional fragment from an Arc or endo-Gag polypeptide of a second species. In some cases, the first Arc or endo-Gag polypeptide is selected from a kingdom member of animalia, plantae, fungi, or protista. In some cases, the first species is selected from a mammal, a rodent, a bird, a reptile, a fish, a vertebrate, a eukaryote, an insect, a fungus, or a plant. In some cases, the second Arc polypeptide is selected from a kingdom member of animalia, plantae, fungi, or protista that is the same or different than the first Arc or endo-Gag polypeptide. In some cases, the second species is selected from a mammal, a rodent, a bird, a reptile, a fish, a vertebrate, a eukaryote, an insect, a fungus, or a plant that is different from the first species.

In some embodiments, an exemplary mammalian Arc or endo-Gag protein for expression as a recombinant or engineered Arc polypeptide is from the species *Homo sapiens*. Additional exemplary species of primate Arc or endo-Gag protein proteins for expression as a recombinant or engineered Arc polypeptide include: *gorilla, Pongo abehi, Pan paniscus, Macaca nemestrina, Chlorocebus sabaeus, Papio anubis, Rhinopithecus roxellana, Macaca fascicularis, Nomascus leucogenys, Callithrix jacchus, Aotus nancymaae, Cebus capucinus imitator, Saimiri boliviensis boliviensis, Otolemur garnettii, Macaca mulatta*, and *Macaca fascicularis*.

An exemplary species list of rodent Arc or endo-Gag proteins for expression as a recombinant or engineered Arc or endo-Gag polypeptide includes: *Fukomys damarensis, Microcebus murinus, Heterocephalus glaber, Propithecus coquereli, Marmota marmota marmota, Galeopterus variegatus, Cavia porcellus, Dipodomys ordii, Octodon degus, Castor canadensis Nannospalax galili, Carlito syrichta, Chinchilla lanigera, Mus musculus, Ictidomys tridecemlineatus, Rattus norvegicus, Microtus ochrogaster, Otolemur* garnettii, Meriones unguiculatus, Cricetulus griseus, Rattus norvegicus, Neotoma lepida, Jaculus jaculus, Mustela putorius furo, Mesocricetus auratus, Tupaia chinensis, Cricetulus griseus, Chrysochloris asiatica, Elephantulus edwardii, Erinaceus europaeus, Ochotona princeps, Sorex araneus, Monodelphis domestica, Echinops telfairi, and Condylura cristata.

An exemplary species list of Arc or endo-Gag proteins for expression as a recombinant or engineered Arc or endo-Gag polypeptide includes: Vulpes vulpes, Canis lupus dingo, Felis catus, Panthera pardus, Callorhinus ursinus, Odobenus rosmarus divergens, Equus asinus, Sus scrofa, Manis javanica, Ceratotherium simum simum, Leptonychotes weddellii, Enhydra lutris kenyoni, Lipotes vexillifer, Bos grunniens, Bubalus bubalis, Camelus dromedarius, Vicugna pacos, Orcinus orca, Neomonachus schauinslandi, Tursiops truncatus, Bos taurus, Capra hircus, Delphinapterus leucas, Ovis aries musimon, Balaenoptera acutorostrata scammoni, Neophocaena asiaeorientalis asiaeorientalis, Miniopterus natalensis, Pteropus alecto, Physeter catodon, Loxodonta africana, Orycteropus afer afer, Bos mutus, Desmodus rotundus, Hipposideros armiger, Ailuropoda melanoleuca, Trichechus manatus latirostris, Rousettus latirostris, Rousettus aegyptiacus, Eptesicus fuscus, Rhinolophus sinicus, Cervus elaphus hippelaphus, Odocoileus virginianus texanus, Pantholops hodgsonii, Camelus bactrianus, Sarcophilus harrisii, Phascolarctos cinereus, and Ornithorhynchus anatinus.

An exemplary species list of bird Arc or endo-Gag proteins for expression as a recombinant or engineered Arc or endo-Gag polypeptide includes: Gallus gallus, Corvus cornix, cornix, Parus major, Corvus brachyrhynchos, Dromaius novaehollandiae, and Apteryx rowi.

An exemplary species list of reptile Arc protein for expression as a recombinant or engineered Arc or endo-Gag polypeptide includes: Python bivittatus, Pogona vitticeps, Anolis carolinensis, Protobothrops mucrosquamatus, Alligator sinensis, Crocodylus porosus, Gavialis gangeticus, Alligator mississippiensis, Pelodiscus sinensis, Terrapene mexicana triunguis, Chrysemys picta bellii, Chelonia mydas, Nanorana parkeri, Xenopus tropicalis, Xenopus laevis, and Latimeria chalumnae, An exemplary species list of fish Arc protein for expression as a recombinant or engineered Arc or endo-Gag polypeptide includes: Oncorhynchus mykiss, Acanthochromis Polyacanthus, Oncorhynchus kisutch, Carassius auratus, and Austrofundulus limnaeus.

An exemplary species list of insect Arc or endo-Gag proteins for expression as a recombinant or engineered Arc or endo-Gag polypeptide includes: Drosophila serrata, Drosophila bipectinata, Solenopsis invicta, Temnothorax curvispinosus, Drosophila melanogaster, Agrilus planipennis, Camponotus floridanus, Pogonomyrmex barbatus, Nilaparvata lugens, Bombyx mori, Tribolium castaneum, and Leptinotarsa decemlineata.

An exemplary species list of plant Arc or endo-Gag proteins for expression as a recombinant or engineered Arc or endo-Gag polypeptide includes Spinacia oleracea and Erythranthe guttata.

An exemplary species list of fungi proteins for expression as a recombinant or engineered Arc or endo-Gag polypeptide includes: Saccharomyces cerevisiae, Rhizopus delemar, Fusarium oxysporum, Cryptococcus neoformans, Rhizophagus irregularis, Fusarium fujikuroi, Candida albicans, Trichophyton rubrum, Pyrenophora tritici-repentis, Rhizopus microsporus, Rhizoctonia solani, Aspergillus flavus, Verticillium dahliae, Fusarium verticillioides, Aspergillus niger, Fusarium graminearum, Aspergillus fumigatus, Zymoseptoria tritici, and Trichoderma harzianum.

An exemplary species list of protists Arc or endo-Gag proteins for expression as a recombinant or engineered Arc or endo-Gag polypeptide includes: Entamoeba histolytica, Paulinella micropora, Guillardia theta, Oxyrrhis marina, Seminavis robusta, Euglena longa, Naegleria gruberi, and Trichomonas vaginalis.

In some instances, Arc or endo-Gag comprises a capsid assembly/forming (CA) domain, a cargo binding domain (e.g., an RNA binding domain), and optionally a matrix (MA) domain, a reverse transcriptase (RT) domain, or a combination thereof. In some cases, the CA domain is further divided into an N-lobe domain and a C-lobe domain. In some cases, the cargo binding domain comprises an RNA binding domain, a DNA binding domain, a protein binding domain, a peptide binding domain, an antibody binding domain, a small molecule binding domain, or a peptidomimetic/nucleotidomimetic binding domain. Exemplary cargo binding domains include, but are not limited to, domains from GPCRs, antibodies or binding fragments thereof, lipoproteins, integrins, tyrosine kinases, DNA-binding proteins, RNA-binding proteins, nucleases, ligases, proteases, integrases, isomerases, phosphatases, GTPases, aromatases, esterases, adaptor proteins, G-proteins, GEFs, cytokines, interleukins, interleukin receptors, interferons, interferon receptors, caspases, transcription factors, neurotrophic factors and their receptors, growth factors and their receptors, signal recognition particle and receptor components, extracellular matrix proteins, integral components of membrane, ribosomal proteins, translation elongation factors, translation initiation factors, GPI-anchored proteins, tissue factors, dystrophin, utrophin, dystrobrevin, any fusions, combinations, subunits, derivatives, or domains thereof.

In some embodiments, one or more non-essential regions which are not involved in capsid formation or nucleic acid binding are removed from an Arc or endo-Gag protein to generate an Arc or endo-Gag polypeptide. In such instances, one or more non-essential regions, e.g., an N-terminal region (e.g., up to 10 amino acids, up to 20 amino acids, up to 30 amino acids, or up to 50 amino acids), a C-terminal region (e.g., up to 10 amino acids, up to 20 amino acids, up to 30 amino acids, or up to 50 amino acids), a RT domain, a MA domain, or a combination thereof, are deleted from an Arc or endo-Gag protein to generate an Arc or endo-Gag polypeptide. In some cases, only the essential regions involved in capsid assembly/forming and cargo binding remain in an Arc or endo-Gag polypeptide. In additional cases, only the essential region involved in capsid assembly/forming (e.g., the N-lobe and/or the C-lobe) remains in an Arc polypeptide.

In certain embodiments, the RT domain, the MA domain, and/or the endogenous RNA binding domain are replaced with other cargo binding domains: for example, replaced with a DNA binding domain, a protein binding domain, a peptide binding domain, an antibody binding domain, a small molecule binding domain, a peptidomimetic binding domain, or a nucleotidomimetic binding domain. In some embodiments, an Arc or endo-Gag polypeptide comprises truncations or modifications of domains involved in capsid forming, nucleic acid binding, or delivery.

In some embodiments, the Arc or endo-Gag polypeptide comprises a MA domain, a CA N-lobe, a CA C-lobe, a cargo binding domain, and a RT domain. In some instances, the Arc polypeptide comprises from N-terminus to C-terminus the following domains: the MA domain, the CA N-lobe, the CA C-lobe, the RT domain, and the cargo binding domain. In some instances, the Arc or endo-Gag polypeptide comprises from N-terminus to C-terminus the following domains: the MA domain, the RT domain, the cargo binding domain, the CA N-lobe, and the CA C-lobe. In some instances, the Arc or endo-Gag polypeptide comprises from N-terminus to C-terminus the following domains: the cargo binding domain, the MA domain, the RT domain, the CA N-lobe, and the CA C-lobe. In some instances, the domains are arranged in an order that does not impede capsid assembly and cargo binding. In some instances, each of the domains is either directly or indirectly fused to the respective two flanking domains.

In some embodiments, the Arc or endo-Gag polypeptide comprises a MA domain, a CA N-lobe, a CA C-lobe, and a cargo binding domain. In some instances, the Arc or endo-Gag polypeptide comprises from N-terminus to C-terminus the following domains: the MA domain, the CA N-lobe, the CA C-lobe, and the cargo binding domain. In some instances, the Arc polypeptide comprises from N-terminus to C-terminus the following domains: the MA domain, the cargo binding domain, the CA N-lobe, and the CA C-lobe. In some instances, the Arc or endo-Gag polypeptide comprises from N-terminus to C-terminus the following domains: the cargo binding domain, the MA domain, the CA N-lobe, and the CA C-lobe. In some instances, the domains are arranged in an order that does not impede capsid assembly and cargo binding. In some instances, each of the domains is either directly or indirectly fused to the respective two flanking domains.

In some embodiments, the Arc or endo-Gag polypeptide comprises a CA N-lobe, a CA C-lobe, and a cargo binding domain. In some instances, the Arc or endo-Gag polypeptide comprises from N-terminus to C-terminus the following domains: the CA N-lobe, the CA C-lobe, and the cargo binding domain. In some instances, the Arc or endo-Gag polypeptide comprises from N-terminus to C-terminus the following domains: the cargo binding domain, the CA N-lobe, and the CA C-lobe. In some instances, the domains are arranged in an order that does not impede capsid assembly and cargo binding. In some instances, each of the domains is either directly or indirectly fused to the respective two flanking domains.

In some embodiments, the Arc or endo-Gag polypeptide comprises a CA N-lobe and a cargo binding domain. In some instances, the Arc or endo-Gag polypeptide comprises from N-terminus to C-terminus the following domains: the CA N-lobe and the cargo binding domain. In some instances, the Arc or endo-Gag polypeptide comprises from N-terminus to C-terminus the following domains: the cargo binding domain and the CA N-lobe. In some instances, the domains are arranged in an order that does not impede capsid assembly and cargo binding. In some instances, the two domains are either directly or indirectly fused to each other.

In some embodiments, the Arc or endo-Gag polypeptide is engineered to comprise a cargo binding domain, a CA domain, a MA domain, or a RT domain from one or more additional species to generate an engineered Arc polypeptide. For example, the engineered Arc or endo-Gag polypeptide comprises a cargo binding domain, a CA domain, a MA domain, or a RT domain from a first species and a cargo binding domain, a CA domain, a MA domain, or a RT domain from a second species. In some cases, the first species is selected from a eukaryote, a vertebrate, a human, a mammal, a rodent, a bird, a reptile, a fish, an insect, a fungus, or a plant. In some cases, the second species is selected from a eukaryote, a vertebrate, a human, a mammal, a rodent, a bird, a reptile, a fish, an insect, a fungus, or a plant that is different from the first species.

In some instances, the engineered or endo-Gag Arc polypeptide comprises a cargo binding domain from a first species and a CA domain (e.g., a CA N-lobe and optionally a CA C-lobe) from a second species. The engineered Arc or endo-Gag polypeptide optionally comprises a MA domain and an RT domain from either the first species or the second species. In some cases, the first species is selected from a eukaryote, a vertebrate, a human, a mammal, a rodent, a bird, a reptile, a fish, an insect, a fungus, or a plant. In some cases, the second species is selected from a eukaryote, a vertebrate, a human, a mammal, a rodent, a bird, a reptile, a fish, an insect, a fungus, or a plant that is different from the first species.

In some instances, the engineered Arc or endo-Gag polypeptide comprises a cargo binding domain, a first CA domain, a second CA domain, and optionally a MA domain and/or a RT domain. In some cases, the cargo binding domain, the first CA domain, and optionally a MA domain and/or a RT domain are from a first species and the second CA domain is from a second species. In some cases, the first CA domain is from a first species and the cargo binding domain, the second CA domain, and optionally a MA domain and/or a RT domain are from a second species. In some instances, the domains are arranged in an order that does not impede capsid assembly and cargo binding. In some instances, each of the domains is either directly or indirectly fused to the respective two adjacent domains.

In some instances, the engineered Arc or endo-Gag polypeptide comprises a cargo binding domain, a first CA domain, and a second CA domain. In some cases, the cargo binding domain and the first CA domain are from a first species and the second CA domain is from a second species. In some cases, the first CA domain is from a first species and the cargo binding domain and the second CA domain are from a second species. In such cases, the engineered Arc or endo-Gag polypeptide comprises from the N-terminus to the C-terminus the following domains: a cargo binding domain, a first CA domain, and a second CA domain. In such cases, the engineered Arc or endo-Gag polypeptide comprises from the N-terminus to the C-terminus the following domains: a first CA domain, a cargo binding domain, and a second CA domain. In such cases, the engineered Arc or endo-Gag polypeptide comprises from the N-terminus to the C-terminus the following domains: a first CA domain, a second CA domain, and a cargo binding domain. In some instances, the domains are arranged in an order that does not impede capsid assembly and cargo binding. In some instances, each of the domains is either directly or indirectly fused to the respective two flanking domains.

In some instances, the engineered Arc or endo-Gag polypeptide further comprises a second polypeptide. In some instances, the second polypeptide is fused directly or indirectly via a linker to one or more of: a cargo binding domain, a first CA domain, a second CA domain, a MA domain if present, or a RT domain if present. In some cases, the second polypeptide is a protein (e.g., a human protein), an antibody or binding fragment thereof, a viral protein, a Gag-like protein (e.g., a human Gag-like protein), or a de novo engineered protein designed to bind to a target receptor of interest. In some instances, the antibody or binding fragment thereof comprises a humanized antibody or binding fragments thereof, a murine antibody or binding fragment thereof, a chimeric antibody or binding fragment thereof, a monoclonal antibody or binding fragment thereof, a multispecific antibody or binding fragment thereof, a bispecific antibody or biding fragment thereof, a monovalent Fab', a divalent $Fab_2$, $F(ab)'_3$ fragments, a single-chain variable fragment (scFv), a bis-scFv, an (scFv)$_2$, a diabody, a mini-body, a nanobody, a triabody, a tetrabody, a disulfide stabi-lized Fv protein (dsFv), a single-domain antibody (sdAb), an Ig NAR, a camelid antibody or binding fragment thereof, or a chemically modified derivative thereof. In some instances, the second polypeptide guides the delivery of a capsid formed by the engineered Arc polypeptide to a target site of interest.

In some embodiments, a nucleic acid sequence or amino acid sequence of the disclosure (for example, encoding an Arc polypeptide or endo-Gag polypeptide) has at least 70% homology, at least 71% homology, at least 72% homology, at least 73% homology, at least 74% homology, at least 75% homology, at least 76% homology, at least 77% homology, at least 78% homology, at least 79% homology, at least 80% homology, at least 81% homology, at least 82% homology, at least 83% homology, at least 84% homology, at least 85% homology, at least 86% homology, at least 87% homology, at least 88% homology, at least 89% homology, at least 90% homology, at least 91% homology, at least 92% homology, at least 93% homology, at least 94% homology, at least 95% homology, at least 96% homology, at least 97% homology, at least 98% homology, at least 99% homology, at least 99.1% homology, at least 99.2% homology, at least 99.3% homology, at least 99.4% homology, at least 99.5% homol-ogy, at least 99.6% homology, at least 99.7% homology, at least 99.8% homology, at least 99.9% or at least 99.99% homology to an amino acid sequence provided herein. Various methods and software programs are used to deter-mine the homology between two or sequences, such as NCBI BLAST, Clustal W, MAFFT, Clustal Omega, AlignMe, Praline, or another suitable method or algorithm.

In certain embodiments, the Arc polypeptide is a human polypeptide having the amino acid sequence of SEQ ID NO: 1 or a sequence having at least 90%, 91%, 92%, 93%, 94%, 95%, 96%, 97%, 98%, or 99% identity to SEQ ID NO: 1.

In certain embodiments, the Arc polypeptide is a killer whale polypeptide having the amino acid sequence of SEQ ID NO: 2 or a sequence having at least 90%, 91%, 92%, 93%, 94%, 95%, 96%, 97%, 98%, or 99% identity to SEQ ID NO: 2.

In certain embodiments, the Arc polypeptide is a white tailed deer polypeptide having the amino acid sequence of SEQ ID NO: 3 or a sequence having at least 90%, 91%, 92%, 93%, 94%, 95%, 96%, 97%, 98%, or 99% identity to SEQ ID NO: 3.

In certain embodiments, the Arc polypeptide is a platypus polypeptide having the amino acid sequence of SEQ ID NO: 4 or a sequence having at least 90%, 91%, 92%, 93%, 94%, 95%, 96%, 97%, 98%, or 99% identity to SEQ ID NO: 4.

In certain embodiments, the Arc polypeptide is a goose polypeptide having the amino acid sequence of SEQ ID NO: 5 or a sequence having at least 90%, 91%, 92%, 93%, 94%, 95%, 96%, 97%, 98%, or 99% identity to SEQ ID NO: 5.

In certain embodiments, the Arc polypeptide is a Dalma-tian pelican polypeptide having the amino acid sequence of SEQ ID NO: 6 or a sequence having at least 90%, 91%, 92%, 93%, 94%, 95%, 96%, 97%, 98%, or 99% identity to SEQ ID NO: 6.

In certain embodiments, the Arc polypeptide is a white tailed eagle polypeptide having the amino acid sequence of SEQ ID NO: 7 or a sequence having at least 90%, 91%, 92%, 93%, 94%, 95%, 96%, 97%, 98%, or 99% identity to SEQ ID NO: 7.

In certain embodiments, the Arc polypeptide is a king cobra polypeptide having the amino acid sequence of SEQ ID NO: 8 or a sequence having at least 90%, 91%, 92%, 93%, 94%, 95%, 96%, 97%, 98%, or 99% identity to SEQ ID NO: 8.

In certain embodiments, the Arc polypeptide is a ray finned fish polypeptide having the amino acid sequence of SEQ ID NO: 9 or a sequence having at least 90%, 91%, 92%, 93%, 94%, 95%, 96%, 97%, 98%, or 99% identity to SEQ ID NO: 9.

In certain embodiments, the Arc polypeptide is a sperm whale polypeptide having the amino acid sequence of SEQ ID NO: 10 or a sequence having at least 90%, 91%, 92%, 93%, 94%, 95%, 96%, 97%, 98%, or 99% identity to SEQ ID NO: 10.

In certain embodiments, the Arc polypeptide is a turkey polypeptide having the amino acid sequence of SEQ ID NO: 11 or a sequence having at least 90%, 91%, 92%, 93%, 94%, 95%, 96%, 97%, 98%, or 99% identity to SEQ ID NO: 11.

In certain embodiments, the Arc polypeptide is a central bearded dragon polypeptide having the amino acid sequence of SEQ ID NO: 12 or a sequence having at least 90%, 91%, 92%, 93%, 94%, 95%, 96%, 97%, 98%, or 99% identity to SEQ ID NO: 12.

In certain embodiments, the Arc polypeptide is a Chinese alligator polypeptide having the amino acid sequence of SEQ ID NO: 13 or a sequence having at least 90%, 91%, 92%, 93%, 94%, 95%, 96%, 97%, 98%, or 99% identity to SEQ ID NO: 13.

In certain embodiments, the Arc polypeptide is an Ameri-can alligator polypeptide having the amino acid sequence of SEQ ID NO: 14 or a sequence having at least 90%, 91%, 92%, 93%, 94%, 95%, 96%, 97%, 98%, or 99% identity to SEQ ID NO: 14.

In certain embodiments, the Arc polypeptide is a Japanese gekko polypeptide having the amino acid sequence of SEQ ID NO: 15 or a sequence having at least 90%, 91%, 92%, 93%, 94%, 95%, 96%, 97%, 98%, or 99% identity to SEQ ID NO: 15.

In certain embodiments, the endo-Gag polypeptide is a human PNMA3 polypeptide having the amino acid sequence of SEQ ID NO: 16 or a sequence having at least 90%, 91%, 92%, 93%, 94%, 95%, 96%, 97%, 98%, or 99% identity to SEQ ID NO: 16.

In certain embodiments, the endo-Gag polypeptide is a human PNMA5 polypeptide having the amino acid sequence of SEQ ID NO: 17 or a sequence having at least 90%, 91%, 92%, 93%, 94%, 95%, 96%, 97%, 98%, or 99% identity to SEQ ID NO: 17.

In certain embodiments, the endo-Gag polypeptide is a human PNMA6A polypeptide having the amino acid sequence of SEQ ID NO: 18 or a sequence having at least 90%, 91%, 92%, 93%, 94%, 95%, 96%, 97%, 98%, or 99% identity to SEQ ID NO: 18.

In certain embodiments, the endo-Gag polypeptide is a human PNMA6B polypeptide having the amino acid sequence of SEQ ID NO: 19 or a sequence having at least 90%, 91%, 92%, 93%, 94%, 95%, 96%, 97%, 98%, or 99% identity to SEQ ID NO: 19.

In certain embodiments, the endo-Gag polypeptide is a human RTL3 polypeptide having the amino acid sequence of SEQ ID NO: 20 or a sequence having at least 90%, 91%, 92%, 93%, 94%, 95%, 96%, 97%, 98%, or 99% identity to SEQ ID NO: 20.

In certain embodiments, the endo-Gag polypeptide is a human RTL6 polypeptide having the amino acid sequence of SEQ ID NO: 21 or a sequence having at least 90%, 91%, 92%, 93%, 94%, 95%, 96%, 97%, 98%, or 99% identity to SEQ ID NO: 21.

In certain embodiments, the endo-Gag polypeptide is a human RTL8A polypeptide having the amino acid sequence of SEQ ID NO: 22 or a sequence having at least 90%, 91%, 92%, 93%, 94%, 95%, 96%, 97%, 98%, or 99% identity to SEQ ID NO: 22.

In certain embodiments, the endo-Gag polypeptide is a human RTL8B polypeptide having the amino acid sequence of SEQ ID NO: 23 or a sequence having at least 90%, 91%, 92%, 93%, 94%, 95%, 96%, 97%, 98%, or 99% identity to SEQ ID NO: 23.

In certain embodiments, the endo-Gag polypeptide is a human BOP polypeptide having the amino acid sequence of SEQ ID NO: 24 or a sequence having at least 90%, 91%, 92%, 93%, 94%, 95%, 96%, 97%, 98%, or 99% identity to SEQ ID NO: 24.

In certain embodiments, the endo-Gag polypeptide is a human LDOC1 polypeptide having the amino acid sequence of SEQ ID NO: 25 or a sequence having at least 90%, 91%, 92%, 93%, 94%, 95%, 96%, 97%, 98%, or 99% identity to SEQ ID NO: 25.

In certain embodiments, the endo-Gag polypeptide is a human ZNF18 polypeptide having the amino acid sequence of SEQ ID NO: 26 or a sequence having at least 90%, 91%, 92%, 93%, 94%, 95%, 96%, 97%, 98%, or 99% identity to SEQ ID NO: 26.

In certain embodiments, the endo-Gag polypeptide is a human MOAP1 polypeptide having the amino acid sequence of SEQ ID NO: 27 or a sequence having at least 90%, 91%, 92%, 93%, 94%, 95%, 96%, 97%, 98%, or 99% identity to SEQ ID NO: 27.

In certain embodiments, the endo-Gag polypeptide is a human PEG10 polypeptide having the amino acid sequence of SEQ ID NO: 28 or a sequence having at least 90%, 91%, 92%, 93%, 94%, 95%, 96%, 97%, 98%, or 99% identity to SEQ ID NO: 28.

In some cases, the recombinant Arc or endo-Gag polypeptide is an Arc polypeptide illustrated in FIG. 1.

Figure 2:
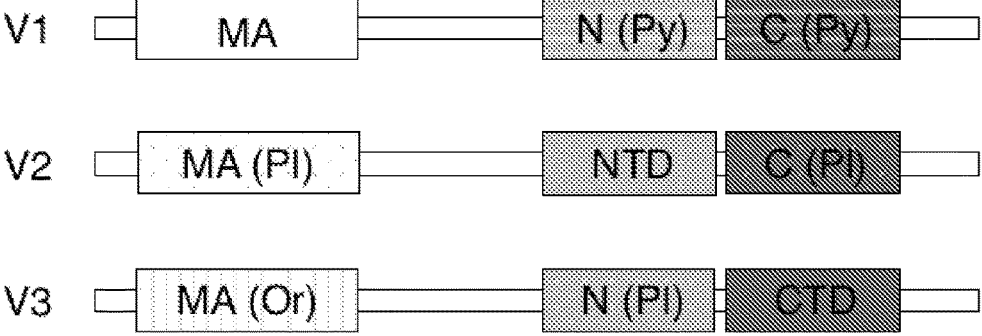
FIG. 2 is a representation of exemplary engineered Arc polypeptides.

In some cases, the engineered Arc or endo-Gag polypeptide is an engineered Arc polypeptide illustrated in FIG. 2.

Linkers

In certain embodiments, a polypeptide of the disclosure comprises a linker. In some embodiments, the linker is a peptide linker. In some instances, the linker is a rigid linker. In other instances, the linker is a flexible linker. In some cases, the linker is a non-cleavable linker. In other cases, the linker is a cleavable linker. In additional cases, the linker comprises a linear structure, or a non-linear structure (e.g., a cyclic structure).

In certain embodiments, non-cleavable linkers comprise short peptides of varying lengths. Exemplary non-cleavable linkers include (EAAAK)n (SEQ ID NO: 70), or (EAAAR)n (SEQ ID NO: 71), where n is from 1 to 5, and up to 30 residues of glutamic acid-proline or lysine-proline repeats. In some embodiments, the non-cleavable linker comprises (GGGGS)n (SEQ ID NO: 72) or (GGGS)n (SEQ ID NO: 73), wherein n is 1 to 10; KESGSVSSEQLAQFRSLD (SEQ ID NO: 74); or EGKSSGSGSESKST (SEQ ID NO: 75). In some embodiments, the non-cleavable linker comprises a poly-Gly/Ala polymer.

In certain embodiments, the linker is a cleavable linker, e.g., an extracellular cleavable linker or an intracellular cleavable linker. In some instances, the linker is designed for cleavage in the presence of particular conditions or in a particular environment (e.g., under physiological condition). For example, the design of a linker for cleavage by specific conditions, such as by a specific enzyme, allows the targeting of cellular uptake to a specific location.

In some embodiments, the linker is a pH-sensitive linker. In one instance, the linker is cleaved under basic pH conditions. In other instance, the linker is cleaved under acidic pH conditions.

In some embodiments, the linker is cleaved in vivo by endogenous enzymes (e.g., proteases) such as serine proteases including but not limited to thrombin, metalloproteases, furin, cathepsin B, necrotic enzymes (e.g., calpains), and the like. Exemplary cleavable linkers include, but are not limited to, GGAANLVRGG (SEQ ID NO: 76); SGRIGFLRTA (SEQ ID NO: 77); SGRSA (SEQ ID NO: 78); GFLG (SEQ ID NO: 79); ALAL (SEQ ID NO: 80); FK; PIC(Et)F-F (SEQ ID NO: 81), where C(Et) indicates S-ethylcysteine; PR(S/T)(L/I)(S/T) (SEQ ID NO: 82); DEVD (SEQ ID NO: 83); GWEHDG (SEQ ID NO: 84); RPLA-LWRS (SEQ ID NO: 85); or a combination thereof.

Capsids

In some embodiments, disclosed herein is a capsid. In some instances, the capsid comprises an Arc polypeptide and/or an endo-Gag polypeptide such as a Copia protein, ASPRV1 protein, a protein from the SCAN domain family, a protein encoded by the Paraneoplastic Ma antigen family, a protein or a combination of proteins chosen from the retrotransposon Gag-like family, or a combination thereof. Exemplary endo-Gag polypeptides are BOP, LDOC1, MOAP1, PEG10, PNMA3, PNMA5, PNMA6A, PNMA6B, RTL3, RTL6, RTL8A, RTL8B, and ZNF18. In some instances, the Arc polypeptide, the Copia protein, the ASPRV1 protein, the protein from the SCAN domain family, the protein encoded by the Paraneoplastic Ma antigen family, and the protein or a combination of proteins chosen from the retrotransposon Gag-like family are each independently a full-length polypeptide. In other instances, the Arc polypeptide, the Copia protein, the ASPRV1 protein, the protein from the SCAN domain family, the protein encoded by the Paraneoplastic Ma antigen family, and the protein or a combination of proteins chosen from the retrotransposon Gag-like family are each independently a functional fragment thereof, e.g., that is capable of forming a subunit of a capsid.

Arc-Based Capsids and Endo-Gag-Based Capsids

In some embodiments, the capsid comprises an Arc-based capsid. In some embodiments, the capsid comprises an endo-Gag-based capsid. In some instances, the Arc-based and/or endo-Gag capsid comprises a plurality of recombinant Arc polypeptides and/or endo-Gag polypeptides described above, a plurality of engineered Arc polypeptides and/or endo-Gag polypeptides described above, or a combination thereof. In some cases, the Arc-based capsid comprises a plurality of recombinant Arc polypeptides. In other cases, the Arc-based capsid comprises a plurality of engineered Arc polypeptides. In some cases, the endo-Gag-based capsid comprises a plurality of recombinant endo-Gag polypeptides. In other cases, the endo-Gag-based capsid comprises a plurality of engineered endo-Gag polypeptides.

In some embodiments, the Arc-based or endo-Gag-based capsid comprises a first plurality of Arc and/or endo-Gag polypeptides from a first species and a second plurality of Arc and/or endo-Gag polypeptides from at least a second species. In some cases, the first species is selected from a eukaryote, a vertebrate, a human, a mammal, a rodent, a bird, a reptile, a fish, an insect, a fungus, or a plant. In some cases, the second species is selected from a eukaryote, a vertebrate, a human, a mammal, a rodent, a bird, a reptile, a fish, an insect, a fungus, or a plant that is different from the first species.

In some instances, the ratio of the first plurality of Arc or endo-Gag polypeptides to the second plurality of Arc or endo-Gag polypeptides is 1:1, 2:1, 3:1, 4:1, 5:1, 6:1, 7:1, 8:1, 9:1, 10:1, 20:1, 50:1, or 100:1. In some cases, the ratio of the first plurality of Arc or endo-Gag polypeptides to the second plurality of Arc or endo-Gag polypeptides is 1:1. In some cases, the ratio of the first plurality of Arc or endo-Gag polypeptides to the second plurality of Arc or endo-Gag polypeptides is 2:1. In some cases, the ratio of the first plurality of Arc or endo-Gag polypeptides to the second plurality of Arc or endo-Gag polypeptides is 4:1. In some cases, the ratio of the first plurality of Arc or endo-Gag polypeptides to the second plurality of Arc or endo-Gag polypeptides is 5:1. In some cases, the ratio of the first plurality of Arc or endo-Gag polypeptides to the second plurality of Arc or endo-Gag polypeptides is 8:1. In some cases, the ratio of the first plurality of Arc or endo-Gag polypeptides to the second plurality of Arc polypeptides is 10:1. In some cases, the ratio of the first plurality of Arc or endo-Gag polypeptides to the second plurality of Arc or endo-Gag polypeptides is 20:1. In some cases, the ratio of the first plurality of Arc or endo-Gag polypeptides to the second plurality of Arc or endo-Gag polypeptides is 50:1. In some cases, the ratio of the first plurality of Arc or endo-Gag polypeptides to the second plurality of Arc or endo-Gag polypeptides is 100:1. In some instances, the ratio is the comparison in molar concentration. In some instances, the ratio is the comparison in the number of capsid forming subunits (e.g., each of the or engineered Arc polypeptide forms a capsid subunit).

In some instances, the ratio of the first plurality of Arc or endo-Gag polypeptides to the second plurality of Arc or endo-Gag polypeptides is 1:2, 1:3, 1:4, 1:5, 1:6, 1:7, 1:8, 1:9, 1:10, 1:20, or 1:50. In some cases, the ratio of the first plurality of Arc or endo-Gag polypeptides to the second plurality of Arc or endo-Gag polypeptides is 1:2. In some cases, the ratio of the first plurality of Arc or endo-Gag polypeptides to the second plurality of Arc or endo-Gag polypeptides is 1:5. In some cases, the ratio of the first plurality of Arc or endo-Gag polypeptides to the second plurality of Arc or endo-Gag polypeptides is 1:8. In some cases, the ratio of the first plurality of Arc or endo-Gag polypeptides to the second plurality of Arc or endo-Gag polypeptides is 1:10. In some cases, the ratio of the first plurality of Arc or endo-Gag polypeptides to the second plurality of Arc or endo-Gag polypeptides is 1:20. In some cases, the ratio of the first plurality of Arc or endo-Gag polypeptides to the second plurality of Arc or endo-Gag polypeptides is 1:50. In some instances, the ratio is the comparison in molar concentration. In some instances, the ratio is the comparison in the number of capsid forming subunits (e.g., each of the recombinant or engineered Arc or endo-Gag polypeptide forms a capsid subunit).

In some embodiments, the Arc-based capsid or endo-Gag-based capsid comprises a plurality of recombinant or engineered Arc polypeptides and a plurality of non-Arc proteins. Exemplary species of non-Arc proteins include but are not limited to, Copia, ASPRV1, a protein or a combination of proteins chosen from the SCAN domain family, a protein or a combination of proteins chosen from the Paraneoplastic Ma antigen family, and a protein or a combination of proteins chosen from the retrotransposon Gag-like family. Exemplary species of non-Arc proteins include BOP, LDOC1, MOAP1, PEG10, PNMA3, PNMA5, PNMA6A, PNMA6B, RTL3, RTL6, RTL8A, RTL8B, and ZNF18.

In some instances, the ratio of the plurality of recombinant or engineered Arc polypeptides to the plurality of non-Arc proteins is 1:1, 2:1, 3:1, 4:1, 5:1, 6:1, 7:1, 8:1, 9:1, 10:1, 20:1, 50:1, or 100:1. In some cases, the ratio of the plurality of recombinant or engineered Arc polypeptides to the plurality of non-Arc proteins is 1:1. In some cases, the ratio of the plurality of recombinant or engineered Arc polypeptides to the plurality of non-Arc proteins is 2:1. In some cases, the ratio of the plurality of recombinant or engineered Arc polypeptides to the plurality of non-Arc proteins is 4:1. In some cases, the ratio of the plurality of recombinant or engineered Arc polypeptides to the plurality of non-Arc proteins is 5:1. In some cases, the ratio of the plurality of recombinant or engineered Arc polypeptides to the plurality of non-Arc proteins is 8:1. In some cases, the ratio of the plurality of recombinant or engineered Arc polypeptides to the plurality of non-Arc proteins is 10:1. In some cases, the ratio of the plurality of recombinant or engineered Arc polypeptides to the plurality of non-Arc proteins is 20:1. In some cases, the ratio of the plurality of recombinant or engineered Arc polypeptides to the plurality of non-Arc proteins is 50:1. In some cases, the ratio of the plurality of recombinant or engineered Arc polypeptides to the plurality of non-Arc proteins is 100:1. In some instances, the ratio is the comparison in molar concentration. In some instances, the ratio is the comparison in the number of capsid forming subunits (e.g., each of the recombinant or engineered Arc polypeptide forms a capsid subunit).

In some instances, the ratio of the plurality of recombinant or engineered Arc polypeptides to the plurality of non-Arc proteins is 1:2, 1:3, 1:4, 1:5, 1:6, 1:7, 1:8, 1:9, 1:10, 1:20, or 1:50. In some cases, the ratio of the plurality of recombinant or engineered Arc polypeptides to the plurality of non-Arc proteins is 1:2. In some cases, the ratio of the plurality of recombinant or engineered Arc polypeptides to the plurality of non-Arc proteins is 1:5. In some cases, the ratio of the plurality of recombinant or engineered Arc polypeptides to the plurality of non-Arc proteins is 1:8. In some cases, the ratio of the plurality of recombinant or engineered Arc polypeptides to the plurality of non-Arc proteins is 1:10. In some cases, the ratio of the plurality of recombinant or engineered Arc polypeptides to the plurality of non-Arc proteins is 1:20. In some cases, the ratio of the plurality of recombinant or engineered Arc polypeptides to the plurality of non-Arc proteins is 1:50. In some instances, the ratio is the comparison in molar concentration. In some instances, the ratio is the comparison in the number of capsid forming subunits (e.g., each of the recombinant or engineered Arc polypeptide forms a capsid subunit).

In some embodiments, the capsid has a diameter of at least 1 nm, or more. In some instances, the capsid has a diameter of at least 2 nm, 3 nm, 4 nm, 5 nm, 10 nm, 15 nm, 20 nm, 25 nm, 30 nm, 40 nm, 50 nm, 60 nm, 70 nm, 80 nm, 90 nm, 100 nm, 150 nm, 200 nm, 300 nm, 400 nm, 500 nm, 600 nm, or more. In some instances, the capsid has a diameter of at least 5 nm, or more. In some cases, the capsid has a diameter of at least 10 nm, or more. In some instances, the capsid has a diameter of at least 20 nm, or more. In some cases, the capsid has a diameter of at least 30 nm, or more. In some cases, the capsid has a diameter of at least 40 nm, or more. In some cases, the capsid has a diameter of at least 50 nm, or more. In some cases, the capsid has a diameter of at least 80 nm, or more. In some cases, the capsid has a diameter of at least 100 nm, or more. In some cases, the capsid has a diameter of at least 200 nm, or more. In some cases, the capsid has a diameter of at least 300 nm, or more. In some cases, the capsid has a diameter of at least 400 nm, or more. In some cases, the capsid has a diameter of at least 500 nm, or more. In some cases, the capsid has a diameter of at least 600 nm, or more.

In some embodiments, the capsid has a diameter of at most 1 nm, or less. In some instances, the capsid has a diameter of at most 2 nm, 3 nm, 4 nm, 5 nm, 10 nm, 15 nm, 20 nm, 25 nm, 30 nm, 40 nm, 50 nm, 60 nm, 70 nm, 80 nm, 90 nm, 100 nm, 150 nm, 200 nm, 300 nm, 400 nm, 500 nm, 600 nm, or less. In some instances, the capsid has a diameter of at most 5 nm, or less. In some cases, the capsid has a diameter of at most 10 nm, or less. In some instances, the capsid has a diameter of at most 20 nm, or less. In some cases, the capsid has a diameter of at most 30 nm, or less. In some cases, the capsid has a diameter of at least 40 nm, or less. In some cases, the capsid has a diameter of at least 50 nm, or less. In some cases, the capsid has a diameter of at least 80 nm, or less. In some cases, the capsid has a diameter of at least 100 nm, or less. In some cases, the capsid has a diameter of at least 200 nm, or less. In some cases, the capsid has a diameter of at least 300 nm, or less. In some cases, the capsid has a diameter of at least 400 nm, or less. In some cases, the capsid has a diameter of at least 500 nm, or less. In some cases, the capsid has a diameter of at least 600 nm, or less.

In some embodiments, the capsid has a diameter of about 1 nm, 2 nm, 3 nm, 4 nm, 5 nm, 10 nm, 15 nm, 20 nm, 25 nm, 30 nm, 40 nm, 50 nm, 60 nm, 70 nm, 80 nm, 90 nm, 100 nm, 150 nm, 200 nm, 300 nm, 400 nm, 500 nm, or 600 nm. In some instances, the capsid has a diameter of about 5 nm. In some cases, the capsid has a diameter of about 10 nm. In some instances, the capsid has a diameter of about 20 nm. In some cases, the capsid has a diameter of about 30 nm. In some cases, the capsid has a diameter of about 40 nm. In some cases, the capsid has a diameter of about 50 nm. In some cases, the capsid has a diameter of about 80 nm. In some cases, the capsid has a diameter of about 100 nm. In some cases, the capsid has a diameter of about 200 nm. In some cases, the capsid has a diameter of about 300 nm. In some cases, the capsid has a diameter of about 400 nm. In some cases, the capsid has a diameter of about 500 nm. In some cases, the capsid has a diameter of about 600 nm.

In some embodiments, the capsid has a diameter of from about 1 nm to about 600 nm. In some instances, the capsid has a diameter of from about 2 nm to about 500 nm, from about 2 nm to about 400 nm, from about 2 nm to about 300 nm, from about 2 nm to about 200 nm, from about 2 nm to about 100 nm, from about 2 nm to about 50 nm, from about 2 nm to about 30 nm, from about 20 nm to about 400 nm, from about 20 nm to about 300 nm, from about 20 nm to about 200 nm, from about 20 nm to about 100 nm, from about 20 nm to about 50 nm, from about 20 nm to about 30 nm, from about 30 nm to about 500 nm, from about 30 nm to about 400 nm, from about 30 nm to about 300 nm, from about 30 nm to about 200 nm, from about 30 nm to about 100 nm, from about 30 nm to about 50 nm, from about 50 nm to about 300 nm, from about 50 nm to about 200 nm, from about 50 nm to about 100 nm, from about 2 nm to about 25 nm, from about 2 nm to about 20 nm, from about 2 nm to about 10 nm, from about 5 nm to about 25 nm, from about 5 nm to about 20 nm, from about 5 nm to about 10 nm, from about 10 nm to about 25 nm, or from about 10 nm to about 20 nm.

In some embodiments, the capsid has a reduced off-target effect. In some cases, the off-target effect is less than 10%, 5%, 4%, 3%, 2%, 1%, or 0.5%. In some cases, the off-target effect is no more than 10%, 5%, 4%, 3%, 2%, 1%, or 0.5%.

In some cases, the capsid does not have an off-target effect.

In certain embodiments, the formation of Arc and/or endo-Gag-based capsids occurs either ex vivo or in vitro.

In some instances, the Arc and/or endo-Gag-based capsids is assembled in vivo.

In some instances, the Arc and/or endo-Gag-based capsids is stable at room temperature. In some cases, the Arc and/or endo-Gag-based capsids is empty. In other cases, the Arc and/or endo-Gag-based capsids is loaded (for example, loaded with a cargo and/or a therapeutic agent, e.g., a DNA or an RNA).

In some instances, the Arc and/or endo-Gag-based capsids is stable at a temperature from about 2° C. to about 37° C. In some instances, the Arc and/or endo-Gag-based capsids is stable at a temperature from about 2° C. to about 8° C., about 2° C. to about 4° C., about 20° C. to about 37° C., about 25° C. to about 37° C., about 20° C. to about 30° C., about 25° C. to about 30° C., or about 30° C. to about 37° C. In some cases, the Arc and/or endo-Gag-based capsid is empty. In other cases, the Arc and/or endo-Gag-based capsids is loaded (for example, loaded with a cargo and/or a therapeutic agent, e.g., a DNA or an RNA).

In some instances, the Arc and/or endo-Gag-based capsids is stable for at least about 1 day, 2 days, 4 days, 5 days, 7 days, 14 days, 28 days, 30 days, 60 days, 2 months, 3 months, 4 months, 5 months, 6 months, 12 months, 18 months, 24 months, 3 years, 5 years, or longer. In some case, the Arc and/or endo-Gag-based capsids has minimum degradation, e.g., less than 10%, 5%, 4%, 3%, 2%, 1%, 0.5% based on the total population of the Arc and/or endo-Gag-based capsids that is degraded. In some cases, the Arc and/or endo-Gag-based capsid is empty. In other cases, the Arc and/or endo-Gag-based capsids is loaded (for example, loaded with a therapeutic agent, e.g., a DNA or an RNA).

Additional Capsids

In some embodiments, the capsid comprises the Copia protein. In some instances, the Copia protein is from *Drosophila melanogaster* (UniProtKB—P04146), *Ceratitis capitate* (UniProtKB—W8BHY5), or *Drosophila simulans* (UniProtKB—Q08461).

In some embodiments, the capsid comprises the protein ASPRV1. The ASPRV1 protein is a structural protein that participates in the development and maintenance of the skin barrier. In some instances, the protein ASPRV1 is from *Homo sapiens* (UniProtKB—Q53RT3).

In some embodiments, the capsid comprises a protein from the SCAN domain family. SCAN domain is a superfamily of zinc finger transcription factors. SCAN domain is also known as leucine rich region (LeR) and functions as protein interaction domain that mediates self-association or selective association with other proteins.

In some embodiments, the capsid comprises a protein from the Paraneoplastic Ma antigen family. The Paraneoplastic Ma antigen family comprises about 14 members of neuro- and testis-specific proteins.

In some embodiments, the capsid comprises a protein encoded by a Retrotransposon Gag-like gene.

In some embodiments, the capsid comprises BOP, LDOC1, MOAP1, PEG10, PNMA3, PNMA5, PNMA6A, PNMA6B, RTL3, RTL6, RTL8A, RTL8B, and/or ZNF18.

Cargos

In some embodiments, a composition of the disclosure (for example, a capsid) comprises a cargo. In some embodiments, the cargo is a therapeutic agent. In some embodiments, the cargo is a nucleic acid molecule, a small molecule, a protein, a peptide, an antibody or binding fragment thereof, a peptidomimetic, or a nucleotidomimetic. In some instances, the cargo is a therapeutic cargo, comprising e.g., one or more drugs. In some instances, the cargo comprises a diagnostic tool, for profiling, e.g., one or more markers (such as markers associates with one or more disease phenotypes). In additional instances, the cargo comprises an imaging tool.

In some instances, the cargo is a nucleic acid molecule. Exemplary nucleic acid molecules include DNA, RNA, or a mixture of DNA and RNA. In some instances, the nucleic acid molecule is a DNA polymer. In some cases, the DNA is a single stranded DNA polymer. In other cases, the DNA is a double stranded DNA polymer. In additional cases, the DNA is a hybrid of single and double stranded DNA polymer.

In some embodiments, the nucleic acid molecule is a RNA polymer, e.g., a single stranded RNA polymer, a double stranded RNA polymer, or a hybrid of single and double stranded RNA polymers. In some instances, the RNA comprises and/or encodes an antisense oligoribonucleotide, a siRNA, an mRNA, a tRNA, an rRNA, a snRNA, a shRNA, microRNA, or a non-coding RNA.

In some embodiments, the nucleic acid molecule comprises a hybrid of DNA and RNA.

In some embodiments, the nucleic acid molecule is an antisense oligonucleotide, optionally comprising DNA, RNA, or a hybrid of DNA and RNA.

In some instances, the nucleic acid molecule comprises and/or encodes an mRNA molecule.

In some embodiments, the nucleic acid molecule comprises and/or encodes an RNAi molecule. In some cases, the RNAi molecule is a microRNA (miRNA) molecule. In other cases, the RNAi molecule is a siRNA molecule. The miRNA and/or siRNA are optionally double-stranded or as a hairpin, and further optionally encapsulated as precursor molecules.

In some embodiments, the nucleic acid molecule is for use in a nucleic acid-based therapy. In some instances, the nucleic acid molecule is for regulating gene expression (e.g., modulating mRNA translation or degradation), modulating RNA splicing, or RNA interference. In some cases, the nucleic acid molecule comprises and/or encodes an anti-sense oligonucleotide, microRNA molecule, siRNA molecule, mRNA molecule, for use in regulation of gene expression, modulating RNA splicing, or RNA interference.

In some instances, the nucleic acid molecule is for use in gene editing. Exemplary gene editing systems include, but are not limited to, CRISPR-Cas systems, zinc finger nuclease (ZFN) systems, and transcription activator-like effector nuclease (TALEN) systems. In some cases, the nucleic acid molecule comprises and/or encodes a component involved in the CRISPR-Cas systems, ZFN systems, or the TALEN systems.

In some cases, the nucleic acid molecule is for use in antigen production for therapeutic and/or prophylactic vaccine production. For example, the nucleic acid molecule encodes an antigen that is expressed and elicits a desirable immune response (e.g., a pro-inflammatory immune response, an anti-inflammatory immune response, an B cell response, an antibody response, a T cell response, a CD4+ T cell response, a CD8+ T cell response, a Th1 immune response, a Th2 immune response, a Th17 immune response, a Treg immune response, or a combination thereof).

In some cases, the nucleic acid molecule comprises a nucleic acid enzyme. Nucleic acid enzymes are RNA molecules (e.g., ribozymes) or DNA molecules (e.g., deoxyribozymes) that have catalytic activities. In some instances, the nucleic acid molecule is a ribozyme. In other instances, the nucleic acid molecule is a deoxyribozyme. In some cases, the nucleic acid molecule is a MNAzyme, which functions as a biosensor and/or a molecular switch (see, e.g., Mokany, et al., "MNAzymes, a versatile new class of nucleic acid enzymes that can function as biosensors and molecular switches," JACS 132(2): 1051-1059 (2010)).

In some instances, exemplary targets of the nucleic acid molecule include, but are not limited to, UL123 (human cytomegalovirus), APOB, AR (androgen receptor) gene, KRAS, PCSK9, CFTR, and SMN (e.g., SMN2).

In some embodiments, the nucleic acid molecule is at least 5 nucleotides or more in length. In some instances, the nucleic acid molecule is at least 6, 7, 8, 9, 10, 11, 12, 13, 14, 15, 16, 17, 18, 19, 20, 21, 22, 23, 24, 25, 26, 27, 28, 29, 30, 35, 40, 50, 60, 70, 80, 90, 100, 150, 200, 250, 300, 400, 500, 1000, 1500, 2000, 3000, 4000, 5000, 6000, 7000, 8000, 9000 nucleotides or more in length. In some instances, the nucleic acid molecule is at least 10 nucleotides or more in length. In some instances, the nucleic acid molecule is at least 12 nucleotides or more in length. In some instances, the nucleic acid molecule is at least 15 nucleotides or more in length. In some instances, the nucleic acid molecule is at least 18 nucleotides or more in length. In some instances, the nucleic acid molecule is at least 19 nucleotides or more in length. In some instances, the nucleic acid molecule is at least 20 nucleotides or more in length. In some instances, the nucleic acid molecule is at least 21 nucleotides or more in length. In some instances, the nucleic acid molecule is at least 22 nucleotides or more in length. In some instances, the nucleic acid molecule is at least 23 nucleotides or more in length. In some instances, the nucleic acid molecule is at least 24 nucleotides or more in length. In some instances, the nucleic acid molecule is at least 25 nucleotides or more in length. In some instances, the nucleic acid molecule is at least 26 nucleotides or more in length. In some instances, the nucleic acid molecule is at least 27 nucleotides or more in length. In some instances, the nucleic acid molecule is at least 28 nucleotides or more in length. In some instances, the nucleic acid molecule is at least 29 nucleotides or more in length. In some instances, the nucleic acid molecule is at least 30 nucleotides or more in length. In some instances, the nucleic acid molecule is at least 40 nucleotides or more in length. In some instances, the nucleic acid molecule is at least 50 nucleotides or more in length. In some instances, the nucleic acid molecule is at least 100 nucleotides or more in length. In some instances, the nucleic acid molecule is at least 200 nucleotides or more in length. In some instances, the nucleic acid molecule is at least 300 nucleotides or more in length. In some instances, the nucleic acid molecule is at least 500 nucleotides or more in length. In some instances, the nucleic acid molecule is at least 1000 nucleotides or more in length. In some instances, the nucleic acid molecule is at least 2000 nucleotides or more in length. In some instances, the nucleic acid molecule is at least 3000 nucleotides or more in length. In some instances, the nucleic acid molecule is at least 4000 nucleotides or more in length. In some instances, the nucleic acid molecule is at least 5000 nucleotides or more in length. In some instances, the nucleic acid molecule is at least 8000 nucleotides or more in length.

In some embodiments, the nucleic acid molecule is at most 12 nucleotides or less in length. In some instances, the nucleic acid molecule is at most 13, 14, 15, 16, 17, 18, 19, 20, 21, 22, 23, 24, 25, 26, 27, 28, 29, 30, 35, 40, 50, 60, 70, 80, 90, 100, 150, 200, 250, 300, 400, 500, 1000, 1500, 2000, 3000, 4000, 5000, 6000, 7000, 8000, 9000 nucleotides or less in length. In some instances, the nucleic acid molecule is at most 15 nucleotides or less in length. In some instances, the nucleic acid molecule is at most 18 nucleotides or less in length. In some instances, the nucleic acid molecule is at most 19 nucleotides or less in length. In some instances, the nucleic acid molecule is at most 20 nucleotides or less in length. In some instances, the nucleic acid molecule is at most 21 nucleotides or less in length. In some instances, the nucleic acid molecule is at most 22 nucleotides or less in length. In some instances, the nucleic acid molecule is at most 23 nucleotides or less in length. In some instances, the nucleic acid molecule is at most 24 nucleotides or less in length. In some instances, the nucleic acid molecule is at most 25 nucleotides or less in length. In some instances, the nucleic acid molecule is at most 26 nucleotides or less in length. In some instances, the nucleic acid molecule is at most 27 nucleotides or less in length. In some instances, the nucleic acid molecule is at most 28 nucleotides or less in length. In some instances, the nucleic acid molecule is at most 29 nucleotides or less in length. In some instances, the nucleic acid molecule is at most 30 nucleotides or less in length. In some instances, the nucleic acid molecule is at most 40 nucleotides or less in length. In some instances, the nucleic acid molecule is at most 50 nucleotides or less in length. In some instances, the nucleic acid molecule is at most 100 nucleotides or less in length. In some instances, the nucleic acid molecule is at most 200 nucleotides or less in length. In some instances, the nucleic acid molecule is at most 300 nucleotides or less in length. In some instances, the nucleic acid molecule is at most 500 nucleotides or less in length. In some instances, the nucleic acid molecule is at most 1000 nucleotides or less in length. In some instances, the nucleic acid molecule is at most 2000 nucleotides or less in length. In some instances, the nucleic acid molecule is at most 3000 nucleotides or less in length. In some instances, the nucleic acid molecule is at most 4000 nucleotides or less in length. In some instances, the nucleic acid molecule is at most 5000 nucleotides or less in length. In some instances, the nucleic acid molecule is at most 8000 nucleotides or less in length.

In some embodiments, the nucleic acid molecule is about 5 nucleotides in length. In some instances, the nucleic acid molecule is about 6, 7, 8, 9, 10, 11, 12, 13, 14, 15, 16, 17, 18, 19, 20, 21, 22, 23, 24, 25, 26, 27, 28, 29, 30, 35, 40, 50, 60, 70, 80, 90, 100, 150, 200, 250, 300, 400, 500, 1000, 1500, 2000, 3000, 4000, 5000, 6000, 7000, 8000, 9000 nucleotides in length. In some instances, the nucleic acid molecule is about 10 nucleotides in length. In some instances, the nucleic acid molecule is about 12 nucleotides in length. In some instances, the nucleic acid molecule is about 15 nucleotides in length. In some instances, the nucleic acid molecule is about 18 nucleotides in length. In some instances, the nucleic acid molecule is about 19 nucleotides in length. In some instances, the nucleic acid molecule is about 20 nucleotides in length. In some instances, the nucleic acid molecule is about 21 nucleotides in length. In some instances, the nucleic acid molecule is about 22 nucleotides in length. In some instances, the nucleic acid molecule is about 23 nucleotides in length. In some instances, the nucleic acid molecule is about 24 nucleotides in length. In some instances, the nucleic acid molecule is about 25 nucleotides in length. In some instances, the nucleic acid molecule is about 26 nucleotides in length. In some instances, the nucleic acid molecule is about 27 nucleotides in length. In some instances, the nucleic acid molecule is about 28 nucleotides in length. In some instances, the nucleic acid molecule is about 29 nucleotides in length. In some instances, the nucleic acid molecule is about 30 nucleotides in length. In some instances, the nucleic acid molecule is about 40 nucleotides in length. In some instances, the nucleic acid molecule is about 50 nucleotides in length. In some instances, the nucleic acid molecule is about 100 nucleotides in length. In some instances, the nucleic acid molecule is about 200 nucleotides in length. In some instances, the nucleic acid molecule is about 300 nucleotides in length. In some instances, the nucleic acid molecule is about 500 nucleotides in length. In some instances, the nucleic acid molecule is about 1000 nucleotides in length. In some instances, the nucleic acid molecule is about 2000 nucleotides in length. In some instances, the nucleic acid molecule is about 3000 nucleotides in length. In some instances, the nucleic acid molecule is about 4000 nucleotides in length. In some instances, the nucleic acid molecule is about 5000 nucleotides in length. In some instances, the nucleic acid molecule is about 8000 nucleotides in length.

In some embodiments, the nucleic acid molecule is from about 5 to about 10,000 nucleotides in length. In some instances, the nucleic acid molecule is from about 5 to about 9000 nucleotides in length, from about 5 to about 8000 nucleotides in length, from about 5 to about 7000 nucleotides in length, from about 5 to about 6000 nucleotides in length, from about 5 to about 5000 nucleotides in length, from about 5 to about 4000 nucleotides in length, from about 5 to about 3000 nucleotides in length, from about 5 to about 2000 nucleotides in length, from about 5 to about 1000 nucleotides in length, from about 5 to about 500 nucleotides in length, from about 5 to about 100 nucleotides in length, from about 5 to about 50 nucleotides in length, from about 5 to about 40 nucleotides in length, from about 5 to about 30 nucleotides in length, from about 5 to about 25 nucleotides in length, from about 5 to about 20 nucleotides in length, from about 10 to about 8000 nucleotides in length, from about 10 to about 7000 nucleotides in length, from about 10 to about 6000 nucleotides in length, from about 10 to about 5000 nucleotides in length, from about 10 to about 4000 nucleotides in length, from about 10 to about 3000 nucleotides in length, from about 10 to about 2000 nucleotides in length, from about 10 to about 1000 nucleotides in length, from about 10 to about 500 nucleotides in length, from about 10 to about 100 nucleotides in length, from about 10 to about 50 nucleotides in length, from about 10 to about 40 nucleotides in length, from about 10 to about 30 nucleotides in length, from about 10 to about 25 nucleotides in length, from about 10 to about 20 nucleotides in length, from about 18 to about 8000 nucleotides in length, from about 18 to about 7000 nucleotides in length, from about 18 to about 6000 nucleotides in length, from about 18 to about 5000 nucleotides in length, from about 18 to about 4000 nucleotides in length, from about 18 to about 3000 nucleotides in length, from about 18 to about 2000 nucleotides in length, from about 18 to about 1000 nucleotides in length, from about 18 to about 500 nucleotides in length, from about 18 to about 100 nucleotides in length, from about 18 to about 50 nucleotides in length, from about 18 to about 40 nucleotides in length, from about 18 to about 30 nucleotides in length, from about 18 to about 25 nucleotides in length, from about 12 to about 50 nucleotides in length, from about 20 to about 40 nucleotides in length, from about 20 to about 30 nucleotides in length, or from about 25 to about 30 nucleotides in length.

In some embodiments, the nucleic acid molecule comprises natural, synthetic, or artificial nucleotide analogues or bases. In some cases, the nucleic acid molecule comprises combinations of DNA, RNA and/or nucleotide analogues. In some instances, the synthetic or artificial nucleotide analogues or bases comprise modifications at one or more of ribose moiety, phosphate moiety, nucleoside moiety, or a combination thereof.

In some embodiments, a nucleotide analogue or artificial nucleotide base described above comprises a nucleic acid with a modification at a 2' hydroxyl group of the ribose moiety. In some instances, the modification includes an H, OR, R, halo, SH, SR, NH2, NHR, NR2, or CN, wherein R is an alkyl moiety. Exemplary alkyl moiety includes, but is not limited to, halogens, sulfurs, thiols, thioethers, thio-esters, amines (primary, secondary, or tertiary), amides, ethers, esters, alcohols and oxygen. In some instances, the alkyl moiety further comprises a modification. In some instances, the modification comprises an azo group, a keto group, an aldehyde group, a carboxyl group, a nitro group, a nitroso, group, a nitrile group, a heterocycle (e.g., imida-zole, hydrazino or hydroxylamino) group, an isocyanate or cyanate group, or a sulfur containing group (e.g., sulfoxide, sulfone, sulfide, or disulfide). In some instances, the alkyl moiety further comprises a hetero substitution. In some instances, the carbon of the heterocyclic group is substituted by a nitrogen, oxygen or sulfur. In some instances, the heterocyclic substitution includes but is not limited to, morpholino, imidazole, and pyrrolidino.

In some instances, the modification at the 2' hydroxyl group is a 2'-O-methyl modification or a 2'-O-methoxyethyl (2'-O-MOE) modification. In some cases, the 2'-O-methyl modification adds a methyl group to the 2' hydroxyl group of the ribose moiety whereas the 2'O-methoxyethyl modi-fication adds a methoxyethyl group to the 2' hydroxyl group of the ribose moiety.

In some instances, the modification at the 2' hydroxyl group is a 2'-O-aminopropyl modification in which an extended amine group comprising a propyl linker binds the amine group to the 2' oxygen. In some instances, this modification neutralizes the phosphate-derived overall nega-tive charge of the oligonucleotide molecule by introducing one positive charge from the amine group per sugar and thereby improves cellular uptake properties due to its zwit-terionic properties.

In some instances, the modification at the 2' hydroxyl group is a locked or bridged ribose modification (e.g., locked nucleic acid or LNA) in which the oxygen molecule bound at the 2' carbon is linked to the 4' carbon by a methylene group, thus forming a 2'-C,4'-C-oxy-methylene-linked bicy-clic ribonucleotide monomer.

In some embodiments, additional modifications at the 2' hydroxyl group include 2'-deoxy, T-deoxy-2'-fluoro, 2-O-aminopropyl (2-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA).

In some embodiments, a nucleotide analogue comprises a modified base such as, but not limited to, 5-propynyluridine, 5-propynylcytidine, 6-methyladenine, 6-methylguanine, N, N, -dimethyladenine, 2-propyladenine, 2propylguanine, 2-aminoadenine, 1-methylinosine, 3-methyluridine, 5-meth-ylcytidine, 5-methyluridine and other nucleotides having a modification at the 5 position, 5-(2-amino) propyl uridine, 5-halocytidine, 5-halouridine, 4-acetylcytidine, 1-methylad-enosine, 2-methyladenosine, 3-methylcytidine, 6-methylu-ridine, 2-methylguanosine, 7-methylguanosine, 2, 2-dimeth-ylguanosine, 5-methylaminoethyluridine, 5-methyloxyuridine, deazanucleotides (such as 7-deaza-ad-enosine, 6-azouridine, 6-azocytidine, or 6-azothymidine), 5-methyl-2-thiouridine, other thio bases (such as 2-thiouri-dine, 4-thiouridine, and 2-thiocytidine), dihydrouridine, pseudouridine, queuosine, archaeosine, naphthyl and sub-stituted naphthyl groups, any O- and N-alkylated purines and pyrimidines (such as N6-methyladenosine, 5-methyl-carbonylmethyluridine, uridine 5-oxyacetic acid, pyridine-4-one, or pyridine-2-one), phenyl and modified phenyl groups such as aminophenol or 2,4, 6-trimethoxy benzene, modified cytosines that act as G-clamp nucleotides, 8-sub-stituted adenines and guanines, 5-substituted uracils and thymines, azapyrimidines, carboxyhydroxyalkyl nucleo-tides, carboxyalkylaminoalkyi nucleotides, and alkylcarbo-nylalkylated nucleotides. Modified nucleotides also include those nucleotides that are modified with respect to the sugar moiety, as well as nucleotides having sugars or analogs thereof that are not ribosyl. For example, the sugar moieties, in some cases are or are based on, mannoses, arabinoses, glucopyranoses, galactopyranoses, 4'-thioribose, and other sugars, heterocycles, or carbocycles. The term nucleotide also includes universal bases. By way of example, universal bases include but are not limited to 3-nitropyrrole, 5-nitroin-dole, or nebularine.

In some embodiments, a nucleotide analogue further comprises a morpholino, a peptide nucleic acid (PNA), a methylphosphonate nucleotide, a thiolphosphonate nucleo-tide, a 2'-fluoro N3-P5'-phosphoramidite, or a 1', 5'-anhy-drohexitol nucleic acid (HNA). Morpholino or phosphoro-diamidate morpholino oligo (PMO) comprises synthetic molecules whose structure mimics natural nucleic acid structure but deviates from the normal sugar and phosphate structures. In some instances, the five member ribose ring is substituted with a six member morpholino ring containing four carbons, one nitrogen, and one oxygen. In some cases, the ribose monomers are linked by a phosphordiamidate group instead of a phosphate group. In such cases, the backbone alterations remove all positive and negative charges making morpholinos neutral molecules capable of crossing cellular membranes without the aid of cellular delivery agents such as those used by charged oligonucle-otides.

In some embodiments, peptide nucleic acid (PNA) does not contain sugar ring or phosphate linkage and the bases are attached and appropriately spaced by oligoglycine-like mol-ecules, therefore, eliminating a backbone charge.

In some embodiments, one or more modifications option-ally occur at the intemucleotide linkage. In some instances, modified internucleotide linkage includes, but is not limited to, phosphorothioates; phosphorodithioates; methylphos-phonates; 5'-alkylenephosphonates; 5'-methylphosphonate; 3'-alkylene phosphonates; borontrifluoridates; borano phos-phate esters and selenophosphates of 3'-5'linkage or 2'-5'linkage; phosphotriesters; thionoalkylphosphotriesters; hydrogen phosphonate linkages; alkyl phosphonates; alkylphosphonothioates; arylphosphonothioates; phospho-roselenoates; phosphorodiselenoates; phosphinates; phos-phoramidates; 3'-alkylphosphoramidates; aminoalkylphos-phoramidates; thionophosphoramidates; phosphoropiperazidates; phosphoroanilothioates; phospho-roanilidates; ketones; sulfones; sulfonamides; carbonates; carbamates; methylenehydrazos; methylenedimethylhydra-zos; formacetals; thioformacetals; oximes; methyleneimi-nos; methylenemethyliminos; thioamidates; linkages with riboacetyl groups; aminoethyl glycine; silyl or siloxane linkages; alkyl or cycloalkyl linkages with or without het-eroatoms of, for example, 1 to 10 carbons that are saturated or unsaturated and/or substituted and/or contain heteroa-toms; linkages with morpholino structures, amides, or poly-amides wherein the bases are attached to the aza nitrogens of the backbone directly or indirectly; and combinations thereof.

In some embodiments, one or more modifications comprise a modified phosphate backbone in which the modification generates a neutral or uncharged backbone. In some instances, the phosphate backbone is modified by alkylation to generate an uncharged or neutral phosphate backbone. As used herein, alkylation includes methylation, ethylation, and propylation. In some cases, an alkyl group, as used herein in the context of alkylation, refers to a linear or branched saturated hydrocarbon group containing from 1 to 6 carbon atoms. In some instances, exemplary alkyl groups include, but are not limited to, methyl, ethyl, n-propyl, isopropyl, n-butyl, isobutyl, sec-butyl, tert-butyl, n-pentyl, isopentyl, neopentyl, hexyl, isohexyl, 1, 1-dimethylbutyl, 2,2-dimethylbutyl, 3.3-dimethylbutyl, and 2-ethylbutyl groups. In some cases, a modified phosphate is a phosphate group as described in U.S. Pat. No. 9,481,905.

In some embodiments, additional modified phosphate backbones comprise methylphosphonate, ethylphosphonate, methylthiophosphonate, or methoxyphosphonate. In some cases, the modified phosphate is methylphosphonate. In some cases, the modified phosphate is ethylphosphonate. In some cases, the modified phosphate is methylthiophosphonate. In some cases, the modified phosphate is methoxyphosphonate.

In some embodiments, one or more modifications further optionally include modifications of the ribose moiety, phosphate backbone and the nucleoside, or modifications of the nucleotide analogues at the 3' or the 5' terminus. For example, the 3' terminus optionally include a 3' cationic group, or by inverting the nucleoside at the 3'-terminus with a 3'-3' linkage. In another alternative, the 3'-terminus is optionally conjugated with an aminoalkyl group, e.g., a 3' C5-aminoalkyl dT. In an additional alternative, the 3'-terminus is optionally conjugated with an abasic site, e.g., with an apurinic or apyrimidinic site. In some instances, the 5'-terminus is conjugated with an aminoalkyl group, e.g., a 5'-O-alkylamino substituent. In some cases, the 5'-terminus is conjugated with an abasic site, e.g., with an apurinic or apyrimidinic site.

In some embodiments, exemplary nucleic acid cargos include, but are not limited to, Fomivirsen, Mipomersen, AZD5312 (AstraZeneca), Nusinersen, and SB010 (Sterna Biologicals).

Small Molecules

In some embodiments, the cargo is a small molecule. In some instances, the small molecule is an inhibitor (e.g., a pan inhibitor or a selective inhibitor). In other instances, the small molecule is an activator. In additional cases, the small molecule is an agonist, antagonist, a partial agonist, a mixed agonist/antagonist, or a competitive antagonist.

In some embodiments, the small molecule is a drug that falls under the class of analgesics, antianxiety drugs, antiarrhythmics, antibacterials, antibiotics, anticoagulants and thrombolytics, anticonvulsants, antidepressants, antidiarrheals, antiemetics, antifungals, antihistamines, antihypertensives, anti-inflammatories, antineoplastics, antipsychotics, antipyretics, antivirals, barbiturates, beta-blockers, bronchodilators, cold cures, corticosteroids, cough suppressants, cytotoxics, decongestants, diuretics, expectorant, hormones, hypoglycemics, immunosuppressives, laxatives, muscle relaxants, sex hormones, sleeping drugs, or tranquilizers.

In some embodiments, the small molecule is an inhibitor, e.g., an inhibitor of a kinase pathway such as the Tyrosine kinase pathway or a Serine/Threonine kinase pathway. In some cases, the small molecule is a dual protein kinase inhibitor. In some cases, the small molecule is a lipid kinase inhibitor.

In some cases, the small molecule is a neuraminidase inhibitor.

In some cases, the small molecule is a carbonic anhydrase inhibitor.

In some embodiments, exemplary targets of the small molecule include, but are not limited to, vascular endothelial growth factor receptor 1 (VEGFR1), vascular endothelial growth factor receptor 2 (VEGFR2), vascular endothelial growth factor receptor 3 (VEGFR3), fibroblast growth factor receptor 1 (FGFR1), fibroblast growth factor receptor 2 (FGFR2), fibroblast growth factor receptor 3 (FGFR3), fibroblast growth factor receptor 4 (FGFR4), cyclin-dependent kinase 4 (CDK4), cyclin-dependent kinase 6 (CDK6), a receptor tyrosine kinase, a phosphoinositide 3-kinase (PI3K) isoform (e.g., PI3Kδ, also known as p110δ), Janus kinase 1 (JAK1), Janus kinase 3 (JAK3), a receptor from the family of platelet-derived growth factor receptors (PDFG-R), and carbonic anhydrase (e.g., carbonic anhydrase I).

In some embodiments, the small molecule targets a viral protein, e.g., a viral envelope protein. In some embodiments, the small molecule decreases viral adsorption to a host cell. In some embodiments, the small molecule decreases viral entry into a host cell. In some embodiments, the small molecule decreases viral replication in a host or a host cell. In some embodiments, the small molecule decreases viral assembly.

In some embodiments, exemplary small molecule cargos include, but are not limited to, lenvatinib, palbociclib, regorafenib, idelalisib, tofacitinib, nintedanib, zanamivir, ethoxzolamide, and artemisinin.

Proteins

In some embodiments, the cargo is a protein. In some instances, the protein is a full-length protein. In other instances, the protein is a fragment, e.g., a functional fragment. In some cases, the protein is a naturally occurring protein. In additional cases, the protein is a de novo engineered protein. In further cases, the protein is a fusion protein. In further cases, the protein is a recombinant protein. Exemplary proteins include, but are not limited to, Fc fusion proteins, anticoagulants, blood factors, bone morphogenetic proteins, enzymes, growth factors, hormones, interferons, interleukins, and thrombolytics.

In some instances, the protein is for use in an enzyme replacement therapy.

In some cases, the protein is for use in antigen production for therapeutic and/or prophylactic vaccine production. For example, the protein comprises an antigen that elicits a desirable immune response (e.g., a pro-inflammatory immune response, an anti-inflammatory immune response, an B cell response, an antibody response, a T cell response, a CD4+ T cell response, a CD8+ T cell response, a Th1 immune response, a Th2 immune response, a Th17 immune response, a Treg immune response, or a combination thereof).

In some instances, exemplary protein cargos include, but are not limited to, romiplostim, liraglutide, a human growth hormone (rHGH), human insulin (BHI), follicle-stimulating hormone (FSH), Factor VIII, erythropoietin (EPO), granulocyte colony-stimulating factor (G-CSF), alpha-galactosidase A, alpha-L-iduronidase, N-acetylgalactosamine-4-sulfatase, dornase alfa, tissue plasminogen activator (TPA), glucocerebrosidase, interferon-beta-1a, insulin-like growth factor 1 (IGF-1), or rasburicase.

Peptides

In some embodiments, the cargo is a peptide. In some instances, the peptide is a naturally occurring peptide. In other instances, the peptide is an artificial engineered peptide or a recombinant peptide. In some cases, the peptide targets a G-protein coupled receptor, an ion channel, a microbe, an anti-microbial target, a catalytic or other Ig-family of receptors, an intracellular target, a membrane-anchored target, or an extracellular target.

In some cases, the peptide comprises at least 2 amino acids. In some cases, the peptide comprises at least 3, 4, 5, 6, 7, 8, 9, 10, 15, 20, 25, 30, 35, 40, 45, 50, 60, 70, 80, 90, 100 amino acids. In some cases, the peptide comprises at least 10 amino acids. In some cases, the peptide comprises at least 15 amino acids. In some cases, the peptide comprises at least 20 amino acids. In some cases, the peptide comprises at least 30 amino acids. In some cases, the peptide comprises at least 40 amino acids. In some cases, the peptide comprises at least 50 amino acids. In some cases, the peptide comprises at least 60 amino acids. In some cases, the peptide comprises at least 70 amino acids. In some cases, the peptide comprises at least 80 amino acids. In some cases, the peptide comprises at least 90 amino acids. In some cases, the peptide comprises at least 100 amino acids.

In some cases, the peptide comprises at most 3 amino acids. In some cases, the peptide comprises at most 4, 5, 6, 7, 8, 9, 10, 15, 20, 25, 30, 35, 40, 45, 50, 60, 70, 80, 90, 100 amino acids. In some cases, the peptide comprises at most 10 amino acids. In some cases, the peptide comprises at most 15 amino acids. In some cases, the peptide comprises at most 20 amino acids. In some cases, the peptide comprises at most 30 amino acids. In some cases, the peptide comprises at most 40 amino acids. In some cases, the peptide comprises at most 50 amino acids. In some cases, the peptide comprises at most 60 amino acids. In some cases, the peptide comprises at most 70 amino acids. In some cases, the peptide comprises at most 80 amino acids. In some cases, the peptide comprises at most 90 amino acids. In some cases, the peptide comprises at most 100 amino acids.

In some cases, the peptide comprises from about 1 to about 10 kDa. In some cases, the peptide comprises from about 1 to about 9 kDa, about 1 to about 6 kDa, about 1 to about 5 kDa, about 1 to about 4 kDa, about 1 to about 3 kDa, about 2 to about 8 kDa, about 2 to about 6 kDa, about 2 to about 4 kDa, about 1.2 to about 2.8 kDa, about 1.5 to about 2.5 kDa, or about 1.5 to about 2 kDa.

In some embodiments, the peptide is a cyclic peptide. In some instances, the cyclic peptide is a macrocyclic peptide. In other instances, the cyclic peptide is a constrained peptide. The cyclic peptides are assembled with varied linkages, such as for example, head-to-tail, head-to-side-chain, side-chain-to-tail, and side-chain-to-side-chain linkages. In some instances, a cyclic peptide (e.g., a macrocyclic or a constrained peptide) has a molecular weight from about 500 Dalton to about 2000 Dalton. In other instances, a cyclic peptide (e.g., a macrocyclic or a constrained peptide) ranges from about 10 amino acids to about 100 amino acids, from about 10 amino acids to about 70 amino acids, or from about 10 amino acids to about 50 amino acids.

In some cases, the peptide is for use in antigen production for therapeutic and/or prophylactic vaccine production. For example, the peptide comprises an antigen that elicits a desirable immune response (e.g., a pro-inflammatory immune response, an anti-inflammatory immune response, an B cell response, an antibody response, a T cell response, a CD4+ T cell response, a CD8+ T cell response, a Th1 immune response, a Th2 immune response, a Th17 immune response, a Treg immune response, or a combination thereof).

In some embodiments, the peptide comprises natural amino acids, unnatural amino acids, or a combination thereof. In some instances, an amino acid residue refers to a molecule containing both an amino group and a carboxyl group. Suitable amino acids include, without limitation, both the D- and L-isomers of the naturally-occurring amino acids, as well as non-naturally occurring amino acids prepared by organic synthesis or other metabolic routes. The term amino acid, as used herein, includes, without limitation, $\alpha$-amino acids, natural amino acids, non-natural amino acids, and amino acid analogs.

In some instances, $\alpha$-amino acid refers to a molecule containing both an amino group and a carboxyl group bound to a carbon which is designated the $\alpha$-carbon.

In some instances, j-amino acid refers to a molecule containing both an amino group and a carboxyl group in a 3 configuration.

In some embodiments, an amino acid analog is a racemic mixture. In some instances, the D isomer of the amino acid analog is used. In some cases, the L isomer of the amino acid analog is used. In some instances, the amino acid analog comprises chiral centers that are in the R or S configuration.

In some embodiments, exemplary peptide cargos include, but are not limited to, peginesatide, insulin, adrenocorticotropic hormone (ACTH), calcitonin, oxytocin, vasopressin, octreolide, and leuprorelin.

In some embodiments, exemplary peptide cargos include, but are not limited to, Telavancin, Dalbavancin, Oritavancin, Anidulafungin, Lanreotide, Pasireotide, Romidepsin, Linaclotide, and Peginesatide.

Antibodies

In some embodiments, the cargo is an antibody or a binding fragment thereof. In some instances, the antibody or binding fragment thereof comprises a humanized antibody or binding fragment thereof, murine antibody or binding fragment thereof, chimeric antibody or binding fragment thereof, monoclonal antibody or binding fragment thereof, bispecific antibody or biding fragment thereof, monovalent Fab', divalent $Fab_2$, F(ab)'3 fragments, single-chain variable fragment (scFv), bis-scFv, $(scFv)_2$, diabody, minibody, nanobody, triabody, tetrabody, disulfide stabilized Fv protein (dsFv), single-domain antibody (sdAb), Ig NAR, camelid antibody or binding fragment thereof, or a chemically modified derivative thereof.

In some instances, the antibody or binding fragment thereof recognizes a cell surface protein. In some instances, the cell surface protein is an antigen expressed by a cancerous cell. In some instances, the cell surface protein is a neoepitope. In some instances, the cell surface protein comprises one or more mutations compared to a wild-type protein. Exemplary cancer antigens include, but are not limited to, alpha fetoprotein, ASLG659, B7-H3, BAFF-R, Brevican, CA125 (MUC16), CA15-3, CA19-9, carcinoembryonic antigen (CEA), CA242, CRIPTO (CR, CR1, CRGF, CRIPTO, TDGF1, teratocarcinoma-derived growth factor), CTLA-4, CXCR5, E16 (LAT1, SLC7A5), FcRH2 (IFGP4, IRTA4, SPAP1A (SH2 domain containing phosphatase anchor protein 1a), SPAPIB, SPAPIC), epidermal growth factor, ETBR, Fc receptor-like protein 1 (FCRH1), GEDA, HLA-DOB (Beta subunit of MHC class II molecule (Ia antigen), human chorionic gonadotropin, ICOS, IL-2 receptor, IL20Ra, Immunoglobulin superfamily receptor translocation associated 2 (IRTA2), L6, Lewis Y, Lewis X, MAGE-1, MAGE-2, MAGE-3, MAGE 4, MART1, mesothelin, MDP, MPF (SMR, MSLN), MCP1 (CCL2), macrophage inhibitory factor (MIF), MPG, MSG783, mucin, MUC1-KLH, Napi3b (SLC34A2), nectin-4, Neu oncogene product, NCA, placental alkaline phosphatase, prostate specific membrane antigen (PMSA), prostatic acid phosphatase, PSCA hlg, anti-transferrin receptor, p97, Purinergic receptor P2X ligand-gated ion channel 5 (P2X5), LY64 (Lymphocyte antigen 64 (RP105), gp100, P21, six transmembrane epithelial antigen of prostate (STEAP1), STEAP2, Sema 5b, tumor-associated glycoprotein 72 (TAG-72), TrpM4 (BR22450, FLJ20041, TRPM4, TRPM4B, transient receptor potential cation channel, subfamily M, member 4) and the like.

In some instances, the cell surface protein comprises clusters of differentiation (CD) cell surface markers. Exemplary CD cell surface markers include, but are not limited to, CD1, CD2, CD3, CD4, CD5, CD6, CD7, CD8, CD9, CD10, CD11a, CD11b, CD11c, CD11d, CDw12, CD13, CD14, CD15, CD15s, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD45RO, CD45RA, CD45RB, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L (L-selectin), CD62P, CD63, CD64, CD65, CD66a, CD66b, CD66c, CD66d, CD66e, CD71, CD79 (e.g., CD79a, CD79b), CD90, CD95 (Fas), CD103, CD104, CD125 (IL5RA), CD134 (OX40), CD137 (4-1BB), CD152 (CTLA-4), CD221, CD274, CD279 (PD-1), CD319 (SLAMF7), CD326 (Ep-CAM), and the like.

In some embodiments, exemplary antibodies or binding fragments thereof include, but are not limited to, zalutumumab (HuMax-EFGr, Genmab), abagovomab (Menarini), abituzumab (Merck), adecatumumab (MT201), alacizumab pegol, alemtuzumab (Campath®, MabCampath, or Campath-1H; Leukosite), AlloMune (BioTransplant), amatuximab (Morphotek, Inc.), anti-VEGF (Genetech), anatumomab mafenatox, apolizumab (huID10), ascrinvacumab (Pfizer Inc.), atezolizumab (MPDL3280A; Genentech/Roche), B43.13 (OvaRex, AltaRex Corporation), basiliximab (Simulect®, Novartis), belimumab (Benlysta®, GlaxoSmithKline), bevacizumab (Avastin®, Genentech), blinatumomab (Blincyto, AMG103; Amgen), BEC2 (ImGlone Systems Inc.), carlumab (Janssen Biotech), catumaxomab (Removab, Trion Pharma), CEAcide (Immunomedics), Cetuximab (Erbitux®, ImClone), citatuzumab bogatox (VB6-845), cixutumumab (IMC-A12, ImClone Systems Inc.), conatumumab (AMG 655, Amgen), dacetuzumab (SGN-40, huS2C6; Seattle Genetics, Inc.), daratumumab (Darzalex®, Janssen Biotech), detumomab, drozitumab (Genentech), durvalumab (MedImmune), dusigitumab (MedImmune), edrecolomab (MAbl7-1A, Panorex, Glaxo Wellcome), elotuzumab (Empliciti™, Bristol-Myers Squibb), emibetuzumab (Eli Lilly), enavatuzumab (Facet Biotech Corp.), enfortumab vedotin (Seattle Genetics, Inc.), enoblituzumab (MGA271, MacroGenics, Inc.), ensituxumab (Neogenix Oncology, Inc.), epratuzumab (LymphoCide, Immunomedics, Inc.), ertumaxomab (Rexomun®, Trion Pharma), etaracizumab (Abegrin, MedImmune), farletuzumab (MORAb-003, Morphotek, Inc), FBTA05 (Lymphomun, Trion Pharma), ficlatuzumab (AVEO Pharmaceuticals), figitumumab (CP-751871, Pfizer), flanvotumab (ImClone Systems), fresolimumab (GC1008, Aanofi-Aventis), futuximab, glaximab, ganitumab (Amgen), girentuximab (Rencarex®, Wilex AG), IMAB362

(Claudiximab, Ganymed Pharmaceuticals AG), imalumab (Baxalta), IMC-1C11 (ImClone Systems), IMC-C225 (Imclone Systems Inc.), imgatuzumab (Genentech/Roche), intetumumab (Centocor, Inc.), ipilimumab (Yervoy®, Bristol-Myers Squibb), iratumumab (Medarex, Inc.), isatuximab (SAR650984, Sanofi-Aventis), labetuzumab (CEA-CIDE, Immunomedics), lexatumumab (ETR2-ST01, Cambridge Antibody Technology), lintuzumab (SGN-33, Seattle Genetics), lucatumumab (Novartis), lumiliximab, mapatumumab (HGS-ETR1, Human Genome Sciences), matuzumab (EMD 72000, Merck), milatuzumab (hLL1, Immunomedics, Inc.), mitumomab (BEC-2, ImClone Systems), narnatumab (ImClone Systems), necitumumab (Portrazza™, Eli Lilly), nesvacumab (Regeneron Pharmaceuticals), nimotuzumab (h-R3, BIOMAb EGFR, TheraCIM, Theraloc, or CIMAher; Biotech Pharmaceutical Co.), nivolumab (Opdivo®, Bristol-Myers Squibb), obinutuzumab (Gazyva or Gazyvaro; Hoffmann-La Roche), ocaratuzumab (AME-133v, LY2469298; Mentrik Biotech, LLC), ofatumumab (Arzerra®, Genmab), onartuzumab (Genentech), Ontuxizumab (Morphotek, Inc.), oregovomab (OvaRex®, AltaRex Corp.), otlertuzumab (Emergent BioSolutions), panitumumab (ABX-EGF, Amgen), pankomab (Glycotope GMBH), parsatuzumab (Genentech), patritumab, pembrolizumab (Keytruda®, Merck), pemtumomab (Theragyn, Antisoma), pertuzumab (Perjeta, Genentech), pidilizumab (CT-011, Medivation), polatuzumab vedotin (Genentech/Roche), pritumumab, racotumomab (Vaxira®, Recombio), ramucirumab (Cyramza®, ImClone Systems Inc.), rituximab (Rituxan®, Genentech), robatumumab (Schering-Plough), Seribantumab (Sanofi/Merrimack Pharmaceuticals, Inc.), sibrotuzumab, siltuximab (Sylvant™, Janssen Biotech), Smart MI95 (Protein Design Labs, Inc.), Smart ID10 (Protein Design Labs, Inc.), tabalumab (LY2127399, Eli Lilly), taplitumomab paptox, tenatumomab, teprotumumab (Roche), tetulomab, TGN1412 (CD28-SuperMAB or TAB08), tigatuzumab (CD-1008, Daiichi Sankyo), tositumomab, trastuzumab (Herceptin®), tremelimumab (CP-672,206; Pfizer), tucotuzumab celmoleukin (EMD Pharmaceuticals), ublituximab, urelumab (BMS-663513, Bristol-Myers Squibb), volociximab (M200, Biogen Idec), and zatuximab.

In some instances, the antibody or binding fragments thereof is an antibody-drug conjugate (ADC). In some cases, the payload of the ADC comprises, for example, but is not limited to, an auristatin derivative, maytansine, a maytansinoid, a taxane, a calicheamicin, cemadotin, a duocarmycin, a pyrrolobenzodiazepine (PDB), or a tubulysin. In some instances, the payload comprises monomethyl auristatin E (MMAE) or monomethyl auristatin F (MMAF). In some instances, the payload comprises DM2 (mertansine) or DM4. In some instances, the payload comprises a pyrrolobenzodiazepine dimer.

Additional Cargos

In some embodiments, the cargo is a peptidomimetic. A peptidomimetic is a small protein-like polymer designed to mimic a peptide. In some instances, the peptidomimetic comprises D-peptides. In other instances, the peptidomimetic comprises L-peptides. Exemplary peptidomimetics include peptoids and β-peptides.

In some embodiments, the cargo is a nucleotidomimetic.

Vectors and Expression Systems

In certain embodiments, the Arc polypeptides, endo-Gag polypeptides, engineered Arc and engineered endo-Gag polypeptides described supra are encoded by plasmid vectors. In some embodiments, vectors include any suitable vectors derived from either a eukaryotic or prokaryotic sources. In some cases, vectors are obtained from bacteria (e.g. *E. coli*), insects, yeast (e.g. *Pichia pastoris*), algae, or mammalian sources.

Exemplary bacterial vectors include pACYC177, pASK75, pBAD vector series, pBADM vector series, pET vector series, pE™ vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Exemplary insect vectors include pFastBac1, pFastBac DUAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

In some cases, yeast vectors include Gateway® pDEST™ 14 vector, Gateway® pDES™ 15 vector, Gateway® pDEST™ 17 vector, Gateway® pDEST™ 24 vector, Gateway® pYES-DEST52 vector, pBAD-DEST49 Gateway® destination vector, pAO815 *Pichia* vector, pFLD1 *Pichi pastoris* vector, pGAPZA, B, & C *Pichia pastoris* vector, pPIC3.5K *Pichia* vector, pPIC6 A, B, & C *Pichia* vector, pPIC9K *Pichia* vector, pTEF1/Zeo, pYES2 yeast vector, pYES2/CT yeast vector, pYES2/NT A, B, & C yeast vector, or pYES3/CT yeast vector.

Exemplary algae vectors include pChlamy-4 vector or MCS vector.

Examples of mammalian vectors include transient expression vectors or stable expression vectors. Mammalian transient expression vectors include p3xFLAG-CMV 8, pFLAG-Myc-CMV 19, pFLAG-Myc-CMV 23, pFLAG-CMV 2, pFLAG-CMV 6a, b, c, pFLAG-CMV 5.1, pFLAG-CMV 5a, b, c, p3xFLAG-CMV 7.1, pFLAG-CMV 20, p3xFLAG-Myc-CMV 24, pCMV-FLAG-MAT1, pCMV-FLAG-MAT2, pBICEP-CMV 3, or pBICEP-CMV 4. Mammalian stable expression vector include pFLAG-CMV 3, p3xFLAG-CMV 9, p3xFLAG-CMV 13, pFLAG-Myc-CMV 21, p3xFLAG-Myc-CMV 25, pFLAG-CMV 4, p3xFLAG-CMV 10, p3xFLAG-CMV 14, pFLAG-Myc-CMV 22, p3xFLAG-Myc-CMV 26, pBICEP-CMV 1, or pBICEP-CMV 2.

In some instances, a cell-free system is a mixture of cytoplasmic and/or nuclear components from a cell and is used for in vitro nucleic acid synthesis. In some cases, a cell-free system utilizes either prokaryotic cell components or eukaryotic cell components. Sometimes, a nucleic acid synthesis is obtained in a cell-free system based on for example *Drosophila* cell, *Xenopus* egg, or HeLa cells (ATCC® CCL-2™). Exemplary cell-free systems include, but are not limited to, *E. coli* S30 Extract system, *E. coli* T7 S30 system, or PURExpress®.

Host Cells

In some embodiments, a host cell includes any suitable cell such as a naturally derived cell or a genetically modified cell. In some instances, a host cell is a production host cell. In some instances, a host cell is a eukaryotic cell. In other instances, a host cell is a prokaryotic cell. In some cases, a eukaryotic cell includes fungi (e.g., a yeast cell), an animal cell, or a plant cell. In some cases, a prokaryotic cell is a bacterial cell. Examples of bacterial cell include gram-positive bacteria or gram-negative bacteria. In some embodiments the gram-negative bacteria is anaerobic, rod-shaped, or both.

In some instances, gram-positive bacteria include Actinobacteria, Firmicutes or Tenericutes. In some cases, gram-negative bacteria include Aquificae, *Deinococcus-Thermus*, Fibrobacteres-Chlorobi Bacteroidetes (FCB group), Fusobacteria, Gemmatimonadetes, Nitrospirae, Planctomycetes-Verrucomicrobia Chlamydiae (PVC group), Proteobacteria, Spirochaetes or Synergistetes. In some embodiments, bacteria is Acidobacteria, Chloroflexi, Chrysiogenetes, Cyanobacteria, Deferribacteres, Dictyoglomi, Thermodesulfobacteria or Thermotogae. In some embodiments, a bacterial cell is *Escherichia coli, Clostridium botulinum*, or *Coli bacilli*.

Exemplary prokaryotic host cells include, but are not limited to, BL21, Machi™, DH10B™, TOP10, DH5u, DH10Bac™, OmniMax™, MegaX™, DH12S™, INV110, TOP10F', INVαF, TOP10/P3, ccdB Survival, PIR1, PIR2, Stbl2™, Stbl3™, or Stbl4™.

In some instances, animal cells include a cell from a vertebrate or from an invertebrate. In some cases, an animal cell includes a cell from a marine invertebrate, fish, insects, amphibian, reptile, mammal, or human. In some cases, a fungus cell includes a yeast cell, such as brewer's yeast, baker's yeast, or wine yeast.

Fungi include ascomycetes such as yeast, mold, filamentous fungi, basidiomycetes, or zygomycetes. In some instances, yeast includes Ascomycota or Basidiomycota. In some cases, Ascomycota includes Saccharomycotina (true yeasts, e.g. *Saccharomyces cerevisiae* (baker's yeast)) or Taphrinomycotina (e.g. Schizosaccharomycetes (fission yeasts)). In some cases, Basidiomycota includes Agaricomycotina (e.g. Tremellomycetes) or Pucciniomycotina (e.g. Microbotryomycetes).

Exemplary yeast or filamentous fungi include, for example, the genus: *Saccharomyces, Schizosaccharomyces, Candida, Pichia, Hansenula, Kluyveromyces, Zygosaccharomyces, Yarrowia, Trichosporon, Rhodosporidi, Aspergillus, Fusarium*, or *Trichoderma*. Exemplary yeast or filamentous fungi include, for example, the species: *Saccharomyces cerevisiae, Schizosaccharomyces pombe, Candida utilis, Candida boidini, Candida albicans, Candida tropicalis, Candida stellatoidea, Candida glabrata, Candida krusei, Candida parapsilosis, Candida guilliermondii, Candida viswanathii, Candida lusitaniae, Rhodotorula mucilaginosa, Pichia metanolica, Pichia angusta, Pichia pastoris, Pichia anomala, Hansenula polymorpha, Kluyveromyces lactis, Zygosaccharomyces rouxii, Yarrowia lipolytica, Trichosporon pullulans, Rhodosporidium toru-Aspergillus niger, Aspergillus nidulans, Aspergillus awamori, Aspergillus oryzae, Trichoderma reesei, Yarrowia lipolytica, Brettanomyces bruxellensis, Candida stellata, Schizosaccharomyces pombe, Torulaspora delbrueckii, Zygosaccharomyces bailii, Cryptococcus neoformans, Cryptococcus gattii*, or *Saccharomyces boulardii*.

Exemplary yeast host cells include, but are not limited to, *Pichia pastoris* yeast strains such as GS115, KM71H, SMD1168, SMD1168H, and X-33; and *Saccharomyces cerevisiae* yeast strain such as INVSc1.

In some instances, additional animal cells include cells obtained from a mollusk, arthropod, annelid or sponge. In some cases, an additional animal cell is a mammalian cell, e.g., from a human, primate, ape, equine, bovine, porcine, canine, feline or rodent. In some cases, a rodent includes mouse, rat, hamster, gerbil, hamster, chinchilla, fancy rat, or guinea pig.

Exemplary mammalian host cells include, but are not limited to, 293A cell line, 293FT cell line, 293F cells, 293 H cells, CHO DG44 cells, CHO-S cells, CHO-K1 cells, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp- In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line.

In some instances, a mammalian host cell is a primary cell. In some instances, a mammalian host cell is a stable cell line, or a cell line that has incorporated a genetic material of interest into its own genome and has the capability to express the product of the genetic material after many generations of cell division. In some cases, a mammalian host cell is a transient cell line, or a cell line that has not incorporated a genetic material of interest into its own genome and does not have the capability to express the product of the genetic material after many generations of cell division.

Exemplary insect host cell include, but are not limited to, *Drosophila* S2 cells, Sf9 cells, Sf21 cells, High Five™ cells, and expresSF+® cells.

In some instances, plant cells include a cell from algae. Exemplary insect cell lines include, but are not limited to, strains from *Chlamydomonas reinhardtii* 137c, or Synechococcus *elongatus* PPC 7942.

Methods of Use

Disclosed herein, in certain embodiments, are methods of preparing a capsid which encapsulates a cargo. In some embodiments, the method comprises incubating a plurality of Arc or endo-Gag polypeptides, engineered Arc or endo-Gag polypeptides, and/or recombinant Arc or endo-Gag polypeptides with a cargo in a solution for a time sufficient to generate a loaded Arc-based capsid or endo-Gag-based capsid.

In some instances, the method comprises mixing a solution comprising a plurality of engineered and/or recombinant Arc polypeptides with a plurality of non-Arc capsid forming subunits prior to incubating with the cargo. In some cases, the plurality of non-Arc capsid forming subunits are mixed with the plurality of engineered and/or recombinant Arc polypeptides at a ratio of 1:1, 2:1, 3:1, 4:1, 5:1, 6:1, 7:1, 8:1, 9:1, or 10:1. In other cases, the plurality of non-Arc capsid forming subunits are mixed with the plurality of engineered and/or recombinant Arc polypeptides at a ratio of 1:2, 1:3, 1:4, 1:5, 1:6, 1:7, 1:8, 1:9, or 1:10.

In some cases, the time sufficient to generate a loaded Arc-based capsid or endo-Gag-based capsid is at least about 5 minutes, at least about 10 minutes, at least about 20 minutes, at least about 30 minutes, at least about 1 hour, at least about 2 hours, at least about 4 hours, at least about 6 hours, at least about 10 hours, at least about 12 hours, at least about 24 hours, or more.

In some cases, the Arc-based capsid or endo-Gag-based capsid is prepared at a temperature from about 2° C. to about 37° C. In some instances, the Arc-based capsid or endo-Gag-based capsid is prepared at a temperature from about 2° C. to about 8° C., about 2° C. to about 4° C., about 20° C. to about 37° C., about 25° C. to about 37° C., about 20° C. to about 30° C., about 25° C. to about 30° C., or about 30° C. to about 37° C.

In some cases, the Arc-based capsid or endo-Gag-based capsid is prepared at room temperature.

In some instances, the Arc-based capsid or endo-Gag-based capsid is further formulated for systemic administration.

In some instances, the Arc-based capsid or endo-Gag-based capsid is further formulated for local administration.

In some instances, the Arc-based capsid or endo-Gag-based capsid is further formulated for parenteral (e.g., intra-arterial, intra-articular, intradermal, intralesional, intramuscular, intraocular, intraosseous infusion, intraperitoneal, intrathecal, intravenous, intravitreal, or subcutaneous) administration.

In some instances, the Arc-based capsid or endo-Gag-based capsid is further formulated for topical administration.

In some instances, the Arc-based capsid or endo-Gag-based capsid is further formulated for oral administration.

In some instances, the Arc-based capsid or endo-Gag-based capsid is further formulated for sublingual administration.

In some instances, the Arc-based capsid or endo-Gag-based capsid is further formulated for aerosol administration.

In certain embodiments, also described herein is a use of an Arc-based capsid or endo-Gag-based capsid for delivery of a cargo to a site of interest. In some instances, the method comprises contacting a cell at the site of interest with an Arc-based capsid or endo-Gag-based capsid for a time sufficient to facilitate cellular uptake of the capsid.

In some cases, the cell is a muscle cell, a skin cell, a blood cell, or an immune cell (e.g., a T cell or a B cell).

In some instances, the cell is a tumor cell, e.g., a solid tumor cell or a cell from a hematologic malignancy. In some cases, the solid tumor cell is a cell from a bladder cancer, breast cancer, brain cancer, colorectal cancer, kidney cancer, liver cancer, lung cancer, pancreatic cancer, prostate cancer, skin cancer, stomach cancer, or thyroid cancer. In some cases, the cell from a hematologic malignancy is from a B-cell malignancy or a T-cell malignancy. In some cases, the cell is from a leukeuma, a lymphoma, a myeloma, chronic lymphocytic leukemia (CLL), small lymphocytic lymphoma (SLL), diffuse large B cell lymphoma (DLBCL), follicular lymphoma, mantle cell lymphoma, Burkitt lymphoma, cutaneous T-cell lymphoma, peripheral T cell lymphoma, multiple myeloma, plasmacytoma, acute lymphoblastic leukemia (ALL), acute myeloid leukemia (AML), or chronic myeloid leukemia (CML).

In some embodiments, the cell is a somatic cell. In some instances, the cell is a blood cell, a skin cell, a connective tissue cell, a bone cell, a muscle cell, or a cell from an organ.

In some embodiments, the cell is an epithelial cell, a connective tissue cell, a muscular cell, or a neuron.

In some instances, the cell is an endodermal cell, a mesodermal cell, or an ectodermal. In some instances, the endoderm comprises cells of the respiratory system, the intestine, the liver, the gallbladder, the pancreas, the islets of Langerhans, the thyroid, or the hindgut. In some cases, the mesoderm comprises osteochondroprogenitor cells, muscle cells, cells from the digestive system, renal stem cells, cells from the reproductive system, cells from the circulatory system (such as endothelial cells). Exemplary cells from the ectoderm comprise epithelial cells, cells of the anterior pituitary, cells of the peripheral nervous system, cells of the neuroendocrine system, cells of the eyes, cells of the central nervous system, cells of the ependymal, or cells of the pineal gland. In some cases, cells derived from the central and peripheral nervous system comprise neurons, Schwann cells, satellite glial cells, oligodendrocytes, or astrocytes. In some cases, neurons further comprise interneurons, pyramidal neurons, gabaergic neurons, dopaminergic neurons, serotoninergic neurons, glutamatergic neurons, motor neurons from the spinal cord, or inhibitory spinal neurons.

In some embodiments, the cell is a stem cell or a progenitor cell. In some cases, the cell is a mesenchymal stem or progenitor cell. In other cases, the cell is a hematopoietic stem or progenitor cell.

In some cases, a target protein is overexpressed or is depleted in the cell. In some cases, the target protein is overexpressed in the cell. In additional cases, the target protein is depleted in the cell.

In some cases, a target gene in the cell has one or more mutations.

In some cases, the cell comprises an impaired splicing mechanism.

In some instances, the Arc-based capsid is administered systemically to a subject in need thereof.

In other instances, the Arc-based capsid or endo-Gag-based capsid is administered locally to a subject in need thereof.

In some embodiments, the Arc-based capsid or endo-Gag-based capsid is administered parenterally, orally, topically, via sublingual, or by aerosol to a subject in need thereof. In some cases, the Arc-based capsid or endo-Gag-based capsid is administered parenterally to a subject in need thereof. In other cases, the Arc-based capsid or endo-Gag-based capsid is administered orally to a subject in need thereof. In additional cases, the Arc-based capsid or endo-Gag-based capsid is administered topically, via sublingual, or by aerosol to a subject in need thereof.

In some embodiments, a delivery component is combined with an Arc-based capsid or endo-Gag-based capsid for a targeted delivery to a site of interest. In some instances, the delivery component comprises a carrier, e.g., an extracellular vesicle such as a micelle, a liposome, or a microvesicle; or a viral envelope.

In some instances, the delivery component serves as a primary delivery vehicle for an Arc-based capsid or endo-Gag-based capsid which does not comprise its own delivery component (e.g., in which the second polypeptide is not present). In such cases, the delivery component directs the Arc-based capsid or endo-Gag-based capsid to a target site of interest and optionally facilitates intracellular uptake.

In other instances, the delivery component enhances target specificity and/or sensitivity of an Arc-based capsid's second polypeptide. In such cases, the delivery component enhances the specificity and/or affinity of the Arc-based capsid or endo-Gag-based capsid to the target site. In additional cases, the delivery components enhances the specificity and/or affinity by about 2-fold, 3-fold, 4-fold, 5-fold, 6-fold, 7-fold, 8-fold, 9-fold, 10-fold, 20-fold, 30-fold, 50-fold, 100-fold, 200-fold, 500-fold, or more. In further cases, the delivery components enhances the specificity and/or affinity by about 10%, 20%, 30%, 40%, 50%, 60%, 70%, 80%, 90%, 100%, 200%, 500%, or more. Further still, the delivery component optionally minimizes off-target effect by about 2-fold, 3-fold, 4-fold, 5-fold, 6-fold, 7-fold, 8-fold, 9-fold, 10-fold, 20-fold, 30-fold, 50-fold, 100-fold, 200-fold, 500-fold, or more. Further still, the delivery component optionally minimizes off-target effect by about 10%, 20%, 30%, 40%, 50%, 60%, 70%, 80%, 90%, 100%, 200%, 500%, or more.

In additional instances, the delivery component serves as a first vehicle that transports an Arc-based capsid to a general target region (e.g., a tumor microenvironment) and the Arc-based or endo-Gag-based capsid's second polypeptide serves as a second delivery molecule that drives the Arc-based capsid or endo-Gag-based capsid to the specific target site and optionally facilitates intracellular uptake. In such cases, the delivery component minimizes off-target effect by about 2-fold, 3-fold, 4-fold, 5-fold, 6-fold, 7-fold, 8-fold, 9-fold, 10-fold, 20-fold, 30-fold, 50-fold, 100-fold, 200-fold, 500-fold, or more. In such cases, the delivery component minimizes off-target effect by about 10%, 20%, 30%, 40%, 50%, 60%, 70%, 80%, 90%, 100%, 200%, 500%, or more.

In further instances, the delivery component serves as a first vehicle that transports an Arc-based capsid to a target site of interest and the Arc-based or endo-Gag-based capsid's second polypeptide serves as a second delivery molecule that facilitates intracellular uptake.

In some embodiments, the delivery component comprises an extracellular vesicle. In some instances, the extracellular vesicle comprises a microvesicle, a liposome, or a micelle. In some instances, the extracellular vesicle has a diameter of from about 10 nm to about 2000 nm, from about 10 nm to about 1000 nm, from about 10 nm to about 800 nm, from about 20 nm to about 600 nm, from about 30 nm to about 500 nm, from about 50 nm to about 200 nm, or from about 80 nm to about 100 nm.

In some embodiments, the delivery component comprises a microvesicle. Also known as circulating microvesicles or microparticles, microvesicles are membrane-bound vesicles that comprise phospholipids. In some instances, the microvesicle has a diameter of from about 50 nm to about 1000 nm, from about 100 nm to about 800 nm, from about 200 nm to about 500 nm, or from about 50 nm to about 400 nm.

In some instances, the microvesicle is originated from cell membrane inversion, exocytosis, shedding, blebbing, or budding. In some instances, the microvesicles are generated from differentiated cells. In other instances, the microvesicles are generated from undifferentiated cells, e.g., by blast cells, progenitor cells, or stem cells.

In some embodiments, the delivery component comprises a liposome. In some instances, the liposome comprises a plurality of lipopeptides, which are presented on the surface of the liposome, for targeted delivery to a site or region of interest. In some cases, the liposomes fuse with the target cell, whereby the contents of the liposome are then emptied into the target cell. In some cases, a liposome is endocytosed by cells that are phagocytic. Endocytosis is then followed by intralysosomal degradation of liposomal lipids and release of the encapsulated agents.

Exemplary liposomes suitable for incorporation include, and are not limited to, multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV). In some instances, a liposome comprises Amphipol (A8-35). Techniques for preparing liposomes are described in, for example, COLLOIDAL DRUG DELIVERY SYSTEMS, vol. 66 (J. Kreuter ed., Marcel Dekker, Inc. (1994)).

Depending on the method of preparation, liposomes are unilamellar or multilamellar, and vary in size with diameters ranging from about 20 nm to greater than about 1000 nm.

In some instances, liposomes provided herein also comprise carrier lipids. In some embodiments the carrier lipids are phospholipids. Carrier lipids capable of forming lipo-somes include, but are not limited to, dipalmitoylphospha-tidylcholine (DPPC), phosphatidylcholine (PC; lecithin), phosphatidic acid (PA), phosphatidylglycerol (PG), phos-phatidylethanolamine (PE), or phosphatidylserine (PS). Other suitable phospholipids further include distearoylphos-phatidylcholine (DSPC), dimyristoylphosphatidylcholine (DMPC), dipalmitoylphosphatidyglycerol (DPPG), dis-tearoylphosphatidyglycerol (DSPG), dimyristoylphosphati-dylglycerol (DMPG), dipalmitoylphosphatidic acid (DPPA); dimyristoylphosphatidic acid (DMPA), distearoylphospha-tidic acid (DSPA), dipalmitoylphosphatidylserine (DPPS), dimyristoylphosphatidylserine (DMPS), distearoylphospha-tidylserine (DSPS), dipalmitoylphosphatidyethanolamine (DPPE), dimyristoylphosphatidylethanolamine (DMPE), distearoylphosphatidylethanolamine (DSPE) and the like, or combinations thereof. In some embodiments, the liposomes further comprise a sterol (e.g., cholesterol) which modulates liposome formation. The carrier lipids are optionally any non-phosphate polar lipids.

In some embodiments, the delivery component comprises a micelle. In some instances, the micelle has a diameter from about 2 nm to about 250 nm, from about 20 nm to about 200 nm, from about 20 nm to about 100 nm, or from about 50 to about 100 nm.

In some instances, the micelle is a polymeric micelle, characterized by a core shell structure, in which the hydro-phobic core is surrounded by a hydrophilic shell. In some cases, the hydrophilic shell further comprises a hydrophilic polymer or copolymer and a pH sensitive component.

Exemplary hydrophilic polymers or copolymers include, but are not limited to, poly(N-substituted acrylamides), poly(N-acryloyl pyrrolidine), poly(N-acryloyl piperidine), poly(N-acryl-L-amino acid amides), poly(ethyl oxazoline), methylcellulose, hydroxypropyl acrylate, hydroxyalkyl cel-lulose derivatives and poly(vinyl alcohol), poly(N-isopro-pylacrylamide), poly(N-vinyl-2-pyrrolidone), polyethyl-eneglycol derivatives, and combinations thereof.

The pH-sensitive moiety includes, but is not limited to, an alkylacrylic acid such as methacrylic acid, ethylacrylic acid, propyl acrylic acid and butyl acrylic acid, or an amino acid such as glutamic acid.

In some instances, the hydrophobic moiety constitutes the core of the micelle and includes, for example, a single alkyl chain, such as octadecyl acrylate or a double chain alkyl compound such as phosphatidylethanolamine or diocta-decylamine. In some cases, the hydrophobic moiety is optionally a water insoluble polymer such as a poly(lactic acid) or a poly(e-caprolactone).

Polymeric micelles exhibiting pH-sensitive properties are also contemplated and are formed, e.g., by using pH-sensitive polymers including, but not limited to, copolymers from methacrylic acid, methacrylic acid esters and acrylic acid esters, polyvinyl acetate phthalate, hydroxypropyl methyl cellulose phthalate, cellulose acetate phthalate, or cellulose acetate trimellitate.

In some embodiments, the delivery component comprises a viral envelope. Viral envelopes comprise glycoproteins, phospholipids, and additional proteins obtained from a host. In some instances, the viral envelope is permissive to a wide range of target cells. In other instances, the viral envelope is non-permissive and is specific to a target cell of interest. In some cases, the viral envelope comprises a cell-specific binding protein and optionally a fusogenic molecule that aids in the fusion of the cargo into a target cell. In some cases, the viral envelope comprises an endogenous viral envelope. In other cases, the viral envelope is a modified envelop, comprising one or more foreign proteins.

In some instances, the viral envelope is derived from a DNA virus. Exemplary enveloped DNA viruses include viruses from the family of Herpesviridae, Poxviridae, and Hepadnavirdae.

In other instances, the viral envelope is derived from an RNA virus. Exemplary enveloped RNA viruses include viruses from the family of Bunyaviridae, Coronaviridae, Filoviridae, Flaviviridae, Orthomyxoviridae, Paramyxoviri-dae, Rhabdoviridae, and Togaviridae.

In additional instances, the viral envelope is derived from a virus from the family of Retroviridae.

In some embodiments, the viral envelope is from an oncolytic virus, such as an oncolytic DNA virus from the family of Herpesviridae (for example, HSV1) or Poxviridae (for example, Vaccinia virus and myxoma virus); or an oncolytic RNA virus from the family of Rhabdoviridae (for example, VSV) or Paramyxoviridae (for example MV and NDV).

In some instances, the viral envelope further comprises a foreign or engineered protein that binds to an antigen or a cell surface molecule. Exemplary antigens and cell surface molecules for targeting include, but are not limited to, P-glycoprotein, Her2/Neu, erythropoietin (EPO), epidermal growth factor receptor (EGFR), vascular endothelial growth factor receptor (VEGF-R), cadherin, carcinoembryonic anti-gen (CEA), CD4. CD8, CD19. CD20, CD33, CD34, CD45, CD117 (c-kit), CD133, HLA-A. HLA-B, HLA-C, chemo-kine receptor 5 (CCRS), stem cell marker ABCG2 trans-porter, ovarian cancer antigen CA125, immunoglobulins, integrins, prostate specific antigen (PSA), prostate stem cell antigen (PSCA), dendritic cell-specific intercellular adhe-sion molecule 3-grabbing nonintegrin (DC-SIGN), thyro-globulin, granulocyte-macrophage colony stimulating factor (GM-CSF), myogenic differentiation promoting factor-1 (MyoD-1), Leu-7 (CD57), LeuM-1, cell proliferation-asso-ciated human nuclear antigen defined by the monoclonal antibody K1-67 (Ki-67), viral envelope proteins, HIV gp120, or transferrin receptor.

In some embodiments, the Arc-based capsid or endo-Gag-based capsid is for in vitro use.

In some instances, the Arc-based capsid or endo-Gag-based capsid is for ex vivo use.

In some cases, the Arc-based capsid or endo-Gag-based capsid is for in vivo use.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

For example, the container(s) include a recombinant or engineered Arc or endo-Gag polypeptide described above. Such kits optionally include an identifying description or label or instructions relating to its use in the methods described herein. For example, a kit typically includes labels listing contents and/or instructions for use, and package inserts with instructions for use. A set of instructions will also typically be included.

Certain Terminologies

Unless defined otherwise, all technical and scientific terms used herein have the same meaning as is commonly understood. It is to be understood that the detailed description are exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the sequence of a CA N-lobe described herein corresponds to the human CA N-lobe. In some instances, the human CA N-lobe comprises residues 207-278 of SEQ ID NO: 1. In some instances, a CA N-lobe described herein comprises about 30%, 40%, 50%, 60%, 70%, 80%, 90%, 91%, 92%, 93%, 94%, 95%, 96%, 97% 98% or 99% sequence identity to residue 207-278 of SEQ ID NO: 1. In some cases, a CA N-lobe described herein shares a structural similarity with the human CA N-lobe. For example, a CA N-lobe described herein shares about 80%, 85%, 90%, 91%, 92%, 93%, 94%, 95%, 96%, 97% 98% or 99% structural similarity with the human CA N-lobe. In some cases, the CA N-lobe shares a high structural similarity (e.g., 80%, 90%, 91%, 92%, 93%, 94%, 95%, 96%, 97% 98% or 99% structural similarity) but does not share a high sequence identity (e.g., the sequence identity is lower than 80%, lower than 70%, lower than 60%, lower than 50%, lower than 40%, or lower than 30%). In some cases, the CA N-lobe comprises residues 207-278 of SEQ ID NO: 1.

As used herein, the sequence of a CA C-lobe described herein corresponds to the human CA C-lobe. In some instances, the human CA C-lobe comprises residues 278-370 of SEQ ID NO: 1. In some instances, a CA C-lobe described herein comprises about 30%, 40%, 50%, 60%, 70%, 80%, 90%, 91%, 92%, 93%, 94%, 95%, 96%, 97% 98% or 99% sequence identity to residue 278-370 of SEQ ID NO: 1. In some cases, a CA C-lobe described herein shares a structural similarity with the human CA C-lobe. For example, a CA C-lobe described herein shares about 80%, 85%, 90%, 91%, 92%, 93%, 94%, 95%, 96%, 97% 98% or 99% structural similarity with the human CA C-lobe. In some cases, the CA C-lobe shares a high structural similarity (e.g., 80%, 90%, 91%, 92%, 93%, 94%, 95%, 96%, 97% 98% or 99% structural similarity) but does not share a high sequence identity (e.g., the sequence identity is lower than 80%, lower than 70%, lower than 60%, lower than 50%, lower than 40%, or lower than 30%). In some cases, the CA C-lobe comprises residues 278-370 of SEQ ID NO: 1.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

EXAMPLES

These examples are provided for illustrative purposes only and not to limit the scope of the claims provided herein.

Figure 3A:
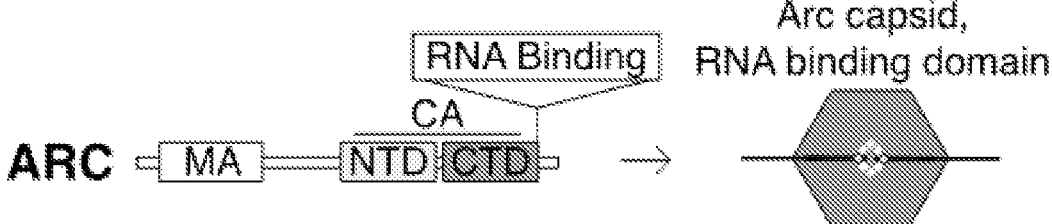
FIGS. 3A and 3B illustrate an exemplary method of engineering an Arc polypeptide to carry a specific cargo (FIG. 3A) (e.g., an RNA payload), or remove an off-function effect (FIG. 3B).
Figure 3B:
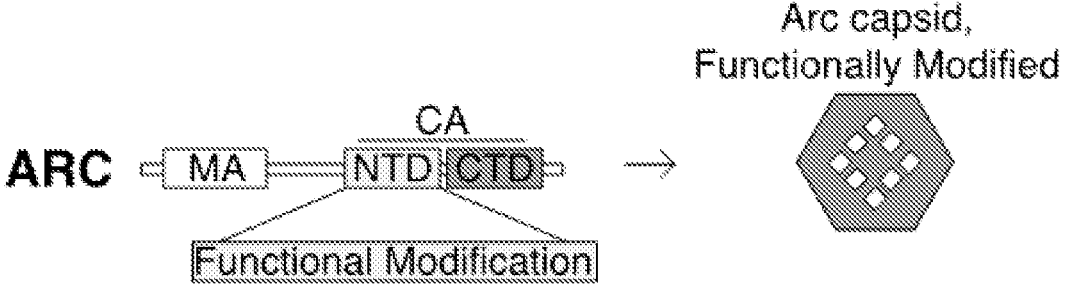

Example 1—Construction of DNA Vectors
Encoding Recombinant Arc Proteins and
Engineered Arc Proteins To construct recombinant DNA vectors for Arc expression, full length cDNA open reading frames, excluding the initial methionine, are inserted into a cloning vector and subsequently transferred into an expression vector according to standard methods. The same approach is used to construct recombinant DNA vectors for expressing endo-Gag proteins. Human Arc cDNA includes an annotated matrix domain (MA) and a capsid domain. The capsid domain has an N-terminal lobe (NTD) and a C-terminal lobe (CTD). FIG. 1 illustrates the structure of the Human Arc protein and the predicted structure of Arc from Python, Platypus, and Orca.

cDNAs encoding engineered Arc proteins are optionally generated by recombining Arc sequences from different species (FIG. 2), by inserting functional domains from other proteins into an Arc protein (FIG. 3A), by modifying the sequence of an Arc protein (FIG. 3B), and/or by any combination of the approaches exemplified in FIGS. 2-3. cDNAs encoding engineered endo-Gag proteins are likewise generated by recombining endo-Gag sequences from different species, by inserting functional domains from other proteins into an endo-Gag protein, by modifying the sequence of an endo-Gag protein, and/or by any combination of these approaches. Furthermore, an engineered endo-Gag protein optionally contains Arc sequences and an engineered Arc protein optionally contains endo-Gag sequences. Engineered Arc and endo-Gag protein monomers assemble into capsids.

cDNAs encoding the Arc and endo-Gag proteins of Table 1 were inserted into an expression vector derived from pET-41 a(+) (EMD Millipore (Novagen) Cat #70566). The entire cloning site of pET-41 a(+) was removed and replaced with the DNA having the nucleotide sequence of SEQ ID NO: 57, which encodes an alternative N-terminal tag having the amino acid sequence of SEQ ID NO: 58 and comprising a 6×His tag (SEQ ID NO: 59), a 6 amino acid spacer (SEQ ID NO: 60), and an AcTEV™ cleavage site (SEQ ID NO: 61). Arc and endo-Gag open reading frames without their starting methionine codon were inserted after the AcTEV™ cleavage site by Gibson assembly. Gibson DG, Young L, Chuang RY, Venter JC, Hutchison CA 3rd, Smith HO (2009). "Enzymatic assembly of DNA molecules up to several hundred kilobases". Nature Methods. 6 (5): 343-345. After expression and AcTEV™ cleavage, the N-terminus of the resulting Arc or endo-Gag protein has a single residual Glycine from the AcTEV™ cleavage site.

SEQ ID NO: 57

ATGCATCACCATCACCATCACGGCTCAGGGTCTGGTAGCGAAAATCTGT      HHHHHH

ACTTCCAGGGG                                    5

GSGSGS

SEQ ID NO: 58                          SEQ ID NO: 59

MHHHHHHGSGSGSENLYFQG                          ENLYFQG

SEQ ID NO: 60

SEQ ID NO: 61

TABLE 1

Sequences of Arc and endo-Gag polypeptides and nucleotides.

| Gene | Species | | | SEQ ID NO: | |
| Name | Common name | Proper name | Sequence ID | Amino acid | DNA |
|---|---|---|---|---|---|
| Arc | Human | *Homo sapiens* | NP_056008.1 | 1 | 29 |
| Arc | Killer Whale | *Orcinus orca* | XP_004265337.1 | 2 | 30 |
| Arc | White Tailed Deer | *Odocoileus virginianus texanus* | XP_020755692.1 | 3 | 31 |
| Arc | Platypus | *Ornithorhynchus anatinus* | XP_001512750.1 | 4 | 32 |
| Arc | Goose | *Anser cygnoides domesticus* | XP_013046406.1 | 5 | 33 |
| Arc | Dalmation Pelican | *Pelecanus crispus* | KFQ60200.1 | 6 | 34 |
| Arc | White Tailed Eagle | *Haliaeetus albicilla* | KFQ04633.1 | 7 | 35 |
| Arc | King Cobra | *Ophiophagus hannah* | ETE60609.1 | 8 | 36 |
| Arc | Ray Finned Fish | *Austrofundulus limnaeus* | XP_013881732.1 | 9 | 37 |
| Arc | Sperm Whale | *Physeter catodon* | XP_007119193.2 | 10 | 38 |
| Arc | Turkey | *Meleagris gallopavo* | XP_010707654.1 | 11 | 39 |
| Arc | Central Bearded Dragon | *Pogona vitticeps* | XP_020633722.1 | 12 | 40 |
| Arc | Chinese Alligator | *Alligator sinensis* | XP_006027442.1 | 13 | 41 |
| Arc | American Alligator | *Alligator mississippiensis* | XP_019337372.1 | 14 | 42 |
| Arc | Japanese Gekko | *Gekko japonicus* | XP_015273745.1 | 15 | 43 |
| PNMA3 | Human | *Homo sapiens* | NP_001269464.1 | 16 | 44 |
| PNMA5 | Human | *Homo sapiens* | NP_001096620.1 | 17 | 45 |
| PNMA6A | Human | *Homo sapiens* | NP_116271.3 | 18 | 46 |
| PNMA6B | Human | *Homo sapiens* | SP_P0C5W0.1 | 19 | 47 |
| RTL3 | Human | *Homo sapiens* | NP_689907.1 | 20 | 48 |
| RTL6 | Human | *Homo sapiens* | NP_115663.2 | 21 | 49 |
| RTL8A | Human | *Homo sapiens* | NP_001071640.1 | 22 | 50 |
| RTL8B | Human | *Homo sapiens* | NP_001071641.1 | 23 | 51 |
| BOP | Human | *Homo sapiens* | NP_078903.3 | 24 | 52 |
| LDOC1 | Human | *Homo sapiens* | NP_036449.1 | 25 | 53 |
| ZNF18 | Human | *Homo sapiens* | NP_001290210.1 | 26 | 54 |

TABLE 1-continued

Sequences of Arc and endo-Gag polypeptides and nucleotides.

| | | | | SEQ ID NO: | |
| | | | | Amino | |
| Gene Name | Common name | Proper name | Sequence ID | acid | DNA |
| MOAP1 | Human | *Homo sapiens* | AAG31786.1 | 27 | 55 |
| PEG10 | Human | *Homo sapiens* | NP_055883.2 | 28 | 56 |

Example 2—Expression and Purification of Arc and Endo-Gag Proteins

Figure 4A:
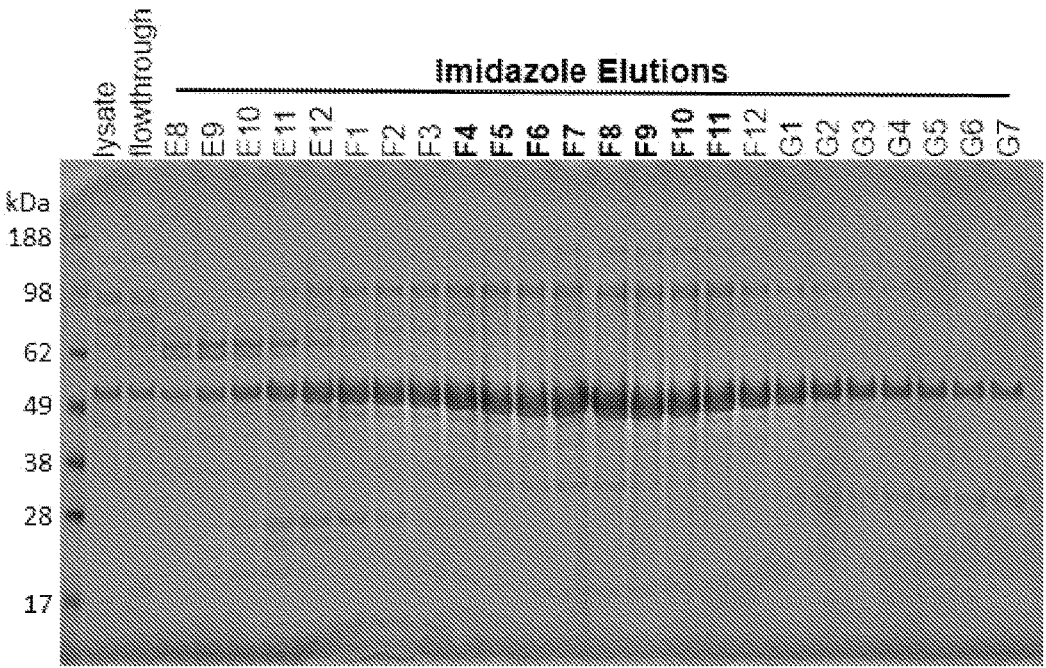
FIG. 4A shows the isolation of 6×His-tagged human Arc by elution from a HisTrap column with an imidazole gradient.

Expression vectors constructs comprising Arc and endo-Gag open reading frames were transformed into the Rosetta 2 (DE3)pLysS *E. coli* strain (Millipore Sigma, Cat #71403). Arc or endo-Gag expression was induced with 0.1 mM IPTG followed by a 16-hour incubation at 16° C. Cell pellets were lysed by sonication in 20 mM sodium phosphate pH 7.4, 0.1M NaCl, 40 mM imidazole, 1 mMv DTT, and 10% glycerol. The lysate was treated with excess TURBO DNase (Thermo Fisher Scientific, Cat #AM2238), RNase Cocktail (Thermo Fisher Scientific, Cat #AMV2286), and Benzonase Nuclease (Millipore Sigma, Cat #71205) to eliminate nucleic acids. NaCl was added to lysate in order to adjust the NaCl concentration to 0.5 M followed by centrifugation and filtration to remove cellular debris. 6xHis-tagged recombinant protein was loaded onto a HisTrap HP column (GE Healthcare, Cat #17-5247-01), washed with buffer A (20 mMv sodium phosphate pH 7.4, 0.5M NaCl, 40 mM imidazole, and 10% glycerol), and eluted with a linear gradient of buffer B (20 mM sodium phosphate pH 7.4, 0.5M NaCl, 500 mMv imidazole, and 10% glycerol). Collection tubes were supplemented in advance with 10 μl of 0.5 M EDTA pH 8.0 per 1 ml eluate. The resulting Arc or endo-Gag protein is generally more than 95% pure as revealed by SDS-PAGE analysis, with a yield of up to 50 mg per 1 L of bacterial culture. FIG. 4A.

Figure 4B:
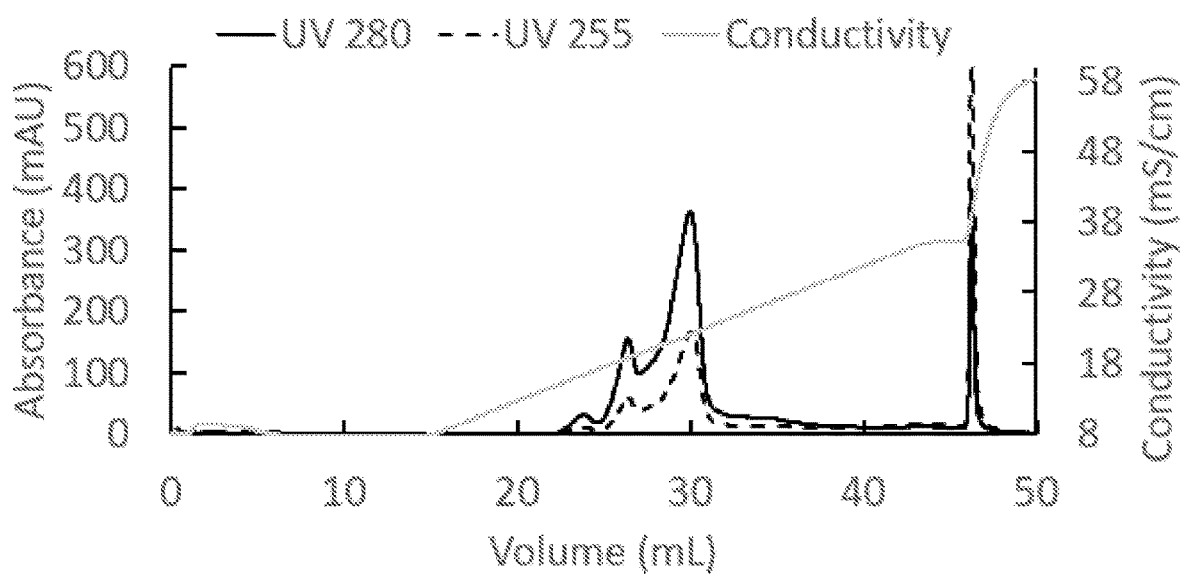
FIG. 4B shows the separation of 6×His-tagged human Arc from residual nucleic acids on a mono Q column eluted with a NaCl gradient.

Residual nucleic acid was removed by anion exchange chromatography on a mono Q 5/50 GL column (GE Healthcare, Cat #17516601). Before loading to the column, recombinant protein was buffer exchanged to buffer C (20 mM Tris-HCl pH 8.0, 100 mM NaCl, and 10% glycerol) using "Pierce Protein Concentrator PES, 10K MWCO, 5-20 ml" (Thermo Scientific, Cat #88528) according to the manufacturer's protocol. After loading, the mono Q resin was washed with 2 ml of buffer C. Arc and endo-Gag proteins were eluted using a linear gradient of buffer D (20 mM Tris-HCl pH 8.0, 500 mM NaCl, and 10% glycerol). RNA efficiently separated from Arc and eluted at 600 mM NaCl (FIG. 4B).

The N-terminal 6xHis tag and spacer were removed from concentrating peak fractions of the mono Q purified Arc using a 10 kDa MWCO PES concentrator and then treating with 10% v/v of AcTEV™ Protease (Invitrogen™ #12575023). The cleavage efficiency is above 99% as revealed by SDS-PAGE assay. The protein is then diluted into HisTrap Buffer A and cleaned with HisTrap HP resin. The resulting purified Arc has an N-terminal Glycine residue and does not contain the initial methionine.

Example 3—Capsid Assembly

Cleaved Arc protein (1 mg/mL) was loaded into a 20 kDa MWCO dialysis cassette and dialyzed overnight in 1M sodium phosphate (pH 7.5) at room temperature. The following day, the solution was removed from the cassette, transferred to microcentrifuge tubes, and spun at max speed for 5 minutes in a tabletop centrifuge. The supernatant was transferred to a 100 kDa MWCO Regenerated Cellulose Amicon Ultrafiltration Centrifugal concentrator. The buffer was exchanged to PBS pH 7.5 and the volume was reduced 20-fold.

Figure 5:
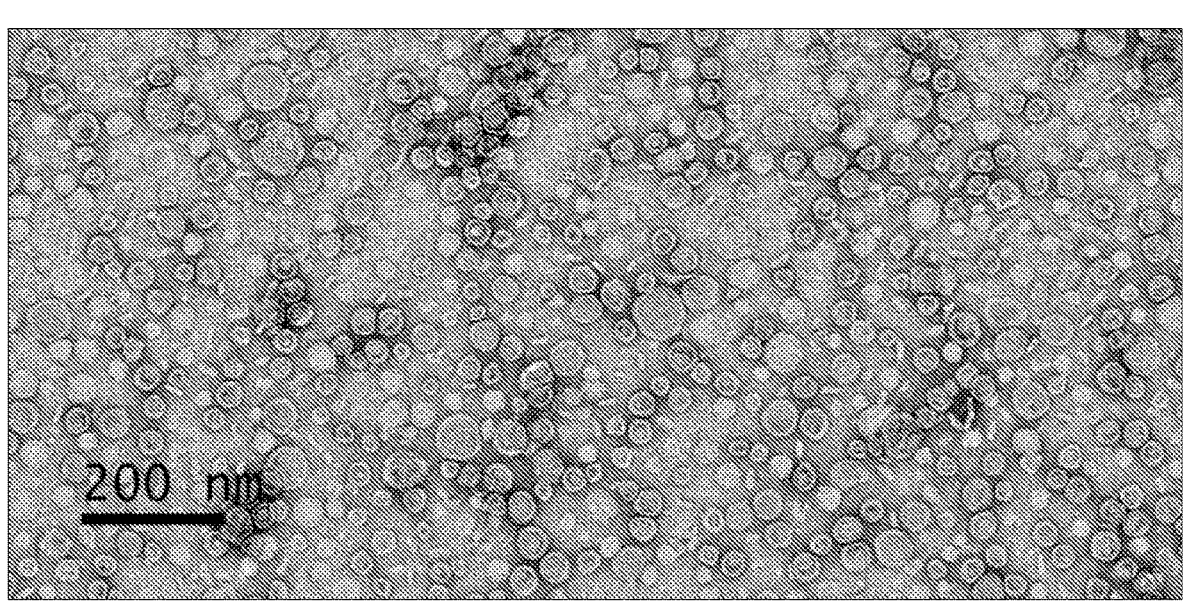
FIG. 5 shows a transmission electron microscope image of negatively stained human Arc capsids.
Figure 6:
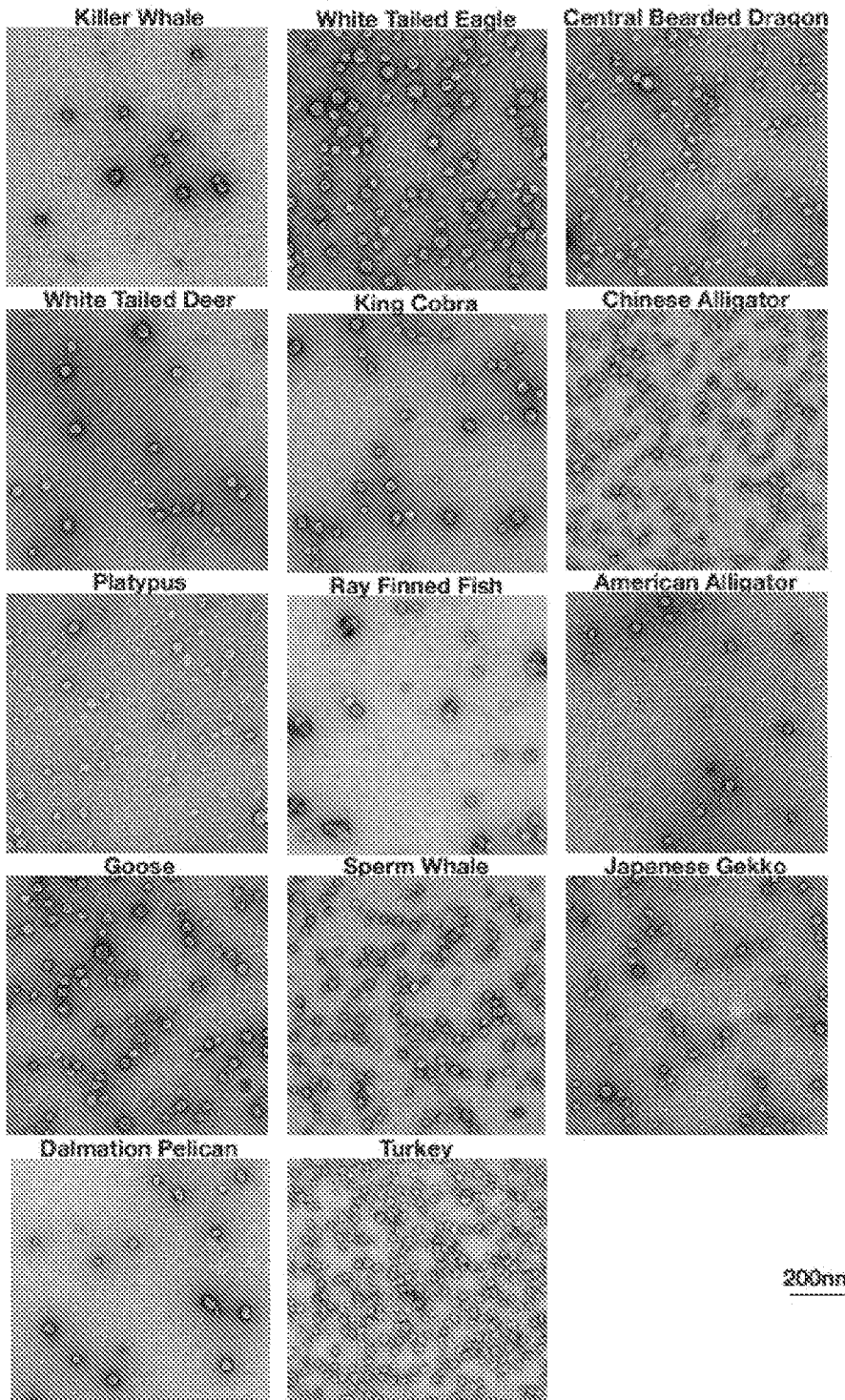
FIG. 6 shows transmission electron microscope images of negatively stained capsids formed from recombinantly expressed Arc orthologs.
Figure 7:
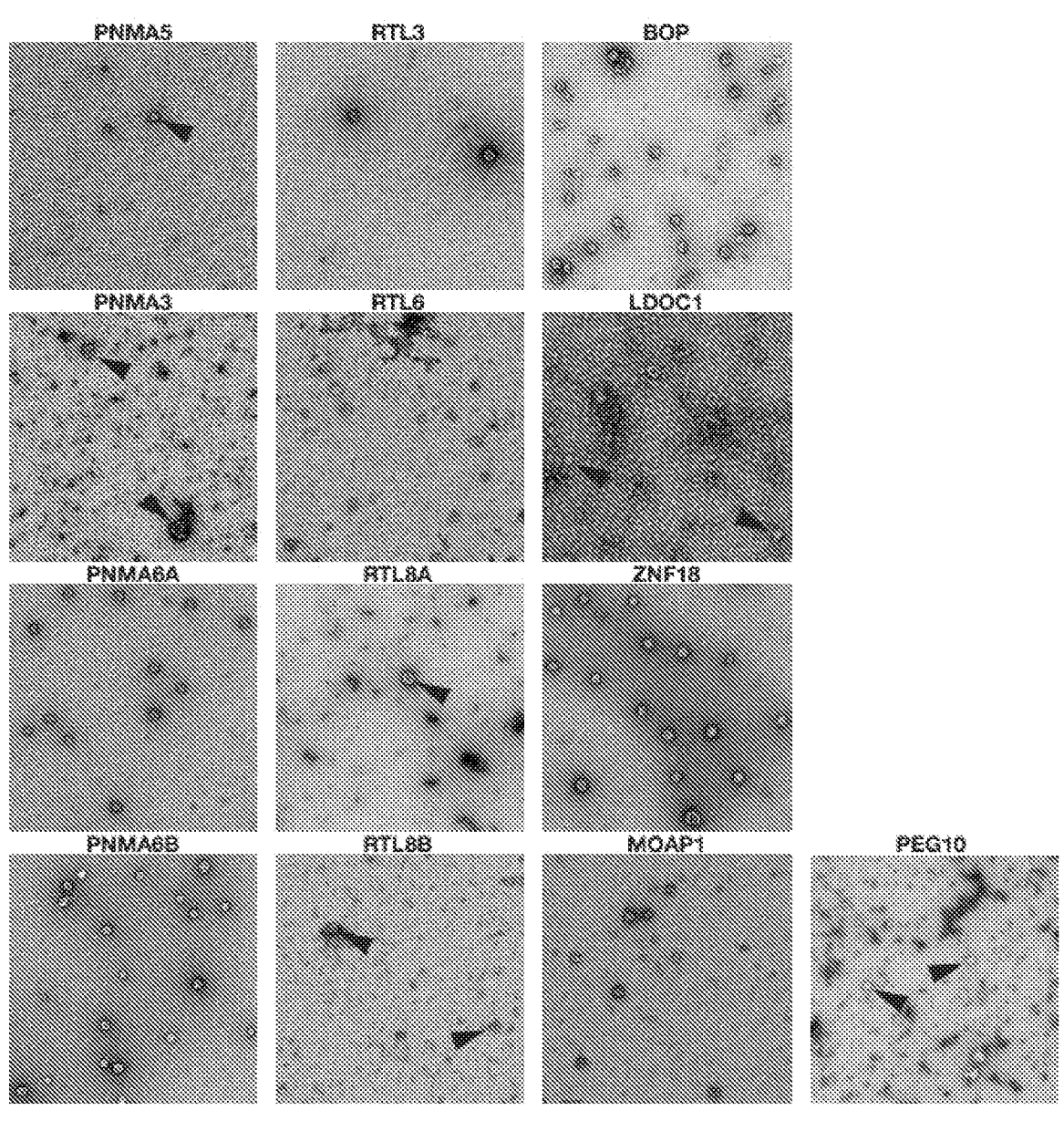
FIG. 7 shows transmission electron microscope images of negatively stained capsids formed from recombinantly expressed endo-Gag proteins.

Capsid assembly was assayed by transmission electron microscopy. EM grids (Carbon Support Film, Square Grid, 400 mesh, 5-6 nm, Copper, CF400-Cu-UL) were prepared by glow discharge. A 5 μL sample of purified Arc was applied to the grid for 20 seconds and then wicked away using filter paper. The grid was then washed with MilliQ H₂O, stained with 5 μL of 1% Uranyl Acetate in H₂O for 30 seconds, and air dried for 1 minute. Images of Arc capsids were acquired using a FEI Talos L120C TEM equipped with a Gatan 4k×4k OneView camera. FIG. 5 shows concentrated human Arc capsids. FIG. 6 shows capsids formed from recombinantly expressed Arc orthologs from other vertebrate species. FIG. 7 shows capsids formed from recombinantly expressed endo-Gag genes from other vertebrate species.

Example 4—Selective Cellular Internalization of Arc Capsids

Capsids assembled from isolated recombinant human Arc protein (0.5 mg/ml) were fluorescently labeled by reacting with a 50-molar excess of NHS ester Alexa Fluor™ 594-NHS dye (Invitrogen™ #A20004) (dissolved in DMSO) in PBS (pH 8.5). Reactions were allowed to proceed for 2-hours in the dark. Alexa594-labeled capsids were then dialyzed with PBS (pH 7.5) overnight at room temperature in the dark with at least two buffer exchanges to remove any unlabeled dye.

Figure 8:
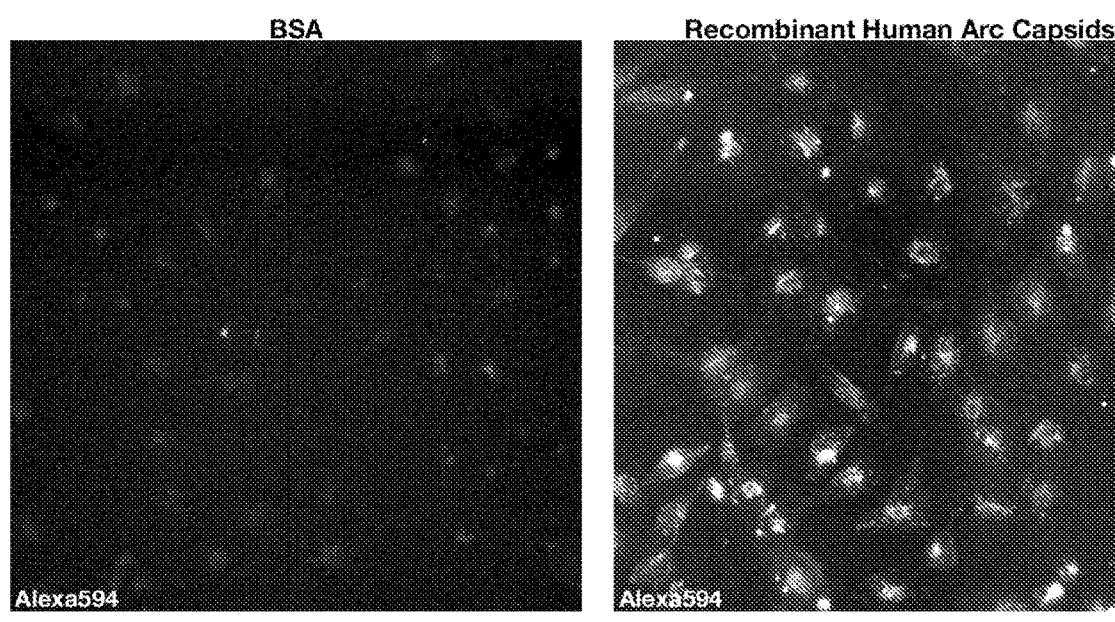
FIG. 8 shows selective internalization of Alexa594-labeled Arc capsids by HeLa cells.

HeLa cells (ATCC® CCL-2™) were seeded 24-hours prior to the experiment in 96-well plates at counts such that they reach ~80% confluency for treatment. Labeled-capsids were then spiked into complete tissue culture media to a final capsid concentration of 0.05 mg/ml. Treatments proceed for 4-hours at 37° C., and then cells are washed 3-times with imaging media (DMEM, no phenol red, with 10% FBS and 20 mM HEPES) containing 10 ug/ml Hoechst nuclear stain prior to imaging. Fluorescence microscopy revealed a punctate staining pattern, suggesting that the Arc capsids were internalized by the HeLa cells (FIG. 8). Little or no intracellular staining was observed after administration of Alexa Fluor™ 594-labeled bovine serum albumin (BSA) (final concentration of 0.05 mg/ml) or 45.6 μM Alexa Fluor™ 594 under identical conditions.

Example 5—Heterologous RNA Delivery by Arc Capsids

Human Arc capsids were loaded with Cre RNA by spiking in excess RNA during capsid formation (by dialysis into 1M sodium phosphate). Cre RNA-loaded capsids were administered to HeLa cells in biological triplicate at a final capsid concentration of 0.05 mg/ml for 4-hours at 37° C. The cells were then washed 3-times with ice-cold 1×PBS prior to RNA extraction (Invitrogen™ TRIzol™ Reagent #15596026). Purified cell-associated RNA was quantified by qPCR in technical triplicate, normalizing values to cellular GAPDH-levels, and comparing to *Escherichia coli* rrsA mRNA and Arc RNA that could have carried over from protein purification. Table 2 shows primers used for the PCR reaction. The amount of cell-associated Cre RNA detected was >27-fold higher when Arc capsid were loaded with Cre RNA compared to control capsids not loaded with Cre RNA (FIG. 9).

TABLE 2

| Primers for qPCR quantification of RNA delivered by Arc capsids to HeLa cells | | |
|---|---|---|
| Gene-Primer | Sequence | SEQ ID NO: |
| GAPDH-F | AAGCTCATTTCCTGGTATGACAACGA | 62 |
| GAPDH-R | AGGGTCTCTCTCTTCCTCTTGTGCT | 63 |
| rrsA-F | GCTCAACCTGGGAACTGCATCTGAT | 64 |
| rrsA-R | TAATCCTGTTTGCTCCCCACGCTTT | 65 |
| Arc CDS-F | GGCCCCTCAGCTCCAGTGATTC | 66 |
| Arc CDS-R | CCTGTTGTCACTCTCCTGGCTCTGA | 67 |
| Cre CDS-F | GCCAAGACATAAGAAACCTCGCCT | 68 |
| Cre CDS-R | GTGAATCAACATCCTCCCTCCGTC | 69 |

FIG. 10 illustrates an alternative method of demonstrating the delivery of a heterologous RNA by an Arc or endo-Gag capsid. 6×His-tagged Arc or endo-Gag genes are expressed in a host cell. The resulting Arc monomers are mixed with translatable Cre mRNA under capsid forming conditions to form Cre mRNA loaded capsids. Cre-loaded capsids are then administered to LoxP-luciferase reporter mice. Upon successful delivery of Cre mRNA into mouse cells and subsequent translation of Cre recombinase protein, LoxP sites of the reporter are recombined, leading to luciferase expression, which is optionally detected by bioluminescence imaging upon administration of luciferin. This method is used to test the transmission potential of candidate Arc and endo-Gag genes. A positive luciferase signal indicates that the candidate Arc or endo-Gag gene encodes an Arc or endo-Gag protein capable of assembling into capsids that incorporate a heterologous cargo and deliver that cargo to a target cell.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TABLE 3

| Arc and endo-Gag amino acid and nucleotide sequences |
|---|

SEQ ID NO: 1
```
GELDHRTSGGLHAYPGPRGGQVAKPNVILQIGKCRAEMLEHVRRTHRHLLAEVSKQVERELKGLHRSVGKLESN
LDGYVPTSDSQRWKKSIKACLCRCQETIANLERWVKREMHVWREVFYRLERWADRLESTGGKYPVGSESARHT
VSVGVGGPESYCHEADGYDYTVSPYAITPPPAAGELPGQEPAEAQQYQPWVPGEDGQPSPGVDTQIFEDPREF
LSHLEEYLRQVGGSEEYWLSQIQNHMNGPAKKWWEFKQGSVKNWVEFKKEFLQYSEGTLSREAIQRELDLPQ
KQGEPLDQFLWRKRDLYQTLYVDADEEEIIQYVVGTLQPKLKRFLRHPLPKTLEQLIQRGMEVQDDLEQAAEPA
GPHLPVEDEAETLTPAPNSESVASDRTQPE
```

SEQ ID NO: 2
```
GELDQRTTGGLHAYPAPRGGPVAKPNVILQIGKCRAEMLEHVRRTHRHLLTEVSKQVERELKGLHRSVGKLESN
LDGYVPTGDSQRWRKSIKACLCRCQETIANLERWVKREMHVWREVFYRLERWADRLESMGGKYPVGSNPSR
HTTSVGVGGPESYGHEADTYDYTVSPYAITPPPAAGELPGQEAVEAQQYPPWGLGEDGQPSPGVDTQIFEDPR
EFLSHLEEYLRQVGGSEEYWLSQIQNHMNGPAKKWWEYKQGSVKNWVEFKKEFLQYSEGALSREAVQRELDL
PQKQGEPLDQFLWRKRDLYQTLYVDADEEEIIQYVVGTLQPKLKRFLRPPLPKTLEQLIQKGMEVEDGLEQVAEP
ASPHLPTEEESEALTPALTSESVASDRTQPE
```

SEQ ID NO: 3
```
GELDHRTTGGLHAYPAPRGGPAAKPNVILQIGKCRAEMLEHVRRTHRHLLAEVSKQVERELKGLHRSVGKLESN
LDGYVPTGDSQRWKKSIKACLSRCQETIANLERWVKREMHVWREVFYRLERWADRLESGGGKYPVGSDPARH
TVSVGVGGPESYCQDADNYDYTVSPYAITPPPAAGQLPGQEEVEAQQYPWAPGEDGQLSPGVDTQVFEDPR
EFLRHLEDYLRQVGGSEEYWLSQIQNHMNGPAKKWWEYKQGSVKNWVEFKKEFLQYSEGTLSREAIQRELDL
PQKQGEPLDQFLWRKRDLYQTLYVDAEEEEIIQYVVGTLQPKLKRFLRPPLPKTLEQLIQKGMEVQDGLEQAAEP
AAEEAEALTPALTNESVASDRTQPE
```

SEQ ID NO: 4
```
GELDRLNPSSGLHPSSGLHPYPGLRGGATAKPNVILQIGKCRAEMLEHVRKTHRHLLTEVSRQVERELKGLHKSV
GKLESNLDGYVPSSDSQRWKKSIKACLSRCQETIAHLERWVKREMNVWREVFYRLERWADRLEAMGGKYPAG
EQARRTVSVGVGGPETCCPGDESYDCPISPYAVPPSTGESPESLDQGDQHYQQWFALPEESPVSPGVDTQIFED
PREFLRHLEKYLKQVGGTEEDWLSQIQNHMNGPAKKWWEYKQGSVKNWLEFKKEFLQYSEGTLTRDALKREL
DLPQKQGEPLDQFLWRKRDLYQTLYVDADEEEIIQYVVGTLQPKLKRFLHHPLPKTLEQLIQRGQEVQNGLEPTD
DPAGQRTQSEDNDESLTPAVTNESTASEGTLPE
```

TABLE 3-continued

Arc and endo-Gag amino acid and nucleotide sequences

SEQ ID NO: 5

```
GQLDNVTNAGIHSFQGHRGVANKPNVILQIGKCRAEMLEHVRRTHRHLLSEVSKQVERELKGLQKSVGKLENN
LEDHVPTDNQRWKKSIKACLARCQETIAHLERWVKREMNVWKEVFFRLEKWADRLESMGGKYCPGEHGKQT
VSVGVGGPEIRPSEGEIYDYALDMSQMYALTPPPGEMPSIPQAHDSYQWVSVSEDAPASPVETQVFEDPREFLS
HLEEYLKQVGGTEEYWLSQIQNHMNGPAKKWWEYKQDSVKNWVEFKKEFLQYSEGTLTRDAIKRELDLPQKE
GEPLDQFLWRKRDLYQTLYVDADEEEIIQYVVGTLQPKLKRFLSYPLPKTLEQLIQRGKEVQGNMDHSDEPSPQR
TPEIQSGDSVESMPPSSTTASPVPSNGTQPEPPSPPATVI
```

SEQ ID NO: 6

```
GQLDNVTNAGIHSFQGHRGVANKPNVILQIGKCRAEMLEHVRRTHRHLLSEVSKQVERELKGLQKSVGKLENN
LEDHVPTDNQRWKKSIKACLARCQETIAHLERWVKREMNVWKEVFFRLEKWADRLESMGGKYCPGEHGKQT
VSVGVGGPEIRPSEGEIYDYALDMSQMYALTPPPGEVPSIPQAHDSYQWVSVSEDAPASPVETQVFEDPREFLS
HLEEYLKQVGGTEEYWLSQIQNHMNGPAKKWWEYKQDSVKNWVEFKKEFLQYSEGTLTRDAIKRELDLPQKE
GEPLDQFLWRKRDLYQTLYVDADEEEIIQYVVGTLQPKLKRFLSYPLPKTLEQLIQRGKEVQGNMDHSEEPSPQR
TPEIQSGDSVDSVPPSSTTASPVPSNGTQPE
```

SEQ ID NO: 7

```
GQLDNVTNAGIHSFQGHRGVANKPNVILQIGKCRAEMLEHVRRTHRHLLSEVSKQVERELKGLQKSVGKLENN
LEDHVPTDNQRWKKSIKACLARCQETIAHLERWVKREMNVWKEVFFRLEKWADRLESMGGKYCPGDHGKQT
VSVGVGGPEIRPSEGEIYDYALDMSQMYALTPPPGEVPSIPQAHDSYQWVSTSEDAPASPVETQVFEDPREFLS
HLEEYLKQVGGTEEYWLSQIQNHMNGPAKKWWEYKQDSVKNWVEFKKEFLQYSEGTLTRDAIKRELDLPQKE
GEPLDQFLWRKRDLYQTLYVDADEEEIIQYVVGTLQPKLKRFLSYPLPKTLEQLIQRGKEVQGNMDHSEEPSPQR
TPEIQSGDSVDSVPPSSTTASPVPSNGTQPE
```

SEQ ID NO: 8

```
GSWGLQRHVADERRGLATPTYGAVCSIREKKASQLSGQSCLEKELLGWKCTEAIVEMMQVDNFNHGNLHSCQ
GHRGMANHKPNVILQIGKCRAEMLDHVRRTHRHLLTEVSKQVERELKSLQKSVGKLENNLEDHVPSAAENQR
WKKSIKACLARCQETIAHLERWVKREINVWKEVFFRLEKWADRLESGGGKYGPGDQSRQTVSVGVGAPEIQPR
KEEIYDYALDMSQMYALTPPPMGEDPNVPQSHDSYQWITISDDSPPSPVETQIFEDPREFLTHLEDYLKQVGGT
EEYWLSQIQNHMNGPAKKWWEYKQDSVKNWLEFKKEFLQYSEGTLTRDAIKQELDLPQKDGEPLDQFLWRK
RDLYQTLYIDAEEEEVIQYVVGTLQPKLKRFLSHPYPKTLEQLIQRGKEVEGNLDNSEEPSPQRSPKHQLGGSVESL
PPSSTASPVASDETHPDVSAPPVTVI
```

SEQ ID NO: 9

```
GDGETQAENPSTSLNNTDEDILEQLKKIVMDQQHLYQKELKASFEQLSRKMFSQMEQMNSKQTDLLLEHQKQ
TVKHVDKRVEYLRAQFDASLGWRLKEQHADITTKIIPEIIQTVKEDISLCLSTLCSIAEDIQTSRATIVTGHAAVQTH
PVDLLGEHHLGTTGHPRLQSTRVGKPDDVPESPVSLFMQGEARSRIVGKSPIKLQFPTFGKANDSSDPLQYLERC
EDFLALNPLTDEELMATLRNVLHGTSRDWWDVARHKIQTWREFNKHFRAAFLSEDYEDELAERVRNIQKEDE
SIRDFAYMYQSLCKRWNPAICEGDVVKLILKNINPQLPSQLRSRVTTVDELVRLGQQLEKDRQNLQYELRKSSG
KIIQKSSSCETSALPNTKSTPNQQNPATSNRPPQVYCWRCKGHHAPASCPQWKADKHRAQPSRSSGPQTLTNL
QAQDI
```

SEQ ID NO: 10

```
GELDQRAAGGLRAYPAPRGGPVAKPSVILQIGKCRAEMLEHVRRTHRHLLTEVSKQVERELKGLHRSVGKLEGN
LDGYVPTGDSQRWKKSIKACLCRCQETIANLERWVKREMHVREVFYRLERWADRLESMGGKYPVGTNPSR
HTVSVGVGGPEGYSHEADTYDYTVSPYAITPPPAAGELPGQEAVEAQQYPPWGLGEDGQPGPGVDTQIFEDP
REFLSHLEEYLRQVGGSEEYWLSQIQNHMNGPAKKWWEFKQGSVKNWVEFKKEFLQYSEGTLSREAIQRELDL
PQKQGEPLDQFLWRKRDLYQTLYVDAEEEEIIQYVVGTLQPKLKRFLRPPLPKTLEQLIQKGMEVQDGLEQAAEP
ASPRLPPEEESEALTPALTSESVASDRTQPE
```

SEQ ID NO: 11

```
GQLDNVTNAGIHSFQGHRGVANKPNVILQIGKCRAEMLEHVRRTHRHLLSEVSKQVERELKGLQKSVGKLENN
LEDHVPTDNQRWKKSIKACLARCQETIAHLERWVKREMNVWKEVFFRLEKWADRLESMGGKYCPGEHGKQT
VSVGVGGPEIRPSEGEIYDYALDMSQMYALTPGPGEVPSIPQAHDSYQWVSVSEDAPASPVETQIFEDPHEFLS
HLEEYLKQVGGTEEYWLSQIQNHMNGPAKKWWEYKQDSVKNWVEFKKEFLQYSEGTLTRDAIKRELDLPQKE
GEPLDQFLWRKRDLYQTLYVDADEEEIIQYVVGTLQPKLKRFLSYPLPKTLEQLIQRGKEVQGNMDHSEEPSPQR
TPEIQSGDSVESMPPSSTTASPVPSNGTQPEPPSPPATVI
```

SEQ ID NO: 12

```
GQLENINQGSLHAFQGHRGVVHNNKPNVILQIGKCRAEMLEHVRRTHRHLLTEVSKQVERELKGLQKSVGKLE
NNLEDHVPSAAENQRWKKSIKACLARCQETIANLERWVKREMNVWKEVFFRLERWADRLESGGGKYCHADQ
GRQTVSVGVGGPEVRPSEGEIYDYALDMSQMYALTPPPMGDVPVIPQHDSYQWVTDPEEAPPSPVETQIFE
DPREFLTHLEDYLKQVGGTEEYWLSQIQNHMNGPAKKWWEYKQDSVKNWLEFKKEFLQYSEGTLTRDAIKQE
LDLPQKEGEPLDQFLWRKRDLYQTLYVEAEEEEVIQYVVGTLQPKLKRFLSHPYPKTLEQLIQRGKEVEGNLDNSE
EPSPQRTPEHQLGDSVESLPPSTTASPAGSDKTQPEISLPPTTVI
```

SEQ ID NO: 13

```
GQLDSVTNAGVHTYQGHRSVANKPNVILQIGKCRTEMLEHVRRTHRHLLTEVSKQVERELKGLQKSVGKLENN
LEDHVPTDNQRWKKSIKACLARCQETIAHLERWVKREMNVWKEVFFRLERWADRLESMGGKYCPTDSARQT
VSVGVGGPEIRPSEGEIYDYALDMSQMYALTPSPGELPSVPQHDSYQWVTSPEDAPASPVETQVFEDPREFLC
HLEEYLKQVGGTEEYWLSQIQNHMNGPAKKWWEYKQDTVKNWVEFKKEFLQYSEGTLTRDAIKRELDLPQKD
GEPLDQFLWRKRDLYQTLYIDADEEQIIQYVVGTLQPKLKRFLSYPLPKTLEQLIQKGKEVQGSLDHSEEPSPQRA
SEARTGDSVETLPPSTTTSPNTSSGTQPEAPSPPATVI
```

SEQ ID NO: 14

```
GQLDSVTNAGVHTYQGHRGVANKPNVILQIGKCRTEMLEHVRRTHRHLLTEVSKQVERELKGLQKSVGKLENN
LEDHVPTDNQRWKKSIKACLARCQETIAHLERWVKREMNVWKEVFFRLERWADRLESMGGKYCPTDSARQT
```

TABLE 3-continued

Arc and endo-Gag amino acid and nucleotide sequences

VSVGVGGPEIRPSEGEIYDYALDMSQMYALTPSPGELPSIPQPHDSYQWVTSPEDAPASPVETQVFEDPREFLC
HLEEYLKQVGGTEEYWLSQIQNHMNGPAKKWWEYKQDTVKNWVEFKKEFLQYSEGTLTRDAIKRELDLPQKD
GEPLDQFLWRKRDLYQTLYIDADEEQIIQYVVGTLQPKLKRFLSYPLPKTLEQLIQKGKEVQGSLDHSEEPSPQRA
SEARTGDSVESLPPSTTTSPNASSGTQPEAPSPPATVI

SEQ ID NO: 15

GQLENVNHGNLHSFQGHRGGVANKPNVILQIGKCRAEMLDHVRRTHRHLLTEVSKQVERELKGLQKSVGKLE
NNLEDHVPSAVENQRWKKSIKACLSRCQETIAHLERWVKREMNVWKEVFFRLERWADRLESGGGKYCHGDN
HRQTVSVGVGGPEVRPSEGEIYDYALDMSQMYALTPPSPGDVPVVSQPHDSYQWVTVPEDTPPSPVETQIFED
PREFLTHLEDYLKQVGGTEEYWLSQIQNHMNGPAKKWWEYKQDSVKNWLEFKKEFLQYSEGTLTRDAIKEELD
LPQKDGEPLDQFLWRKRDLYQTLYVEADEEEVIQYVVGTLQPKLKRFLSHPYPKTLEQLIQRGKEVEGNLDNSEE
PTPQRTPEHQLCGSVESLPPSSTVSPVASDGTQPETSPLPATVI

SEQ ID NO: 16

GPLTLLQDWCRGEHLNTRRCMLILGIPEDCGEDEFEETLQEACRHLGRYRVIGRMFRREENAQAILLELAQDIDY
ALLPREIPGKGGPWEVIVKPRNSDGEFLNRLNRFLEEERRTVSDMNRVLGSDTNCSAPRVTISPEFWTWAQTLG
AAVQPLLEQMLYRELRVFSGNTISIPGALAFDAWLEHTTEMLQMWQVPEGEKRRRLMECLRGPALQVVSGLR
ASNASITVEECLAALQQVFGPVESHKIAQVKLCKAYQEAGEKVSSFVLRLEPLLQRAVENNVVSRRNVNQTRLKR
VLSGATLPDKLRDKLKLMKQRRKPPGFLALVKLLREEEEWEATLGPDRESLEGLEVAPRPPARITGVGAVPLPAS
GNSFDARPSQGYRRRRGRGQHRRGGVARAGSRGSRKRKRHTFCYSCGEDGHIRVQCINPSNLLLAKETKEILEG
GEREAQTNSR

SEQ ID NO: 17

GALTLLEDWCKGMDMDPRKALLIVGIPMECSEVEIQDTVKAGLQPLCAYRVLGRMFRREDNAKAVFIELADTV
NYTTLPSHIPGKGGSWEVVVKPRNPDDEFLSRLNYFLKDEGRSMTDVARALGCCSLPAESLDAEVMPQVRSPPL
EPPKESMWYRKLKVFSGTASPSPGEETFEDWLEQVTEIMPIWQVSEVEKRRRLLESLRGPALSIMRVLQANNDS
ITVEQCLDALKQIFGDKEDFRASQFRFLQTSPKIGEKVSTFLLRLEPLLQKAVHKSPLSVRSTDMIRLKHLLARVAM
TPALRGKLELLDQRGCPPNFLELMKLIRDEEEWENTEAVMKNKEKPSGRGRGASGRQARAEEASVSAPQATVQA
RSFSDSSPQTIQGGLPPLVKRRRLLGSESTRGEDHGQATYPKAENQTPGREGPQAAGEELGNEAGAGAMSHPK
PWET

SEQ ID NO: 18

GAVTMLQDWCRWMGVNARRGLLILGIPEDCDDAEFQESLEAALRPMGHFTVLGKAFREEDNATAALVELDRE
VNYALVPREIPGTGGPWNVVFVPRCSGEEFLGLGRVFHFPEQEGQMVESVAGALGVGLRRVCWLRSIGQAVQ
PWVEAVRCQSLGVFSGRDQPAPGEESFEVWLDHTTEMLHVWQGVSERERRRRLLEGLRGTALQLVHALLAEN
PARTAQDCLAALAQVFGDNESQATIRVKCLTAQQQSGERLSAFVLRLEVLLQKAMEKEALARASADRVRLRQM
LTRAHLTEPLDEALRKLRMAGRSPSFLEMLGLVRESEAWEASLARSVRAQTQEGAGARAGAQAVARASTKVEA
VPGGPGREPEGLLQAGGQEAEELLQEGLKPVLEECDN

SEQ ID NO: 19

GAVTMLQDWCRWMGVNARRGLLILGIPEDCDDAEFQESLEAALRPMGHFTVLGKVFREEDNATAALVELDRE
VNYALVPREIPGTGGPWNVVFVPRCSGEEFLGLGRVFHFPEQEGQMVESVAGALGVGLRRVCWLRSIGQAVQ
PWVEAVRYQSLGVFSGRDQPAPGEESFEVWLDHTTEMLHVWQGVSERERRRRLLEGLRGTALQLVHALLAEN
PARTAQDCLAALAQVFGDNESQATIRVKCLTAQQQSGERLSAFVLRLEVLLQKAMEKEALARASADRVRLRQM
LTRAHLTEPLDEALRKLRMAGRSPSFLEMLGLVRESEAWEASLARSVRAQTQEGAGARAGAQAVARASTKVEA
VPGGPGREPEGLRQAGGQEAEELLQEGLKPVLEECDN

SEQ ID NO: 20

GVEDLAASYIVLKLENEIRQAQVQWLMEENAALQAQIPELQKSQAAKEYDLLRKSSEAKEPQKLPEHMNPPAA
WEAQKTPEFKEPQKPPEPQDLLPWEPPAAWELQEAPAAPESLAPPATRESQKPPMAHEIPTVLEGQGPANTQ
DATIAQEPKNSEPQDPPNIEKPQEAPEYQETAAQLEFLELPPPQEPLEPSNAQEFLELSAAQESLEGLIVVETSAAS
EFPQAPIGLEATDFPLQYTLTFSGDSQKLPEFLVQLYSYMRVRGHLYPTEAALVSFVGNCFSGRAGWWFQLLLDI
QSPLLEQCESFIPVLQDTFDNPENMKDANQCIHQLCQGEGHVATHFHLIAQELNWDESTLWIQFQEGLASSIQ
DELSHTSPATNLSDLITQCISLEEKPDPNPLGKSSSAEGDGPESPPAENQPMQAAINCPHISEAEWVRWHKGRL
CLYCGYPGHFARDCPVKPHQALQAGNIQACQ

SEQ ID NO: 21

GVQPQTSKAESPALAASPNAQMDDVIDTLTSLRLTNSALRREASTLRAEKANLTNMLESVMAELTLLRTRARIPG
ALQITPPISSITSNGTRPMTTPPTSLPEPFSGDPGRLAGFLMQMDRFMIFQASRFPGEAERVAFLVSRLTGEAEK
WAIPHMQPDSPLRNNYQGFLAELRRTYKSPLRHARRAQIRKTSASNRAVRERQMLCRQLASAGTGPCPVHPAS
NGTSPAPALPARARNL

SEQ ID NO: 22

GDGRVQLMKALLAGPLRPAARRWRNPIPFPETFDGDTDRLPEFIVQTSSYMFVDENTFSNDALKVTFLITRLTGP
ALQWVIPYIRKESPLLNDYRGFLAEMKRVFGWEEDEDF

SEQ ID NO: 23

GEGRVQLMKALLARPLRPAARRWRNPIPFPETFDGDTDRLPEFIVQTSSYMFVDENTFSNDALKVTFLITRLTGP
ALQWVIPYIKKESPLLSDYRGFLAEMKRVFGWEEDEDF

SEQ ID NO: 24

GPRGRCRQQGPRIPIWAAANYANAHPWQQMDKASPGVAYTPLVDPWIERPCCGDTVCVRTTMEQKSTASG
TCGGKPAERGPLAGHMPSSRPHRVDFCWVPGSDPGTFDGSPWLLDRFLAQLGDYMSFHFEHYQDNISRVCEI
LRRLTGRAQAWAAPYLDGDLPLPDDYELFCQDLKEVVQDPNSFAEYHAVVICPLPLASSQLPVAPQLPVVRQYL
ARFLEGLALDMGTAPRSLPAAMATPAVSGSNSVSRSALFEQQLTKESTPGPKEPPVLPSSTCSSKPGPVEPASSQ
PEEAAPTPVPRLSESANPPAQRPDPAHPGGPKPQKTEEEVLETEGDQEVSLGTPQEVVEAPETPGEPPLSPGF

TABLE 3-continued

Arc and endo-Gag amino acid and nucleotide sequences

SEQ ID NO: 25

GVDELVLLLHALLMRHRALSIENSQLMEQLRLLVCERASLLRQVRPPSCPVPFPETFNGESSRLPEFIVQTASYML
VNENRFCNDAMKVAFLISLLTGEAEEWVVPYIEMDSPILGDYRAFLDEMKQCFGWDDDEDDDDEEEEDDY

SEQ ID NO: 26

GPVDLGQALGLLPSLAKAEDSQFSESDAALQEELSSPETARQLFRQFRYQVMSGPHETLKQLRKLCFQWLQPEV
HTKEQILEILMLEQFLTILPGEIQMWVRKQCPGSGEEAVTLVESLKGDPQRLWQWISIQVLGQDILSEKMESPSC
QVGEVEPHLEVVPQELGLENSSSGPGELLSHIVKEESDTEAELALAASQPARLEERLIRDQDLGASLLPAAPQEQ
WRQLDSTQKEQYWDLMLETYGKMVSGAGISHPKSDLTNSIEFGEELAGIYLHVNEKIPRPTCIGDRQENDKENL
NLENHRDQELLHASCQASGEVPSQASLRGFFTEDEPGCFGEGENLPEALQNIQDEGTGEQLSPQERISEKQLGQ
HLPNPHSGEMSTMWLEEKRETSQKGQPRAPMAQKLPTCRECGKTFYRNSQLIFHQRTHTGETYFQCTICKKAF
LRSSDFVKHQRTHTGEKPCKCDYCGKGFSDFSGLRHHEKIHTGEKPYKCPICEKSFIQRSNFNRHQRVHTGEKPY
KCSHCGKSFSWSSSLDKHQRSHLGKKPFQ

SEQ ID NO: 27

GTLRLLEDWCRGMDMNPRKALLIAGISQSCSVAEIEEALQAGLAPLGEYRLLGRMFRRDENRKVALVGLTAETS
HALVPKEIPGKGGIWRVIFKPPDPDNTFLSRLNEFLAGEGMTVGELSRALGHENGSLDPEQGMIPEMWAPMLA
QALEALQPALQCLKYKKLRVFSGRESPEPGEEEFGRWMFHTTQMIKAWQVPDVEKRRRLLESLRGPALDVIRVL
KINNPLITVDECLQALEEVFGVTDNPRELQVKYLTTYHKDEEKLSAYVLRLEPLLQKLVQRGAIERDAVNQARLDQ
VIAGAVHKTIRRELNLPEDGPAPGFLQLLVLIKDYEAAEEEEEALLQAILEGNFT

SEQ ID NO: 28

GTERRRDELSEEINNLREKVMKQSEENNNLQSQVQKLTEENTTLREQVEPTPEDEDDDIELRGAAAAAAPPPPIE
EECPEDLPEKFDGNPDMLAPFMAQCQIFMEKSTRDFSVDRVRVCFVTSMMTGRAARWASAKLERSHYLMHN
YPAFMMEMKHVFEDPQRREVAKRKIRRLRQGMGSVIDYSNAFQMIAQDLDWNEPALIDQYHEGLSDHIQEEL
SHLEVAKSLSALIGQCIHIERRLARAAAARKPRSPPRALVLPHIASHHQVDPTEPVGGARMRLTQEEKERRRKLNL
CLYCGTGGHYADNCPAKASKSSPAGKLPGPAVEGPSATGPEIIRSPQDDASSPHLQVMLQIHLPGRHTLFVRAM
IDSGASGNFIDHEYVAQNGIPLRIKDWPILVEAIDGRPIASGPVVHETHDLIVDLGDHREVLSFDVTQSPFFPVVL
GVRWLSTHDPNITWSTRSIVFDSEYCRYHCRMYSPIPPSLPPPAPQPPLYYPVDGYRVYQPVRYYYVQNVYTPV
DEHVYPDHRLVDPHIEMIPGAHSIPSGHVYSLSEPEMAALRDFVARNVKDGLITPTIAPNGAQVLQVKRGWKL
QVSYDCRAPNNFTIQNQYPRLSIPNLEDQAHLATYTEFVPQIPGYQTYPTYAAYPTYPVGFAWYPVGRDGQGRS
LYVPVMITWNPHWYRQPPVPQYPPPQPPPPPPPPPPPPPSYSTL

SEQ ID NO: 29

GGGGAGCTGGACCACCGGACCAGCGGCGGGCTCCACGCCTACCCCGGGCCGCGGGGCGGGCAGGTGGCC
AAGCCCAACGTGATCCTGCAGATCGGGAAGTGCCGGGCCGAGATGCTGGAGCACGTGCGGCGGACGCAC
CGGCACCTGCTGGCCGAGGTGTCCAAGCAGGTGGAGCGCGAGCTGAAGGGGCTGCACCGGTCGGTCGGG
AAGCTGGAGAGCAACCTGGACGGCTACGTGCCCACGAGCGACTCGCAGCGCTGGAAGAAGTCCATCAAG
GCCTGCCTGTGCCGCTGCCAGGAGACCATCGCCAACCTGGAGCGCTGGGTCAAGCGCGAGATGCACGTGT
GGCGCGAGGTGTTCTACCGCCTGGAGCGCTGGGCCGACCGCCTGGAGTCCACGGGCGGCAAGTACCCGGT
GGGCAGCGAGTCAGCCCGCCACACCGTTTCCGTGGGCGTGGGGGGTCCCGAGAGCTACTGCCACGAGGC
AGACGGCTACGACTACACCGTCAGCCCCTACGCCATCACCCCGCCCCCAGCCGCTGGCGAGCTGCCCGGGC
AGGAGCCCGCCGAGGCCCAGCAGTACCAGCCGTGGGTCCCCGGCGAGGACGGGCAGCCCAGCCCCGGCG
TGGACACGCAGATCTTCGAGGACCCTCGAGAGTTCCTGAGCCACCTAGAGGAGTACTTGCGGCAGGTGGG
CGGCTCTGAGGAGTACTGGCTGTCCCAGATCCAGAATCACATGAACGGGCCGGCCAAGAAGTGGTGGGA
GTTCAAGCAGGGCTCCGTGAAGAACTGGGTGGAGTTCAAGAAGGAGTTCCTGCAGTACAGCGAGGGCAC
GCTGTCCCGAGAGGCCATCCAGCGCGAGCTGGACCTGCCGCAGAAGCGGGCGAGCCGCTGGACCAGTTC
CTGTGGCGCAAGCGGGACCTGTACCAGACGCTCTACGTGGACGCGGACGAGGAGGAGATCATCCAGTAC
GTGGTGGGCACCCTGCAGCCCAAGCTCAAGCGTTTCCTGCGCCACCCCCTGCCCAAGACCCTGGAGCAGCT
CATCCAGAGGGGCATGGAGGTGCAGGATGACCTGGAGCAGGCGGCCGAGCCGGCCGGCCCCCACCTCCC
GGTGGAGGATGAGGCGGAGACCCTCACGCCCGCCCCCAACAGCGAGTCCGTGGCCAGTGACCGGACCCA
GCCCGAG

SEQ ID NO: 30

GGGGAATTGGATCAACGTACTACCGGTGGCCTTCACGCATACCCTGCACCACGCGGGGGCCCTGTCGCGA
AGCCAAATGTCATCCTGCAGATTGGGAAGTGCCGGGCTGAGATGCTGGAGCACGTCCGTCGGACGCATCG
TCATCTTCTTACTGAGGTGTCAAAACAGGTGGAGCGTGAACTCAAAGGCTTGCACCGCAGCGTTGGGAAAC
TTGAAAGCAACTTAGATGGCTATGTGCCGACTGGCGACAGCCAGCGTTGGCGTAAGTCCATCAAAGCATGT
TTGTGTCGTTGCCAGGAAACGATTGCAAACCTGGAGCGTTGGGTCAAACGGGAGATGCATGTCTGGCGTG
AAGTATTTTATCGTTTAGAGCGTTGGGCCGATCGTTTAGAGAGACATGGGTGGTAAGTACCCTGTGGGGAGC
AACCCTTCTCGGCATACGACGTCAGTCGGTGTTGGCGGGCCGGAGTCCTACGGTCATGAAGCGGACACCTA
CGACTATACCGTAAGCCCTTATGCTATTACCCCACCACCTGCGGCCGGCGAATTACCTGGCCAGGAAGCCG
TTGAGGCTCAACAATACCCTCCTTGGGGGCTGGGCGAGGATGGTCAACCTAGCCCAGGGGTAGACACGCA
AATCTTTGAGGACCCACGGGAGTTTCTTTCCCACCTGGAAGAATACCTGCGTCAGGTTGGTGGGACGCGAAG
AATACTGGCTGTCACAAATTCAAAACCATATGAATGGTCCTGCAAAAAAATGGTGGGAATATAAACAGGGT
TCCGTGAAAAACTGGGTTGAGTTTAAAAAGGAGTTTCTTCAATATTCCGAGGGCGCCCTCAGTCGGGAGGC
GGTCCAACGCGAGTTGGACTTGCCACAGAAACAGGGGGAACCACTCGATCAATTCCTTTGGCGGAAACGT
GACCTTTACCAGACATTGTACGTGGATGCAGATGAGGAAGAAATTACCTGCGTCAGGTTGGTGGGACCTGCA
GCCGAAACTGAAACGTTTCCTTCGCCCGCCGCTGCCTAAAACGTTGGAACAACTTATTCAGAAAGGTATGG
AGGTCGAGGATGGCTTAGAACAAGTCGCAGAGCCGGCCTCGCCACACTTGCCTACAGAGGAGGAATCGGA
GGCGCTGACCCCAGCACTTACATCAGAGTCAGTGGCATCAGACCGGACACAACCAGAG

SEQ ID NO: 31

GGGGAGTTAGATCACCGTACAACGGGGGGGTTGCACGCATACCCTGCTCCACGTGGCGGGCCGGCAGCTA
AGCCAAACGTAATCCTGCAGATTGGGAAGTGCCGGGCAGAGATGTTGGAGCACGTCCGGCGGACCCACCG
GCACCTCCTGGCTGAAGTGTCTAAACAAGTAGAACGGGAACTCAAAGGTCTTCATCGTAGCGTCGGGAAAT
TGGAATCGAATTTGGACGGGTATGTTCCTACAGGCGACTCACAGCGGTGGAAAAAGAGCATCAAGGCCTG

TABLE 3-continued

Arc and endo-Gag amino acid and nucleotide sequences

```
CCTGAGTCGCTGCCAGGAGACGATTGCTAACCTCGAACGCTGGGTTAAGCGGGAGATGCACGTTTGGCGC
GAAGTCTTCTACCGGCTGGAGCGTTGGGCTGATCGGCTCGAATCTGGTGGGGGTAAGTATCCAGTTGGGT
CCGACCCTGCTCGCCACACAGTCTCAGTTGGCGTAGGTGGGCCGGAGTCGTATTGCCAAGATGCGGACAA
CTATGATTATACAGTTTCCCCATACGCGATCACACCACCGCCGGCAGCAGGGCAGCTGCCAGGTCAGGAAG
AGGTTGAGGCCCAGCAGTATCCACCATGGGCCCCAGGGGAAGACGGCCAGCTTTCTCCTGGGGTGGACAC
TCAAGTTTTTGAAGATCCGCGTGAATTTCTGCGGCATTTGAAGATTATCTCCGCCAGGTCGGGGGGTCTG
AAGAGTATTGGTTAAGCCAAATTCAAAACCATATGAACGGCCCGGCCAAGAAGTGGTGGGAGTACAAGCA
AGGGTCTGTGAAAAATTGGGTGGAGTTTAAGAAAGAATTCTTGCAATATTCTGAGGGCACTCTTTCGCGTG
AAGCCATCCAACGCGAACTCGACTTACCGCAGAAACAAGGGGAACCTCTCGACCAATTTCTGTGGCGCAAA
CGCGACCTGTACCAGACTCTTTACGTCGATGCTGAGGAGGAAGAAATTATTCAATACGTAGTTGGCACACT
GCAGCCTAAGCTTAAACGGTTTTTACGTCCACCATTGCCGAAGACGCTTGAACAACTCATCCAGAAGGGTA
TGGAGGTTCAAGATGGTCTGGAACAGGCAGCGGAACCAGCGGCGGAGGAGGCAGAAGCCCTGACACCTG
CGTTAACTAACGAGTCTGTCGCGAGCGACCGCACCCAGCCGGAA
```

SEQ ID NO: 32

```
GGGGAATTAGACCGCCTGAACCCAAGCTCAGGCCTGCATCCATCCTCTGGTTTGCATCCATACCCAGGTCTC
CGGGGCGGGGCAACCGCGAAGCCTAATGTCATTTTGCAAATTGGCAAATGCCGTGCGGAAATGCTTGAAC
ACGTCCGCAAAACTCACCGTCATCTCCTCACAGAAGTATCGCGCCAAGTAGAACGCGAGCTCAAAGGCCTT
CACAAAAGTGTTGGCAAGTTGGAATCAAATCTTGATGGGTACGTACCGTCAAGCGACTCCCAACGCTGGAA
GAAAAGCATTAAGGCGTGCTTATCCCGTTGCCAAGAGACGATTGCGCATTTAGAACGCTGGGTTAAACGTG
AAATGAATGTATGGCGTGAGGTGTTCTACCGTTTGGAACGTTGGGCGGACCGTCTGGAGGCTATGGGCGG
TAAGTATCCTGCCGGTGAGCAGGCCCGGCGTACAGTTTCAGTGGGCGTTGGGGGCCCTGAGACATGTTGT
CCAGGGGATGAAAGTTATGATTGTCCGATTTCTCCGTATGCAGTTCCACCTTCCACCGGCGAGTCTCCGGAA
TCCTTAGACCAAGGGGATCAGCACTATCAGCAGTGGTTTGCCCTCCCGGAGGAGTCCCCTGTTAGCCCTGG
GGTTGATACCCAGATCTTTGAAGATCCTCGCGAGTTTTTACGTCATCTGGAGAAGTACCTGAAACAAGTCG
GCGGGACAGAGGAAGACTGGCTTTCTCAAATCCAGAATCACATGAATGGGCCGGCGAAGAAGTGGTGGG
AGTACAAGCAAGGGAGTGTTAAGAATTGGCTTGAATTTAAGAAGGAATTTTTACAGTATTCGGAGGGCAC
ACTGACGCGGGACGCGTTGAAACGTGAACTGGATCTCCCACAGAAACAAGGCGAACCACTTGATCAATTTT
TATGGCGGAAGCGCGACTTATATCAGACACTCTACGTTGACGCCGATGAAGAGGAAATCATTCAGTACGTC
GTGGGCACTCTTCAGCCGAAATTAAAACGCTTTCTCCATCACCCACTCCCTAAGACGCTTGAGCAGCTTATC
CAACGGGGCCAAGAAGTTCAGAATGGTCTGGAGCCTACCGACGATCCTGCAGGCCAACGCACTCAATCGG
AGGACAACGACGAAAGCCTTACCCCTGCCGTCACCAATGAGAGTACTGCAAGCGAGGGCACCCTGCCAGA
G
```

SEQ ID NO: 33

```
GGGCAGCTTGATAACGTTACAAACGCGGGCATCCACTCCTTCCAGGGGCATCGTGGCGTAGCGAATAAGC
CAAATGTCATTCTGCAAATTGGTAAATGTCGTGCGGAAATGCTGGAGCACGTTCGCCGCACCCACCGCCAT
TTATTATCTGAAGTATCTAAGCAGGTAGAACGTGAGCTGAAAGGGCTGCAAAAGTCCGTGGGCAAGCTCG
AGAATAACTTGGAGGATCATGTCCCTACAGATAACCAACGCTGGAAGAAGTCCATTAAAGCGTGCTTGGCT
CGTTGTCAAGAGACTATCGCGCATTTAGAGCGTTGGGTGAAACGCGAAATGAACGTCTGGAAGGAGGTGT
TTTTCCGGCTGGAAAAGTGGGCAGACCGGCTGGAGTCAATGGGTGGCAAGTACTGCCCGGGCGAACACG
GGAAACAAACCGTCAGTGTAGGCGTGGGGGGTCCTGAAATCCGGCCTTCGGAGGGGGAAATTTATGATTA
TGCTCTGGATATGAGCCAGATGTATGCACTCACCCCCACCTCCAGGCGAAATGCCATCAATCCCACAAGCCCA
TGACAGCTATCAGTGGGTTAGTGTCTCAGAAGATGCCCCGGCGAGCCCTGTCGAAACCCAGGTATTTGAGG
ACCCTCGGGAATTCCTGTCTCACCTGGAGGAATACCTGAAGCAGGTAGGCGGCACGGAGGAGTATTGGTT
GTCCCAGATCCAGAATCACATGAATGGTCCGGCAAAAAAATGGTGGGAATATAAACAGGACTCCGTTAAA
AACTGGGTTGAGTTTAAAAAGGAATTCTTGCAATACTCTGAAGGTACTTTAACTCGGGATGCTATTAAGCGT
GAACTCGACTTGCCGCAAAAGGAAGGTGAACCTCTTGACCAATTCCTTTGGCGGAAGCGGGACCTCTATCA
GACACTTTACGTGGACGCGGATGAGGAGGAGATCATTCAGTATGTGGTCGGTACCCTGCAGCCGAAGCTC
AAGCGTTTCCTGAGCTATCCTCTCCCAAAGACTTTAGAACAGCTCATCCAGCGCGGTAAAGAAGTGCAGGG
TAACATGGATCACTCCGATGAGCCTTCGCCGCAGCGTACACCTGAAATTCAATCAGGTGACTCCGTAGAAT
CTATGCCACCTTCAACAACGGCATCTCCGGTTCCATCTAATGGTACCCAACCTGAGCCGCCGAGCCCGCCAG
CCACCGTTATC
```

SEQ ID NO: 34

```
GGGCAACTTGACAACGTAACAAACGCTGGGATTCACTCCTTTCAGGGCCACCGCGGTGTCGCCAACAAGCC
AAACGTAATCTTGCAAATTGGCAAATGCCGTGCGGAGATGTTGGAACACGTTCGTCGTACACATCGTCACT
TGCTGTCGGAAGTCTCTAAACAAGTAGAACGTGAACTTAAAGGGCTTCAAAGTCAGTCGGCAAATTGGAA
AACAACCTTGAAGACCATGTACCAACCGACAATCAGCGTTGGAAAAAGTCTATCAAAGCTTGCCTGGCCCG
TTGTCAAGAGACGATTGCTCACCTGGAGCGGTGGGTAAAGCGCGAGATGAATGTGTGGAAAGAGGTCTTC
TTCCGCTTGGAAAAATGGGCCGACCGTTTGGAGTCCATGGGCGGTAAATATTGTCCGGGTGAACATGGTA
AGCAAACAGTCTCTGTGGGCGTTGGTGGGCCGGAGATTCGGCCTTCTGAAGGCGAGATTTACGATTATGC
GCTCGACATGTCCCAGATGTATGCGCTTACACCACCACCGGGCGAGGTACCAAGCATTCCTCAAGCGCATG
ACAGTTATCAGTGGGTTAGCGTATCCGAAGACGCTCCTGCCTCGCCGGTAGAGACCCAGGTTTTTGAAGAT
CCTCGTGAATTTTTAAGCCACTTGGAGGAGTATTTGAAGCAGGTAGGGGGACAGAGGAATATTGGCTGT
CTCAGATCCAGAACCACATGAATGGCCCGGCTAAAAAGTGGTGGGAATACAAACAAGATTCGGTAAAGAA
TTGGGTAGAATTTAAAAAGGAGTTTTTACAGTACTCAGAGGGGACTCTCACGCGTGATGCGATCAAACGCG
AGTTGGATCTTCCTCAAAAAGAGGGGGAGCCACTCGATCAGTTCCTCTGGCGCAAGCGGGATCTCTACCAA
ACACTCTACGTAGACGCAGACGAAGAAGAGATCATCCAGTACGTGGTGGGTACGCTCCAGCCGAAACTCA
AACGTTTCCTCAGCTACCCACTTCCTAAGACTCTGGAACAACTGATTCAGCGGGCAAAGAGGTCCAGGGT
AACATGGACCATTCAGAGGAACCTAGTCCGCAACGTACACCTGAGATCCAATCTGGGGATTCTGTCGATTC
GGTTCCACCTTCTACAACAGCGTCTCCGGTGCCGTCAAATGGGACCCAACCAGAG
```

SEQ ID NO: 35

```
GGGCAGCTTGATAATGTAACCAATGCAGGTATCCACTCTTTCCAGGGTCACCGCGGTGTGGCAAACAAGCC
AAATGTTATTCTGCAAATTGGTAAGTGTCGCGCTGAGATGTTAGAACACGTCCGGCGCACGCATCGGCATC
TCCTGTCAGAGGTTTCAAAGCAGGTAGAGCGTGAATTAAAGGGCCTCCAGAAGTCCGTAGGTAAACTCGA
AAATAATCTTGAAGACCACGTTCCTACCGATAATCAACGGTGGAAAAAGTCAATCAAGGCGTGCTTAGCAC
```

TABLE 3-continued

Arc and endo-Gag amino acid and nucleotide sequences

```
GGTGTCAGGAAACGATCGCGCACCTCGAACGTTGGGTGAAGCGCGAAATGAATGTCTGGAAAGAAGTGTT
CTTCCGGCTTGAGAAGTGGGCTGATCGGCTCGAATCCATGGGTGGCAAATATTGTCCAGGTGATCATGGCA
AGCAAACGGTCTCCGTCGGTGTTGGTGGTCCGGAAATCCGGCCGAGCGAGGGTGAAATCTATGACTACGC
TCTTGATATGTCCCAGATGTATGCACTCACTCCTCCGCCGGGTGAGGTCCCGTCGATCCCGCAGGCGCATGA
CTCATACCAATGGGTGTCGACTAGCGAAGACGCACCAGCCTCCCCTGTTGAAACTCAAGTATTCGAGGACC
CGCGTGAGTTCCTGAGCCATTTAGAGGAGTACCTTAAGCAGGTTGGTGGTACCGAGGAATACTGGTTGAG
CCAGATTCAGAATCACATGAACGGGCCGGCTAAGAAATGGTGGGAATACAAGCAGGATTCAGTCAAGAAT
TGGGTCGAATTTAAGAAGGAGTTTTTGCAGTACAGTGAGGGGACGCTCACACGCGACGCTATCAAACGGG
AGCTGGACCTGCCACAAAAGGAGGGTGAACCGCTTGATCAGTTTCTTTGGCGCAAGCGTGATCTGTATCAA
ACCCTGTATGTGGACGCTGACGAAGAAGAGATCATTCAGTACGTGGTTGGGACTCTGCAACCAAAGCTGA
AGCGTTTTCTTTCTTATCCTCTCCCTAAGACACTGGAACAGTTAATCCAACGTGGCAAGGAGGTCCAGGGTA
ATATGGACCACTCTGAGGAACCGAGCCCGCAACGTACTCCTGAAATTCAGAGCGGGGATAGTGTCGACTC
AGTTCCTCCAAGTACGACCGCATCCCCGGTCCCAAGTAACGGTACCCAACCAGAG
```

SEQ ID NO: 36

```
GGGTCTTGGGGCTTGCAACGTCACGTGGCTGATGAACGTCGTGGCCTCGCTACGCCTACCTACGGCGCGGT
TTGTTCCATTCGGGAGAAAAAGCCTCCCAACTGAGCGGCCAGAGCTGTTTGGAGAAAGAGTTGCTTGGTT
GGAAATGTACGGAGGCAATCGTGGAAATGATGCAAGTCGATAACTTTAACCACGGTAACTTACATAGCTGC
CAAGGCCATCGGGGGATGGCAAATCACAAACCGAACGTAATCCTTCAAATCGGGAAATGTCGCGCAGAAA
TGTTAGACCACGTGCGTCGCACCCACCGCCATCTCTTGACGGAGGTTTCGAAGCAGGTAGAACGCGAATTG
AAGTCTCTCCAAAAGTCGGTTGGCAAGCTCGAGAATAATCTGGAAGACCACGTGCCATCGGCAGCGGAGA
ACCAACGTTGGAAGAAATCAATTAAAGCCTGCCTGGCCCGGTGCCAAGAAACAATTGCTCACCTCGAACGC
TGGGTTAAACGCGAAATCAACGTCTGGAAAGAAGTATTCTTTCGTCTGGAGAAGTGGGCGGACCGCCTTG
AGTCGGGTGGGGGCAAGTATGGGCCTGGTGACCAAAGTCGTCAAACTGTAAGTGTCGGTGTTGGGGCCCC
AGAAATCCAACCGCGGAAAGAAGAAATCTATGACTACGCTCTCGACATGTCGCAGATGTATGCCTTAACAC
CACCGCCGATGGGTGAAGACCCAAACGTACCTCAATCCCACGATAGCTACCAGTGGATTACCATCTCAGAC
GATTCACCTCCGTCGCCAGTGGAAACTCAAATTTTCGAGGATCCACGCGAATTCCTTACCCATCTCGAGGAT
TATCTTAAGCAAGTGGGCGGGACTGAAGAATATTGGTTGAGTCAGATTCAAAATCATATGAACGGTCCGGC
CAAGAAATGGTGGGAGTACAAACAAGATTCCGTGAAAAACTGGTTGGAATTCAAGAAGGAATTCCTTCAA
TACTCTGAGGGGTACTTTGACACGTGACGCAATTAAACAAGAACTTGACTTACCGCAGAAGGACGGCGAGCC
ATTGGATCAATTTCTTTGGCGGAAGCGGGACCTGTATCAGACGCTCTATATTGATGCAGAGGAGGAAGAA
GTAATCCAATACGTTGTTGGCACACTCCAACCGAAATTAAAACGTTTCCTTTCCCACCCGTATCCGAAAACTT
TGGAACAGTTAATCCAACGTGGGAAAGAGGTGGAAGGCAACCTCGATAACTCTGAGGAGCCTAGCCCGCA
ACGGAGTCCAAAGCACCAATTGGGTGGTAGCGTCGAGAGCCTCCCACCTTCGTCGACCGCAAGTCCTGTTG
CGTCAGACGAGACTCACCCAGACGTGAGCGCACCTCCGGTAACGGTGATT
```

SEQ ID NO: 37

```
GGGGACGGCGAGACTCAAGCTGAGAATCCATCTACCAGCTTGAACAACACTGACGAAGATATCTTGGAAC
AGCTCAAGAAAATTGTCATGGATCAACAACACCTGTATCAGAAAGAATTAAAGGCATCTTTTGAACAACTC
AGTCGCAAAATGTTTTCCCAGATGGAACAAATGAATAGCAAGCAACGGATCTGCTTTTAGAACATCAAAA
ACAGACTGTCAAACATGTAGACAAGCGCGTGGAGTATTTGCGGGCGCAATTCGATGCATCGTTAGGCTGG
CGGTTGAAAGAGCAACACGCGGATATTACGACCAAAATCATTCCTGAGATCATCCAAACGGTGAAGGAAG
ATATTAGCCTGTGTCTTTCTACGCTCTGCAGTATCGCTGAAGATATCCAGACATCACGGGCTACCACTGTCA
CAGGGCATGCTGCCGTACAAACCCATCCTGTGGATCTTTTGGGTGAACACCATTTAGGGACCCACGGGGCAC
CCACGCTTACAGTCGACCCGTGTAGGGAAACCAGACGACGTACCTGAGTCGCCGGTAAGCCTGTTTATGCA
AGGTGAGGCGCGTTCCCGGATCGTTGGCAAGAGTCCGATTAAACTGCAATTTCCGACGTTCGGCAAAGCA
AACGATTCTTCCGACCCACTCCAATATCTGGAGCGGTGTGAGGACTTTCTTGCTCTTAACCCTTTAACTGATG
AGGAACTTATGGCTACTTTGCGGAATGTGTTACATGGCACCTCTCGGGATTGGTGGGATGTCGCACGTCAT
AAAATCCAAACTTGGCGTGAGTTTAATAAACATTCCGGGCGGCTTTCCTCAGCGAGGATTATGAAGATGA
GTTGGCTGAGCGCGTCCGTAACCGCATCCAAAAAGAAGATGAGTCTATCCGCGATTTCGCTTATATGTATC
AGTCCTTGTGCAAGCGGTGGAACCCTGCTATCTGCGAAGGTGATGTAGTAAAGCTCATCCTGAAGAACATC
AATCCACAACTGCCGTCTCAGTTACGCTCCCGGGTCACGACCGTGGATGAGCTTGTTCGCTTGGGCCAGCA
GCTTGAAAAAGATCGTCAGAATCAGCTCCAATATGAGCTTCGGAAGAGTTCCGGCAAAATTATCCAAAAT
CTAGTTCGTGCGAAACTTCAGCGCTCCCGAACACGAAGAGTACACCTAATCAACAAAACCCTGCTACCAGT
AACCGTCCTCCACAGGTGTATTGCTGGCGGTGTAAGGGTCACCATGCCCCTGCCTCTTGTCCGCAATGGAA
AGCTGATAAGCACCGTGCGCAACCTTCGCGGAGTTCTGGGCCACAAACTCTGACTAATCTCCAAGCTCAAG
ACATC
```

SEQ ID NO: 38

```
GGGGAATTGGATCAACGTGCGGCAGGGGGCTTGCGCGCGTACCCGGCGCCGCGTGGTGGTCCAGTTGCC
AAACCGAGCGTAATTCTTCAGATTGGTAAGTGCCGCGCTGAGATGCTGGAACACGTCCGCCGCACGCATCG
CCATCTTCTGACGGAGGTAAGTAAACAAGTGGAGCGCGAACTCAAGGGGTTACATCGGTCTGTCGGTAAG
TTGGAGGGCAATTTAGACGGCTATGTGCCTACCGGTGATTCCCAACGCTGGAAAAAAAGTATCAAGGCGT
GTCTCTGCCGGTGTCAGGAAACAATTGCAAATCTCGAGCGTTGGGTGAAACGTGAGATGCATGTTTGGCGT
GAGGTATTCTATCGTTTGGAACGGTGGGCAGACCGTTTGGAGTCTGGGGGGCAAGTATCCGGTGGGCA
CTAACCCGTCGCGCACACAGTAAGTGTCGGGGTAGGGGCCCGGAAGGCTATTCTCATGAAGCGGATAC
TTATGACTACACGGTGTCTCCGTATGCTATCACGCCACCGCCTGCCGCGGGTGAGTTGCCTGGTCAAGAGG
CTGTCGAGGCACAACAGTACCCTCCATGGGGTCTGGGGGAGGACGGGCAACCAGGTCCGGGCGTGGACA
CGCAGATTTTTGAGGACCCTCGCGAATTTTTGAGCCACTTAGAGGAGTACCTGCGGCAAGTAGGGGGGAG
TGAAGAGTACTGGTTATCGCAAATTCAAAATCATATGAATGGCCCTGCGAAGAAATGGTGGGAGTTCAAAC
AGGGGTCAGTCAAGAATTGGGTCGAGTTTAAGAAAGAATTTTTGCAATACAGTGAGGGTACGTTGAGTCG
CGAGGCCATCCAACGTGAACTGGACCTCCCTCAGAAGCAGGGGGAGCCGTTAGATCAATTTTTATGGCGG
AAACGTGACTTATACCAAACCCTCTACGTTGACGCTGAGGAAGAAGAAATTATTCAATATGTTGTCGGTAC
GCTGCAGCCAAAGCTGAAGCGGTTCCTCCGTCCTCCACTCCCTAAAAACCTTAGAACAATTAATCCAAAAGG
CATGGAAGTTCAGGACGGGTTAGAACAAGCGGCCGAACCGGCCTCTCCGCGTCTGCCGCCGGAAGAGGA
GAGTGAGGGCTCTTACGCCTGCGCTCACGAGCGAATCAGTAGCCTCCGATCGGACACAGCCAGAG
```

TABLE 3-continued

Arc and endo-Gag amino acid and nucleotide sequences

SEQ ID NO: 39
```
GGGCAGCTTGACAATGTGACGAACGCGGGGATTCACAGCTTTCAAGGGCACCGCGGCGTCGCCAACAAAC
CGAATGTCATTCTGCAAATCGGTAAATGTCGTGCTGAAATGCTTGAGCACGTTCGTCGTACCCATCGTCACT
TGCTTTCTGAAGTATCAAAACAAGTGGAGCGGGAACTCAAAGGCCTGCAAAAGTCAGTGGGTAAATTGGA
GAATAACCTCGAAGACCATGTACCTACAGACAACCAGCGGTGGAAAAAATCTATCAAGGCATGCCTCGCTC
GTTGCCAGGAGACTATTGCCCATCTTGAGCGGTGGGTGAAACGTGAAATGAACGTATGGAAGGAAGTATT
TTTTCGCTTAGAGAAGTGGGCTGATCGTCTTGAATCGATGGGCGGCAAGTACTGTCCTGGGGAACACGGC
AAACAAACTGTATCTGTCGGCGTGGGGGGGCCCGGAGATCCGGCCATCGGAAGGGGAAATTTATGATTATG
CTCTCGACATGTCCCAAATGTATGCTCTCACACCAGGGCCAGGGGAAGTACCGTCAATTCCGCAAGCACAC
GACAGCTACCAATGGGTATCTGTGAGCGAGGACGCGCCTGCCTCTCCGGTTGAGACGCAAATCTTTGAGG
ACCCACATGAATTTTTGTCTCATCTTGAAGAATATCTCAAACAGGTTGGCGGCACAGAAGAATACTGGTTAT
CTCAGATCCAGAATCACATGAACGGCCCGGCTAAAAAGTGGTGGGAGTATAAGCAAGATTCCGTAAAGAA
CTGGGTCGAATTCAAGAAAGAGTTTCTTCAATACTCTGAGGGTACTCTGACGCGCGATGCAATTAAGCGGG
AGTTAGACCTTCCACAAAAAGAGGGGGAGCCTCTTGACCAGTTCCTGTGGCGTAAGCGCGACCTCTATCAG
ACACTTTACGTCGACGCTGATGAAGAAGAGATTATTCAATATGTTGTGGGTACCCTGCAGCCAAAGCTTAA
GCGTTTCCTTAGCTACCCACTTCCGAAAACTCTGGAGCAGCTCATTCAACGCGGTAAGGAAGTGCAGGGCA
ACATGGACCACTCTGAAGAGCCTAGCCCGCAGCGCACTCCTGAAATCCAATCAGGTGACAGTGTGGAGTCA
ATGCCGCCGTCAACCACCGCTTCTCCGGTACCTAGCAACGGGACGCAACCAGAGCCTCCAAGCCCACCGGC
TACAGTCATC
```

SEQ ID NO: 40
```
GGGCAACTTGAGAATATTAACCAAGGTTCCCTGCACGCGTTTCAGGGTCATCGCGGCGTGGTCCATAACAA
CAAGCCTAACGTTATTCTCCAGATCGGGAAGTGCCGCGCCGAAATGCTGGAGCATGTGCGGCGCACCCATC
GCCATTTGCTCACTGAAGTATCAAAACAGGTGGAGCGTGAGTTGAAGGGGTTGCAGAAAAGTGTAGGCAA
ACTTGAAAATAATTTAGAAGACCACGTACCAAGTGCGGCTGAGAACCAACGCTGGAAGAAGTCGATTAAA
GCCTGCTTAGCGCGTTGTCAGGAGACCATTGCGAACTTGGAACGCTGGGTTAAACGTGAGATGAATGTTTG
GAAGGAGGTCTTTTTCCGCTTAGAGCGCTGGGCAGATCGCCTCGAATCCGGGGGTGGCAAGTACTGCCAT
GCAGACCAGGGTCGCCAAACTGTCAGCGTAGGTGTTGGTGGTCCTGAAGTGCGTCCGTCTGAAGGTGAAA
TTTACGATTACGCGTTGGATATGAGCCAAATGTACGCCTTGACTCCGCCGCCTATGGGTGATGTTCCAGTAA
TTCCTCAGCCGCCATGACAGTTATCAGTGGGTGACAGATCCGGGAAGAAGCGCCACCAAGTCCGGTTGAGAC
ACAAATTTTCGAGGACCCTCGGGAGTTTCTGACCCATCTTGAGGATTATTTAAAACAAGTCGGCGGGACAG
AGGAATATTGGCTCTCACAGATCCAAAATCATATGAATGGGCCAGCGAAAAGTGGTGGGAATATAAACA
GGATAGTGTGAAGAACTGGCTTGAGTTCAAAAAAGAATTCTTGCAGTACTCAGAAGGCACGTTAACGCGG
GACGCTATTAAACAGGAACTTGACCTTCCACAAAAAGAAGGGGAACCGCTGGATCAATTCCTCTGGCGCAA
ACGCGATTTGTACCAAACTCTCTACGTCGAGGCAGAAGAAGAGGAGGTCATCCAATATGTAGTTGGTACGCACAC
TGCAACCAAAACTGAAGCGGTTTCTTTCTCATCCGTACCCTAAAAACCCTGGAGCAACTCATCCAGCGCGGGA
AGGAAGTTGAGGGGAATTTGGACAATAGTGAAGAACCGTCTCCACAGCGGACCCCAGAACATCAGCTGGG
GGACAGTGTGGAATCTTTGCCGCCTAGTACTACGGCTTCGCCTGCCGGTTCGGATAAAACGCAACCTGAGA
TTAGCTTACCTCCAACTACAGTCATT
```

SEQ ID NO: 41
```
GGGCAATTAGATTCGGTAACCAATGCGGGCGTCCACACCTACCAGGGCCATCGGAGCGTCGCCAATAAAC
CTAACGTCATTCTTCAAATCGGGAAATGTCGGACTGAGATGCTGGAGCATGTCCGTCGGACTCATCGCCAC
CTGCTCACAGAAGTGTCAAAGCAAGTGGAACGTGAACTCAAGGGCTTACAGAAGAGCGTGGGCAAACTGG
AAAACAATCTTGAAGACCATGTCCCAACTGACAATCAGCGGTGGAAGAAGTCAATCAAGGCATGTCTCGCG
CGTTGCCAAGAGACCATTGCTCACCTTGAGCGGTGGGTGAAACGTGAAATGAACGTGTGGAAGGAGGTGT
TCTTCCGGTTAGAACGCTGGGCCGACCGCCTTGAATCAATGGGTGGTAAATACTGCCCGACGGACTCTGCA
CGTCAGACAGTTAGCGTTGGGGTGGGGGGCCCGGAAATTCGGCCTAGTGAAGGCGAAATCTATGACTACG
CGCTCGATATGAGCCAAATGTACGCTCTTACGCCGTCACCGGGCGAATTGCCGTCCGTCCCTCAACCGCATG
ATTCATACCAGTGGGTCACTAGTCCGGAAGACGCTCCGGCGTCACCAGTTGAAACGCAGGTATTCGAGGAT
CCTCGGGAGTTCTTGTGTCATTTGGAAGAGTACCTGAAGCAGGTTGGCGGTACAGAGGAATATTGGCTGA
GCCAGATTCAGAATCATATGAATGGTCCTGCAAAAAAGTGGTGGGAATATAAACAAGACACGGTTAAGAA
TTGGGTGGAATTCAAGAAGGAGTTCTTACAATACAGTGAGGGTACACTTACCCGTGATGCGATTAAGCGG
GAATTAGACCTCCCGCAAAAGGACGGTGAGCCTCTGGATCAATTTTTTATGGCGTAAGCGTGACCTCTATCA
GACATTATACATTGATGCCGATGAAGAACAGATCATTCAGTACGTTCGTGGGGACATTGCAACCTAAACTCA
AGCGGTTCTTGTCCTATCCACTTCCAAAAACTCTTGAACAATTAATCCAGAAAGGGAAGGAGGTGCAGGGT
TCACTTGACCACAGCGAGGAGCCGAGTCCTCAACGTGCGAGCGAGGCTCGGACGGGCGATAGTGTGGAA
ACCTTGCCGCCTTCTACCACTACATCACCAAATACGTCATCTGGTACACAGCCAGAGGCACCATCGCCTCCA
GCGACGGTAATC
```

SEQ ID NO: 42
```
GGGCAGTTAGACAGTGTGACTAACGCCGGGGTGCATACGTACCAGGGGCACCGCGGGGTCGCCAATAAG
CCAAATGTAATTCTCCAGATTGGGAAGTGTCGTACAGAGATGTTGGAACATGTCCGTCGCACTCATCGCCA
CTTGCTCACCGAGGTCTCCAAACAAGTAGAACGCGAACTCAAGGGGCTCCAGAAGAGTGTTGGGAAGTTG
GAGAATAACCTCGAAGACCACGTTCCGACAGATAACCAACGGTGGAAAAAGTCTATTAAAGCCTGTCTCGC
CCGTTGTCAAGAGACAATCGCACACTTGGAACGCTGGGTCAAACGGGAGATGAATGTGTGGAAGGAAGTC
TTCTTCCGTCTCGAGCGGTGGGCGGATCGTTTAGAAAGTATGGGCGGTAAATATTGCCCAACTGACTCGGC
TCGTCAAACGGTGTCGGTTGGCGTAGGCGGGCCCGGAAATTCGCCTAGCGAGGGTGAGATCTATGACTAT
GCACTTGACATGAGTCAGATGTATGCGTTAACTCCGTCGCCAGGGGAGCTTCCAAGTATTCCACAGCCTCA
CGATAGTTATCAATGGGTAACTTCTCCTGAAGACGCCCCAGCATCCCCAGTTGAGACACAAGTATTCGAGG
ACCCTCGTGAGTTTCTCTGTCACCTCGAGGAGTACCTTAAACAGGTAGGCGGGACCGAAGAGTACTGGTTA
TCGCAAATCCAAAACCATATGAATGGTCCTGCCAAAAAGTGGTGGGAGTATAAACAAGATACTGTGAAGA
ATTGGGTAGAGTTCAAGAAAGAGTTCTTACAGTACTCTGAGGGGACGTTAACTCGTGATGCGATCAAGCGC
GAATTGGATTTACCTCAGAAGGACGGCGAGCCACTCGACCAGTTCTTATGGCGCAAGCGTGACTTGTATCA
AACCCTTTATATCGATGCTGACGAGGAACAAATTATCCAGTACGTAGTCGGTACGTTGCAACCAAAACTTAA
ACGCTTTCTGAGCTACCCATTACCTAAAACGTTGGAGCAACTGATCCAGAAAGGTAAAGAGGTGCAAGGG
AGCCTGGATCATAGTGAAGAACCGAGCCCTCAGCGGGCTTCTGAAGCTCGGACCGGTGATAGCGTCGAAT
```

TABLE 3-continued

Arc and endo-Gag amino acid and nucleotide sequences

CTTTACCACCTAGTACCACAACCAGCCCGAATGCGTCATCTGGTACCCAACCTGAAGCGCCTTCCCCACCTG
CTACAGTCATT

SEQ ID NO: 43

GGGCAGCTCGAGAATGTCAACCATGGGAACCTCCATTCTTTTCAAGGTCATCGCGGCGGCGTCGCCAACAA
GCCAAACGTTATCTTGCAGATCGGTAAATGTCGTGCAGAGATGCTGGACCACGTCCGGCGGACCCACCGG
CATTTACTGACAGAGGTATCGAAACAGGTTGAACGTGAGTTGAAGGGGTTACAGAAATCAGTAGGGAAAT
TAGAAAATAACTTAGAAGACCATGTCCCTTCAGCCGTTGAAAACCAGCGTTGGAAAAAATCGATCAAGGCC
TGCCTTTCCCGCTGCCAAGAGACCATTGCCCACCTTGAGCGTTGGGTGAAGCGCGAGATGAACGTATGGAA
AGAGGTTTTCTTCCGCTTAGAGCGGTGGGCAGATCGGTTGGAATCTGGGGGCGGGAAATATTGTCACGGT
GATAATCATCGTCAAACAGTATCAGTCGGTGTTGGCGGCCCTGAGGTACGTCCATCTGAAGGCGAAATTTA
CGATTACGCTCTCGACATGTCGCAAATGTACGCTTTAACACCGCCTAGCCCAGGGGATGTGCCTGTAGTTA
GCCAGCCGCACGACAGCTATCAGTGGGTTACGGTTCCGGAGGATACCCCTCCATCCCCGGTGGAGACGCA
AATCTTCGAGGACCCACGGGAGTTCTTGACCCACTTAGAGGATTACTTAAAGCAAGTGGGGGGTACAGAG
GAATATTGGTTATCTCAGATCCAGAATCACATGAACGGGCCAGCCAAGAAGTGGTGGGAGTATAAGCAAG
ACTCAGTAAAAAATTGGCTCGAGTTTAAGAAGGAATTCCTTCAGTATTCCGAGGGGACACTTACGCGCGAC
GCTATCAAGGAAGAACTTGACCTCCCGCAAAAGGACGGGGAACCTCTTGATCAGTTCCTGTGGCGCAAGC
GCGACTTGTACCAGACCCTGTACGTGGAGGCGGATGAGGAGGAGGTGATCCAGTATGTTGTGGGGACTTT
ACAACCTAAATTAAAGCGTTTTCTCTCACACCCTTACCCGAAAACGTTAGAGCAACTTATCCAACGGGGCAA
AGAGGTGGAAGGGAACCTCGACAATTCAGAGGAACCAACACCTCAGCGTACTCCAGAACACCAACTGTGT
GGTTCTGTAGAATCGCTGCCTCCTTCCTCTACCGTCAGTCCAGTGGCTAGCGATGGTACTCAACCTGAGACT
TCGCCATTGCCAGCGACTGTTATT

SEQ ID NO: 44

GGGCCATTGACGTTGTTACAAGACTGGTGTCGTGGTGAACATTTAAACACCCGCCGGTGCATGTTGATCCT
CGGTATCCCAGAAGATTGCGGCGAGGATGAGTTCGAAGAGACACTTCAGGAGGCGTGTCGCCATTTAGGG
CGGTACCGCGTGATCGGCCGCATGTTCCGTCGTGAGGAAAATGCCCAAGCGATCCTCTTGGAATTGGCGCA
GGATATTGACTATGCCTTACTCCCTCGGGAAATCCCTGGGAAAGGCGGGCCTTGGGAGGTAATTGTGAAG
CCGCGTAATTCCGACGGCGAATTCTTAAATCGGCTTAATCGCTTTCTTGAAGAGGAGCGCCGTACGGTCTCC
GATATGAACCGTGTTTTGGGCTCGGATACTAACTGTTCAGCTCCTCGTGTCACCATTAGTCCTGAATTCTGG
ACTTGGGCACAGACGCTGGGCGCAGCTGTCCAACCATTGCTCGAACAGATGCTCTACCGGGAGTTACGGG
TCTTCAGTGGCAATACGATTTCCATCCCAGGTGCTCTCGCTTTTGACGCGTGGCTGGAGCATACCACGGAAA
TGCTTCAAATGTGGCAGGTGCCTGAAGGGGAGAAACGGCGGCGCTTGATGGAGTGTTTGCGGGGGCCAG
CCCTGCAAGTCGTTAGTGGGTTACGTGCATCGAATGCCAGTATCACTGTCGAAGAGTGTCTTGCTGCACTG
CAGCAGGTATTCGGTCCAGTGGAAAGTCATAAGATTGCCCAAGTAAAGTTATGCAAAGCTTACCAGGAGG
CTGGGGAAAAAGTAAGCAGCTTCGTTTTGCGTTTGGAGCCCACTGCTTCAAGCGTGCTGTAGAAAACAACGTG
GTCAGTCGCCGCAATGTCAACCAAACACGTCTTAAGCGTGTTCTGTCGGGCGCCACCCTTCCTGACAAGCTG
CGTGATAAATTGAAGTTAATGAAACAGCGCCGTAAACCGCCGGGTTTCTTGGCGTTGGTTAAACTGTTACG
TGAAGAGGAGGAGTGGGAGGCCACCTTAGGGCCAGACCGCGAGTCATTGGAGGGGTTAGAAGTGGCACC
GCGCCCGCCAGCACGGATTACGGGTGTTGGCGCAGTACCTCTTCCGGCATCCGGGAATTCATTTGATGCCC
GTCCTTCGCAAGGGTACCGGCGCCGTCGGGGTCGTGGTCAGCACCGTCGGGGCGGCGTTGCTCGTGCAGG
CTCTCGTGGCTCTCGTAAGCGGAAACGGCACACCTTCTGCTATTCCTGTGGTGAGGATGGCCATATTCGTGT
CCAATGCATTAACCCTAGCAATCTCCTGTTGGCTAAGGAGACCAAAGAGATTTTGGAAGGGGGAGAACGT
GAAGCGCAAACGAATTCACGT

SEQ ID NO: 45

GGGGCTCTTACGCTCTTAGAAGACTGGTGTAAGGGTATGGACATGGACCCGCGGAAGGCTCTCCTGATTGT
AGGTATTCCGATGGAATGCAGTGAGGTGGAAATCCAGGATACAGTTAAAGCTGGTCTTCAACCTCTGTGCG
CTTATCGTGTACTCGGCCGTATGTTCCGGCGGGAGGATAATGCGAAGGCTGTTTTCATTGAGCTGGCAGAC
ACCGTGAATTACACCACGTTACCGTCTCACATTCCGGGTAAAGGGGGTTCCTGGGAAGTCGTTGTTAAACC
TCGGAACCCTGACGACGAGTTCCTTTCTCGGCTTAACTACTTCTTGAAAGATGAGGGCCGCTCGATGACGG
ATGTCGCCCGGGCACTGGGGTGCTGTAGCTTACCTGCGGAATCACTGGACGCGGAAGTAATGCCACAGGT
CCGCTCCCCACCATTAGAACCTCCAAAAGAGAGTATGTGGTACCGTAAGTTAAAAGTGTTTAGTGGTACCG
CGTCGCCTTCGCCGGGGGAGGAGACATTTGAGGACTGGTTAGAGCAAGTCACCGAGATCATGCCTATCTG
GCAAGTATCTGAAGTTGAAAAGCGCCGTCGGTTACTGGAGTCACTCCGGGGCCCGGCACTCTCAATTATGC
GCGTGTTACAAGCCAATAACGATAGCATTACCGTTGAACAGTGTTTGAACAGTCATTAAAGCAGATCTTTGGC
GACAAGGAAGACTTCCGTGCCTCTCAATTTCGTTTTCTTCAAACGTCCCCTAAAATTGGGGAGAAGGTGAGT
ACGTTCCTGCTGCGTTTAGAGCCACTCTTGCAAAAGGCCGTTCACAAGAGCCCACTTTCGGTACGTAGTACT
GATATGATTCGGTTAAAGCACCTGTTGGCACGCGTAGCCATGACCCCGGCACTGCGTGGTAAACTCGAATT
ACTCGACCAACGCGGGTGCCCACCTAATTTTCTTGAGCTGATGAAGCTGATCCGGGATGAGGAAGAGTGG
GAGAATACTGAAGCTGTGATGAAAAATAAAGAGAAACCTTCAGGTCGTGGCCGCGGTGCATCAGGCCGTC
AAGCTCGCGCCGAGGCCAGTGTAAGTGCTCCGCAAGCAACAGTCCAAGCACGTAGCTTCTCTGATTCTAGC
CCGCAGACGATTCAGGGGGGCTTACCACCTCTTGTCAAGCGTCGGCGCCTTTTGGGTTCGGAGAGCACACG
TGGGGAAGACCACGGGCAAGCTACTTATCCGAAAGCAGAGAATCAGACTCCAGGGCGTGAGGGCCCGCA
GGCGGCTGGGGAGGAACTTGGTAATGAGGCCGGGGCCGGCGCGATGTCCCACCCGAAACCGTGGGAAAC
C

SEQ ID NO: 46

GGGGCTGTGACAATGCTCCAGGACTGGTGCCGTTGGATGGGCGTGAACGCTCGGCGGGGGCTGTTAATCT
TAGGTATCCCTGAAGACTGTGACGATGCAGAGTTCCAAGAGTCGTTAGAAGCTGCACTCCGTCCTATGGGT
CACTTTACTGTACTCGGTAAGGCCTTCCGCGAGGAAGACAACGCTACCGCTGCGCTGGTGGAATTAGATCG
CGAGGTTAATTACGCACTTGTTCCACGCGAAATTCCGGGCACCGGCGGGCCTTGGAACGTCGTGTTCGTTC
CTCGGTGCTCCGGCGAGGAATTCCTGGGGTTAGGCCGCGTGTTCCACTTTCCTGAACAGGAGGGCCAAATG
GTAGAATCGGTTGCGGGGGGCACTGGGGGTAGGTCTGCGCCGCGTGTGTTGGTTACGCTCGATCGGGCAA
GCTGTACAACCATGGGTAGAAGCTGTTCGCTGCCAAAGCTTAGGGGTATTTAGTGGTCGTGATCAACCTGC
ACCTGGTGAAGAAAGCTTCGAGGTCTGGTTGGATCATACGACCGAGATGTTGCATGTGTGGCAAGGCGTG
TCGGAACGGGAACGGCGCCGTCGTCTGCTGGAAGGGCTGCGTGGCACAGCCTTACAACTTGTACATGCCTT
ACTGGCAGAAAATCCGGCACGGACAGCACAAGATTGCTTGGCTGCATTAGCCCAAGTTTTTGGTGATAACG

TABLE 3-continued

Arc and endo-Gag amino acid and nucleotide sequences

```
AAAGCCAGGCAACGATTCGTGTTAAATGTTTGACAGCCCAACAGCAGAGTGGCGAACGCCTCTCTGCGTTC
GTTCTCCGCTTAGAAGTACTTCTGCAAAAGGCTATGGAGAAGGAAGCATTGGCGCGCGCGTCAGCGGATC
GGGTGCGTCTTCGTCAGATGCTGACACGCGCACATCTCACAGAGCCGTTGGATGAAGCCTTACGGAAATTG
CGTATGGCAGGGCGTTCTCCGTCTTTTTTGGAAATGCTCGGCTTAGTACGCGAGTCAGAGGCCTGGGAGGC
AAGTCTGGCTCGGTCCGTCCGGGCGCAAACCCAGGAGGGTGCAGGGGCCCGGCGGGGGCCCAAGCAGT
TGCGCGTGCCAGCACTAAGGTTGAAGCTGTACCTGGTGGCCCTGGCCGGGAGCCAGAAGGTCTCCTCCAA
GCCGGGGGCCAAGAAGCGGAAGAACTTCTCCAAGAGGGCTTAAAGCCGGTTTTAGAGGAATGTGACAAT
```

SEQ ID NO: 47
```
GGGGCGGTCACCATGTTGCAAGACTGGTGTCGGTGGATGGGCGTGAATGCTCGGCGGGGTTTATTGATCT
TGGGTATCCCAGAAGACTGTGACGACGCCGAGTTTCAGGAGTCGCTCGAGGCCGCCCTTCGTCCAATGGG
GCATTTTACGGTTCTGGGCAAGGTGTTCCGTGAAGAGGATAACGCTACAGCAGCTCTTGTGGAGCTTGACC
GTGAGGTGAATTATGCGTTAGTACCTCGCGAGATTCCAGGTACCGGTGGGCCATGGAACGTAGTCTTCGTC
CCACGTTGCTCGGGGGAGGAATTTCTGGGGCTTGGGCGCGTATTCCACTTTCCAGAACAGGAAGGGCAGA
TGGTCGAAAGCGTAGCAGGCGCTCTTGGCGTTGGTCTCCGGCGCTGTGCTGGTTACGCTCCATCGGCCAA
GCAGTCCAACCATGGGTTGAAGCCGTACGCTATCAATCTTTAGGTGTCTTCTCAGGCCGTGACCAGCCGGC
GCCTGGTGAGGAATCCTTCGAAGTCTGGCTCGATCATACAACTGAGATGCTGCATGTATGGCAAGGTGTCT
CAGAGCGGGAACGGCGGCGGCGGTTATTAGAGGGGCTCCGTGGGACTGCGCTCCAATTAGTACATGCGCT
TTTGGCCGAAAATCCAGCCCGTACTGCCCAAGATTGTCTGGCAGCACTCGCCCAAGTATTCGGCGACAACG
AATCGCAGGCAACAATCCGCGTAAAGTGTCTTACAGCACAGCAGCAGTCAGGGGAACGTCTTAGTGCGTTC
GTTCTGCGGCTGGAAGTGTTACTCCAGAAAGCCATGGAAAAGGAGGCATTGGCTCGCGCGAGCGCTGACC
GTGTACGTCTGCGGCAAATGCTTACTCGCGCACATCTCACCGAGCCTCTCGATGAAGCACTGCGGAAACTG
CGCATGGCAGGCCGCAGCCCGTCTTTCCTGGAAATGTTAGGCTTAGTCCGGGAGTCCGAAGCCTGGGAGG
CCAGTCTGGCACGGTCAGTGCGGGCACAAACGCAAGAGGGTGCAGGGGCACGGGCGGGTGCACAAGCA
GTTGCACGTGCCTCCACTAAAGTTGAGGCAGTGCCGGGTGGGCCAGGCCGTGAACCGGAGGGTTTGCGCC
AAGCCGGCGGGCAGGAAGCCGAAGAATTACTCCAAGAAGGTTTAAAACCGGTTTTGGAGGAATGCGATAA
C
```

SEQ ID NO: 48
```
GGGGTGGAAGATTTGGCGGCATCTTACATCGTATTAAAGCTTGAGAACGAAATCCGGCAGGCGCAGGTCC
AATGGTTAATGGAGGAAAACGCCGCCCTGCAGGCCCAGATCCCTGAACTTCAAAAGTCGCAAGCCGCGAA
GGAGTATGATCTTCTGCGTAAATCTTCGGAGGCGAAGGAGCCGCAAAAACTGCCAGAACATATGAATCCAC
CGGCCGCTTGGGAAGCACAAAAGACTCCAGAGTTTAAGGAACCACAGAAACCTCCTGAACCACAGGATTT
GCTTCCTTGGGAGCCGCCTGCTGCCTGGGAGTTGCAAGAAGCACCGGCTGCCCCTGAGTCACTGGCTCCGC
CTGCAACCCGTGAGTCTCAGAAACCACCTATGGCGCATGAAATCCCTACTGTATTGGAGGGGCAAGGGCCT
GCCAACACAAGACGCTACGATTGCTCAAGAACCAAAGAATAGCGAGCCGCAAGACCCTCCAAATATCG
AGAAACCTCAGGAAGCTCCGGAATATCAAGAAACAGCGGCACAGTTGGAGTTTTTAGAACTTCCTCCACCT
CAGGAGCCACTCGAACCGAGCAATGCGCAAGAATTTCTCGAGTTGTCGGCTGCCCAGGAGTCCTTAGAAG
GCCTCATTGTAGTTGAAACGTCCGCGGCTTCGGAGTTCCCACAGGCTCCTATCGGGCTTGAAGCCACCGAC
TTTCCGCTGCAGTACACGCTTACCTTCTCTGGCGACAGCCAGAAGTTGCCAGAATTTTTGGTCCAACTCTAC
AGTTATATGCGGGTACGTGGGCACTTATACCCTACCGAGGCGGCGTTAGTGTCGTTTGTAGGCAATTGTTT
CTCAGGGCGCGCGGGCTGGTGGTTTCAGTTGCTTTTGGATATCCAGTCGCCTCTGTTAGAACAGTGTGAAA
GTTTTATCCCGGTTCTCCAAGACACATTTGACAATCCGGAAAACATGAAGGACGCAAACCAATGCATCCACC
AGCTTTGTCAGGGCGAGGGTCATGTGGCCACACACTTCCACCTCATTGCACAAGAGCTTAATTGGGATGAA
AGCACGCTGTGGATCCAGTTCCAGGAAGGCCTGGCCTCATCCATCCAGGATGAACTTTCCCATACATCGCCT
GCTACCAACCTGAGTGATCTGATTACTCAATGCATCTCATTAGAGGAAAAGCCTGACCCAAACCCGTTAGG
GAAGTCCTCCTCGGCGGAGGGGGATGGCCCGGAAAGTCCGCCAGCAGAAAACCAACCTATGCAAGCTGCG
ATCAATTGTCCTCACATTTCCGAAGCAGAGTGGGTTCGTTGGCACAAAGGCCGGCTTTGTCTCTATTGCGGC
TATCCGGGTCACTTCGCACGTGATTGCCCAGTGAAGCCACACCAGGCGTTACAGGCAGGGAACATTCAGGC
TTGCCAA
```

SEQ ID NO: 49
```
GGGGTGCAGCCGCAGACTAGCAAAGCTGAATCGCCGGCTCTCGCTGCCTCACCGAACGCACAAATGGATG
ACGTTATTGATACATTAACCTCCCTGCGTCTGACGAATTCGGCTCTGCGGCGGGAGGCTAGCACTCTTCGG
GCCGAGAAAGCAAATTTAACTAATATGCTCGAGTCAGTGATGGCCGAGTTAACGCTGTTACGGACCCGTGC
GCGGATTCCGGGGGCCCTGCAGATTACGCCACCAATTTCGTCTATTACTAGCAACGGTACTCGCCCGATGA
CGACTCCTCCAACTAGTTTACCTGAACCGTTTTCTGGCGATCCTGGCCGGTTAGCTGGTTTCCTTATGCAGAT
GGACCGTTTTATGATCTTTCAAGCTAGCCGGTTTCCAGGGGAGGCAGAGCGTGTTGCGTTCCTGGTGTCGC
GCTTAACTGGCGAAGCAGAAAATGGGCCATTCCTCACATGCAACCAGACTCTCCTTTGCGTAACAACTATC
AAGGCTTCTTAGCAGAGTTACGGCGGACCTATAAGAGCCCGTTGCGTCACGCCCGGCGGGCGCAAATCCG
GAAGACATCGGCCTCGAACCGGGCAGTCCGTGAACGCCAAATGCTTTGCCGGCAACTTGCATCAGCAGGT
ACAGGCCCATGCCCGGTACACCCTGCTAGTAACGGGACTTCCCCGGCACCGGCATTACCAGCACGGGCGC
GTAACTTA
```

SEQ ID NO: 50
```
GGGGACGGTCGGGTACAGTTGATGAAGGCTTTATTGGCTGGCCCTTTACGTCCGGCGGCACGCCGTTGGC
GGAATCCTATTCCATTTCCAGAGACTTTTGATGGGGATACTGATCGCCTCCGGAGTTTATCGTCCAAACTT
CGTCCTACATGTTCGTTGACGAAAATACTTTCTCTAACGACGCTCTGAAAGTGACATTTCTCATTACCCGGCT
GACAGGTCCAGCCTTGCAATGGGTCATTCCGTACATTCGTAAAGAAAGCCCGCTTCTTAACGACTATCGGG
GTTTCCTGGCCGAGATGAAGCGGGTTTTTGGGTGGGAAGAGGACGAGGACTTT
```

SEQ ID NO: 51
```
GGGGAAGGTCGGGTGCAACTTATGAAAGCGTTGCTTGCCCGCCCGCTTCGTCCAGCAGCACGTCGCTGGC
GGAATCCAATTCCTTTCCCGGAGACTTTTGACGGGGACACCGATCGGCTCCCAGAGTTCATTGTGCAGACG
TCAAGCTATATGTTCGTGGATGAGAACACGTTCTCTAACGACGCGTTGAAAGTGACTTTCTTAATTACGCGT
TTGACTGGCCCGGCTTTACAATGGGTGATTCCATACATTAAGAAAGAGTCACCGCTTCTCAGTGATTATCGC
GGTTTTTTAGCCGAGATGAAGCGGGTCTTCGGGTGGGAAGAAGACGAAGACTTT
```

TABLE 3-continued

Arc and endo-Gag amino acid and nucleotide sequences

SEQ ID NO: 52

```
GGGCCGCGTGGGCGTTGCCGTCAACAAGGTCCTCGGATTCCGATTTGGGCAGCGGCCAACTATGCCAACG
CCCACCCGTGGCAACAAATGGATAAGGCTTCGCCAGGCGTTGCTTACACACCTTTGGTTGATCCTTGGATTG
AGCGGCCTTGTTGCGGTGACACGGTTTGTGTGCGCACCACAATGGAACAGAAGAGCACAGCGTCAGGCAC
TTGTGGTGGTAAGCCTGCTGAGCGTGGTCCTCTCGCGGGGCATATGCCGAGCTCACGCCCACATCGGGTTG
ATTTCTGTTGGGTTCCTGGTAGCGACCCAGGCACATTCGACGGCAGTCCATGGCTCTTAGATCGCTTTTTGG
CGCAACTTGGTGATTACATGAGTTTTCACTTTGAACACTACCAGGACAATATCAGCCGTGTCTGCGAGATTC
TTCGTCGGTTAACGGGCCGCGCTCAGGCATGGGCTGCTCCTTACCTGGACGGGGACCTTCCACTGCCAGAC
GACTACGAATTGTTTTGTCAAGACCTTAAGGAGGTAGTACAGGACCCTAACAGTTTCGCCGAGTATCACGC
CGTGGTGACTTGTCCACTCCCTCTTGCTTCGTCCCAACTTCCTGTAGCTCCTCAGCTTCCGGTGGTACGCCAA
TACCTTGCGCGCTTCTTGGAGGGCCTTGCTTTGGATATGGGTACGGCGCCTCGGTCACTCCCGGCCGCTAT
GGCCACACCGGCAGTCTCCGGCTCGAACTCCGTTTCTCGTTCTGCCTTATTTGAACAACAACTCACAAAGGA
ATCCACTCCAGGCCCGAAAGAGCCACCTGTTCTCCCTAGCTCGACTTGCTCTAGCAAACCGGGTCCTGTCGA
ACCAGCCAGTTCACAACCTGAAGAGGCTGCTCCTACCCCGGTGCCGCGTTTGTCAGAGTCGGCTAACCCAC
CGGCTCAGCGTCCAGACCCTGCTCACCCTGGTGGTCCTAAACCACAAAAAACCGAAGAGGAAGTTTTAGAA
ACTGAGGGGGACCAGGAAGTTAGCCTGGGGACGCCGCAGGAGGTCGTAGAAGCGCCGGAAACACCAGG
TGAACCACCGCTCAGCCCTGGGTTC
```

SEQ ID NO: 53

```
GGGGTTGATGAATTGGTGCTCTTGTTGCACGCGCTGTTAATGCGCCATCGGGCGCTTTCCATTGAAAATTCT
CAGTTGATGGAGCAACTTCGCTTGTTGGTCTGCGAACGGGCGAGCCTTCTTCGTCAGGTACGTCCGCCGAG
CTGTCCAGTGCCATTTCCTGAGACTTTTAACGGGGAGTCATCACGGTTACCTGAGTTCATCGTCCAAACCGC
AAGCTATATGTTAGTTAATGAAAATCGCTTTTGCAATGACGCAATGAAAGTCGCTTTTTTGATTAGCCTTCTT
ACTGGTGAAGCAGAAGAATGGGTCGTCCCATACATTGAGATGGATTCACCAATTCTTGGGGACTACCGTGC
GTTCTTGGATGAGATGAAGCAGTGTTTTGGGTGGGACGATGATGAAGATGACGACGATGAGGAAGAGGA
GGATGACTAT
```

SEQ ID NO: 54

```
GGGCCTGTGGATTTAGGTCAGGCTTTGGGGTTGTTGCCATCCCTCGCTAAGGCCGAAGATTCCCAATTTAG
CGAAAGCGATGCAGCTTTACAGGAGGAATTGTCTTCTCCGGAAACCGCACGGCAACTTTTTCGTCAATTTCG
CTATCAAGTCATGTCGGGGCCTCATGAAACACTGAAACAGTTACGGAAGTTATGTTTTCAGTGGCTGCAAC
CTGAAGTCCATACAAAGGAACAAATCCTCGAAATTCTGATGCTGGAACAGTTCTTGACCATTCTGCCTGGTG
AAATTCAGATGTGGGTCCGCAAGCAGTGCCCTGGTAGTGGGGAGGAGGCGGTTACGTTAGTAGAATCCCT
GAAAGGTGATCCACAACGGCTCTGGCAATGGATCTCCATCCAAGTCCTGGGTCAGGATATCCTGTCTGAGA
AAATGGAGTCACCTTCTTGCCAGGTGGGCGAAGTGGAGCCACACCTGGAAGTTGTACCTCAGGAACTGGG
GTTAGAGAATTCATCTTCAGGGCCGGGGGAACTTCTTTCGCACATCGTGAAAGAGGAGTCTGACACTGAAG
CAGAGTTGGCGTTAGCGGCATCCCAGCCAGCTCGTTTGGAAGAACGGCTGATTCGGGATCAGGACCTTGG
GGCGTCCTCCTCCCGGCAGCACCGCAGGAGCAATGGCGTCAATTAGACAGCACTCAAAAAGAACAATATT
GGGACCTGATGCTGGAGACCTACGGCAAAATGGTATCCGGCGCGGGTATCTCACACCCGAAGTCCGATTT
AACGAACTCAATTGAGTTCGGTGAAGAGTTGGCAGGTATTTATTTACATGTAAACGAAAAGATTCCGCGGC
CTACCTGCATTGGTGACCGCCAAGAAAACGACAAAGAAAACCTTAATTTGGAAAACCATCGTGACCAGGAA
TTATTACATGCCAGCTGCCAGGCCTCGGGCGAAGTGCCATCCCAGGCATCGTTACGTGGCTTCTTTACCGAG
GACGAACCTGGTTGCTTCGGCGAAGGGGAGAACCTTCCTGAGGCACTTCAGAATATCCAGGATGAGGGGA
CTGGCGAACAGCTGAGCCCGCAAGAACGCATTAGTGAAAAACAGTTGGGTCAACATTTGCCAAATCCGCAC
TCGGGGGAGATGTCGACGATGTGGCTTGAAGAAAAACGGGAGACCAGCCAGAAAGGCCAACCACGTGCA
CCAATGGCGCAGAAATTGCCAACGTGCCGCGAATGTGGCAAAACGTTTTATCGCAATAGTCAACTTATCTTT
CACCAACGCACACACACCGGTGAGACATATTTTCAATGCACCATCTGCAAAAAGGCGTTTCTCCGGTCATCT
GATTTCGTGAAACATCAGCGGACTCATACTGGCGAAAAACCTTGTAAATGTGACTATTGTGGCAAGAGGCTT
TAGTGATTTTAGCGGGCTTCGGCATCACGAGAAGATCCATACCGGCGAGAAGCCATACAAGTGTCCAATCT
GTGAGAAATCTTTCATCCAGCGCAGTAATTTTAACCGCCACCAACGGGTTCACACCGGTGAAAAGCCTTATA
AATGCTCGCATTGTGGCAAGAGCTTCAGCTGGAGCTCCTCGCTCGATAAGCATCAACGTTCACATCTGGGG
AAGAAGCCGTTCCAA
```

SEQ ID NO: 55

```
GGGACTCTCCGCTTACTTGAGGATTGGTGTCGGGGGATGGACATGAACCCACGTAAGGCCCTTCTTATCGC
CGGGATTTCCCAGTCATGTTCAGTCGCCGAGATTGAAGAGGCGCTCCAAGCCGGGCTTGCTCCTTTAGGCG
AGTATCGTCTCCTTGGGCGGATGTTTCGCCGCGATGAAAATCGCAAAGTAGCGTTGGTTGGTCTCACAGCT
GAAACTAGCCATGCGCTTGTACCTAAAGAAATTCCTGGTAAAGGCGGGATCTGGCGGGTTATTTTTAAACC
ACCGGACCCGGACAATACGTTTCTTTCTCGTTTGAATGAGTTCCTCGCGGGCGAGGGGATGACGGTGGGG
GAACTTAGTCGTGCTCTTGGTCACGAAAATGGGTCATTAGACCCTGAACAGGGTATGATTCCGGGAAATGTG
GGCGCCGATGCTGGCACAGGCTCTGGAGGCTCTCCAACCGGCTTTACAGTGCCTTAAGTACAAGAAGCTGC
GCGTTTTTTCAGGGCGCGAGTCTCCAGAGCCGGGTGAGGAGGAATTCGGCCGTTGGATGTTCCATACCACC
CAGATGATCAAAGCGTGGCAGGTGCCGGATGTCGAGAAACGCCGCCGGCTGTTGAATCACTCCGCGGGC
CGGCACTTGACGTTATTCGGGTTCTGAAAATTAACAACCCGTTAATTACGGTAGATGAATGTTTGCAAGCAC
TTGAAGAGGTCTTTGGGGTGACTGACAATCCTCGGGAATTGCAGGTAAAATACTTAACGACCTACCATAAG
GACGAGGAGAAATTATCAGCCTACGTACTGCGGCTGGAACCGCTGCTGCAGAAGCTCGTCCAGCGGGGGG
CTATTGAACGGGACGCTGTTAATCAGGCTCGCCTGGATCAGGTAATCGCTGGGGCGGTACATAAAACTATC
CGCCGTGAGCTGAACCTGCCTGAAGACGGGCCGGCGCCAGGCTTTCTTCAACTCCTCGTTTTGATTAAGGA
TTACGAGGCAGCTGAAGAGGAGGAAGCATTACTTCAGGCCATTCTTGAAGGGAACTTTACT
```

SEQ ID NO: 56

```
GGGACAGAACGGCGTCGCGACGAATTAAGTGAAGAAATTAATAATCTTCGTGAAAAGGTTATGAAACAGA
GTGAGGAAAACAACAATCTTCAATCCCAAGTCCAGAAACTCACTGAGGAGAATACTACACTCCGTGAGCAA
GTTGAACCTACACCTGAAGATGAAGATGACGACATTGAGTTGCGGGGCGCAGCAGCCGCAGCCGCGCCTC
CGCCGCCGATCGAGGAGGAATGCCCGGAGGATTTACCGGAAAAATTTGATGGTAATCCGGACATGTTAGC
GCCATTCATGGCCCAGTGCCAAATTTTTATGGAAAAGTCTACGCGCGATTTTAGTGTAGATCGCGTACGTGT
ATGTTTTGTGACGAGCATGATGACTGGTCGCGCAGCCCGTTGGGCGTCAGCGAAATTGGAGCGGTCGCAC
TACCTGATGCATAATTACCCGGCGTTCATGATGGAGATGAAACACGTGTTTGAAGACCCGCAGCGGCGGGG
```

TABLE 3-continued

Arc and endo-Gag amino acid and nucleotide sequences

```
AGGTGGCCAAACGCAAGATCCGGCGGTTGCGGCAGGGCATGGGCAGCGTAATTGATTATAGTAATGCGTT
TCAAATGATTGCGCAGGATCTGGATTGGAATGAACCTGCTCTCATTGATCAATATCATGAAGGGCTTAGTG
ACCATATTCAAGAGGAACTCTCTCACCTGGAAGTGGCTAAATCTCTCTCCGCCCTTATTGGCCAATGCATTC
ATATTGAGCGCCGTCTTGCACGTGCTGCTGCCGCTCGGAAACCGCGTAGTCCACCACGGGCTTTAGTGCTC
CCACATATCGCGTCACACCATCAAGTAGATCCTACTGAGCCAGTGGGGGGTGCACGCATGCGCTTAACCCA
AGAAGAAAAGGAACGTCGTCGTAAGCTGAATTTATGCCTGTACTGCGGCCACTGGTGGCCATTATGCCGATA
ACTGTCCTGCCAAAGCCAGTAAGTCAAGCCCGGCTGGGAAACTTCCAGGTCCTGCCGTCGAGGGCCCTTCT
GCTACCGGCCCAGAGATTATCCGCTCCCCGCAAGACGATGCGTCGTCGCCTCATCTCCAGGTAATGCTCCAA
ATCCACCTCCCTGGCCGGCACACACTCTTTGTCCGGGCGATGATTGACTCTGGGGCGTCTGGTAATTTTATT
GATCACGAGTATGTTGCTCAAAATGGTATCCCTCTCCGGATCAAAGACTGGCCTATTCTGGTTGAAGCCATC
GATGGCCGTCCGATCGCGAGCGGTCCTGTGGTTCATGAAACGCATGACCTCATCGTTGATCTGGGTGACCA
CCGTGAAGTATTATCCTTTGATGTGACTCAGTCACCGTTTTTTCCAGTTGTTTGGGCGTCCGTTGGCTTTCG
ACTCACGATCCTAACATCACGTGGTCGACACGGTCGATTGTCTTCGATTCGGAATATTGTCGTTATCATTGC
CGCATGTATTCACCAATTCCGCCGTCTCTCCCGCCGCCTGCGCCGCAACCTCCTCTGTATTACCCGGTGGAC
GGTTACCGTGTTTACCAGCCAGTTCGCTACTACTACGTACAAACGTGTACACGCCTGTTGATGAACACGTG
TACCCAGATCACCGCCTGGTCGACCCTCATATTGAGATGATCACCGATAGGCCGCACTCGATCCCATCGGGCCAT
GTTTATTCCTTGTCTGAGCCAGAAATGGCCGCCTTACGGGATTTTGTGGCCCGGAATGTCAAAGACGGCCT
GATTACCCCGACAATTGCACCAAACGGTGCTCAGGTGTTGCAGGTGAAGCGGGGCTGGAAGTTGCAAGTC
AGCTATGATTGTCGTGCGCAAACAACTTCACTATTCAGAACCAATATCCACGTCTCAGCATCCCTAATCTCG
AGGACCAGGCACATCTTGCAACATATACTGAATTTGTACCTCAGATTCCTGGCTATCAGACTTATCCTACGT
ATGCTGCCTACCCAACATACCCGGTAGGTTTCGCATGGTACCCAGTAGGCCGGGACGGGCAGGGCCGCTCT
TTATATGTTCCTGTCTCATGATTACATGGAACCCGCATTGGTACCGCAGCCTCCGGTCCCACAGTACCCACCTC
CTCAACCTCCACCACCTCCGCCGCCTCCTCCACCGCCACCTTCTTACTCGACATTA
```

SEQUENCE LISTING

Sequence total quantity: 85
SEQ ID NO: 1              moltype = AA   length = 396
FEATURE                   Location/Qualifiers
source                    1..396
                          mol_type = protein
                          organism = Homo sapiens
SEQUENCE: 1
GELDHRTSGG LHAYPGPRGG QVAKPNVILQ IGKCRAEMLE HVRRTHRHLL AEVSKQVERE   60
LKGLHRSVGK LESNLDGYVP TSDSQRWKKS IKACLCRCQE TIANLERWVK REMHVWREVF  120
YRLERWADRL ESTGGKYPVG SESARHTVSV GVGGPESYCH EADGYDYTVS PYAITPPPAA  180
GELPGQEPAE AQQYQPWVPG EDGQPSPGVD TQIFEDPREF LSHLEEYLRQ VGGSEEYWLS  240
QIQNHMNGPA KKWWEFKQGS VKNWVEFKKE FLQYSEGTLS REAIQRELDL PQKQGEPLDQ  300
FLWRKRDLYQ TLYVDADEEE IIQYVVGTLQ PKLKRFLRHP LPKTLEQLIQ RGMEVQDDLE  360
QAAEPAGPHL PVEDEAETLT PAPNSESVAS DRTQPE                            396

SEQ ID NO: 2              moltype = AA   length = 396
FEATURE                   Location/Qualifiers
source                    1..396
                          mol_type = protein
                          organism = Orcinus orca
SEQUENCE: 2
GELDQRTTGG LHAYPAPRGG PVAKPNVILQ IGKCRAEMLE HVRRTHRHLL TEVSKQVERE   60
LKGLHRSVGK LESNLDGYVP TGDSQRWRKS IKACLCRCQE TIANLERWVK REMHVWREVF  120
YRLERWADRL ESMGGKYPVG SNPSRHTTSV GVGGPESYGH EADTYDYTVS PYAITPPPAA  180
GELPGQEAVE AQQYPPWGLG EDGQPSPGVD TQIFEDPREF LSHLEEYLRQ VGGSEEYWLS  240
QIQNHMNGPA KKWWEYKQGS VKNWVEFKKE FLQYSEGALS REAVQRELDL PQKQGEPLDQ  300
FLWRKRDLYQ TLYVDADEEE IIQYVVGTLQ PKLKRFLRPP LPKTLEQLIQ KGMEVEDGLE  360
QVAEPASPHL PTEEESEALT PALTSESVAS DRTQPE                            396

SEQ ID NO: 3              moltype = AA   length = 390
FEATURE                   Location/Qualifiers
source                    1..390
                          mol_type = protein
                          note = subspecies texanus
                          organism = Odocoileus virginianus
SEQUENCE: 3
GELDHRTTGG LHAYPAPRGG PAAKPNVILQ IGKCRAEMLE HVRRTHRHLL AEVSKQVERE   60
LKGLHRSVGK LESNLDGYVP TGDSQRWKKS IKACLSRCQE TIANLERWVK REMHVWREVF  120
YRLERWADRL ESGGGKYPVG SDPARHTVSV GVGGPESYCQ DADNYDYTVS PYAITPPPAA  180
GQLPGQEEVE AQQYPPWAPG EDGQLSPGVD TQVFEDPREF LRHLEDYLRQ VGGSEEYWLS  240
QIQNHMNGPA KKWWEYKQGS VKNWVEFKKE FLQYSEGTLS REAIQRELDL PQKQGEPLDQ  300
FLWRKRDLYQ TLYVDAEEEE IIQYVVGTLQ PKLKRFLRPP LPKTLEQLIQ KGMEVQDGLE  360
QAAEPAAEEA EALTPALTNE SVASDRTQPE                                   390

SEQ ID NO: 4              moltype = AA   length = 401
FEATURE                   Location/Qualifiers
source                    1..401

-continued

```
                              mol_type = protein
                              organism = Ornithorhynchus anatinus
SEQUENCE: 4
GELDRLNPSS GLHPSSGLHP YPGLRGGATA KPNVILQIGK CRAEMLEHVR KTHRHLLTEV   60
SRQVERELKG LHKSVGKLES NLDGYVPSSD SQRWKKSIKA CLSRCQETIA HLERWVKREM  120
NVWREVFYRL ERWADRLEAM GGKYPAGEQA RRTVSVGVGG PETCCPGDES YDCPISPYAV  180
PPSTGESPES LDQGDQHYQQ WFALPEESPV SPGVDTQIFE DPREFLRHLE KYLKQVGGTE  240
EDWLSQIQNH MNGPAKKWWE YKQGSVKNWL EFKKEFLQYS EGTLTRDALK RELDLPQKQG  300
EPLDQFLWRK RDLYQTLYVD ADEEEIIQYV VGTLQPKLKR FLHHPLPKTL EQLIQRGQEV  360
QNGLEPTDDP AGQRTQSEDN DESLTPAVTN ESTASEGTLP E                     401

SEQ ID NO: 5              moltype = AA  length = 404
FEATURE                   Location/Qualifiers
source                    1..404
                          mol_type = protein
                          note = subspecies domesticus
                          organism = Anser cygnoides
SEQUENCE: 5
GQLDNVTNAG IHSFQGHRGV ANKPNVILQI GKCRAEMLEH VRRTHRHLLS EVSKQVEREL   60
KGLQKSVGKL ENNLEDHVPT DNQRWKKSIK ACLARCQETI AHLERWVKRE MNVWKEVFFR  120
LEKWADRLES MGGKYCPGEH GKQTVSVGVG GPEIRPSEGE IYDYALDMSQ MYALTPPPGE  180
MPSIPQAHDS YQWVSVSEDA PASPVETQVF EDPREFLSHL EEYLKQVGGT EEYWLSQIQN  240
HMNGPAKKWW EYKQDSVKNW VEFKKEFLQY SEGTLTRDAI KRELDLPQKE GEPLDQFLWR  300
KRDLYQTLYV DADEEEIIQY VVGTLQPKLK RFLSYPLPKT LEQLIQRGKE VQGNMDHSDE  360
PSPQRTPEIQ SGDSVESMPP STTASPVPSN GTQPEPPSPP ATVI                  404

SEQ ID NO: 6              moltype = AA  length = 395
FEATURE                   Location/Qualifiers
source                    1..395
                          mol_type = protein
                          organism = Pelecanus crispus
SEQUENCE: 6
GQLDNVTNAG IHSFQGHRGV ANKPNVILQI GKCRAEMLEH VRRTHRHLLS EVSKQVEREL   60
KGLQKSVGKL ENNLEDHVPT DNQRWKKSIK ACLARCQETI AHLERWVKRE MNVWKEVFFR  120
LEKWADRLES MGGKYCPGEH GKQTVSVGVG GPEIRPSEGE IYDYALDMSQ MYALTPPPGE  180
VPSIPQAHDS YQWVSVSEDA PASPVETQVF EDPREFLSHL EEYLKQVGGT EEYWLSQIQN  240
HMNGPAKKWW EYKQDSVKNW VEFKKEFLQY SEGTLTRDAI KRELDLPQKE GEPLDQFLWR  300
KRDLYQTLYV DADEEEIIQY VVGTLQPKLK RFLSYPLPKT LEQLIQRGKE VQGNMDHSEE  360
PSPQRTPEIQ SGDSVDSVPP STTASPVPSN GTQPE                            395

SEQ ID NO: 7              moltype = AA  length = 395
FEATURE                   Location/Qualifiers
source                    1..395
                          mol_type = protein
                          organism = Haliaeetus albicilla
SEQUENCE: 7
GQLDNVTNAG IHSFQGHRGV ANKPNVILQI GKCRAEMLEH VRRTHRHLLS EVSKQVEREL   60
KGLQKSVGKL ENNLEDHVPT DNQRWKKSIK ACLARCQETI AHLERWVKRE MNVWKEVFFR  120
LEKWADRLES MGGKYCPGDH GKQTVSVGVG GPEIRPSEGE IYDYALDMSQ MYALTPPPGE  180
VPSIPQAHDS YQWVSTSEDA PASPVETQVF EDPREFLSHL EEYLKQVGGT EEYWLSQIQN  240
HMNGPAKKWW EYKQDSVKNW VEFKKEFLQY SEGTLTRDAI KRELDLPQKE GEPLDQFLWR  300
KRDLYQTLYV DADEEEIIQY VVGTLQPKLK RFLSYPLPKT LEQLIQRGKE VQGNMDHSEE  360
PSPQRTPEIQ SGDSVDSVPP STTASPVPSN GTQPE                            395

SEQ ID NO: 8              moltype = AA  length = 465
FEATURE                   Location/Qualifiers
source                    1..465
                          mol_type = protein
                          organism = Ophiophagus hannah
SEQUENCE: 8
GSWGLQRHVA DERRGLATPT YGAVCSIREK KASQLSGQSC LEKELLGWKC TEAIVEMMQV   60
DNFNHGNLHS CQGHRGMANH KPNVILQIGK CRAEMLDHVR RTHRHLLTEV SKQVERELKS  120
LQKSVGKLEN NLEDHVPSAA ENQRWKKSIK ACLARCQETI AHLERWVKRE INVWKEVFFR  180
LEKWADRLES GGGKYGPGDQ SRQTVSVGVG APEIQPRKEE IYDYALDMSQ MYALTPPPMG  240
EDPNVPQSHD SYQWITISDD SPPSPVETQI FEDPREFLTH LEDYLKQVGG TEEYWLSQIQ  300
NHMNGPAKKW WEYKQDSVKN WLEFKKEFLQ YSEGTLTRDA IKQELDLPQK DGEPLDQFLW  360
RKRDLYQTLY IDAEEEEVIQ YVVGTLQPKL KRFLSHPYPK TLEQLIQRGK EVEGNLDNSE  420
EPSPQRSPKH QLGGSVESLP PSSTASPVAS DETHPDVSAP PVTVI                 465

SEQ ID NO: 9              moltype = AA  length = 451
FEATURE                   Location/Qualifiers
source                    1..451
                          mol_type = protein
                          organism = Austrofundulus limnaeus
SEQUENCE: 9
GDGETQAENP STSLNNTDED ILEQLKKIVM DQQHLYQKEL KASFEQLSRK MFSQMEQMNS   60
KQTDLLLEHQ KQTVKHVDKR VEYLRAQFDA SLGWRLKEQH ADITTKIIPE IIQTVKEDIS  120
LCLSTLCSIA EDIQTSRATT VTGHAAVQTH PVDLLGEHHL GTTGHPRLQS TRVGKPDDVP  180
ESPVSLFMQG EARSRIVGKS PIKLQFPTFG KANDSSDPLQ YLERCEDFLA LNPLTDEELM  240
```

```
ATLRNVLHGT SRDWWDVARH KIQTWREFNK HFRAAFLSED YEDELAERVR NRIQKEDESI    300
RDFAYMYQSL CKRWNPAICE GDVVKLILKN INPQLPSQLR SRVTTVDELV RLGQQLEKDR    360
QNQLQYELRK SSGKIIQKSS SCETSALPNT KSTPNQQNPA TSNRPPQVYC WRCKGHHAPA    420
SCPQWKADKH RAQPSRSSGP QTLTNLQAQD I                                   451

SEQ ID NO: 10             moltype = AA   length = 396
FEATURE                   Location/Qualifiers
source                    1..396
                          mol_type = protein
                          organism = Physeter catodon
SEQUENCE: 10
GELDQRAAGG LRAYPAPRGG PVAKPSVILQ IGKCRAEMLE HVRRTHRHLL TEVSKQVERE    60
LKGLHRSVGK LEGNLDGYVP TGDSQRWKKS IKACLCRCQE TIANLERWVK REMHVWREVF    120
YRLERWADRL ESMGGKYPVG TNPSRHTVSV GVGGPEGYSH EADTYDYTVS PYAITPPPAA    180
GELPGQEAVE AQQYPPWGLG EDGQPGPGVD TQIFEDPREF LSHLEEYLRQ VGGSEEYWLS    240
QIQNHMNGPA KKWWEFKQGS VKNWVEFKKE FLQYSEGTLS REAIQRELDL PQKQGEPLDQ    300
FLWRKRDLYQ TLYVDAEEEE IIQYVVGTLQ PKLKRFLRPP LPKTLEQLIQ KGMEVQDGLE    360
QAAEPASPRL PPEEESEALT PALTSESVAS DRTQPE                             396

SEQ ID NO: 11             moltype = AA   length = 404
FEATURE                   Location/Qualifiers
source                    1..404
                          mol_type = protein
                          organism = Meleagris gallopavo
SEQUENCE: 11
GQLDNVTNAG IHSFQGHRGV ANKPNVILQI GKCRAEMLEH VRRTHRHLLS EVSKQVEREL    60
KGLQKSVGKL ENNLEDHVPT DNQRWKKSIK ACLARCQETI AHLERWVKRE MNVWKEVFFR    120
LEKWADRLES MGGKYCPGEH GKQTVSVGVG GPEIRPSEGE IYDYALDMSQ MYALTPGPGE    180
VPSIPQAHDS YQWVSVSEDA PASPVETQIF EDPHEFLSHL EEYLKQVGGT EEYWLSQIQN    240
HMNGPAKKWW EYKQDSVKNW VEFKKEFLQY SEGTLTRDAI KRELDLPQKE GEPLDQFLWR    300
KRDLYQTLYV DADEEIIQY VVGTLQPKLK RFLSYPLPKT LEQLIQRGKE VQGNMDHSEE    360
PSPQRTPEIQ SGDSVESMPP STTASPVPSN GTQPEPPSPP ATVI                    404

SEQ ID NO: 12             moltype = AA   length = 409
FEATURE                   Location/Qualifiers
source                    1..409
                          mol_type = protein
                          organism = Pogona vitticeps
SEQUENCE: 12
GQLENINQGS LHAFQGHRGV VHNNKPNVIL QIGKCRAEML EHVRRTHRHL LTEVSKQVER    60
ELKGLQKSVG KLENNLEDHV PSAAENQRWK KSIKACLARC QETIANLERW VKREMNVWKE    120
VFFRLERWAD RLESGGGKYC HADQGRQTVS VGVGGPEVRP SEGEIYDYAL DMSQMYALTP    180
PPMGDVPVIP QPHDSYQWVT DPEEAPPSPV ETQIFEDPRE FLTHLEDYLK QVGGTEEYWL    240
SQIQNHMNGP AKKWWEYKQD SVKNWLEFKK EFLQYSEGTL TRDAIKQELD LPQKEGEPLD    300
QFLWRKRDLY QTLYVEAEEE EVIQYVVGTL QPKLKRFLSH PYPKTLEQLI QRGKEVEGNL    360
DNSEEPSPQR TPEHQLGDSV ESLPPSTTAS PAGSDKTQPE ISLPPTTVI               409

SEQ ID NO: 13             moltype = AA   length = 404
FEATURE                   Location/Qualifiers
source                    1..404
                          mol_type = protein
                          organism = Alligator sinensis
SEQUENCE: 13
GQLDSVTNAG VHTYQGHRSV ANKPNVILQI GKCRTEMLEH VRRTHRHLLT EVSKQVEREL    60
KGLQKSVGKL ENNLEDHVPT DNQRWKKSIK ACLARCQETI AHLERWVKRE MNVWKEVFFR    120
LERWADRLES MGGKYCPTDS ARQTVSVGVG GPEIRPSEGE IYDYALDMSQ MYALTPSPGE    180
LPSVPQPHDS YQWVTSPEDA PASPVETQVF EDPREFLCHL EEYLKQVGGT EEYWLSQIQN    240
HMNGPAKKWW EYKQDTVKNW VEFKKEFLQY SEGTLTRDAI KRELDLPQKD GEPLDQFLWR    300
KRDLYQTLYI DADEEQIIQY VVGTLQPKLK RFLSYPLPKT LEQLIQKGKE VQGSLDHSEE    360
PSPQRASEAR TGDSVETLPP STTTSPNTSS GTQPEAPSPP ATVI                    404

SEQ ID NO: 14             moltype = AA   length = 404
FEATURE                   Location/Qualifiers
source                    1..404
                          mol_type = protein
                          organism = Alligator mississippiensis
SEQUENCE: 14
GQLDSVTNAG VHTYQGHRGV ANKPNVILQI GKCRTEMLEH VRRTHRHLLT EVSKQVEREL    60
KGLQKSVGKL ENNLEDHVPT DNQRWKKSIK ACLARCQETI AHLERWVKRE MNVWKEVFFR    120
LERWADRLES MGGKYCPTDS ARQTVSVGVG GPEIRPSEGE IYDYALDMSQ MYALTPSPGE    180
LPSIPQPHDS YQWVTSPEDA PASPVETQVF EDPREFLCHL EEYLKQVGGT EEYWLSQIQN    240
HMNGPAKKWW EYKQDTVKNW VEFKKEFLQY SEGTLTRDAI KRELDLPQKD GEPLDQFLWR    300
KRDLYQTLYI DADEEQIIQY VVGTLQPKLK RFLSYPLPKT LEQLIQKGKE VQGSLDHSEE    360
PSPQRASEAR TGDSVESLPP STTTSPNASS GTQPEAPSPP ATVI                    404

SEQ ID NO: 15             moltype = AA   length = 408
FEATURE                   Location/Qualifiers
source                    1..408
                          mol_type = protein
```

```
                        organism = Gekko japonicus
SEQUENCE: 15
GQLENVNHGN LHSFQGHRGG VANKPNVILQ IGKCRAEMLD HVRRTHRHLL TEVSKQVERE   60
LKGLQKSVGK LENNLEDHVP SAVENQRWKK SIKACLSRCQ ETIAHLERWV KREMNVWKEV   120
FFRLERWADR LESGGGKYCH GDNHRQTVSV GVGGPEVRPS EGEIYDYALD MSQMYALTPP   180
SPGDVPVVSQ PHDSYQWVTV PEDTPPSPVE TQIFEDPREF LTHLEDYLKQ VGGTEEYWLS   240
QIQNHMNGPA KKWWEYKQDS VKNWLEFKKE FLQYSEGTLT RDAIKEELDL PQKDGEPLDQ   300
FLWRKRDLYQ TLYVEADEEE VIQYVVGTLQ PKLKRFLSHP YPKTLEQLIQ RGKEVEGNLD   360
NSEEPTPQRT PEHQLCGSVE SLPPSSTVSP VASDGTQPET SPLPATVI               408

SEQ ID NO: 16             moltype = AA   length = 455
FEATURE                   Location/Qualifiers
source                    1..455
                          mol_type = protein
                          organism = Homo sapiens
SEQUENCE: 16
GPLTLLQDWC RGEHLNTRRC MLILGIPEDC GEDEFEETLQ EACRHLGRYR VIGRMFRREE   60
NAQAILLELA QDIDYALLPR EIPGKGGPWE VIVKPRNSDG EFLNRLNRFL EEERRTVSDM   120
NRVLGSDTNC SAPRVTISPE FWTWAQTLGA AVQPLLEQML YRELRVFSGN TISIPGALAF   180
DAWLEHTTEM LQMWQVPEGE KRRRLMECLR GPALQVVSGL RASNASITVE ECLAALQQVF   240
GPVESHKIAQ VKLCKAYQEA GEKVSSFVLR LEPLLQRAVE NNVVSRRNVN QTRLKRVLSG   300
ATLPDKLRDK LKLMKQRRKP PGFLALVKLL REEEEWEATL GPDRESLEGL EVAPRPPARI   360
TGVGAVPLPA SGNSFDARPS QGYRRRRGRG QHRRGGVARA GSRGSRKRKR HTFCYSCGED   420
GHIRVQCINP SNLLLAKETK EILEGGEREA QTNSR                            455

SEQ ID NO: 17             moltype = AA   length = 448
FEATURE                   Location/Qualifiers
source                    1..448
                          mol_type = protein
                          organism = Homo sapiens
SEQUENCE: 17
GALTLLEDWC KGMDMDPRKA LLIVGIPMEC SEVEIQDTVK AGLQPLCAYR VLGRMFRRED   60
NAKAVFIELA DTVNYTTLPS HIPGKGGSWE VVVKPRNPDD EFLSRLNYFL KDEGRSMTDV   120
ARALGCCSLP AESLDAEVMP QVRSPPLEPP KESMWYRKLK VFSGTASPSP GEETFEDWLE   180
QVTEIMPIWQ VSEVEKRRRL LESLRGPALS IMRVLQANND SITVEQCLDA LKQIFGDKED   240
FRASQFRFLQ TSPKIGEKVS TFLLRLEPLL QKAVHKSPLS VRSTDMIRLK HLLARVAMTP   300
ALRGKLELLD QRGCPPNFLE LMKLIRDEEE WENTEAVMKN KEKPSGRGRG ASGRQARAEA   360
SVSAPQATVQ ARSFSDSSPQ TIQGGLPPLV KRRRLLGSES TRGEDHGQAT YPKAENQTPG   420
REGPQAAGEE LGNEAGAGAM SHPKPWET                                     448

SEQ ID NO: 18             moltype = AA   length = 399
FEATURE                   Location/Qualifiers
source                    1..399
                          mol_type = protein
                          organism = Homo sapiens
SEQUENCE: 18
GAVTMLQDWC RWMGVNARRG LLILGIPEDC DDAEFQESLE AALRPMGHFT VLGKAFREED   60
NATAALVELD REVNYALVPR EIPGTGGPWN VVFVPRCSGE EFLGLGRVFH FPEQEGQMVE   120
SVAGALGVGL RRVCWLRSIG QAVQPWVEAV RCQSLGVFSG RDQPAPGEES FEVVWLDHTTE  180
MLHVWQGVSE RERRRRLLEG LRGTALQLVH ALLAENPART AQDCLAALAQ VFGDNESQAT   240
IRVKCLTAQQ QSGERLSAFV LRLEVLLQKA MEKEALARAS ADRVRLRQML TRAHLTEPLD   300
EALRKLRMAG RSPSFLEMLG LVRESEAWEA SLARSVRAQT QEGAGARAGA QAVARASTKV   360
EAVPGGPGRE PEGLLQAGGQ EAEELLQEGL KPVLEECDN                        399

SEQ ID NO: 19             moltype = AA   length = 399
FEATURE                   Location/Qualifiers
source                    1..399
                          mol_type = protein
                          organism = Homo sapiens
SEQUENCE: 19
GAVTMLQDWC RWMGVNARRG LLILGIPEDC DDAEFQESLE AALRPMGHFT VLGKVFREED   60
NATAALVELD REVNYALVPR EIPGTGGPWN VVFVPRCSGE EFLGLGRVFH FPEQEGQMVE   120
SVAGALGVGL RRVCWLRSIG QAVQPWVEAV RYQSLGVFSG RDQPAPGEES FEVVWLDHTTE  180
MLHVWQGVSE RERRRRLLEG LRGTALQLVH ALLAENPART AQDCLAALAQ VFGDNESQAT   240
IRVKCLTAQQ QSGERLSAFV LRLEVLLQKA MEKEALARAS ADRVRLRQML TRAHLTEPLD   300
EALRKLRMAG RSPSFLEMLG LVRESEAWEA SLARSVRAQT QEGAGARAGA QAVARASTKV   360
EAVPGGPGRE PEGLRQAGGQ EAEELLQEGL KPVLEECDN                        399

SEQ ID NO: 20             moltype = AA   length = 475
FEATURE                   Location/Qualifiers
source                    1..475
                          mol_type = protein
                          organism = Homo sapiens
SEQUENCE: 20
GVEDLAASYI VLKLENEIRQ AQVQWLMEEN AALQAQIPEL QKSQAAKEYD LLRKSSEAKE   60
PQKLPEHMNP PAAWEAQKTP EFKEPQKPPE PQDLLPWEPP AAWELQEAPA APESLAPPAT   120
RESQKPPMAH EIPTVLEGQG PANTQDATIA QEPKNSEPQD PPNIEKPQEA PEYQETAAQL   180
EFLELPPPQE PLEPSNAQEF LELSAAQESL EGLIVVETSA ASEFPQAPIG LEATDFPLQY   240
TLTFSGDSQK LPEFLVQLYS YMRVRGHLYP TEAALVSFVG NCFSGRAGWW FQLLLLDIQSP  300
```

```
LLEQCESFIP VLQDTFDNPE NMKDANQCIH QLCQGEGHVA THFHLIAQEL NWDESTLWIQ  360
FQEGLASSIQ DELSHTSPAT NLSDLITQCI SLEEKPDPNP LGKSSSAEGD GPESPPAENQ  420
PMQAAINCPH ISEAEWVRWH KGRLCLYCGY PGHFARDCPV KPHQALQAGN IQACQ       475

SEQ ID NO: 21               moltype = AA   length = 239
FEATURE                     Location/Qualifiers
source                      1..239
                            mol_type = protein
                            organism = Homo sapiens
SEQUENCE: 21
GVQPQTSKAE SPALAASPNA QMDDVIDTLT SLRLTNSALR REASTLRAEK ANLTNMLESV  60
MAELTLLRTR ARIPGALQIT PPISSITSNG TRPMTTPPTS LPEPFSGDPG RLAGFLMQMD  120
RFMIFQASRF PGEAERVAFL VSRLTGEAEK WAIPHMQPDS PLRNNYQGFL AELRRTYKSP  180
LRHARRAQIR KTSASNRAVR ERQMLCRQLA SAGTGPCPVH PASNGTSPAP ALPARARNL   239

SEQ ID NO: 22               moltype = AA   length = 113
FEATURE                     Location/Qualifiers
source                      1..113
                            mol_type = protein
                            organism = Homo sapiens
SEQUENCE: 22
GDGRVQLMKA LLAGPLRPAA RRWRNPIPFP ETFDGDTDRL PEFIVQTSSY MFVDENTFSN  60
DALKVTFLIT RLTGPALQWV IPYIRKESPL LNDYRGFLAE MKRVFGWEED EDF         113

SEQ ID NO: 23               moltype = AA   length = 113
FEATURE                     Location/Qualifiers
source                      1..113
                            mol_type = protein
                            organism = Homo sapiens
SEQUENCE: 23
GEGRVQLMKA LLARPLRPAA RRWRNPIPFP ETFDGDTDRL PEFIVQTSSY MFVDENTFSN  60
DALKVTFLIT RLTGPALQWV IPYIKKESPL LSDYRGFLAE MKRVFGWEED EDF         113

SEQ ID NO: 24               moltype = AA   length = 364
FEATURE                     Location/Qualifiers
source                      1..364
                            mol_type = protein
                            organism = Homo sapiens
SEQUENCE: 24
GPRGRCRQQG PRIPIWAAAN YANAHPWQQM DKASPGVAYT PLVDPWIERP CCGDTVCVRT  60
TMEQKSTASG TCGGKPAERG PLAGHMPSSR PHRVDFCWVP GSDPGTFDGS PWLLDRFLAQ  120
LGDYMSFHFE HYQDNISRVC EILRRLTGRA QAWAAPYLDG DLPLPDDYEL FCQDLKEVVQ  180
DPNSFAEYHA VVTCPLPLAS SQLPVAPQLP VVRQYLARFL EGLALDMGTA PRSLPAAMAT  240
PAVSGSNSVS RSALFEQQLT KESTPGPKEP PVLPSSTCSS KPGPVEPASS QPEEAAPTPV  300
PRLSESANPP AQRPDPAHPG GPKPQKTEEE VLETEGDQEV SLGTPQEVVE APETPGEPPL  360
SPGF                                                              364

SEQ ID NO: 25               moltype = AA   length = 146
FEATURE                     Location/Qualifiers
source                      1..146
                            mol_type = protein
                            organism = Homo sapiens
SEQUENCE: 25
GVDELVLLLH ALLMRHRALS IENSQLMEQL RLLVCERASL LRQVRPPSCP VPFPETFNGE  60
SSRLPEFIVQ TASYMLVNEN RFCNDAMKVA FLISLLTGEA EEWVVPYIEM DSPILGDYRA  120
FLDEMKQCFG WDDDEDDDDE EEDDY                                        146

SEQ ID NO: 26               moltype = AA   length = 549
FEATURE                     Location/Qualifiers
source                      1..549
                            mol_type = protein
                            organism = Homo sapiens
SEQUENCE: 26
GPVDLGQALG LLPSLAKAED SQFSESDAAL QEELSSPETA RQLFRQFRYQ VMSGPHETLK  60
QLRKLCFQWL QPEVHTKEQI LEILMLEQFL TILPGEIQMW VRKQCPGSGE EAVTLVESLK  120
GDPQRLWQWI SIQVLGQDIL SEKMESPSCQ VGEVEPHLEV VPQELGLENS SSGPGELLSH  180
IVKEESDTEA ELALAASQPA RLEERLIRDQ DLGASLLPAA PQEQWRQLDS TQKEQYWDLM  240
LETYGKMVSG AGISHPKSDL TNSIEFGEEL AGIYLHVNEK IPRPTCIGDR QENDKENLNL  300
ENHRDQELLH ASCQASGEVP SQASLRGFFT EDEPGCFGEG ENLPEALQNI QDEGTGEQLS  360
PQERISEKQL GQHLPNPHSG EMSTMWLEEK RETSQKGQPR APMAQKLPTC RECGKTFYRN  420
SQLIFHQRTH TGETYFQCTI CKKAFLRSSD FVKHQRTHTG EKPCKCDYCG KGFSDFSGLR  480
HHEKIHTGEK PYKCPICEKS FIQRSNFNRH QRVHTGEKPY KCSHCGKSFS WSSSLDKHQR  540
SHLGKKPFQ                                                         549

SEQ ID NO: 27               moltype = AA   length = 351
FEATURE                     Location/Qualifiers
source                      1..351
                            mol_type = protein
                            organism = Homo sapiens
```

-continued

```
SEQUENCE: 27
GTLRLLEDWC RGMDMNPRKA LLIAGISQSC SVAEIEEALQ AGLAPLGEYR LLGRMFRRDE   60
NRKVALVGLT AETSHALVPK EIPGKGGIWR VIFKPPDPDN TFLSRLNEFL AGEGMTVGEL  120
SRALGHENGS LDPEQGMIPE MWAPMLAQAL EALQPALQCL KYKKLRVFSG RESPEPGEEE  180
FGRWMPHTTQ MIKAWQVPDV EKRRRLLESL RGPALDVIRV LKINNPLITV DECLQALEEV  240
FGVTDNPREL QVKYLTTYHK DEEKLSAYVL RLEPLLQKLV QRGAIERDAV NQARLDQVIA  300
GAVHKTIRRE LNLPEDGPAP GFLQLLVLIK DYEAAEEEEA LLQAILEGNF T           351

SEQ ID NO: 28          moltype = AA   length = 708
FEATURE                Location/Qualifiers
source                 1..708
                       mol_type = protein
                       organism = Homo sapiens
SEQUENCE: 28
GTERRRDELS EEINNLREKV MKQSEENNNL QSQVQKLTEE NTTLREQVEP TPEDEDDDIE   60
LRGAAAAAAP PPPIEEECPE DLPEKFDGNP DMLAPFMAQC QIFMEKSTRD FSVDRVRVCF  120
VTSMMTGRAA RWASAKLERS HYLMHNYPAF MMEMKHVFED PQRREVAKRK IRRLRQGMGS  180
VIDYSNAFQM IAQDLDWNEP ALIDQYHEGL SDHIQEELSH LEVAKSLSAL IGQCIHIERR  240
LARAAAARKP RSPPRALVLP HIASHHQVDP TEPVGGARMR LTQEEKERRR KLNLCLYCGT  300
GGHYADNCPA KASKSSPAGK LPGPAVEGPS ATGPEIIRSP QDDASSPHLQ VMLQIHLPGR  360
HTLFVRAMID SGASGNFIDH EYVAQNGIPL RIKDWPILVE AIDGRPIASG PVVHETHDLI  420
VDLGDHREVL SFDVTQSPFF PVVLGVRWLS THDPNITWST RSIVFDSEYC RYHCRMYSPI  480
PPSLPPPAPQ PPLYYPVDGY RVYQPVRYYY VQNVYTPVDE HVYPDHRLVD PHIEMIPGAH  540
SIPSGHVYSL SEPEMAALRD FVARNVKDGL ITPTIAPNGA QVLQVKRGWK LQVSYDCRAP  600
NNFTIQNQYP RLSIPNLEDQ AHLATYTEFV PQIPGYQTYP TYAAYPTYPV GFAWYPVGRD  660
GQGRSLYVPV MITWNPHWYR QPPVPQYPPP QPPPPPPPPP PPPSYSTL              708

SEQ ID NO: 29          moltype = DNA   length = 1188
FEATURE                Location/Qualifiers
source                 1..1188
                       mol_type = other DNA
                       organism = Homo sapiens
SEQUENCE: 29
ggggagctgg accaccggac cagcggcggg ctccacgcct accccgggcc gcggggcggg   60
caggtggcca agcccaacgt gatcctgcag atcgggaagt gccgggccga gatgctggag  120
cacgtgcggc ggacgcaccg gcacctgctg gccgaggtgt ccaagcaggt ggagcgcgag  180
ctgaaggggc tgcaccggtc ggtcgggaag ctggagagca acctggacgg ctacgtgccc  240
acgagcgact cgcagcgctg gaagaagtcc atcaaggcct gcctgtgccg ctgccaggag  300
accatcgcca acctggagcg ctgggtcaag cgcgagatgc acgtgtggcg cgaggtgttc  360
taccgcctgg agcgctgggc cgaccgcctg gagtccacgg gcggcaagta cccggtgggc  420
agcgagtcag cccgccacac cgtttccgtg ggcgtggggg gtcccgagag ctactgccac  480
gaggcagacg gctacgacta caccgtcagc ccctacgcca tcaccccgcc cccagccgct  540
ggcgagcggc ccgggcagga gcccgccgag gcccagcagt accagccgtg ggtccccggc  600
gaggacgggc agcccagccc cggcgtggac acgcagatct cgaggacccc tcgagagttc  660
ctgagccacc tagaggagta cttgcggcag gtgggcggct ctgaggagta ctggctgtcc  720
cagatccaga atcacatgaa cgggccggcc aagaagtggt gggagttcaa gcagggctcc  780
gtgaagaact gggtggagtt caagaaggag ttcctgcagt acagcgaggg cacgctgtcc  840
cgagaggcca tccagcgcga gctggacctg ccgcagaagc agggcgagcc gctggaccag  900
ttcctgtggc gcaagcggga cctgtaccag acgctctacg tggacgcgga cgaggaggag  960
atcatccagt acgtggtggg cacccctgcag cccaagctca agcgtttcct gcgccacccc 1020
ctgcccaaga ccctggagca gctcatccag aggggcatgg aggtgcagga tgacctggag 1080
caggcggccg agccggccgg cccccacctc ccggtggagg atgaggcgga gaccctcacg 1140
cccgcccca acagcgagtc cgtggccagt gaccggaccc agcccgag              1188

SEQ ID NO: 30          moltype = DNA   length = 1188
FEATURE                Location/Qualifiers
source                 1..1188
                       mol_type = other DNA
                       organism = Orcinus orca
SEQUENCE: 30
ggggaattgg atcaacgtac taccggtggc cttcacgcat accctgcacc acgcgggggc   60
cctgtcgcga agccaaatgt catcctgcag attgggaagt gccgggctga gatgctggag  120
cacgtccgtc ggacgcatcg tcatcttctt actgaggtgt caaaacaggt ggagcgtgaa  180
ctcaaaggct tgcaccgcag cgttgggaaa cttgaaagca acttagatgg ctatgtgccg  240
actggcgaca gccagcgttg gcgtaagtcc atcaaagcat gtttgtgtcg ttgccaggaa  300
acgattgcaa acctggagcg ttgggtcaaa cgggagatgc atgtctggcg tgaagtattt  360
tatcgtttag agcgttgggc cgatcgttta gagagcatgg gtggtaagta ccctgtgggg  420
agcaaccctt ctcggcatac gacgtcagtc ggtgttggcg ggcgggagtc ctacggtcat  480
gaagcggaca cctacgacta taccgtaagc ccttatgcta ttaccccacc acctgcggcc  540
ggcgaattac ctggccagga agccgttgag gctcaacaat accctccttg ggggctgggc  600
gaggatggtc aacctagccc aggggtagac acgcaaatct ttgaggaccc acgggagttt  660
ctttcccacc tggaagaata cctgcgtcag gttggtggga gcaagaata ctggctgtca  720
caaattcaaa accatatgaa tggtcctgca aaaaaatggt gggaatataa acagggttcc  780
gtgaaaaact gggttgagtt taaaaaggag tttcttcaat attcggaggg cgccctcagt  840
cgggaggcgc tccaacgcga gttggacttg ccacagaaac aggggggaacc actcgatcaa  900
ttcctttggc ggaaacgtga cctttaccag acattgtacg tggatgcaga tgaggaagaa  960
attatccaat atgttgtggg gaccctgcag ccgaaactga aacgtttcct tcgcccgccg 1020
ctgcctaaaa cgttggaaca acttattcag aaaggtatgg aggtcgagga tggcttagaa 1080
caagtcgcag agccggcctc gccacacttg cctacagagg aggaatcgga ggcgctgacc 1140
```

```
ccagcactta catcagagtc agtggcatca gaccggacac aaccagag              1188

SEQ ID NO: 31           moltype = DNA  length = 1170
FEATURE                 Location/Qualifiers
source                  1..1170
                        mol_type = other DNA
                        organism = Odocoileus virginianus
                        sub_species = texanus
SEQUENCE: 31
ggggagttag atcaccgtac aacggggggg ttgcacgcat accctgctcc acgtggcggg   60
ccggcagcta agccaaacgt aatcctgcag attgggaagt gccgggcaga gatgttggag  120
cacgtccggc ggacccaccg gcacctcctg gctgaagtgt ctaaacaagt agaacgggaa  180
ctcaaaggtc ttcatcgtag cgtcgggaaa ttggaatcga atttggacgg gtatgttcct  240
acaggcgact cacagcggtg gaaaaagagc atcaaggcct gcctgagtcg ctgccaggag  300
acgattgcta acctcgaacg ctgggttaag cgggagatgc acgtttggcg cgaagtcttc  360
taccggctgg agcgttgggc tgatcggctc gaatctggtg ggggtaagta tccagttggg  420
tccgaccctg ctcgccacac agtctcagtt ggcgtaggtg ggccggagtc gtattgccaa  480
gatgcggaca actatgatta tacagtttcc ccatacgcga tcacaccacc gccggcagca  540
gggcagctgc caggtcagga agaggttgag gcccagcagt atccaccatg ggcccccaggg  600
gaagacggcc agctttctcc tggggtggac actcaagttt ttgaagatcc gcgtgaattt  660
ctgcggcatt tagaagatta tctccgccag gtcgggggggt ctgaagagta ttggttaagc  720
caaattcaaa accatatgaa cggcccggcc aagaagtggt ggagtacaa gcaagggtct  780
gtgaaaaatt gggtggagtt taagaaagaa ttcttgcaat attctgaggg cactctttcg  840
cgtgaagcca tccaacgcga actcgactta ccgcagaaac aaggggaacc tctcgaccaa  900
tttctgtggc gcaaacgcga cctgtaccag actctttacg tcgatgctga ggaggaagaa  960
attattcaat acgtagttgg cacactgcag cctaagctta aacggttttt acgtccacca 1020
ttgccgaaga cgcttgaaca actcatccag aagggtatgg aggttcaaga tggtctggaa 1080
caggcagcgg aaccagcggc ggaggaggca gaagccctga cacctgcgtt aactaacgag 1140
tctgtcgcga gcgaccgcac ccagccggaa                                  1170

SEQ ID NO: 32           moltype = DNA  length = 1203
FEATURE                 Location/Qualifiers
source                  1..1203
                        mol_type = other DNA
                        organism = Ornithorhynchus anatinus
SEQUENCE: 32
ggggaattag accgcctgaa cccaagctca ggcctgcatc catcctctgg tttgcatcca   60
tacccaggtc tccggggcgg ggcaaccgcg aagcctaatg tcattttgca aattggcaaa  120
tgccgtgcgg aaatgcttga acacgtccgc aaaactcacc gtcatctcct cacagaagta  180
tcgcgccaag tagaacgcga gctcaaaggc cttcacaaaa gtgttggcaa gttggaatca  240
aatcttgatg ggtacgtacc gtcaagcgac tcccaacgct ggaagaaaag cattaaggcg  300
tgcttatccc gttgccaaga gacgattgcg catttagaac gctgggttaa acgtgaaatg  360
aatgtatggc gtgaggtgtt ctaccgtttg gaacgttcag gggaccgtct ggaggctatg  420
ggcggtaagt atcctgccgg tgagcaggcc cggcgtacag tttcagtggg cgttgggggc  480
cctgagacat gttgtccagg ggatgaaagt tatgattgtc cgatttctcc gtatgcagtt  540
ccaccttcca ccggcgagtc tccggaatcc ttagaccaag gggatcagca ctatcagcag  600
tggtttgccc tcccggagga gtccctgtt agccctgggg ttgatacacca gatctttgaa  660
gatcctcgcg agttttttacg tcatctggag aagtacctga aacaagtcgg cgggacagag  720
gaagactggc tttctcaaat ccagaatcac atgaatgggc cggcgaagaa gtggtgggag  780
tacaagcaag ggagtgttaa gaattggctt gaatttaaga aggaatttttt acagtattcg  840
gagggcacac tgacgcggga cgcgttgaaa cgtgaactgg atctcccaca gaaacaaggc  900
gaaccacttg atcaattttt atggcgggaag cgcgacttat atcagacact ctacgttgac  960
gccgatgaag aggaaatcat tcagtacgtc gtgggcactc ttcagccgaa attaaaacgc 1020
tttctccatc acccactccc taagacgctt gagcagctta tccaacgggg ccaagaagtt 1080
cagaatggtc tggagcctac cgacgatcct gcaggcaac gcactcaatc ggaggacaac 1140
gacgaaagcc ttaccccctgc cgtcaccaat gagagtactg caagcgaggg cacccctgcca 1200
gag                                                              1203

SEQ ID NO: 33           moltype = DNA  length = 1212
FEATURE                 Location/Qualifiers
source                  1..1212
                        mol_type = other DNA
                        organism = Anser cygnoides
                        sub_species = domesticus
SEQUENCE: 33
gggcagcttg ataacgttac aaacgcgggc atccactcct tccaggggca tcgtggcgta   60
gcgaataagc caaatgtcat tctgcaaatt ggtaaatgtc gtgcgaaat gctggagcac  120
gttcgccgca cccaccgcca tttattatct gaagtatcta agcaggtaga agtgagctg  180
aaagggctgc aaaagtccgt gggcaagctc gagaataact tggaggatca tgtccctaca  240
gataaccaac gctggaagaa gtccattaaa gcgtgcttgg ctcgttgtca agagactatc  300
gcgcatttag agcgttgggt gaaacgcgaa atgaacgtct ggaaggaggt gtttttccgg  360
ctggaaaagt gggcagaccg gctggagtca atggtggca agtactgccc gggcgaacac  420
gggaaacaaa ccgtcagtgt aggcgtgggg ggtcctgaaa tccggccttc ggagggggaa  480
atttatgatt atgctctgga tatgagccag atgtatgcac tcaccccacc tccaggcgaa  540
atgccatcaa tcccacaagc ccatgacagc tatcagtggg ttagtgtctc agaagatgcc  600
ccggcgagcc ctgtcgaaac ccaggtattt gaggaccctc gggaattcct gtctcacctg  660
gaggaatacc tgaagcaggt aggcggcacg gaggagtatt ggttgtccca gatccagaat  720
cacatgaatg gtccggcaaa aaaatggtgg gaatataaac aggactccgt taaaaactgg  780
gttgagttta aaaaggaatt cttgcaatac tctgaaggta cttttaactcg ggatgctatt  840
```

```
aagcgtgaac tcgacttgcc gcaaaaggaa ggtgaacctc ttgaccaatt cctttggcgg    900
aagcgggacc tctatcagac actttacgtg gacgcggatg aggaggagat cattcagtat    960
gtggtcggta ccctgcagcc gaagctcaag cgtttcctga gctatcctct cccaaagact   1020
ttagaacagc tcatccagcg cggtaaagaa gtgcagggta acatggatca ctccgatgag   1080
ccttcgccgc agcgtacacc tgaaattcaa tcaggtgact ccgtagaatc tatgccacct   1140
tcaacaacgg catctccggt tccatctaat ggtacccaac ctgagccgcc gagcccgcca   1200
gccaccgtta tc                                                       1212

SEQ ID NO: 34               moltype = DNA  length = 1185
FEATURE                     Location/Qualifiers
source                      1..1185
                            mol_type = other DNA
                            organism = Pelecanus crispus
SEQUENCE: 34
gggcaacttg acaacgtaac aaacgctggg attcactcct ttcagggcca ccgcggtgtc    60
gccaacaagc caaacgtaat cttgcaaatt ggcaaatgcc gtgcggagat gttggaacac   120
gttcgtcgta cacatcgtca cttgctgtcg gaagtctcta aacaagtaga acgtgaactt   180
aaagggcttc aaaagtcagt cggcaaattg gaaaacaacc ttgaagacca tgtaccaacc   240
gacaatcagc gttggaaaaa gtctatcaaa gcttgcctgg cccgttgtca agagacgatt   300
gctcacctgg agcggtgggt aaagcgcgag atgaatgtgt ggaaagaggt cttcttccgc   360
ttggaaaaat gggccgaccg tttggagtcc atgggcggta aatattgtcc gggtgaacat   420
ggtaagcaaa cagtctctgt gggcgttggt gggccggaaa ttcggccttc tgaaggcgag   480
atttacgatt atgcgctcga catgtcccag atgtatgcgc ttacaccacc accgggcgag   540
gtaccaagca ttcctcaagc gcatgacagt tatcagtggg ttagcgtatc cgaagacgct   600
cctgcctcgc cggtagagac ccaggttttt gaagatcctc gtgaatttt aagccacttg   660
gaggagtatt tgaagcaggt aggggggaca gaggaatatt ggctgtctca gatccagaac   720
cacatgaatg gcccggctaa aaagtggtgg gaatacaaac aagattcggt aaagaattgg   780
gtagaattta aaaaggagtt tttacagtac tcagagggga ctctcacgcg tgatgcgatc   840
aaacgcgagt tggatcttcc tcaaaaagag ggggagccac tcgatcagtt cctctggcgc   900
aagcgggatc tctaccaaac actctacgta gacgcagacg aagaagagat catccagtac   960
gtggtgggta cgctccagcc gaaactcaaa cgtttcctca gctacccact tcctagaact  1020
ctggaacaac tgattcagcg gggcaaagag gtccagggta acatggacca ttcgaggaa   1080
cctagtccgc aacgtacacc tgagatccaa tctggggatt ctgtcgattc ggttccacct  1140
tctacaacag cgtctccggt gccgtcaaat gggacccaac agag                    1185

SEQ ID NO: 35               moltype = DNA  length = 1185
FEATURE                     Location/Qualifiers
source                      1..1185
                            mol_type = other DNA
                            organism = Haliaeetus albicilla
SEQUENCE: 35
gggcagcttg ataatgtaac caatgcaggt atccactctt tccagggtca ccgcggtgtg    60
gcaaacaagc caaatgttat tctgcaaatt ggtaagtgtc gcgctgagat gttagaaacc   120
gtccggcgca cgcatcggca tctcctgtca gaggtttcaa agcaggtaga gcgtgaatta   180
aagggcctcc agaagtccgt aggtaaactc gaaaataatc ttgaagacca cgttcctacc   240
gataatcaac ggtggaaaaa gtcaatcaag gcgtgcttag cacggtgtca ggaaacgatc   300
gcgcacctcg aacgttgggt gaagcgcgaa atgaatgtct ggaaagaagt gttcttccgg   360
cttgagaagt gggctgatcg gctcgaatcc atgggtggca aatattgtcc aggtgatcat   420
ggcaagcaaa cggtctccgt cggtgttggt ggtccggaaa tccggccgag cgagggtgaa   480
atctatgact acgctcttga tatgtcccag atgtatgcac tcactcctcc gccgggtgag   540
gtcccgtcga tcccgcaggc gcatgactca taccaatggg tgtcgactag cgaagacgca   600
ccagcctccc ctgttgaaac tcaagtattc gaggacccgc gtgagttcct gagccatta   660
gaggagtacc ttaagcaggt tggtggtacc gaggaatact ggttgagcca gattcagaat   720
cacatgaacg ggcggctaa gaaatggtgg gaatacaagc aggattcagt caagaattg   780
gtcgaattta agaaggagtt tttgcagtac agtgagggga cgctcacacg cgacgctatc   840
aaacgggagc tggacctgcc acaaaaggag ggtgaacgc ttgatcagtt tctttggcgc    900
aagcgtgatc tgtatcaaac cctgtatgtg gacgctgacg aagaagagat cattcagtac   960
gtggttggga ctctgcaacc aaagctgaag cgttttcttt cttatcctct ccctaagaca  1020
ctggaacagt taatccaacg tggcaaggag gtccagggta atatggacca ctctgaggaa   1080
ccgagcccgc aacgtactcc tgaaattcag agcggggata gtgtcgactc agttcctcca   1140
agtacgaccg catcccggt cccaagtaac ggtacccaac agag                     1185

SEQ ID NO: 36               moltype = DNA  length = 1395
FEATURE                     Location/Qualifiers
source                      1..1395
                            mol_type = other DNA
                            organism = Ophiophagus hannah
SEQUENCE: 36
gggtcttggg gcttgcaacg tcacgtggct gatgaacgtc gtggcctcgc tacgcctacc    60
tacggcgcgg tttgttccat tcgggagaaa aaagcctccc aactgagcgg ccagagctgt   120
ttggagaaag agttgcttgg ttggaaatgt acggaggcaa tcgtgaaat gatgcaagtc    180
gataacttta ccacggtaa cttacatagc tgccaaggcc atcgggggat ggcaaatcac   240
aaaccgaacg taatccttca aatcgggaaa tgtcgcgcag aaatgttaga ccacgtgcgt   300
cgcacccacc gccatctctt gacggaggtt tcgaagcagg tagaacgcga attgaagtct   360
ctccaaaagt cggttggcaa gctcgagaat aatctggaag accacgtgcc atcggcagcg   420
gagaaccaac gttggaagaa atcaattaaa gcctgcctgg cccggtgcca agaaacaatt   480
gctcacctcg aacgctgggt taaacgcgaa atcaacgtct ggaaagaagt attctttcgt   540
ctggagaagt gggcggaccg ccttgagtcg ggtggggca agtatgggcc tggtgaccaa   600
agtcgtcaaa ctgtaagtgt cggtgttggg gccccagaaa tccaaccgcg gaaagaagaa   660
```

```
atctatgact acgctctcga catgtcgcag atgtatgcct taacaccacc gccgatgggt   720
gaagacccaa acgtacctca atcccacgat agctaccagt ggattaccat ctcagacgat   780
tcacctccgt cgccagtgga aactcaaatt ttcgaggatc cacgcgaatt ccttaccat    840
ctcgaggatt atcttaagca agtgggcggg actgaagaat attggttgag tcagattcaa   900
aatcatatga acggtccggc caagaaatgg tgggagtaca acaagattc cgtgaaaaac    960
tggttggaat tcaagaagga attccttcaa tactctgagg gtactttgac acgtgacgca  1020
attaaacaag aacttgactt accgcagaag gacggcgagc cattggatca atttctttgg  1080
cggaagcggg acctgtatca gacgctctat attgatgcag aggaggaaga agtaatccaa  1140
tacgttgttg gcacactcca accgaaatta aaacgtttcc tttcccaccc gtatccgaaa  1200
actttggaac agttaatcca acgtgggaaa gaggtggaag gcaacctcga taactctgag  1260
gagcctagcc cgcaacggag tccaaagcac caattgggtg gtagcgtcga gagcctccca  1320
ccttcgtcga ccgcaagtcc tgttgcgtca gacgagactc acccagacgt gagcgcacct  1380
ccggtaacgg tgatt                                                    1395
```

```
SEQ ID NO: 37              moltype = DNA  length = 1353
FEATURE                    Location/Qualifiers
source                     1..1353
                           mol_type = other DNA
                           organism = Austrofundulus limnaeus
SEQUENCE: 37
ggggacggcg agactcaagc tgagaatcca tctaccagct tgaacaacac tgacgaagat   60
atcttggaac agctcaagaa aattgtcatg gatcaacaac acctgtatca gaaagaatta   120
aaggcatctt ttgaacaact cagtcgcaaa atgtttttccc agatggaaca aatgaatagc   180
aagcaaacgg atctgctttt agaacatcaa aaacagactg tcaaacatgt agacaagcgc   240
gtggagtatt tgcgggcgca attcgatgca tcgttaggct ggcggttgaa agagcaacac   300
gcggatatta cgaccaaaat cattcctgag atcatccaaa cggtgaagga agatattagc   360
ctgtgtcttt ctacgctctg cagtatcgct gaagatatcc agacatcacg ggctaccact   420
gtcacagggc atgctgccgt acaaacccat cctgtggatc ttttgggtga acaccattta   480
gggaccacgg ggcacccacg cttacagtcg acccgtgtag ggaaaccaga cgacgtacct   540
gagtcgccgg taagcctgtt tatgcaaggt gaggcgcgtt cccggatcgt tggcaagagt   600
ccgattaaac tgcaatttcc gacgttcggc aaagcaaacg attcttccga cccactccaa   660
tatctggagc ggtgtgagga cttttcttgct cttaacccctt taactgatga ggaacttatg   720
gctactttgc ggaatgtgtt acatggcacc tctcgggatt ggtgggatgt cgcacgtcat   780
aaaatccaaa cttggcgtga gtttaataaa cacttccggg cggctttcct cagcgaggat   840
tatgaagatg agttggctga gcgcgtccgt aaccgtatcc aaaaagaaga tgagtctatc   900
cgcgatttcg cttatatgta tcagtccttg tgcaagcggt ggaaccctgc tatctgcgaa   960
ggtgatgtag taaagctcat cctgaagaac atcaatccac aactgccgtc tcagttacgc  1020
tcccgggtca cgaccgtgga tgagcttgtt cgcttgggcc agcagcttga aaaagatcgt  1080
cagaatcagc tccaatatga gcttcggaag agttccggca aaattatcca aaaatctagt  1140
tcgtgcgaaa cttcagcgct cccgaacacg aagagtacac ctaatcaaca aaaccctgct  1200
accagtaacc gtcctccaca ggtgtattgc tggcggtgta agggtcacca tgcccctgcc  1260
tcttgtccgc aatggaaagc tgataagcac cgtgcgcaac cttcgcggag ttctgggcca  1320
caaactctga ctaatctcca agctcaagac atc                               1353
```

```
SEQ ID NO: 38              moltype = DNA  length = 1188
FEATURE                    Location/Qualifiers
source                     1..1188
                           mol_type = other DNA
                           organism = Physeter catodon
SEQUENCE: 38
ggggaattgg atcaacgtgc ggcaggggc ttgcgcgcgt acccggcgcc gcgtggtggt    60
ccagttgcca aaccgagcgt aattcttcag attggtaagt gccgcgctga gatgctggaa   120
cacgtccgcc gcacgcatcg ccatcttctg acggaggtaa gtaaacaagt ggagcgcgaa   180
ctcaaggggt tacatcggtc tgtcggtaag ttggagggca atttagacgg ctatgtgcct   240
accggtgatt cccaacgctg gaaaaaaagt atcaaggcgt gtctctgccg gtgtcaggaa   300
acaattgcaa atctcgagcg ttgggtgaaa cgtgagatgc atgtttggcg tgaggtattc   360
tatcgtttgg aacggtgggc agaccgtttg gagtctatgg ggggcaagta tccggtgggc   420
actaacccgt cgcggcacac agtaagtgtc ggggtagggg gcccggaagg ctattctcat   480
gaagcggata cttatgacta cacggtgtct ccgtatgcta tcacgccacc gcctgccgcg   540
ggtgagttgc ctggtcaaga ggctgtcgag gcacaacagt accctccatg gggtctgggg   600
gaggacgggc aaccaggtcc gggcgtggac acgcagattt ttgaggaccc tcgcgaattt   660
ttgagccact tagaggagta cctgcggcaa gtaggggggga gtgaagagta ctggttatcg   720
caaattcaaa atcatatgaa tggccctgcg aagaaatggt gggagttcaa acaggggtca   780
gtcaagaatt gggtgcgaatt taagaaagaa tttttgcaat acagtgaggg tacgttgagt   840
cgcgaggcca tccaacgtga actggaccttc cctcagaagc aggggggagcc gttagatcaa   900
tttttatggc ggaaacgtga cttataccaa accctctacg ttgacgctga ggaagaagaa   960
attattcaat atgttgtcgg tacgctgcag ccaaagctga agcggttcct ccgtcctcca  1020
ctccctaaaa ccttagaaca attaatccaa aaaggcatgg aagttcagga cgggttagaa  1080
caagcggccg aaccggcctc tccgcgtctg ccgccggaag aggagagtga ggctcttacg  1140
cctgcgctca cgagcgaatc agtagcctcc gatcggcacg agccagag               1188
```

```
SEQ ID NO: 39              moltype = DNA  length = 1212
FEATURE                    Location/Qualifiers
source                     1..1212
                           mol_type = other DNA
                           organism = Meleagris gallopavo
SEQUENCE: 39
gggcagcttg acaatgtgac gaacgcgggg attcacagct ttcaagggca ccgcggcgtc    60
gccaacaaac cgaatgtcat tctgcaaatc ggtaaatgtc gtgctgaaat gcttgagcac   120
```

```
gttcgtcgta cccatcgtca cttgctttct gaagtatcaa aacaagtgga gcgggaactc   180
aaaggcctgc aaaagtcagt gggtaaattg gagaataacc tcgaagacca tgtacctaca   240
gacaaccagc ggtggaaaaa atctatcaag gcatgcctcg ctcgttgcca ggagactatt   300
gcccatcttg agcggtgggt gaaacgtgaa atgaacgtat ggaaggaagt attttttcgc   360
ttagagaagt gggctgatcg tcttgaatcg atgggcggca agtactgtcc tggggaaaac   420
ggcaaacaaa ctgtatctgt cggcgtgggg ggcccggaga tccggccatc ggaaggggaa   480
atttatgatt atgctctcga catgtcccaa atgtatgctc tcacaccagg gccaggggaa   540
gtaccgtcaa ttccgcaagc acacgacagc taccaatggg tatctgtgag cgaggacgcg   600
cctgcctctc cggttgagac gcaaatcttt gaggacccac atgaattttt gtctcatctt   660
gaagaatatc tcaaacaggt tggcggcaca gaagaatact ggttatctca gatccagaat   720
cacatgaacg gcccggctaa aaagtggtgg gagtataagc aagattccgt aaagaactgg   780
gtcgaattca agaaagagtt tcttcaatac tctgagggta ctctgacgcg cgatgcaatt   840
aagcgggagt tagaccttcc acaaaaagag ggggagcctc ttgaccagtt cctgtggcgt   900
aagcgcgacc tctatcagac actttacgtc gacgctgatg aagaagagat tattcaatat   960
gttgtgggta ccctgcagcc aaaagcttaag cgtttcctta gctacccact tccgaaaact  1020
ctggagcagc tcattcaacg cggtaaggaa gtgcagggca acatggacca ctctgaagag  1080
cctagcccgc agcgcactcc tgaaatccaa tcaggtgaca gtgtggagtc aatgccgccg  1140
tcaaccaccg cttctccggt acctagcaac gggacgcaac cagagcctcc aagcccaccg  1200
gctacagtca tc                                                       1212
```

SEQ ID NO: 40         moltype = DNA  length = 1227
FEATURE                 Location/Qualifiers
source                  1..1227
                           mol_type = other DNA
                           organism = Pogona vitticeps
SEQUENCE: 40

```
gggcaacttg agaatattaa ccaaggttcc ctgcacgcgt ttcagggtca tcgcggcgtg    60
gtccataaca acaagcctaa cgttattctc cagatcggga agtgccgcgc cgaaatgctg   120
gagcatgtgc ggcgcaccca tcgccatttg ctcactgaag tatcaaaaca ggtggagcgt   180
gagttgaagg ggttgcagaa aagtgtaggc aaacttgaaa ataatttaga agaccacgta   240
ccaagtgcgg ctgagaacca acgctggaag aagtcgatta aagcctgctt agcgcgttgt   300
caggagacca ttgcgaactt ggaacgctgg gttaaacgtg agatgaatgt ttggaaggag   360
gtcttttttcc gcttagagcg ctgggcagat cgcctcgaat ccgggggtgg caagtactgc   420
catgcagacc agggtcgcca aactgtcagc gtaggtgttg gtggtcctga agtgcgtccg   480
tctgaaggtg aaatttacga ttacgcgttg gatatgagcc aaatgtacgc cttgactccg   540
ccgcctatgg gtgatgttcc agtaattcct cagccgcatg acagttatca gtgggtgaca   600
gatccggaag aagcgccacc aagtccggtt gagacacaaa ttttcgagga ccctcgggag   660
tttctgaccc atcttgagga ttatttaaaa caagtcggcg ggacagagga atattggctc   720
tcacagatcc aaaatcatat gaatgggcca gcgaaaaagt ggtgggaata taaacaggat   780
agtgtgaaga actggcttga gttcaaaaaa gaattcttgc agtactcaga aggcacgtta   840
acgcgggacg ctattaaaca ggaacttgac cttccacaaa aagaagggga accgctggat   900
caattcctct ggcgcaaacg cgatttgtac caaactctct acgtcgaggc agaagaagag   960
gaggtcatcc aatatgtagt tggcacactg caaccaaaac tgaagcggtt tcttttctcat  1020
ccgtacccta aaaccctgga gcaactcatc cagcgcggga aggaagttga ggggaatttg  1080
gacaatagtg aagaaccgtc tccacagcgg accccagaac atcagctggg ggacagtgtg  1140
gaatctttgc cgcctagtac tacggcttcg cctgccggtt cggataaaac gcaacctgag  1200
attagcttac ctccaactac agtcatt                                       1227
```

SEQ ID NO: 41         moltype = DNA  length = 1212
FEATURE                 Location/Qualifiers
source                  1..1212
                           mol_type = other DNA
                           organism = Alligator sinensis
SEQUENCE: 41

```
gggcaattag attcggtaac caatgcgggc gtccacacct accagggcca tcggagcgtc    60
gccaataaac ctaacgtcat tcttcaaatc gggaaatgtc ggactgagat gctggagcat   120
gtccgtcgga ctcatcgcca cctgctcaca gaagtgtcaa agcaagtgga acgtgaactc   180
aagggcttac agaagagcgt gggcaaactg gaaaacaatc ttgaagacca tgtcccaact   240
gacaatcagc ggtggaagaa gtcaatcaag gcatgtctcg cgcgttgcca agagaccatt   300
gctcaccttg agcggtgggt gaaacgtgaa atgaacgtgt ggaaggaggt gttcttccgg   360
ttagaacgct gggccgaccg ccttgaatca atgggtggta aatactgccc gacggactct   420
gcacgtcaga cagttagcgt tggggtgggg ggcccggaaa ttcggcctag tgaaggcgaa   480
atctatgact acgcgctcga tatgagccaa atgtacgctc ttacgccgtc accgggcgaa   540
ttgccgtccg tccctcaacc gcatgattca taccagtggg tcactagtcc ggaagacgct   600
ccggcgtcac cagttgaaac gcaggtattc gaggatcctc gggagttctt gtgtcatttg   660
gaagagtacc tgaagcaggt tggcggtaca gaggaatatt ggctgagcca gattcagaat   720
catatgaatg gtcctgcaaa aaagtggtgg gaatataaac aagacacggt taagaattgg   780
gtggaattca agaaggagtt cttacaatac agtgagggta cacttaccg tgatgcgatt   840
aagcgggaat tagacctccc gcaaaaggac ggtgagcctc tggatcaatt tttatggcgt   900
aagcgtgacc tctatcagac attatacatt gatgccgatg aagaacagat cattcagtac   960
gtcgtgggga cattgcaacc taaactcaag cggttcttgt cctatccact tccaaaaact  1020
cttgaacaat taatccagaa agggaaggag gtgcagggtt cacttgacca cagcgaggag  1080
ccgagtcctc aacgtgcgag cgaggctcgg acgggcgata gtgtggaaac cttgccgcct  1140
tctaccacta catcaccaaa tacgtcatct ggtacacagc cagaggcacc atcgcctcca  1200
gcgacggtaa tc                                                       1212
```

SEQ ID NO: 42         moltype = DNA  length = 1212
FEATURE                 Location/Qualifiers
source                  1..1212

```
                    mol_type = other DNA
                    organism = Alligator mississippiensis
SEQUENCE: 42
gggcagttag acagtgtgac taacgccggg gtgcatacgt accaggggca ccgcggggtc    60
gccaataagc caaatgtaat tctccagatt gggaagtgtc gtacagagat gttggaacat   120
gtccgtcgca ctcatcgcca cttgctcacc gaggtctcca aacaagtaga acgcgaactc   180
aaggggctcc agaagagtgt tgggaagttg gagaataacc tcgaagacca cgttccgaca   240
gataaccaac ggtggaaaaa gtctattaaa gcctgtctcg cccgttgtca agagacaatc   300
gcacacttgg aacgctgggt caaacgggag atgaatgtgt ggaaggaagt cttcttccgt   360
ctcgagcggt gggcggatcg tttagaaagt atgggcggta aatattgccc aactgactcg   420
gctcgtcaaa cggtgtcggt tggcgtaggc ggcccggaaa ttcgccctag cgagggtgag   480
atctatgact atgcacttga catgagtcag atgtatgcgt taactccgtc gccaggggag   540
cttccaagta ttccacagcc tcacgatagt tatcaatggg taacttctcc tgaagacgcc   600
ccagcatccc cagttgagac acaagtattc gaggaccctc gtgagtttct ctgtcacctc   660
gaggagtacc ttaaacaggt aggcgggacc gaagagtact ggttatcgca aatccaaaac   720
catatgaatg tcctgccaa aaagtggtgg gagtataaac aagatactgt gaagaattgg   780
gtagagttca agaaagagtt cttacagtac tctgagggga cgttaactcg tgatgcgatc   840
aagcgcgaat tggatttacc tcagaaggac ggcgagccac tcgaccagtt cttatggcgc   900
aagcgtgact tgtatcaaac cctttatatc gatgctgacg aggaacaaat tatccagtac   960
gtagtcggta cgttgcaacc aaaacttaaa cgctttctga gctacccatt acctaaaacg  1020
ttggagcaac tgatccagaa aggtaaagag gtgcaaggga gcctggatca tagtgaagaa  1080
ccgagccctc agcgggcttc tgaagctcgg accggtgata gcgtcgaatc tttaccacct  1140
agtaccacaa ccagcccgaa tgcgtcatct ggtacccaac ctgaagcgcc ttccccacct  1200
gctacagtca tt                                                      1212

SEQ ID NO: 43        moltype = DNA  length = 1224
FEATURE              Location/Qualifiers
source               1..1224
                     mol_type = other DNA
                     organism = Gekko japonicus
SEQUENCE: 43
gggcagctcg agaatgtcaa ccatgggaac ctccattctt ttcaaggtca tcgcggcggc    60
gtcgccaaca agccaaacgt tatcttgcag atcggtaaat gtcgtgcaga gatgctggac   120
cacgtccggc ggacccaccg gcatttactg acagaggtat cgaaacaggt tgaacgtgag   180
ttgaaggggt tacagaaatc agtaggggaa ttagaaaata acttagaagg ccatgtccct   240
tcagccgttg aaaaccagcg ttggaaaaaa tcgatcaagg cctgcctttc ccgctgccaa   300
gagaccattg cccaccttga gcgttgggtg aagcgcgaga tgaacgtatg gaaagaggtt   360
ttcttccgct tagagcggtg ggcagatcgg ttggaatctg ggggcgggaa atattgtcac   420
ggtgataatc atcgtcaaac agtatcagtc ggtgttggcg gccctgaggt acgtccatct   480
gaaggcgaaa tttacgatta cgctctcgac atgtcgcaaa tgtacgcttt aacaccgcct   540
agcccagggg atgtgcctgt agttagccag ccgcacgaca gctatcagtg ggttacggtt   600
ccggaggata cccctccatc cccggtggag acgcaaatct tcgaggaccc acgggagttc   660
ttgacccact tagaggatta cttaaagcaa gtgggggata cagagggaata ttggttatct   720
cagatccaga atcacatgaa cgggccagcc aagaagtggt gggagtataa gcaagactca   780
gtaaaaaatt ggctcgagtt taagaaggaa ttccttcagt attccgaggg gacacttacg   840
cgcgacgcta tcaaggaaga acttgacctc ccgcaaaagg acgggggaacc tcttgatcag   900
ttcctgtggc gcaagcgcga cttgtaccag accctgtacg tcgatgctgg gaggaggag   960
gtgatccagt atgttgtggg gactttacaa cctaaattaa agcgttttct ctcacaccct  1020
tacccgaaaa cgttagagca acttatccaa cggggcaaag aggtgaaggg aacctcgac   1080
aattcagagg aaccaacacc tcagcgtact ccagaacacc aactgtgtgg ttctgtagaa  1140
tcgctgcctc cttcctctac cgtcagtcca gtggctagcg atggtactca acctgagact  1200
tcgccattgc cagcgactgt tatt                                          1224

SEQ ID NO: 44        moltype = DNA  length = 1365
FEATURE              Location/Qualifiers
source               1..1365
                     mol_type = other DNA
                     organism = Homo sapiens
SEQUENCE: 44
gggccattga cgttgttaca agactggtgt cgtggtgaac atttaaacac ccgccggtgc    60
atgttgatcc tcggtatccc agaagattgc ggcgaggatg agttcgaaga gacacttcag   120
gaggcgtgtc gccatttagg gcggtaccgc gtgatcggcc gcatgttccg tcgtgaggaa   180
aatgcccaag cgatcctctt ggaattggcg caggatattg actatgcctt actccctcgg   240
gaaatccctg ggaaaggcgg gccttgggag gtaattgtga agccgcgtaa ttccgacggc   300
gaattcttaa atcggcttaa tcgctttctt gaagaggagc gccgtacggt ctccgatatg   360
aaccgtgttt tgggctcgga tactaactgt tcagctcctc gtgtcaccat tagtcctgaa   420
ttctggactt gggcacagac gctgggcgca gctgtccaac cattgctcga acagatgctc   480
tacgggagt tacgggtctt cagtggcaat acgatttcca tcccaggtgc tctcgctttt   540
gacgcgtggc tggagcatac cacggaaatg cttcaaatgt ggcaggtgc tgaaggggag   600
aaacggcggc gcttgatgga gtgtgtttgcg gggccagccc tgcaagtcgt tagtgggtta   660
cgtgcatcga atgccagtat cactgtcgaa gagtgtcttg ctgcactgca gcaggtattc   720
ggtccagtgg aaagtcataa gattgcccaa gtaaagttat gcaaagctta ccaggaggct   780
gggaaaaag taagcagctt cgttttgcgt ttggagccac tgcttcagcg tgctgtagaa   840
aacaacgtgg tcagtcgccg caatgtcaac caaacacgtc ttaagcgtgt tctgtcgggag   900
gccaccctc ctgacaagct gcgtgataaa ttgaagttaa tgaaacacg ccgtaaaccg   960
ccgggtttct tggcgttggt taaactgtta cgtgaagagg aggagtggga ggccacctta  1020
gggccagacc gcgagtcatt ggaggggtta gaagtggcac cgcgcccgcc agcacggatt  1080
acgggtgttg gcgcagtacc tcttccggca tccgggaatt catttgatgc ccgtccttcg  1140
caagggtacc ggcgccgtcg gggtcgtggt cagcaccgtc ggggcggcgt tgctcgtgca  1200
```

-continued

```
ggctctcgtg gctctcgtaa gcggaaacgg cacaccttct gctattcctg tggtgaggat   1260
ggccatattc gtgtccaatg cattaaccct agcaatctcc tgttggctaa ggagaccaaa   1320
gagattttgg aaggggggaga acgtgaagcg caaacgaatt cacgt                   1365

SEQ ID NO: 45          moltype = DNA  length = 1344
FEATURE                Location/Qualifiers
source                 1..1344
                       mol_type = other DNA
                       organism = Homo sapiens
SEQUENCE: 45
ggggctctta cgctcttaga agactggtgt aagggtatgg acatggaccc gcggaaggct   60
ctcctgattg taggtattcc gatggaatgc agtgaggtgg aaatccagga tacagttaaa   120
gctggtcttc aacctctgtg cgcttatcgt gtactcggcc gtatgttccg gcgggaggat   180
aatgcgaagg ctgtttttcat tgagctggca gacaccgtga attacaccac gttaccgtct   240
cacattccgg gtaaaggggg ttcctgggaa gtcgttgtta aacctcggaa ccctgacgac   300
gagttccttt ctcggcttaa ctacttcttg aaagatgagg gccgctcgat gacggatgtc   360
gcccgggcac tggggtgctg tagcttacct gcggaatcac tggacgcgga agtaatgcca   420
caggtccgct ccccaccatt agaacctcca aaagagagta tgtggtaccg taagttaaaa   480
gtgtttagtg gtaccgcgtc gccttcgccg ggggaggaga catttgagga ctggttagag   540
caagtcaccg agatcatgcc tatctggcaa gtatctgaag ttgaaaagcg ccgtcggtta   600
ctggagtcac tccggggccc ggcactctca attatgcgcg tgttacaagc caataacgat   660
agcattaccg ttgaacagtg tttggatgca ttaaagcaga tctttggcga caaggaagac   720
ttccgtgcct ctcaatttcg ttttcttcaa acgtcccca aaattgggga gaaggtgagt   780
acgttcctgc tgcgtttaga gccactcttg caaaaggccg ttcacaagag cccactttcg   840
gtacgtagta ctgatatgat tcggttaaag cacctgttgg cacgcgtagc catgacccg   900
gcactgcgtg gtaaactcga attactcgac caacgcggt gcccacctaa ttttcttgag  960
ctgatgaagc tgatccggga tgaggaagag tgggagaata ctgaagctgt gatgaaaaat   1020
aaagagaaac cttcaggtcg tggccgcggt gcatcaggcc gtcaagctcg cgccgaggcc   1080
agtgtaagtg ctccgcaagc aacagtccaa gcacgtagct tctctgattc tagcccgcag   1140
acgattcagg ggggcttacc acctcttgtc aagcgtcggc gcctttggg ttcggagagc   1200
acacgtgggg aagaccacgg gcaagctact tatccgaaag cagagaatca gactccaggg   1260
cgtgagggcc cgcaggcggc tggggaggaa cttggtaatg aggccggggc cggcgcgatg   1320
tcccaccccga aaccgtggga aacc                                          1344

SEQ ID NO: 46          moltype = DNA  length = 1197
FEATURE                Location/Qualifiers
source                 1..1197
                       mol_type = other DNA
                       organism = Homo sapiens
SEQUENCE: 46
ggggctgtga caatgctcca ggactggtgc cgttggatgg gcgtgaacgc tcggcggggg   60
ctgttaatct taggtatccc tgaagactgt gacgatgcag agttccaaga gtcgttagaa   120
gctgcactcc gtcctatggg tcactttact gtactcggta aggccttccg cgaggaagac   180
aacgctaccg ctgcgctggt ggaattagat cgcgcaggtta attacgcact tgttccacgc   240
gaaattccgg gcaccggcgg gccttggaac gtcgtgttcg ttcctcggtg ctccggcgag   300
gaattcctgg ggttaggccg cgtgttccac tttcctgaac aggagggcca aatggtagaa   360
tcggttgcgg gggcactggg ggtaggtctg cgccgcgtgt gttggttacg ctcgatcggg   420
caagctgtac aaccatgggt agaagctgtt cgctgccaaa gcttaggggt atttagtggt   480
cgtgatcaac ctgcacctgg tgaagaaagc ttcgaggtct ggttggatca tacgaccgag   540
atgttgcatg tgtggcaagg cgtgtcggaa cgggaacggc gccgtcgtct gctggaaggg   600
ctgcgtggca cagccttaca acttgtacat gccttactgg cagaaaatcc ggcacggaca   660
gcacaagatt gcttggctgc attagcccaa gtttttggtg ataacgaaag ccaggcaacg   720
attcgtgtta aatgtttgac agcccaacag cagagtggcg aacgcctctc tgcgttcgtt   780
ctccgcttag aagtacttct gcaaaaggct atggagaagg aagcattggc gcgcgcgtca   840
gcggatcggg tgcgtcttcg tcagatgctg acacgcgcac atctcacaga gccgttggat   900
gaagccttac ggaaattgcg tatggcaggg cgttctccgt cttttttgga aatgctcggc   960
ttagtacgcg agtcagaggc ctgggaggca agtctggctc ggtccgtccg ggcgcaaacc   1020
caggagggtg caggggcccg ggcggggggcc caagcagttg cgcgtgccag cactaaggtt   1080
gaagctgtac ctggtggccc tggccgggag ccagaaggtc tcctccaagc cggggggcaa   1140
gaagcggaag aacttctcca agagggctta aagccggttt tagaggaatg tgacaat       1197

SEQ ID NO: 47          moltype = DNA  length = 1197
FEATURE                Location/Qualifiers
source                 1..1197
                       mol_type = other DNA
                       organism = Homo sapiens
SEQUENCE: 47
ggggcggtca ccatgttgca agactggtgt cggtggatgg gcgtgaatgc tcggcgggt   60
ttattgatct tgggtatccc agaagactgt gacgacgccg agtttcagga gtcgctcgag   120
gccgcccttc gtccaatggg gcattttacg gttctgggca aggtgttccg tgaagaggat   180
aacgctacag cagctcttgt ggagcttgac cgtgaggtga attatgcgtt agtacctcgc   240
gagattccag gtaccggtgg gccatggaac gtagtcttcg tcccacgttg ctcggggggag   300
gaatttctgg ggcttgggcg cgtattccac tttccagaac aggaagggca gatggtcgaa   360
agcgtagcag gcgctcttgg cgttggtctc cggcgcgtgt gcttggttacg ctccatcggc   420
caagcagtcc aaccatgggt tgaagccgta cgctatcaat ctttaggtgt cttctcaggc   480
cgtgaccagc cggcgcctgg tgaggaatcc ttcgaagtct ggctcgatca tacaactgag   540
atgctgcatg tatggcaagg tgtctcagag cgggaacggc ggcggcgtgt attagagggg   600
ctccgtggga ctgcgctcca attagtacat gcgcttttgg ccgaaaatcc agcccgtact   660
gcccaagatt gtctggcagc actcgcccaa gtattcggca caacgaatc gcaggcaaca   720
```

-continued

```
atccgcgtaa agtgtcttac agcacagcag cagtcagggg aacgtcttag tgcgttcgtt   780
ctgcggctgg aagtgttact ccagaaagcc atggaaaagg aggcattggc tcgcgcgagc   840
gctgaccgtg tacgtctgcg gcaaatgctt actcgcgcac atctcaccga gcctctcgat   900
gaagcactgc ggaaactgcg catggcaggc cgcagcccgt ctttcctgga aatgttaggc   960
ttagtcggaa agtccgaagc ctgggaggcc agtctggcac ggtcagtgcg ggcacaaacg   1020
caagagggtg caggggcacg ggcgggtgca caagcagttg cacgtgcctc cactaaagtt   1080
gaggcagtgc cgggtgggcc aggccgtgaa ccggagggtt tgcgccaagc cggcgggcag   1140
gaagccgaag aattactcca agaaggttta aaaccggttt tggaggaatg cgataac      1197
```

SEQ ID NO: 48          moltype = DNA  length = 1425
FEATURE                Location/Qualifiers
source                 1..1425
                          mol_type = other DNA
                          organism = Homo sapiens
SEQUENCE: 48

```
ggggtggaag atttggcggc atcttacatc gtattaaagc ttgagaacga aatccggcag   60
gcgcaggtcc aatggttaat ggaggaaaac gccgccctgc aggcccagat ccctgaactt   120
caaaagtcgc aagccgcgaa ggagtatgat cttctgcgta aatcttcgga ggcgaaggag   180
ccgcaaaaac tgccagaaca tatgaatcca ccggccgctt gggaagcaca aaagactcca   240
gagtttaagg aaccacagaa acctcctgaa ccacaggatt tgcttccttg ggagccgcct   300
gctgcctggg agttgcaaga agcaccggct gccctgagt cactggctcc gcctgcaacc   360
cgtgagtctc agaaaccacc tatggcgcat gaaatcccta ctgtattgga ggggcaaggg   420
cctgccaaca cacaagacgc tacgattgct caagaaccaa agaatagcga gccgcaagac   480
cctccaaata tcgagaaacc tcaggaagct ccggaatatc aagaaacagc ggcacagttg   540
gagtttttag aacttcctcc acctcaggag ccactcgaac cgagcaatgc gcaagaattt   600
ctcgagttgt cggctgccca ggagtcctta gaaggcctca ttgtagttga aacgtccgcg   660
gcttcggagt cccacaggc tcctatcggg cttgaagcca ccgactttcc gctgcagtac   720
acgcttacct tctctggcga cagccagaag ttgccagaat ttttggtcca actctacagt   780
tatatgcggg tacgtgggca cttataccct accgaggcgg cgttagtgtc gtttgtaggc   840
aattgtttct cagggcgcgc gggctggtgg tttcagttgc ttttggatat ccagtcgcct   900
ctgttagaac agtgtgaaag ttttatcccg gttctccaag acacatttga caatccggaa   960
aacatgaagg acgcaaacca atgcatccac cagctttgtc agggcgaggg tcatgtggcc   1020
acacacttcc acctcattgc acaagagctt aattgggatg aaagcacgct gtggatccag   1080
ttccaggaag gcctggcctc atccatccag gatgaacttt cccatacatc gcctgctacc   1140
aacctgagtg atctgattac tcaatgcatc tcattagagg aaaagcctga cccaaacccg   1200
ttagggaagt cctcctcggc ggaggggggat ggcccggaaa gtccgccagc agaaaaccaa   1260
cctatgcaag ctgcgatcaa ttgtcctcac atttccgaag cagagtgggt tcgttggcac   1320
aaaggccggc tttgtctcta ttgcggctat ccgggtcact tcgcacgtga ttgcccagtg   1380
aagccacacc aggcgttaca ggcagggaac attcaggctt gccaa                   1425
```

SEQ ID NO: 49          moltype = DNA  length = 717
FEATURE                Location/Qualifiers
source                 1..717
                          mol_type = other DNA
                          organism = Homo sapiens
SEQUENCE: 49

```
ggggtgcagc cgcagactag caaagctgaa tcgccggctc tcgctgcctc accgaacgca   60
caaatggatg acgttattga tacattaacc tccctgcgtc tgacgaattc ggctctgcgg   120
cgggaggcta gcactcttcg ggccgagaaa gcaaatttaa ctaatatgct cgagtcagtg   180
atggccgagt taacgctgtt acggacccgt gcgcggattc cggggggccct gcagattacg   240
ccaccaattt cgtctattac tagcaacggt actcgcccga tgactgactcc tccaactagt   300
ttacctgaac cgtttctgg cgatcctggc cggttagctg gtttccttat gcagatggac   360
cgttttatga tctttcaagc tagccggttt ccaggggagg cagagcgtgt tgcgttcctg   420
gtgtcgcgct taactggcga agcagaaaaa tgggccattc ctcacatgca accagactct   480
cctttggcgta acaactatca aggcttctta gcagagttac ggcggaccta taagagcccg   540
ttgcgtcacg cccggcgggc gcaaatccgg aagacatcgg cctcgaaccg ggcagtccgt   600
gaacgccaaa tgctttgccg gcaacttgca tcagcaggta caggcccatg cccggtacac   660
cctgctagta acgggacttc cccggcaccg gcattaccag cacgggcgcg taactta      717
```

SEQ ID NO: 50          moltype = DNA  length = 339
FEATURE                Location/Qualifiers
source                 1..339
                          mol_type = other DNA
                          organism = Homo sapiens
SEQUENCE: 50

```
ggggacggtc gggtacagtt gatgaaggct ttattggctg gccctttacg tccggcggca   60
cgccgttggc ggaatcctat tccatttcca gagactttg atggggatac tgatcgcctc   120
ccggagttta tcgtccaaac ttcgtcctac atgttcgttg acgaaaatac tttctctaac   180
gacgctctga aagtgacatt tctcattacc cggctgacag gtccagcctt gcaatgggtc   240
attccgtaca ttcgtaaaga aagcccgctt cttaacgact atcggggttt cctggccgag   300
atgaagcggg tttttgggtg ggaagaggac gaggacttt                          339
```

SEQ ID NO: 51          moltype = DNA  length = 339
FEATURE                Location/Qualifiers
source                 1..339
                          mol_type = other DNA
                          organism = Homo sapiens
SEQUENCE: 51

```
ggggaaggtc gggtgcaact tatgaaagcg ttgcttgccc gcccgcttcg tccagcagca   60
```

-continued

```
cgtcgctggc ggaatccaat tcctttcccg gagacttttg acggggacac cgatcggctc  120
ccagagttca ttgtgcagac gtcaagctat atgttcgtgg atgagaacac gttctctaac  180
gacgcgttga aagtgacttt cttaattacg cgtttgactg gcccggcttt acaatgggtg  240
attccataca ttaagaaaga gtcaccgctt ctcagtgatt atcgcggttt tttagccgag  300
atgaagcggg tcttcgggtg ggaagaagac gaagacttt                          339

SEQ ID NO: 52          moltype = DNA   length = 1092
FEATURE                Location/Qualifiers
source                 1..1092
                       mol_type = other DNA
                       organism = Homo sapiens SEQUENCE: 52
gggccgcgtg ggcgttgccg tcaacaaggt cctcggattc cgatttgggc agcggccaac  60
tatgccaacg cccacccgtg gcaacaaatg gataaggctt cgccagcgt tgcttacaca   120
cctttggttg atccttggat tgagcggcct tgttgcggtg acacggtttg tgtgcgcacc  180
acaatggaac agaagagcac agcgtcaggc acttgtggtg gtaagcctgc tgagcgtggt  240
cctctcgcgg ggcatatgcc gagctcacgc ccacatcggg ttgatttctg ttgggttcct  300
ggtagcgacc caggcacatt cgacggcagt ccatggctct tagatcgctt tttggcgcaa  360
cttggtgatt acatgagttt tcactttgaa cactaccagg acaatatcag ccgtgtctgc  420
gagattcttc gtcggttaac gggccgcgct caggcatggg ctgctcctta cctggacggg  480
gaccttccac tgccagacga ctacgaattg ttttgtcaag accttaagga ggtagtacag  540
gaccctaaca gtttcgccga gtatcacgcc gtggtgactt gtccactccc tcttgcttcg  600
tcccaacttc ctgtagctcc tcagcttccg gtggtacgcc aataccttgc gcgcttcttg  660
gagggccttg ctttggatat gggtacggcg cctcggtcac tcccggccgc tatggccaca  720
ccggcagtct ccggctcgaa ctccgtttct cgttctgcct tatttgaaca acaactcaca  780
aaggaatcca ctccaggccc gaaagagcca cctgttctcc ctagctcgac ttgctctagc  840
aaaccgggtc ctgtcgaacc agccagttca caacctgaag aggctgctcc taccccggtg  900
ccgcgtttgt cagagtcggc taacccaccg gctcagcgtc cagaccctgc tcaccctggt  960
ggtcctaaac cacaaaaaac cgaagaggaa gttttagaaa ctgaggggga ccaggaagtt  1020
agcctggggga cgccgcagga ggtcgtagaa gcgccggaaa caccaggtga accaccgctc 1080
agccctgggt tc                                                       1092

SEQ ID NO: 53          moltype = DNA   length = 438
FEATURE                Location/Qualifiers
source                 1..438
                       mol_type = other DNA
                       organism = Homo sapiens SEQUENCE: 53
ggggttgatg aattggtgct cttgttgcac gcgctgttaa tgcgccatcg ggcgctttcc  60
attgaaaatt ctcagttgat ggagcaactt cgcttgttgg tctgcgaacg ggcgagcctt  120
cttcgtcagg tacgtccgcc gagctgtcca gtgccatttc ctgagacttt taacgggggag 180
tcatcacggt tacctgagtt catcgtcaa accgcaagct atatgttagt taatgaaaat  240
cgcttttgca atgacgcaat gaaagtcgct tttttgatta gccttcttac tggtgaagca  300
gaagaatggg tcgtcccata cattgagatg gattcaccaa ttcttgggga ctaccgtgcg  360
ttcttggatg agatgaagca gtgttttggg tgggacgatg atgaagatga cgacgatgag  420
gaagaggagg atgactat                                                 438

SEQ ID NO: 54          moltype = DNA   length = 1647
FEATURE                Location/Qualifiers
source                 1..1647
                       mol_type = other DNA
                       organism = Homo sapiens SEQUENCE: 54
gggcctgtgg atttaggtca ggctttgggg ttgttgccat ccctcgctaa ggccgaagat  60
tcccaattta gcgaaagcga tgcagcttta caggaggaat tgtcttctcc ggaaaccgca  120
cggcaacttt ttcgtcaatt tcgctatcaa gtcatgtcgg ggcctcatga aacactgaaa  180
cagttacgga agttatgttt tcagtggctg caacctgaag tccatacaaa ggaacaaatc  240
ctcgaaattc tgatgctgga acagttcttg accattctgc ctggtgaaat tcagatgtgg  300
gtccgcaagc agtgccctgg tagtggggag gaggcggtta cgttagtaga atccctgaaa  360
ggtgatccac aacggctctg gcaatggatc tccatccaag tcctgggtca ggatatcctg  420
tctgagaaaa tggagtcacc ttcttgccag gtgggcgaag tggagccaca cctggaagtt  480
gtacctcagg aactgggggtt agagaattca tcttcagggc cggggggaact tctttcgcac  540
atcgtgaaag aggagtctga cactgaagca gagttggcgt tagcggcatc ccagccagct  600
cgtttggaag aacggctgat tcgggatcag gaccttgggg cgtccctcct ccgggcagca  660
ccgcaggagc aatggcgtca attagacagc actcaaaaag aacaatattg ggacctgatg  720
ctggagacct acggcaaaat ggtatccggc gcgggtatct cacacccgaa gtccgattta  780
acgaactcaa ttgagttcgg tgaagagttg gcaggtattt atttacatgt aaacgaaaag  840
attccgcggc ctacctgcat tggtgaccgc caagaaacg acaaagaaaa ccttaatttg   900
gaaaaccatc gtgaccagga attattacat gccagctcgg aggcctcggg cgaagtgcca  960
tcccaggcat cgttacgtgg cttctttacc gaggacgaac ctggttgctt cggcgaaggg  1020
gagaaccttc ctgaggcact tcagaatatc caggatgagg ggactggcga acagctgagc  1080
ccgcaagaac gcattagtga aaaacagttg ggtcaacatt tgccaaatcc gcactcgggg  1140
gagatgtcga cgatgtggct tgaagaaaaa cgggagacca gccagaaagg ccaaccacgt  1200
gcaccaatgg cgcagaaatt gccaacgtgc cgcgaagtgt gcaaaacgtt ttatcgcaat  1260
agtcaactta tctttcacca acgcacacac accggtgaga catattttca atgcaccatc  1320
tgcaaaaagt cgtttctccg gtcatctgat ttcgtgaaac atcagcggac tcatactggc  1380
gaaaaacctt gtaaatgtga ctattgtggc aagggcttta gtgattttag cgggcttcgg  1440
catcacgaga agatccatac cggcgagaag ccatacaagt gtccaatctg tgagaaatct  1500
ttcatccagc gcagtaattt taaccgccac caacgggttc acaccggtga aaagccttat  1560
```

```
aaatgctcgc attgtggcaa gagcttcagc tggagctcct cgctcgataa gcatcaacgt   1620
tcacatctgg ggaagaagcc gttccaa                                       1647

SEQ ID NO: 55         moltype = DNA  length = 1053
FEATURE               Location/Qualifiers
source                1..1053
                      mol_type = other DNA
                      organism = Homo sapiens
SEQUENCE: 55
gggactctcc gcttacttga ggattggtgt cgggggatgg acatgaaccc acgtaaggcc   60
cttcttatcg ccgggatttc ccagtcatgt tcagtcgccg agattgaaga ggcgctccaa   120
gccgggcttg ctcctttagg cgagtatcgt ctccttgggc ggatgtttcg ccgcgatgaa   180
aatcgcaaag tagcgttggt tggtctcaca gctgaaacta gccatgcgct tgtacctaaa   240
gaaattcctg gtaaaggcgg gatctggcgg gttattttta aaccaccgga cccggacaat   300
acgtttcttt ctcgtttgaa tgagttcctc gcgggcgagg ggatgacggt ggggaacttt   360
agtcgtgctc ttggtcacga aaatgggtca ttagaccctg aacagggtat gattccggaa   420
atgtgggcgc cgatgctggc acaggctctg gaggctctcc aaccggcttt acagtgcctt   480
aagtacaaga agctgcgcgt tttttcaggg cgcgagtcgt cagagccggg tgaggaggaa   540
ttcggccgtt ggatgttcca taccacccag atgatcaaag cgtggcaggt gccggatgtc   600
gagaaacgcc gccggctgtt ggaatcactc cgcgggccgg cacttgacgt tattcgggtt   660
ctgaaaatta acaacccgtt aattacggta gatgaatgtt tgcaagcact tgaagaggtc   720
tttggggtga ctgacaatcc tcgggaattg caagtaaaat acttaacgac ctaccataag   780
gacgaggaga aattatcagc ctacgtactg cggctggaac cgctgctgca gaagctcgtc   840
cagcgggggg ctattgaacg ggacgctgtt aatcaggctc gcctggatca ggtaatcgct   900
ggggcggtac ataaaactat ccgccgtgag ctgaacctgc ctgaagacgg gccggcgcca   960
ggctttcttc aactcctcgt tttgattaag gattacgagg cagctgaaga ggaggaagca   1020
ttacttcagg ccattcttga agggaacttt act                               1053

SEQ ID NO: 56         moltype = DNA  length = 2124
FEATURE               Location/Qualifiers
source                1..2124
                      mol_type = other DNA
                      organism = Homo sapiens
SEQUENCE: 56
gggacagaac ggcgtcgcga cgaattaagt gaagaaatta ataatcttcg tgaaaaggtt   60
atgaaacaga gtgaggaaaa caacaatctt caatcccaag tccagaaact cactgaggag   120
aatactcac tccgtgagca agttgaacct acacctgaag atgaagatga cgacattgag    180
ttgcggggcg cagcagccgc agccgcgcct ccgccgccga tcgaggagga atgcccggag   240
gatttaccgg aaaaatttga tggtaatccg gacatgttag cgccattcat ggcccagtgc   300
caaattttta tggaaaagtc tacgcgcgat tttagtgtag atcgcgtacg tgtatgtttt   360
gtgacgagca tgatgactgg tcgcgcagcc cgttgggcgt cagcgaaatt ggagcggtcg   420
cactacctga tgcataatta cccggcgttc atgatggaga tgaaacacgt gtttgaagac   480
ccgcagcggc gggaggtggc caaacgcaag atccggcggt tgcggcaggg catgggcagc   540
gtaattgatt atagtaatgc gtttcaaatg attgcgcagg atctggattg gaatgaacct   600
gctctcattg atcaatatca tgaagggctt agtgaccata ttcaagagga actctctcac   660
ctggaagtgg ctaaatctct ctccgccctt attggccaat gcattcatat tgagcgccgt   720
cttgcacggt ctgctgccgc tcggaaaccg cgtagtccac cacgggcttt agtgctccca   780
catatcgcgt cacaccatca agtagatcct actgagccag tggggggtgc acgcatgcgc   840
ttaacccaag aagaaaagga acgtcgtcgt aagctgaatt tatgcctgta ctgcggcact   900
ggtggccatt atgccgataa ctgtcctgcc aaagccagta agtcaagccc ggctgggaaa   960
cttccaggtc ctgccgtcga gggcccttct gctaccggcc cagagattat ccgctccccg   1020
caagacgatg cgtcgtcgcc tcatctccag gtaatgctcc aaatccacct ccctggccgg   1080
cacacactct ttgtccgggc gatgattgac tctgggggcgt ctggtaattt tattgatcac   1140
gagtatgttg ctcaaaatgg tatccctctc cggatcaaag actggcctat tctggttgaa   1200
gccatcgatg gccgtccgat cgcgagcggt cctgtggttc atgaaacgca tgacctcatc   1260
gttgatctgg gtgaccaccg tgaagtatta tcctttgatg tgactcagtc accgttttt   1320
ccagttgttt tgggcgtccg ttggctttcg actcacgatc ctaacatcac gtggtcgaca   1380
cggtcgattg tcttcgattc ggaatattgt cgttatcatt gccgcatgta ttcaccaatt   1440
ccgccgtctc tcccgccgcc tgcgccgcaa cctcctctgt attacccggt ggacggttac   1500
cgtgtttacc agccagttcg ctactactac gtacaaaacg tgtacacgcc tgttgatgaa   1560
cacgtgtacc cagatcaccg cctggtcgac cctcatattg agatgatccc gggtgcgcac   1620
tcgatcccat cgggccatgt ttattccttg tctgagccag aaatggccgc cttacgggat   1680
tttgtggccc ggaatgtcaa agacggcctg attaccccga caattgcacc aaacggtgct   1740
caggtgttgc aggtgaagcg gggctggaag ttgcaagtca gctatgattg tcgtgcgcca   1800
aacaacttca ctattcagaa ccaatatcca cgtctcagca tccctaatct cgaggaccag   1860
gcacatcttg caacatatac tgaatttgta cctcagattc ctggctatca gacttatcct   1920
acgtatgctc cctacccaac ataccggta ggtttcgcat ggtacccagt aggccgggac    1980
gggcagggcc gctctttata tgttcctgtc atgattacat ggaacccgca ttggtaccgc   2040
cagcctccgg tcccacagta cccacctcct caacctccac cacctccgcc gcctcctcca   2100
ccgccacctt cttactcgac atta                                          2124

SEQ ID NO: 57         moltype = DNA  length = 60
FEATURE               Location/Qualifiers
misc_feature         1..60
                      note = Description of Artificial Sequence:
                      Syntheticoligonucleotide
source                1..60
                      mol_type = other DNA
                      organism = synthetic construct
```

```
SEQUENCE: 57
atgcatcacc atcaccatca cggctcaggg tctggtagcg aaaatctgta cttccagggg  60

SEQ ID NO: 58            moltype = AA  length = 20
FEATURE                  Location/Qualifiers
REGION                   1..20
                         note = Description of Artificial Sequence: Syntheticpeptide
source                   1..20
                         mol_type = protein
                         organism = synthetic construct
SEQUENCE: 58
MHHHHHHGSG SGSENLYFQG                                                20

SEQ ID NO: 59            moltype = AA  length = 6
FEATURE                  Location/Qualifiers
REGION                   1..6
                         note = Description of Artificial Sequence: Synthetic6xHis
                          tag
source                   1..6
                         mol_type = protein
                         organism = synthetic construct
SEQUENCE: 59
HHHHHH                                                                6

SEQ ID NO: 60            moltype = AA  length = 6
FEATURE                  Location/Qualifiers
REGION                   1..6
                         note = Description of Artificial Sequence: Syntheticpeptide
source                   1..6
                         mol_type = protein
                         organism = synthetic construct
SEQUENCE: 60
GSGSGS                                                                6

SEQ ID NO: 61            moltype = AA  length = 7
FEATURE                  Location/Qualifiers
REGION                   1..7
                         note = Description of Artificial Sequence: Syntheticpeptide
source                   1..7
                         mol_type = protein
                         organism = synthetic construct
SEQUENCE: 61
ENLYFQG                                                               7

SEQ ID NO: 62            moltype = DNA  length = 26
FEATURE                  Location/Qualifiers
misc_feature             1..26
                         note = Description of Artificial Sequence: Syntheticprimer
source                   1..26
                         mol_type = other DNA
                         organism = synthetic construct
SEQUENCE: 62
aagctcattt cctggtatga caacga                                         26

SEQ ID NO: 63            moltype = DNA  length = 25
FEATURE                  Location/Qualifiers
misc_feature             1..25
                         note = Description of Artificial Sequence: Syntheticprimer
source                   1..25
                         mol_type = other DNA
                         organism = synthetic construct
SEQUENCE: 63
agggtctctc tcttcctctt gtgct                                          25

SEQ ID NO: 64            moltype = DNA  length = 25
FEATURE                  Location/Qualifiers
misc_feature             1..25
                         note = Description of Artificial Sequence: Syntheticprimer
source                   1..25
                         mol_type = other DNA
                         organism = synthetic construct
SEQUENCE: 64
gctcaacctg ggaactgcat ctgat                                          25

SEQ ID NO: 65            moltype = DNA  length = 25
FEATURE                  Location/Qualifiers
misc_feature             1..25
                         note = Description of Artificial Sequence: Syntheticprimer
source                   1..25
```

```
                        mol_type = other DNA
                        organism = synthetic construct
SEQUENCE: 65
taatcctgtt tgctccccac gcttt                                       25

SEQ ID NO: 66          moltype = DNA   length = 22
FEATURE                Location/Qualifiers
misc_feature           1..22
                       note = Description of Artificial Sequence: Syntheticprimer
source                 1..22
                       mol_type = other DNA
                       organism = synthetic construct
SEQUENCE: 66
ggcccctcag ctccagtgat tc                                          22

SEQ ID NO: 67          moltype = DNA   length = 25
FEATURE                Location/Qualifiers
misc_feature           1..25
                       note = Description of Artificial Sequence: Syntheticprimer
source                 1..25
                       mol_type = other DNA
                       organism = synthetic construct
SEQUENCE: 67
cctgttgtca ctctcctggc tctga                                       25

SEQ ID NO: 68          moltype = DNA   length = 24
FEATURE                Location/Qualifiers
misc_feature           1..24
                       note = Description of Artificial Sequence: Syntheticprimer
source                 1..24
                       mol_type = other DNA
                       organism = synthetic construct
SEQUENCE: 68
gccaagacat aagaaacctc gcct                                        24

SEQ ID NO: 69          moltype = DNA   length = 24
FEATURE                Location/Qualifiers
misc_feature           1..24
                       note = Description of Artificial Sequence: Syntheticprimer
source                 1..24
                       mol_type = other DNA
                       organism = synthetic construct
SEQUENCE: 69
gtgaatcaac atcctccctc cgtc                                        24

SEQ ID NO: 70          moltype = AA   length = 25
FEATURE                Location/Qualifiers
REGION                 1..25
                       note = Description of Artificial Sequence: SyntheticPeptide
REGION                 1..25
                       note = MISC_FEATURE - This sequence may encompass 1-5 "Glu
                        Ala Ala Ala Lys"repeating units
source                 1..25
                       mol_type = protein
                       organism = synthetic construct
SEQUENCE: 70
EAAAKEAAAK EAAAKEAAAK EAAAK                                       25

SEQ ID NO: 71          moltype = AA   length = 25
FEATURE                Location/Qualifiers
REGION                 1..25
                       note = Description of Artificial Sequence: SyntheticPeptide
REGION                 1..25
                       note = MISC_FEATURE - This sequence may encompass 1-5 "Glu
                        Ala Ala Ala Arg"repeating units
source                 1..25
                       mol_type = protein
                       organism = synthetic construct
SEQUENCE: 71
EAAAREAAAR EAAAREAAAR EAAAR                                       25

SEQ ID NO: 72          moltype = AA   length = 50
FEATURE                Location/Qualifiers
REGION                 1..50
                       note = Description of Artificial Sequence:
                        SyntheticPolypeptide
REGION                 1..50
                       note = MISC_FEATURE - This sequence may encompass 1-10 "Gly
                        Gly Gly Gly Ser"repeating units
```

```
source                  1..50
                        mol_type = protein
                        organism = synthetic construct
SEQUENCE: 72
GGGGSGGGGS GGGGSGGGGS GGGGSGGGGS GGGGSGGGGS GGGGSGGGGS          50

SEQ ID NO: 73           moltype = AA  length = 40
FEATURE                 Location/Qualifiers
REGION                  1..40
                        note = Description of Artificial Sequence:
                        SyntheticPolypeptide
REGION                  1..40
                        note = MISC_FEATURE - This sequence may encompass 1-10 "Gly
                        Gly Gly Ser"repeating units
source                  1..40
                        mol_type = protein
                        organism = synthetic construct
SEQUENCE: 73
GGGSGGGSGG GSGGGSGGGS GGGSGGGSGG GSGGGSGGGS                     40

SEQ ID NO: 74           moltype = AA  length = 18
FEATURE                 Location/Qualifiers
REGION                  1..18
                        note = Description of Artificial Sequence: SyntheticPeptide
source                  1..18
                        mol_type = protein
                        organism = synthetic construct
SEQUENCE: 74
KESGSVSSEQ LAQFRSLD                                             18

SEQ ID NO: 75           moltype = AA  length = 14
FEATURE                 Location/Qualifiers
REGION                  1..14
                        note = Description of Artificial Sequence: Syntheticpeptide
source                  1..14
                        mol_type = protein
                        organism = synthetic construct
SEQUENCE: 75
EGKSSGSGSE SKST                                                 14

SEQ ID NO: 76           moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 76
GGAANLVRGG                                                      10

SEQ ID NO: 77           moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 77
SGRIGFLRTA                                                      10

SEQ ID NO: 78           moltype = AA  length = 5
FEATURE                 Location/Qualifiers
REGION                  1..5
                        note = Description of Artificial Sequence: Syntheticpeptide
source                  1..5
                        mol_type = protein
                        organism = synthetic construct
SEQUENCE: 78
SGRSA                                                            5

SEQ ID NO: 79           moltype = AA  length = 4
FEATURE                 Location/Qualifiers
REGION                  1..4
                        note = Description of Artificial Sequence: Syntheticpeptide
source                  1..4
                        mol_type = protein
                        organism = synthetic construct
SEQUENCE: 79
GFLG                                                             4
```

-continued

```
SEQ ID NO: 80          moltype = AA  length = 4
FEATURE                Location/Qualifiers
REGION                 1..4
                       note = Description of Artificial Sequence: Syntheticpeptide
source                 1..4
                       mol_type = protein
                       organism = synthetic construct
SEQUENCE: 80
ALAL                                                                     4

SEQ ID NO: 81          moltype = AA  length = 5
FEATURE                Location/Qualifiers
REGION                 1..5
                       note = Description of Artificial Sequence: SyntheticPeptide
MOD_RES                3
                       note = S-ethylcysteine
source                 1..5
                       mol_type = protein
                       organism = synthetic construct
SEQUENCE: 81
PICFF                                                                    5

SEQ ID NO: 82          moltype =   length =
SEQUENCE: 82
000

SEQ ID NO: 83          moltype = AA  length = 4
FEATURE                Location/Qualifiers
REGION                 1..4
                       note = Description of Artificial Sequence: Syntheticpeptide
source                 1..4
                       mol_type = protein
                       organism = synthetic construct
SEQUENCE: 83
DEVD                                                                     4

SEQ ID NO: 84          moltype = AA  length = 6
FEATURE                Location/Qualifiers
REGION                 1..6
                       note = Description of Artificial Sequence: Syntheticpeptide
source                 1..6
                       mol_type = protein
                       organism = synthetic construct
SEQUENCE: 84
GWEHDG                                                                   6

SEQ ID NO: 85          moltype = AA  length = 8
FEATURE                Location/Qualifiers
REGION                 1..8
                       note = Description of Artificial Sequence: Syntheticpeptide
source                 1..8
                       mol_type = protein
                       organism = synthetic construct
SEQUENCE: 85
RPLALWRS                                                                 8
```

What is claimed is:

1. A capsid comprising a recombinant endogenous Gag polypeptide and a heterologous cargo, wherein (a) the endogenous Gag polypeptide comprises (i) at least one capsid forming subunit from an endogenous Gag polypeptide that is not an Arc polypeptide and (ii) an RNA binding domain modified to bind to a heterologous cargo, and (b) the RNA binding domain is fused to the at least one capsid forming subunit through a linker.

2. The capsid of claim 1, wherein the cargo is an RNA and is bound to the RNA binding domain.

3. The capsid of claim 1, wherein the at least one capsid forming subunit is from an endogenous Gag polypeptide that is not an Arc polypeptide.

4. The capsid of claim 1, wherein the endogenous Gag polypeptide is a Paraneoplastic Ma antigen family polypeptide, a retrotransposon Gag-like (RTL) family polypeptide, or a SCAN domain family polypeptide.

5. The capsid of claim 1, wherein the linker is non-cleavable.

6. The capsid of claim 5, wherein the linker is selected from (EAAAK)$_n$ (SEQ ID NO: 70), or (EAAAR)$_n$ (SEQ ID NO: 71), where n is from 1 to 5, and up to 30 residues of glutamic acid-proline or lysine-proline repeats.

7. The capsid of claim 5, wherein the linker comprises (a) (GGGGS)$_n$ (SEQ ID NO: 72) or (GGGS)$_n$ (SEQ ID NO: 73), wherein n is 1 to 10, (b) KESGSVSSEQLAQFRSLD (SEQ ID NO: 74), or (c) EGKSSGSGSESKST (SEQ ID NO: 75).

8. The capsid of claim 1, wherein the linker is cleavable.

9. The capsid of claim 8, wherein the linker is cleaved by endogenous enzymes.

10. The capsid of claim 1, wherein the linker is fused to the C-terminus of the at least one capsid forming subunit.

11. The capsid of claim 1, wherein the linker is fused to the N-terminus of the at least one capsid forming subunit.

* * * * *